(12) United States Patent
TenBrink et al.

(10) Patent No.: US 7,312,360 B2
(45) Date of Patent: Dec. 25, 2007

(54) SUBSTITUTED HYDROXYETHYLAMINES

(75) Inventors: Ruth TenBrink, Kalamazoo, MI (US); Michel Maillard, Redwood Shores, CA (US); Martha Warpehoski, Portage, MI (US)

(73) Assignees: Elan Pharmaceuticals, Inc., So. San Francisco, CA (US); Pharmacia & Upjohn Company, Kalamazoo, MI (US)

( * ) Notice: Subject to any disclaimer, the term of this patent is extended or adjusted under 35 U.S.C. 154(b) by 91 days.

(21) Appl. No.: 10/313,849

(22) Filed: Dec. 6, 2002

(65) Prior Publication Data

US 2004/0044072 A1 Mar. 4, 2004

Related U.S. Application Data

(60) Provisional application No. 60/338,452, filed on Dec. 6, 2001.

(51) Int. Cl.
C07C 233/65 (2006.01)
A61K 31/165 (2006.01)

(52) U.S. Cl. ............ 564/185; 564/157; 560/27; 560/29; 514/616; 514/617; 514/478

(58) Field of Classification Search .......... 564/185, 564/157; 514/616, 617, 478; 560/27, 29
See application file for complete search history.

(56) References Cited

FOREIGN PATENT DOCUMENTS

| WO | WO96/22287 | 7/1996 |
|---|---|---|
| WO | WO99/64001 | 12/1999 |
| WO | WO 00/47618 | 8/2000 |
| WO | WO 00/56335 | 9/2000 |
| WO | WO 00/77030 | 12/2000 |
| WO | WO 01/10387 | 2/2001 |
| WO | WO 01/66564 | 9/2001 |
| WO | WO 02/02505 | 1/2002 |
| WO | WO 02/02512 | 1/2002 |
| WO | WO 02/098849 | 12/2002 |
| WO | WO 02/100856 | 12/2002 |
| WO | WO 03/006423 | 1/2003 |

OTHER PUBLICATIONS

Alcon, et al., (1997) *Enantioselective*, 8:29676-2974.
Arrowsmith, et al., (1987) *Tetrahedron Letters*, 28:5569-5572.
Barrish, et al., (1994) *J. Med. Chem. Amer. Chem. Soc.* 37:1758-1768.
Ciganek, (1992) *J. Org. Chem.*, 57:4521-4527.
Dantzig, et al., (1996) *Cancer Research*, 56:4171-4179.
Getman, et al., (1993) *J. Med. Chem.*, 36:288-291.
Hyafil, F., (1993) *Cancer Research*, 53:4595-4602.
Norman, et al., (2000) *J. Med. Chem.*, 43:4288-4312.
Shibata, et al., (1997) *Tetrahedron Letters*, 38:619-620.
Snyder, et al., (1938) *J. Am. Chem. Soc.*, 60:105-111.
Vazquez, (1994) *J. Med. Chem.*, 38:581-584.
Witherspoon, et al., (1996) *Clin. Cancer Res.*, 2:7-12.
International Search Report for International Application No. PCT/US02/39050, 2002.

*Primary Examiner*—Shailendra Kumar
(74) *Attorney, Agent, or Firm*—McDonnell Boehnen Hulbert & Berghoff LLP

(57) ABSTRACT

Disclosed are compounds of the formula

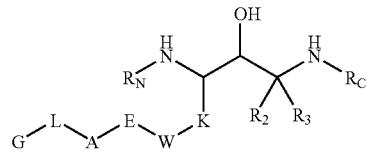

and the pharmaceutically acceptable salts thereof wherein the variables G, L, A, W, E, R2, R3, R4, R5, $R_N$, and $R_c$ are defined herein. These compounds interact with and inhibit the activity of the enzyme beta-secretase. These compounds are therefore useful in treating Alzheimer's disease and other similar diseases. Pharmaceutical compositions and methods of treatment of these diseases are also disclosed.

11 Claims, No Drawings

SUBSTITUTED HYDROXYETHYLAMINES

This application claims benefit of 60/338,452, filed Dec. 6, 2001.

BACKGROUND OF THE INVENTION

1. Field of the Invention

The present invention relates to α-aminoalcohol derivatives and to such compounds that are capable of inhibiting beta-secretase, an enzyme that cleaves amyloid precursor protein to produce amyloid beta peptide (A beta), a major component of the amyloid plaques found in the brains of Alzheimer's sufferers. The invention also relates to the use of such compounds in the treatment of Alzheimer's Disease.

2. Description of the Related Art

Alzheimer's disease (AD) is a progressive degenerative disease of the brain primarily associated with aging. Clinical presentation of AD is characterized by loss of memory, cognition, reasoning, judgement, and orientation. As the disease progresses, motor, sensory, and linguistic abilities are also affected until there is global impairment of multiple cognitive functions. These cognitive losses occur gradually, but typically lead to severe impairment and eventual death in the range of four to twelve years.

Alzheimer's disease is characterized by two major pathologic observations in the brain: neurofibrillary tangles and beta amyloid (or neuritic) plaques, comprised predominantly of an aggregate of a peptide fragment know as A beta. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Smaller numbers of these lesions in a more restricted anatomical distribution are found in the brains of most aged humans who do not have clinical AD. Amyloidogenic plaques and vascular amyloid angiopathy also characterize the brains of individuals with Trisomy 21 (Down's Syndrome), Hereditary Cerebral Hemorrhage with Amyloidosis of the Dutch-Type (HCHWA-D), and other neurogenerative disorders. Beta-amyloid is a defining feature of AD, now believed to be a causative precursor or factor in the development of disease. Deposition of A beta in areas of the brain responsible for cognitive activities is a major factor in the development of AD. Beta-amyloid plaques are predominantly composed of amyloid beta peptide (A beta, also sometimes designated betaA4). A beta peptide is derived by proteolysis of the amyloid precursor protein (APP) and is comprised of 39–42 amino acids. Several proteases called secretases are involved in the processing of APP.

Cleavage of APP at the N-terminus of the A beta peptide by beta-secretase and at the C-terminus by one or more gamma-secretases constitutes the beta-amyloidogenic pathway, i.e. the pathway by which A beta is formed. Cleavage of APP by alpha-secretase produces alpha-sAPP, a secreted form of APP that does not result in beta-amyloid plaque formation. This alternate pathway precludes the formation of A beta peptide. A description of the proteolytic processing fragments of APP is found, for example, in U.S. Pat. Nos. 5,441,870; 5,721,130; and 5,942,400.

An aspartyl protease has been identified as the enzyme responsible for processing of APP at the beta-secretase cleavage site. The beta-secretase enzyme has been disclosed using varied nomenclature, including BACE, Asp, am Mamepsin. See, for example, Sindha et al., 1999, *Nature* 402:537–554 (p501) and published PCT application WO00/17369.

Several lines of evidence indicate that progressive cerebral deposition of beta-amyloid peptide (A beta) plays a seminal role in the pathogenesis of AD and can precede cognitive symptoms by years or decades. See, for example, Selkoe, 1991, *Neuron* 6:487. Release of A beta from neuronal cells grown in culture and the presence of A beta in cerebrospinal fluid (CSF) of both normal individuals and AD patients has been demonstrated. See, for example, Seubert et al., 1992, *Nature* 359:325–327.

It has been proposed that A beta peptide accumulates as a result of APP processing by beta-secretase, thus inhibition of this enzyme's activity is desirable for the treatment of AD. In vivo processing of APP at the beta-secretase cleavage site is thought to be a rate-limiting step in A beta production, and is thus a therapeutic target for the treatment of AD. See for example, Sabbagh, M., et al., 1997, *Alz. Dis. Rev.* 3, 1–19.

BACE1 knockout mice fail to produce A beta, and present a normal phenotype. When crossed with transgenic mice that overexpress APP, the progeny show reduced amounts of A beta in brain extracts as compared with control animals (Luo et al., 2001 *Nature Neuroscience* 4:231–232). This evidence further supports the proposal that inhibition of beta-secretase activity and reduction of A beta in the brain provides a therapeutic method for the treatment of AD and other beta amyloid disorders.

Published PCT application WO00/47618 entitled "Beta-Secretase Enzyme Compositions and Methods" identifies the beta-secretase enzyme and methods of its use. This publication also discloses oligopeptide inhibitors that bind the enzyme's active site and are useful in affinity column purification of the enzyme. In addition, WO00/77030 discloses tetrapeptide inhibitors of beta-secretase activity that are based on a statine molecule Various pharmaceutical agents have been proposed for the treatment of Alzheimer's disease but without any real success. U.S. Pat. No. 5,175,281 discloses 21-aminosteroids as being useful for treating Alzheimer's disease. U.S. Pat. No. 5,502,187 discloses bicyclic heterocyclic amines as being useful for treating Alzheimer's disease.

At present there are no effective treatments for halting, preventing, or reversing the progression of Alzheimer's disease. Therefore, there is an urgent need for pharmaceutical agents capable of slowing the progression of Alzheimer's disease and/or preventing it in the first place.

Compounds that are effective inhibitors of beta-secretase, that inhibit beta-secretase-mediated cleavage of APP, that are effective inhibitors of A beta production, and/or are effective to reduce amyloid beta deposits or plaques, are needed for the treatment and prevention of disease characterized by amyloid beta deposits or plaques, such as AD.

SUMMARY OF INVENTION

The invention provides compounds capable of interacting with and inhibiting beta-secretase. More specifically, the invention encompasses compounds represented by formula I

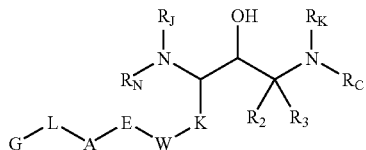

and the pharmaceutically acceptable salts thereof, wherein

E is a bond or $C_1$–$C_3$ alkylene;

$R_J$ is H, $C_1$–$C_4$ alkoxycarbonyl or benzyloxycarbonyl;

$R_K$ is H, $C_1$–$C_4$ alkoxycarbonyl or benzyloxycarbonyl;

K is —$(CR_4R_5)_n$—; wherein $R_4$ and $R_5$ are independently hydrogen, halogen, $C_1$–$C_6$ alkoxy or $C_1$–$C_4$ alkyl optionally substituted with halogen, —CN, —$CF_3$, or —OH;

n is 0, 1 or 2;

A is:
  (I) aryl or cycloalkyl where each aryl or cycloalkyl is optionally substituted with one, two or three independently selected $R_{100}$ groups, where $R_{100}$ is
    (A) —$NO_2$,
    (B) —C≡N,
    (C) —N(R)CO(R')R, where R and R' are independently hydrogen, $C_1$–$C_6$ alkyl, or —$(CH_2)_{0-2}$-aryl or —$(CH_2)_{0-2}$-cycloalkyl, where each aryl or cycloalkyl is optionally substituted with halogen, hydroxy, $C_1$–$C_6$ alkyl, $C_1$–$C_6$ alkyl, amino, mono$(C_1$–$C_6)$alkylamino, or di$(C_1$–$C_6)$alkylamino,
    (D) —$CO_2$—$R_{25}$, where $R_{25}$ is selected from the group consisting of:
      (a) $C_1$–$C_6$ alkyl,
      (b) —$(CH_2)_{0-2}$-cycloalkyl,
      (c) —$(CH_2)_{0-2}$-aryl, where the aryl is optionally substituted with halogen, hydroxy, $C_1$–$C_6$ alkyl, $C_1$–$C_6$ alkyl, amino, mono$(C_1$–$C_6)$alkylamino, or di$(C_1$–$C_6)$alkylamino, and
      (d) hydrogen,
    (E) —NH—$CO_2$—$R_{25}$,
    (F) —O—$(C_2$–$C_6$ alkyl)—$CO_2H$,
    (G) —NRR',
    (H) —SR,
    (I) —$CH_2OH$,
    (J) —C(O)—$(C_1$–$C_6)$alkyl,
    (K) —C(O)NRR',
    (L) —$SO_2NRR'$,
    (M) —$CO_2H$,
    (N) $C_1$–$C_6$ alkyl, $C_1$–$C_6$ alkenyl with one or two double bonds, —$C_1$–$C_6$ alkynyl with one or two triple bonds, —$CF_3$, —F, —Cl, —Br, —I, $C_1$–$C_3$ alkoxy, —$OCF_3$, —$NH_2$, —OH, or —CN,
    (O) halogen, and
    (P) —$(CH_2)_{0-2}$—O—$(CH_2)_{0-2}$—OH;
  (II) heteroaryl, provided that, when E is a bond, the heteroaryl group is bonded through one of its carbon atoms to W, and where the heteroaryl is optionally substituted with one or two independently selected $R_{100}$ groups;
    (III) heterocycle, provided that, when E is a bond, the heterocycle group is bonded through one of its carbon atoms to W, where the heterocycle is optionally substituted with one or two independently selected $R_{200}$ groups, where $R_{200}$ is (1) =O,
(2) $C_1$–$C_3$ alkyl,
(3) —$CF_3$,
(4) —F, Cl, —Br and —I,
(5) $C_1$–$C_3$ alkoxy,
(6) —$OCF_3$,
(7) —$NH_2$,
(8) —OH, or
(9) —C≡N;

W is a bond, —S—, —S(O)—, —$SO_2$—, —O—, —N(R)— where R is hydrogen or $C_1$–$C_4$ alkyl;

L is a bond or absent when G is absent, or L is —C(O)—, —S(O)—, —$SO_2$—, —O—, —C($R_{110}$)($R_{112}$)O—, —OC($R_{110}$)($R_{112}$)—, —N($R_{110}$)—, —CON($R_{110}$)—, —N($R_{110}$)CO—, —C($R_{110}$)(R')—, —C(OH)$R_{110}$—, —$SO_2NR_{110}$—, —N($R_{110}$)$SO_2$—, —N($R_{110}$)CON($R_{112}$)—, N($R_{110}$)CSN($R_{112}$)—, —$OCO_2$—, —$NCO_2$—, or —OCON($R_{110}$)—, where $R_{110}$ and $R_{112}$ are independently hydrogen, or $C_1$–$C_4$ alkyl, where $C_1$–$C_4$ alkyl is optionally substituted with OH, $C_1$–$C_4$ alkoxy, or one to five F;

G is absent or:
  (I) $C_1$–$C_{10}$ alkyl, optionally substituted with up to three groups independently selected from
    (A) —$CO_2H$,
    (B) —$CO_2(C_1$–$C_4$ alkyl)
    (C) $C_1$–$C_6$ alkoxy,
    (D) —OH,
    (E) —NRR',
    (F) —$C_1$–$C_6$ haloalkyl,
    (G) —$(C_1$–$C_{10}$ alkyl)—O—$(C_1$–$C_3$ alkyl),
    (H) —$C_1$–$C_{10}$ alkenyl with one or two double bonds,
    (I) —$C_1$–$C_{10}$ alkynyl with one or two triple bonds,
    (J) —$C_1$–$C_{10}$ alkyl chain with one double bond and one triple bond,
    (K) aryl optionally substituted with $R_{100}$,
    (L) heteroaryl optionally substituted with $R_{100}$,
    (M) $C_1$–$C_6$ alkyl,
  (II) —$(CH_2)_{0-3}$—$(C_3$–$C_7)$ cycloalkyl where cycloalkyl is optionally substituted with one, two or three substituents selected from the group consisting of:
    (A) —$CO_2H$,
    (B) —$CO_2$—$(C_1$–$C_4$ alkyl),
    (C) $C_1$–$C_6$ alkoxy,
    (D) —OH,
    (E) —$NH_2$,
    (F) —$C_1$–$C_6$ haloalkyl,
    (G) —$(C_1$–$C_{10}$ alkyl) —O—$(C_1$–$C_3$ alkyl)
    (H) —$C_1$–$C_{10}$ alkenyl with one or two double bonds,
    (I) —$C_1$–$C_{10}$ alkynyl with one or two triple bonds,
    (J) —$C_1$–$C_{10}$ alkyl chain with one double bond and one triple bond,
    (K) aryl optionally substituted with $R_{100}$,
    (L) heteroaryl optionally substituted with $R_{100}$,
    (m) mono$(C_1$–$C_6$ alkyl)amino, and
  (n) di$(C_1$–$C_6$ alkyl) amino,
  (o) $C_1$–$C_6$ alkyl,
  (III) —$(CRR)_{0-4}$-aryl where aryl is optionally substituted with $R_{100}$,
  (IV) —$(CH_2)_{0-4}$-heteroaryl where the heteroaryl is optionally substituted with one, two, or three independently selected $R_{100}$ groups,
  (V) —$(CH_2)_{0-4}$-heterocycle, where the heterocycle is optionally substituted with one or two $R_{200}$ groups,
  (VI) —C($R_{10}$)($R_{12}$)—CO—NH—$R_{14}$ where $R_{10}$ and $R_{12}$ are the same or different and are selected from the group consisting of:

(A) —H,
(B) —$C_1$–$C_6$ alkyl,
(C) —($C_1$–$C_4$ alkyl)-aryl, where the aryl is optionally substituted with one, two, or three independently selected $R_{100}$ groups,
(D) —($C_1$–$C_4$ alkyl)-heteroaryl where the heteroaryl is optionally substituted with one, two, or three independently selected $R_{100}$ groups,
(E) —($C_1$–$C_4$ alkyl)-heterocycle, where the heterocycle is optionally substituted with one or two $R_{200}$ groups,
(F) heteroaryl where the heteroaryl is optionally substituted with one, two, or three independently selected $R_{100}$ groups,
(G) heterocycle, where the heterocycle is optionally substituted with one or two $R_{200}$ groups,
(H) —$(CH_2)_{1-4}$—OH,
(I) —$(CH_2)_{1-4}$—Y—$(CH_2)_{1-4}$-aryl where Y is —O—, —S— or
—$NR_{C-5}$— where $R_{16}$ is hydrogen or $C_1$–$C_6$ alkyl, and where the aryl is optionally substituted with one, two, or three independently selected $R_{100}$ groups,
(J) —$(CH_2)_{1-4}$—Y—$(CH_2)_{1-4}$— heteroaryl where the heteroaryl is optionally substituted with one, two, or three independently selected $R_{100}$ groups, and
(K)-aryl, where the aryl is optionally substituted with one, two, or three independently selected $R_{100}$ groups, and
$R_{14}$ is:
(A) —H,
(B) —$C_1$–$C_6$ alkyl,
(C) -aryl, where the aryl is optionally substituted with one, two, or three independently selected $R_{100}$ groups,
(D) -heteroaryl where the heteroaryl is optionally substituted with one, two, or three independently selected $R_{100}$ groups,
(E) -heterocycle, where the heterocycle is optionally substituted with one or two $R_{200}$ groups,
(F) —($C_1$–$C_4$ alkyl)-aryl, where the aryl is optionally substituted with one, two, or three independently selected $R_{100}$ groups,
(G) —($C_1$–$C_4$ alkyl)-heteroaryl where the heteroaryl is optionally substituted with one, two, or three independently selected $R_{100}$ groups,
(H) —($C_1$–$C_4$ alkyl)-heterocycle, where the heterocycle is optionally substituted with one or two $R_{200}$ groups, or
(I) —$(CH_2)_{0-2}$—O—$(CH_2)_{0-2}$—OH;
$R_2$ is selected from the group consisting of:
(I) hydrogenH,
(II) $C_1$–$C_6$ alkyl,
(III) —$(CH_2)_{0-4}$-aryl, where the aryl is optionally substituted with one, two, or three independently selected $R_{100}$ groups,
(IV) —$(CH_2)_{0-4}$-heteroaryl where the heteroaryl is optionally substituted with one, two, or three independently selected $R_{100}$ groups,
where $R_3$ is selected from the group consisting of:
(I) —H,
(II) $C_1$–$C_6$ alkyl, and
(III) —$(CH_2)_{0-4}$-aryl, where the aryl is optionally substituted with one, two, or three independently selected $R_{100}$ groups, (IV) —$(CH_2)_{0-4}$-heteroaryl where the heteroaryl is optionally substituted with one, two, or three independently selected $R_{100}$ groups,
$R_N$ is:
(I) $R_{N-1}$—$X_N$— where $X_N$ is selected from the group consisting of:
(A) —CO—,
(B) —$SO_2$—,
(C) —$(CR'''R''')_{1-6}$ wherein
R''' and R''' at each occurrence are the same or different and are —H or $C_1$–$C_4$ alkyl,
(D) —CO—$(CR''R''')_{1-6}$—$X_{N-1}$ wherein
$X_{N-1}$ is selected from the group consisting of –O—, —S— and —NR''—,
(E) a single bond, and
(F) —CO—$(CR''R''')_{1-6}$—
where $R_{N-1}$ is selected from the group consisting of:
(A) $R_{N-aryl}$ wherein $R_{N-aryl}$ at each occurrence is independently phenyl; naphthyl; tetralinyl; indanyl; indenyl; dihydronaphthyl; or 6,7,8,9-tetrahydro-5H-benzo[a]cycloheptenyl; each of which is optionally substituted with one, two or three of the following substituents which can be the same or different and are:
(1) $C_1$–$C_6$ alkyl, optionally substituted with one, two or three substituents selected from the group consisting of $C_1$–$C_3$ alkyl, —F, —Cl, —Br, —I, —OH, —SH, —C≡N, —$CF_3$, $C_1$–$C_3$ alkoxy, and —$NR_{1-a}R_{1-b}$,
wherein $R_{1-a}$ and $R_{1-b}$ at each occurrence are independently H or $C_1$–$C_6$ alkyl,
(2) —OH,
(3) —$NO_2$,
(4) —F, —Cl, —Br, —I,
(5) —$CO_2H$,
(6) —C≡N,
(7) —$(CH_2)_{0-4}$—CO—$NR_{N-2}R_{N-3}$ where $R_{N-2}$ and $R_{N-3}$ are the same or different and are selected from the group consisting of:
(a) —H,
(b) —$C_1$–$C_8$ alkyl optionally substituted with one substituent selected from the group consisting of:
(i) —OH,
(ii) —$NH_2$,
(iii) phenyl,
(c) —$C_1$–$C_8$ alkyl optionally substituted with 1, 2, or 3 groups that are independently —F, —Cl, —Br, or —I,
(d) —$C_3$–$C_8$ cycloalkyl,
(e) —($C_1$–$C_2$ alkyl)—($C_3$–$C_8$ cycloalkyl),
(f) —($C_1$–$C_6$ alkyl) —O—($C_1$–$C_3$ alkyl)
(g) —$C_2$–$C_6$ alkenyl,
(h) —$C_2$–$C_6$ alkynyl,
(i) —$C_1$–$C_6$ alkyl chain with one double bond and one triple bond,
(j) —$R_{1-aryl}$, wherein
$R_{1-aryl}$ at each occurrence is independently phenyl, naphthyl, indanyl, indenyl, dihydronaphthyl, or tetralinyl each of which is optionally substituted with 1, 2, 3, or 4 groups that are independently:
(i) $C_1$–$C_6$ alkyl optionally substituted with one, two or three substituents independently selected from the group consisting of $C_1$–$C_3$ alkyl, —F, —Cl, —Br, —I, —OH, —SH, —$NR_{1-a}R_{1-b}$, —C≡N, —$CF_3$, and $C_1$–$C_3$ alkoxy, (ii) $C_2$–$C_6$ alkenyl with one or two double bonds, optionally substituted with one, two or three substituents independently selected from the group consisting of —F, —Cl, —OH, —SH, —C≡N, —CF$_3$, $C_1$–$C_3$ alkoxy, and —NR$_{1-a}$R$_{1-b}$, (iii) $C_2$–$C_6$ alkynyl optionally substituted with 1, 2, or 3 groups that are independently selected from the group consisting of —F, —Cl, —OH, —SH, —C≡N, —CF$_3$, $C_1$–$C_3$ alkoxy, and —NR$_{1-a}$R$_{1-b}$, (iv) —F, Cl, —Br and —I, (v) —$C_1$–$C_6$ alkoxy optionally substituted with 1, 2, or 3 —F, (vi) —NR$_{N-2}$R$_{N-3}$, (vii) —OH, (viii) —C≡N, (ix) $C_3$–$C_7$ cycloalkyl, optionally substituted with 1, 2, or 3 groups that are selected from the group consisting of —F, —Cl, —OH, —SH, —C≡N, —CF$_3$, $C_1$–$C_3$ alkoxy, and —NR$_{1-a}$R$_{1-b}$, (x) —CO—($C_1$–$C_4$ alkyl), (xi) —SO$_2$—NR$_{1-a}$R$_{1-b}$, (xii) —CO—NR$_{1-a}$R$_{1-b}$, or (xiii) —SO$_2$—($C_1$–$C_4$ alkyl), (k) —R$_{1\text{-}heteroaryl}$, wherein R$_{1\text{-}heteroaryl}$ at each occurrence is independently selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide, where the R$_{1\text{-}heteroaryl}$ group is optionally substituted with 1, 2, 3, or 4 groups that are independently:

(i) $C_1$–$C_6$ alkyl optionally substituted with 1, 2, or 3 groups independently selected from the group consisting of $C_1$–$C_3$ alkyl, —F, —Cl, —Br, —I, —OH, —SH, —NR$_{1-a}$R$_{1-b}$, —C≡N, —CF$_3$, and $C_1$–$C_3$ alkoxy, (ii) $C_2$–$C_6$ alkenyl optionally substituted with 1, 2, or 3 groups that are independently —F, —Cl, —OH, —SH, —C≡N, —CF$_3$, $C_1$–$C_3$ alkoxy, or —NR$_{1-a}$R$_{1-b}$, (iii) $C_2$–$C_6$ alkynyl optionally substituted with 1, 2, or 3 groups that are independently —F, —Cl, —OH, —SH, —C≡N, —CF$_3$, $C_1$–$C_3$ alkoxy, or —NR$_{1-a}$R$_{1-b}$, (iv) —F, —Cl, —Br and —I, (v) —$C_1$–$C_6$ alkoxy optionally substituted with one, two, or three —F, (vi) —(CH$_2$)$_{0-4}$—NR$_{N-2}$R$_{N-3}$, (vii) —OH, (viii) —C≡N, (ix) (CH$_2$)$_{0-4}$—$C_3$–$C_7$ cycloalkyl, optionally substituted with 1, 2, or 3 groups that are independently selected from the group consisting of —F, —Cl, —OH, —SH, —C≡N, —CF$_3$, $C_1$–$C_3$ alkoxy, and —NR$_{1-a}$R$_{1-b}$, (x) (CH$_2$)$_{0-4}$—CO—($C_1$–$C_6$ alkyl)

(xi) (CH$_2$)$_{0-4}$—SO$_2$—NR$_{N-2}$R$_{N-3}$, (xii) (CH$_2$)$_{0-4}$—CO—NR$_{N-2}$R$_{N-3}$, (xiii) (CH$_2$)$_{0-4}$—SO$_2$—($C_1$–$C_6$ alkyl), (xiv) (CH$_2$)$_{0-4}$—N(R$_{N-2}$)—SO$_2$—, and (xv) (CH$_2$)$_{0-4}$—N(R$_{N-2}$)—C(O)—, (l) —R$_{1\text{-}heterocyle}$, wherein R$_{1\text{-}heterocycle}$ at each occurrence is independently selected from the group consisting of morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide, and homothiomorpholinyl S-oxide, where the R$_{1\text{-}heterocycle}$ group is bonded by any atom of the parent R$_{1\text{-}heterocycle}$ group substituted by hydrogen such that the new bond to the R$_{1\text{-}heterocycle}$ group replaces the hydrogen atom and its bond, where heterocycle is optionally substituted with 1, 2, 3, or 4 groups that are independently:

(a) $C_1$–$C_6$ alkyl optionally substituted with one, two or three substituents independently selected from the group consisting of $C_1$–$C_3$ alkyl, halogen, —OH, —SH, —NR$_{1-a}$R$_{1-b}$—C≡N, —CF$_3$, and $C_1$–$C_3$ alkoxy, (b) $C_2$–$C_6$ alkenyl with one or two double bonds, optionally substituted with one, two or three substituents independently selected from the group consisting of —F, —Cl, —OH, —SH, —C≡N, —CF$_3$, $C_1$–$C_3$ alkoxy, and —NR$_{1-a}$R$_{1-b}$ (c) $C_2$–$C_6$ alkynyl with one or two triple bonds, optionally substituted with one, two or three substituents independently selected from the group consisting of —F, —Cl, —OH, —SH, —C≡N, —CF$_3$, $C_1$–$C_3$ alkoxy, and —NR$_{1-a}$R$_{1-b}$,
(d) halogen,
(e) $C_1$–$C_6$ alkoxy,
(f) —$C_1$–$C_6$ alkoxy optionally substituted with one, two, or three —F,
(g) —NR$_{N-2}$R$_{N-3}$,
(h) —OH,
(i) —C≡N,
(j) —(CH$_2$)$_{0-4}$—($C_3$–$C_8$ cycloalkyl), optionally substituted with 1, 2, or 3 groups independently selected from the group consisting of —F, —Cl, —OH, —SH, —C≡N, —CF$_3$, $C_1$–$C_3$ alkoxy, and —NR$_{1-a}$R$_{1-b}$,
(k) —(CH$_2$)$_{0-4}$—CO—($C_1$–$C_4$ alkyl),
(l) —(CH$_2$)$_{0-4}$—SO$_2$—NR$_{1-a}$R$_{1-b}$,
(m) —(CH$_2$)$_{0-4}$—CO—NR$_{1-a}$R$_{1-b}$,
(n) —(CH$_2$)$_{0-4}$—SO$_2$—($C_1$–$C_6$ alkyl), and
(o) =O,
(p) —(CH$_2$)$_{0-4}$—N(R$_{N-2}$)—SO$_2$—
(q) —(CH$_2$)$_{0-4}$—N(R$_{N-2}$)—C(O)—
(8) —(CH$_2$)$_{0-4}$—CO—($C_1$–$C_{12}$ alkyl),
(9) —(CH$_2$)$_{0-4}$—CO—($C_2$–$C_{12}$ alkenyl)
(10) —(CH$_2$)$_{0-4}$—CO—($C_2$–$C_{12}$ alkynyl)
(11) —(CH$_2$)$_{0-4}$—CO—($C_3$–$C_8$ cycloalkyl)
(12) —(CH$_2$)$_{0-4}$CO —R$_{1-aryl}$,
(13) —(CH$_2$)$_{0-4}$—CO—R$_{1-heteroaryl}$,
(14) —(CH$_2$)$_{0-4}$—CO—R$_{1-heterocycle}$,
(15) —(CH$_2$)$_{0-4}$—CO—R$_{N-4}$ wherein R$_{N-4}$ is selected from the group consisting of phenyl, morpholinyl, thiomorpholinyl, piperazinyl, piperidinyl, homomorpholinyl, homothiomorpholinyl, homothiomorpholinyl S-oxide, homothiomorpholinyl S,S-dioxide, pyrrolinyl, thienyl, pyrazolyl, pyridyl N-oxide, oxazolyl, thiazolyl, imidazolyl, and pyrrolidinyl where each group is optionally substituted with one, two, three, or four groups that are independently $C_1$–$C_6$ alkyl,
(16) —(CH$_2$)$_{0-4}$—CO—O—R$_{N-5}$ where R$_{N-5}$ is selected from the group consisting of:
(a) $C_1$–$C_6$ alkyl,
(b) —(CH$_2$)$_{0-2}$—(R$_{1-aryl}$),
(c) $C_2$–$C_6$ alkenyl,
(d) $C_2$–$C_6$ alkynyl,
(e) —(CH$_2$)$_{0-2}$—$C_3$$C_8$ cycloalkyl,
(f) —(CH$_2$)$_{0-2}$—(R$_{1-heteroaryl}$), and
(g) —(CH$_2$)$_{0-2}$—(R$_{1-heterocycle}$),
(17) —(CH$_2$)$_{0-4}$—SO$_2$—NR$_{N-2}$R$_{N-3}$,
(18) —(CH$_2$)$_{0-4}$—SO—($C_1$–$C_8$ alkyl),
(19) —(CH$_2$)$_{0-4}$—SO$_2$—($C_1$–$C_{12}$ alkyl),
(20) —(CH$_2$)$_{0-4}$—SO$_2$—($C_3$–$C_8$ cycloalkyl),
(21) —(CH$_2$)$_{0-4}$—N(H or R$_{N-5}$)—CO—O—R$_{N-5}$,
(22) —(CH$_2$)$_{0-4}$—N(H or R$_{N-5}$)—CO—N(R$_{N-5}$)$_2$,
(23) —(CH$_2$)$_{0-4}$—N—CS—N(R$_{N-5}$)$_2$,
(24) —(CH$_2$)$_{0-4}$—N(H or R$_{N-5}$)—CO—R$_{N-2}$,
(25) —(CH$_2$)$_{0-4}$—NR$_{N-2}$R$_{N-3}$,
(26) —(CH$_2$)$_{0-4}$—R$_{N-4}$,
(27) —(CH$_2$)$_{0-4}$—O—CO—($C_1$–$C_6$ alkyl),
(28) —(CH$_2$)$_{0-4}$—O—P(O)—(OR$_{100}$)$_2$ wherein R$_{100}$ at each occurrence is independently —H or $C_1$–$C_4$ alkyl,
(29) —(CH$_2$)$_{0-4}$—O—CO—N(R$_{N-5}$)$_2$,
(30) —(CH$_2$)$_{0-4}$—O—CS—N(R$_{N-5}$)$_2$,
(31) —(CH$_2$)$_{0-4}$—O—(R$_{N-5}$),
(32) —(CH$_2$)$_{0-4}$—O—(R$_{N-5}$)—COOH,
(33) —(CH$_2$)$_{0-4}$—S—(R$_{N-5}$),
(34) —(CH$_2$)$_{0-4}$—O—($C_1$–$C_6$ alkyl optionally substituted with one, two, three, four, or five of —F),
(35) $C_3$–$C_8$ cycloalkyl,
(36) $C_2$–$C_6$ alkenyl optionally substituted with $C_1$–$C_3$ alkyl, —F, —Cl, —Br, —I, —OH, —SH, —C≡N, —CF$_3$, $C_1$–$C_3$ alkoxy, or —NR$_{1-a}$R$_{1-b}$,
(37) $C_2$–$C_6$ alkynyl optionally substituted with $C_1$–$C_3$ alkyl, —F, —Cl, —Br, —I, —OH, —SH, —C≡N, —CF$_3$, $C_1$–$C_3$ alkoxy, or —NR$_{1-a}$R$_{1-b}$,
(38) —(CH$_2$)$_{0-4}$—N(H or R$_{N-5}$)—SO$_2$—R$_{N-2}$,
(39) —(CH$_2$)$_{1-4}$—($C_3$–$C_8$ cycloalkyl)
(B) —R$_{N-heteroaryl}$ where R$_{N-heteroaryl}$ is selected from the group consisting of: pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzisothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, henoxazinyl, phenothiazinyl, pteridinyl, benzothiazolyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyridinyl-N-oxide, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide, imidazopyrazolyl, quinazolinonyl, pyrazopyridyl, benzooxadiazolyl, dihydropyrimidinonyl, and dihydrobenzfuranonyl,
where the R$_{N-heteroaryl}$ group is bonded by any atom of the parent R$_{N-heteroaryl}$ group substituted by hydrogen such that the new bond to the R$_{N-heteroaryl}$ group replaces the hydrogen atom and its bond, where heteroaryl is optionally substituted with one, two, three, or four of:
(1) $C_1$–$C_6$ alkyl, optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, and —NR$_{1-a}$R$_{1-b}$,
(2) —OH,
(3) —NO$_2$,
(4) —F, —Cl, —Br, —I,
(5) —CO$_2$H, (6) —C≡N,
(7) —(CH$_2$)$_{0-4}$—CO—NR$_{N-2}$R$_{N-3}$,
(8) —(CH$_2$)$_{0-4}$—CO—(C$_1$–C$_{12}$ alkyl),
(9) —(CH$_2$)$_{0-4}$—CO—(C$_2$–C$_{12}$ alkenyl),
(10) —(CH$_2$)$_{0-4}$—CO—(C$_2$–C$_{12}$ alkynyl),
(11) —(CH$_2$)$_{0-4}$—CO—(C$_3$–C$_8$ cycloalkyl),
(12) —(CH$_2$)$_{0-4}$—C—R$_{1\text{-}aryl}$,
(13) —(CH$_2$)$_{0-4}$—CO—R$_{1\text{-}heteroaryl}$,
(14) —(CH$_2$)$_{0-4}$—CO—R$_{1\text{-}heterocycle}$,
(15) —(CH$_2$)$_{0-4}$—CO—R$_{N-4}$,
(16) —(CH$_2$)$_{0-4}$—CO—O—R$_{N-5}$,
(17) —(CH$_2$)$_{0-4}$—SO$_2$—NR$_{N-2}$R$_{N-3}$,
(18) —(CH$_2$)$_{0-4}$—SO—(C$_1$–C$_8$ alkyl),
(19) —(CH$_2$)$_{0-4}$—SO$_2$ (C$_1$–C$_{12}$ alkyl),
(20) —(CH$_2$)$_{0-4}$—SO$_2$—(C$_3$–C$_8$ cycloalkyl),
(21) —(CH$_2$)$_{0-4}$—N(H or R$_{N-5}$)—CO—O—R$_{N-5}$,
(22) —(CH$_2$)$_{0-4}$—N(H or R$_{N-5}$)—CO—N(R$_{N-5}$)$_2$,
(23) —(CH$_2$)$_{0-4}$—N—CS—N(R$_{N-5}$)$_2$,
(24) —(CH$_2$)$_{0-4}$—N(—H or R$_{N-5}$)—CO—R$_{N-2}$,
(25) —(CH$_2$)$_{0-4}$—NR$_{N-2}$R$_{N-3}$,
(26) —(CH$_2$)$_{0-4}$—R$_{N-4}$,
(27) —(CH$_2$)$_{0-4}$—O—CO—(C$_1$–C$_6$ alkyl),
(28) —(CH$_2$)$_{0-4}$—O—P(O)—(OR$_{100}$)$_2$,
(29) —(CH$_2$)$_{0-4}$—O—CO—N(R$_{N-5}$)$_2$,
(30) —(CH$_2$)$_{0-4}$—O—CS—N(R$_{N-5}$)$_2$,
(31) —(CH$_2$)$_{0-4}$—O—(R$_{N-5}$),
(32) —(CH$_2$)$_{0-4}$—O—(R$_{N-5}$)—COOH,
(33) —(CH$_2$)$_{0-4}$—S—(R$_{N-5}$),
(34) —(CH$_2$)$_{0-4}$—O—(C$_1$–C$_6$ alkyl optionally substituted with one, two, three, four, or five of —F),
(35) C$_3$–C$_8$ cycloalkyl,
(36) C$_2$–C$_6$ alkenyl optionally substituted with C$_1$–C$_3$ alkyl, —F, —Cl, —Br, —I, —OH, —SH, —C≡N, —CF$_3$, C$_1$–C$_3$ alkoxy, or —NR$_{1\text{-}a}$R$_{1\text{-}b}$,
(37) C$_2$–C$_6$ alkynyl optionally substituted with C$_1$–C$_3$ alkyl, —F, —Cl, —Br, —I, —OH, —SH, —C≡N, —CF$_3$, C$_1$–C$_3$ alkoxy, or —NR$_{1\text{-}a}$R$_{1\text{-}b}$,
(38) —(CH$_2$)$_{0-4}$—N(—H or R$_{N-5}$)—SO$_2$—R$_{N-2}$,
(39) —(CH$_2$)$_{1-4}$—C$_3$–C$_8$ cycloalkyl,
(C) R$_{N\text{-}aryl}$—W—R$_{N\text{-}aryl}$,
(D) R$_{N\text{-}aryl}$—W—R$_{N\text{-}heteroaryl}$,
(E) R$_{N\text{-}aryl}$—W—R$_{1\text{-}heterocycle}$,
(F) R$_{N\text{-}heteroaryl}$—W—R$_{N\text{-}aryl}$,
(G) R$_{N\text{-}heteroaryl}$—W—R$_{N\text{-}heteroaryl}$,
(H) R$_{N\text{-}heteroaryl}$—W—R$_{N\text{-}1\text{-}heterocycle}$,
(I) R$_{N\text{-}heterocycle}$—W—R$_{N\text{-}aryl}$,
(J) R$_{N\text{-}heterocycle}$—W—R$_{N\text{-}heteroaryl}$,
(K) R$_{N\text{-}heterocycle}$—W—R$_{N\text{-}1\text{-}heterocycle}$,
where W is
(1) —(CH$_2$)$_{1-4}$—,
(2) —O—,
(3) —S(O)$_{0-2}$—,
(4) —N(R$_{N-5}$)—,
(5) —CO—; or
(6) a bond;
(II) —CO—(C$_1$–C$_{10}$ alkyl) wherein the alkyl is optionally substituted with one two or three substituents independently selected from the group consisting of:
(A) —OH,
(B) —C$_1$–C$_6$ alkoxy,
(C) —C$_1$–C$_6$ thioalkoxy,
(D) —CO—O—R$_{N-8}$ where R$_{N-8}$ at each occurrence is independently —H, C$_1$–C$_6$ alkyl or -phenyl,
(E) —CO—NR$_{N-2}$R$_{N-3}$,
(F) —CO—R$_{N-4}$,
(G) —SO$_2$—(C$_1$–C$_8$ alkyl),
(H) —SO$_2$—NR$_{N-2}$R$_{N-3}$,
(I) —NH—CO—(C$_1$–C$_6$ alkyl),
(J) —NH—CO—O—R$_{N-8}$,
(K) —NR$_{N-2}$R$_{N-3}$,
(L) —R$_{N-4}$,
(M) —O—CO—(C$_1$–C$_6$ alkyl),
(N) —O—CO—NR$_{N-8}$R$_{N-8}$,
(O) —O—(C$_1$–C$_5$ alkyl)—COOH,
(P) —O—(C$_1$–C$_6$ alkyl optionally substituted with one, two, or three of —F, —Cl, —Br, —I),
(Q) —NH—SO$_2$—(C$_1$–C$_6$ alkyl),
(R) halogen,
(S) —N(H or R$_{N-5}$)—SO$_2$—R$_{N-2}$,
(T) —N(H or R$_{N-5}$)—CO—(R$_{N-2}$), and
(U) —SO$_2$—R$_{N-2}$,
(III) —CO—(C$_1$–C$_6$ alkyl)—O—(C$_1$–C$_6$ alkyl) wherein each alkyl is unsubstituted or independently substituted with one, two, or three substituents selected from the group consisting of:
(A) —OH,
(B) —C$_1$–C$_6$ alkoxy,
(C) —C$_1$–C$_6$ thioalkoxy,
(D) —CO—O—R$_{N-8}$,
(E) —CO—NR$_{N-2}$R$_{N-3}$,
(F) —CO—R$_{N-4}$,
(G) —SO$_2$—(C$_1$–C$_8$ alkyl),
(H) —SO$_2$—NR$_{N-2}$R$_{N-3}$,
(I) —NH—CO—(C$_1$–C$_6$ alkyl),
(J) —NH—CO—O—R$_{N-8}$,
(K) —NR$_{N-2}$R$_{N-3}$,
(L) —R$_{N-4}$,
(M) —O—CO—(C$_1$–C$_6$ alkyl),
(N) —O—CO—NR$_{N-8}$R$_{N-8}$,
(O) —O—(C$_1$–C$_5$ alkyl)—CO$_2$H,
(P) —O—(C$_1$–C$_6$ alkyl optionally substituted with one, two, or three groups that are independently —F, —Cl, —Br, or —I),
(Q) —NH—SO$_2$—(C$_1$–C$_6$ alkyl),
(R) halogen,
(S) —N(H or R$_{N-5}$)—SO$_2$—R$_{N-2}$,
(T) —N(H or R$_{N-5}$)—CO—(R$_{N-2}$), and
(U) —SO$_2$—R$_{N-2}$,
(IV) —CO—(C$_1$–C$_6$ alkyl)—S—(C$_1$–C$_6$ alkyl) wherein each alkyl is unsubstituted or substituted with one, two, or three of substituents independently selected from the group consisting of:
(A) —OH,
(B) —C$_1$–C$_6$ alkoxy,
(C) —C$_1$–C$_6$ thioalkoxy,
(D) —CO—O—R$_{N-8}$,
(E) —CO—NR$_{N-2}$R$_{N-3}$,
(F) —CO—R$_{N-4}$,
(G) —SO$_2$—(C$_1$–C$_8$ alkyl),
(H) —SO$_2$—NR$_{N-2}$R$_{N-3}$,
(I) —NH—CO—(C$_1$–C$_6$ alkyl),
(J) —NH—CO—O—R$_{N-8}$,
(K) —NR$_{N-2}$R$_{N-3}$,
(L) —R$_{N-4}$,
(M) —O—CO—(C$_1$–C$_6$ alkyl),
(N) —O—CO—NR$_{N-8}$R$_{N-8}$,
(O) —O—(C$_1$–C$_5$ alkyl)—COOH,
(P) —O—(C$_1$–C$_6$ alkyl optionally substituted with one, two, or three groups that are independently —F, —Cl, —Br, or —I),
(Q) —NH—SO$_2$—(C$_1$–C$_6$ alkyl),
(R) halogen,
(S) —N(H or R$_{N-5}$)—SO$_2$—R$_{N-2}$, (T) —N(H or $R_{N-5}$)—CO—($R_{N-2}$), and
(U) —SO$_2$—$R_{N-2}$,
(V) —CO—CH (—(CH$_2$)$_{0-2}$—O—$R_{N-10}$)—(CH$_2$)$_{0-2}$—$R_{N-aryl}$/$R_{N-heteroaryl}$) wherein
$R_{N-10}$ is selected from the group consisting of:
(A) —H,
(B) $C_1$–$C_6$ alkyl,
(C) $C_3$–$C_8$ cycloalkyl,
(D) $C_2$–$C_6$ alkenyl with one double bond,
(E) $C_2$–$C_6$ alkynyl with one triple bond,
(F) $R_{1-aryl}$,
(G) $R_{N-heteroaryl}$,
(H) $R_{N-heterocycle}$,
(VI) —CO—($C_3$–$C_8$ cycloalkyl) where the cycloalkyl group is optionally substituted with one or two substituents independently selected from the group consisting of:
(A) —(CH$_2$)$_{0-4}$—OH,
(B) —(CH$_2$)$_{0-4}$—$C_1$–$C_6$ alkoxy,
(C) —(CH$_2$)$_{0-4}$—$C_1$–$C_6$ thioalkoxy,
(D) —(CH$_2$)$_{0-4}$—CO—O—$R_{N-8}$,
(E) —(CH$_2$)$_{0-4}$—CO—NR$_{N-2}$R$_{N-3}$,
(F) —(CH$_2$)$_{0-4}$—CO—$R_{N-4}$,
(G) —(CH$_2$)$_{0-4}$—SO$_2$—($C_1$–$C_8$ alkyl),
(H) —(CH$_2$)$_{0-4}$—SO$_2$—NR$_{N-2}$R$_{N-3}$,
(I) —(CH$_2$)$_{0-4}$—NH—CO—($C_1$–$C_6$ alkyl),
(J) —NH—CO—O—$R_{N-8}$,
(K) —(CH$_2$)$_{0-4}$—NR$_{N-2}$R$_{N-3}$,
(L) —(CH$_2$)$_{0-4}$—$R_{N-4}$,
(M) —O—CO—($C_1$–$C_6$ alkyl),
(N) —O—CO—NR$_{N-8}$R$_{N-8}$,
(O) —O—($C_1$–$C_6$ alkyl)—CO$_2$H,
(P) —O—($C_1$–$C_6$ alkyl optionally substituted with one, two, or three groups that are independently selected from —F, —Cl, —Br, and —I),
(Q) —NH—SO$_2$—($C_1$–$C_6$ alkyl),
(R) halogen,
(S) —N(H or $R_{N-5}$)—SO$_2$—$R_{N-2}$, and
(T) —N(H or $R_{N-5}$)—CO—($R_{N-2}$), and
(U) —SO$_2$—$R_{N-2}$; and $R_C$ is selected from the group consisting of:
(I) —$C_1$–$C_{10}$ alkyl optionally substituted with one, two or three groups independently selected from the group consisting of $C_1$–$C_3$ alkyl, halogen, —OH, —SH, —C≡N, —CF$_3$, $C_1$–$C_6$ alkoxy, —O-phenyl, —NR$_{1-a}$R$_{1-b}$, —OC=O NR$_{1-a}$R$_{1-b}$, —S(=O)$_{0-2}$R$_{1-a}$, —NR$_{1-a}$C=O NR$_{1-a}$R$_{1-b}$, —C=O NR$_{1-a}$R$_{1-b}$, and —S(=O)$_2$NR$_{1-a}$R$_{1-b}$ wherein
$R_{1-a}$ and $R_{1-b}$ at each occurrence are independently H or $C_1$–$C_6$ alkyl,
(II) —(CH$_2$)$_{0-3}$—($C_3$–$C_8$) cycloalkyl where cycloalkyl can be optionally substituted with one, two or three substituents independently selected from the group consisting of $C_1$–$C_3$ alkyl, halogen, —OH, —SH, —C≡N, —CF$_3$, $C_1$–$C_6$ alkoxy, —O-phenyl, —CO$_2$H, —CO$_2$—($C_1$–$C_4$ alkyl), and —NR$_{1-a}$R$_{1-b}$
(III) —(CR$_{C-x}$R$_{C-y}$)$_{0-4}$—R$_{C-aryl}$ where R$_{C-x}$ and R$_{C-y}$ are independently selected from the group consisting of
—H,
$C_1$–$C_4$ alkyl optionally substituted with 1 or 2 —OH,
$C_1$–$C_4$ alkoxy optionally substituted with 1, 2, or 3 halogen,
—(CH$_2$)$_{0-4}$—$C_3$–$C_8$ cycloalkyl,
$C_2$–$C_6$ alkenyl containing one or two double bonds,
$C_2$–$C_6$ alkynyl containing one or two triple bonds, and
phenyl, or R$_{C-x}$ and R$_{C-y}$ are taken together with the carbon to which they are attached to form a carbocycle of three, four, five, six or seven carbon atoms, where one carbon atom is optionally replaced by a group selected from —O—, —S—, —SO$_2$—, —NR$_{N-2}$— and R$_{C-aryl}$, wherein
R$_{C-aryl}$ at each occurrence is independently phenyl; naphthyl; tetralinyl; indanyl; dihydronaphthyl; or 6,7,8,9-tetrahydro-5H-benzo[a]cycloheptenyl,
each of which is optionally substituted with 1, 2, or 3 groups that are independently:
(1) $C_1$–$C_6$ alkyl, optionally substituted with one, two or three substituents selected from the group consisting of $C_1$–$C_3$ alkyl, halogen, —OH, —SH, —C≡N, —CF$_3$, $C_1$–$C_3$ alkoxy, and —NR$_{1-a}$R$_{1-b}$,
(2) —OH,
(3) —NO$_2$,
(4) halogen,
(5) —CO$_2$H,
(6) —C≡N,
(7) —(CH$_2$)$_{0-4}$—CO—NR$_{N-2}$R$_{N-3}$ where
R$_{N-2}$ and R$_{N-3}$ are independently selected from the group consisting of:
(a) —H,
(b) —$C_1$–$C_6$ alkyl optionally substituted with one substituent selected from the group consisting of:
(i) —OH, and
(ii) —NH$_2$,
(c) —$C_1$–$C_6$ alkyl optionally substituted with 1, 2, or 3 groups that are independently —F, —Cl, —Br, —I, or OH,
(d) —$C_3$–$C_7$ cycloalkyl,
(e) —($C_1$–$C_2$ alkyl)—($C_3$–$C_7$ cycloalkyl),
(f) —($C_1$–$C_6$ alkyl)—O—($C_1$–$C_3$ alkyl),
(g) —$C_2$–$C_6$ alkenyl
(h) —$C_2$–$C_6$ alkynyl
(i) —$C_1$–$C_6$ alkyl chain with one double bond and one triple bond,
(j) —R$_{1-aryl}$ wherein R$_{1-aryl}$, at each occurrence is independently phenyl, naphthyl, indanyl, indenyl, dihydronaphthyl, or tetralinyl each of which is optionally substituted with 1, 2, 3, or 4 groups that are independently:
(i) $C_1$–$C_6$ alkyl optionally substituted with one, two or three substituents independently selected from the group consisting of $C_1$–$C_3$ alkyl, —F, —Cl, —Br, —I, —OH, —SH, —NR$_{1-a}$R$_{1-b}$, —C≡N, —CF$_3$, and $C_1$–$C_3$ alkoxy,
(ii) $C_2$–$C_6$ alkenyl with one or two double bonds, optionally substituted with one, two or three substituents independently selected from the group consisting of —F, —Cl, —OH, —SH, —C≡N, —CF$_3$, $C_1$–$C_3$ alkoxy, and —NR$_{1-a}$R$_{1-b}$,
(iii) $C_2$–$C_6$ alkynyl optionally substituted with 1, 2, or 3 groups that are independently selected from the group consisting of —F, —Cl, —OH, —SH, —C≡N, —CF$_3$, $C_1$–$C_3$ alkoxy, and —NR$_{1-a}$R$_{1-b}$,
(iv) —F, Cl, —Br and —I,
(v) —$C_1$–$C_6$ alkoxy optionally substituted with 1, 2, or 3—F,
(vi) —NR$_{N-2}$R$_{N-3}$,
(vii) —OH,
(viii) —C≡N, (ix) $C_3$–$C_7$ cycloalkyl, optionally substituted with 1, 2, or 3 groups that are selected from the group consisting of —F, —Cl, —OH, —SH, —C≡N, —$CF_3$, $C_1$–$C_3$ alkoxy, and —$NR_{1-a}R_{1-b}$, (x) —CO—($C_1$–$C_4$ alkyl), (xi) —$SO_2$—$NR_{1-a}R_{1-b}$, (xii) —CO—$NR_{1-a}R_{1-b}$, or (xiii) —$SO_2$—($C_1$–$C_4$ alkyl), (k) —$R_{1\text{-}heteroaryl}$ wherein $R_{1\text{-}heteroaryl}$ at each occurrence is independently selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide, where the $R_{1\text{-}heteroaryl}$ group is optionally substituted with 1, 2, 3, or 4 groups that are independently:

(i) $C_1$–$C_6$ alkyl optionally substituted with 1, 2, or 3 groups independently selected from the group consisting of $C_1$–$C_3$ alkyl, —F, —Cl, —Br, —I, —OH, —SH, —$NR_{1-a}R_{1-b}$, —C≡N, —$CF_3$, and $C_1$–$C_3$ alkoxy, (ii) $C_2$–$C_6$ alkenyl optionally substituted with 1, 2, or 3 groups that are independently —F, —Cl, —OH, —SH, —C≡N, —$CF_3$, $C_1$–$C_3$ alkoxy, and —$NR_{1-a}R_{1-b}$, (iii) $C_2$–$C_6$ alkynyl optionally substituted with 1, 2, or 3 groups that are independently selected from the group consisting of —F, —Cl, —OH, —SH, —C≡N, —$CF_3$, $C_1$–$C_3$ alkoxy, and —$NR_{1-a}R_{1-b}$, (iv) —F, —Cl, —Br and —I, (v) —$C_1$–$C_6$ alkoxy optionally substituted with one, two, or three —F, (vi) —$(CH_2)_{0-4}$—$NR_{N-2}R_{N-3}$, (vii) —OH, (viii) —C≡N, (ix) $(CH_2)_{0-4}$—$C_3$–$C_7$ cycloalkyl, optionally substituted with 1, 2, or 3 groups that are independently selected from the group consisting of —F, —Cl, —OH, —SH, —C≡N, —$CF_3$, $C_1$–$C_3$ alkoxy, and —$NR_{1-a}R_{1-b}$, (x) $(CH_2)_{0-4}$—CO—($C_1$–$C_6$ alkyl), (xi) $(CH_2)_{0-4}$—$SO_2$—$NR_{N-2}R_{N-3}$, (xii) $(CH_2)_{0-4}$—CO—$NR_{N-2}R_{N-3}$, (xiii) $(CH_2)_{0-4}$—$SO_2$—($C_1$–$C_6$ alkyl), (xiv) $(CH_2)_{0-4}$—$N(R_{N-2})$—$SO_2$—, and (xv) $(CH_2)_{0-4}$—$N(R_{N-2})$—C(O)—, (8) —$(CH_2)_{0-4}$—CO—($C_1$–$C_{12}$ alkyl), (9) —$(CH_2)_{0-4}$—CO—($C_2$–$C_{12}$ alkenyl),

(10) —$(CH_2)_{0-4}$—CO—($C_2$–$C_{12}$ alkynyl),

(11) —$(CH_2)_{0-4}$—CO—$(CH_2)_{0-4}$($C_3$–$C_7$ cycloalkyl),

(12) —$(CH_2)_{0-4}$—CO—$R_{1\text{-}aryl}$,

(13) —$(CH_2)_{0-4}$—CO—$R_{1\text{-}heteroaryl}$,

(14) —$(CH_2)_{0-4}$—CO—$R_{1\text{-}heterocycle}$ wherein $R_{1\text{-}heterocycle}$ at each occurrence is independently selected from the group consisting of morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide, and homothiomorpholinyl S-oxide, where the $R_{1\text{-}heterocycle}$ group is bonded by any atom of the parent $R_{1\text{-}heterocycle}$ group substituted by hydrogen such that the new bond to the $R_{1\text{-}heterocycle}$ group replaces the hydrogen atom and its bond, where heterocycle is optionally substituted with 1, 2, 3, or 4 groups that are independently:

(a) $C_1$–$C_6$ alkyl optionally substituted with one, two or three substituents independently selected from the group consisting of $C_1$–$C_3$ alkyl, halogen, —OH, —SH, —$NR_{1-a}R_{1-b}$—C≡N, —$CF_3$, and $C_1$–$C_3$ alkoxy, (b) $C_2$–$C_6$ alkenyl with one or two double bonds, optionally substituted with one, two or three substituents independently selected from the group consisting of —F, —Cl, —OH, —SH, —C≡N, —$CF_3$, $C_1$–$C_3$ alkoxy, and —$NR_{1-a}R_{1-b}$ (c) $C_2$–$C_6$ alkynyl with one or two triple bonds, optionally substituted with one, two or three substituents independently selected from the group consisting of —F, —Cl, —OH, —SH, —C≡N, —$CF_3$, $C_1$–$C_3$ alkoxy, and —$NR_{1-a}R_{1-b}$ (d) halogen, (e) $C_1$–$C_6$ alkoxy,
(f) —$C_1$–$C_6$ alkoxy optionally substituted with one, two, or three —F,
(g) —$NR_{N-2}R_{N-3}$,
(h) —OH,
(i) —C≡N,
(j) $(CH_2)_{0-4}(C_3$–$C_7$ cycloalkyl), optionally substituted with 1, 2, or 3 groups independently selected from the group consisting of —F, —Cl, —OH, —SH, —C≡N, —$CF_3$, $C_1$–$C_3$ alkoxy, and —$NR_{1-a}R_{1-b}$,
(k) —$(CH_2)_{0-4}$—CO—($C_1$–$C_4$ alkyl),
(l) —$(CH_2)_{0-4}$—$SO_2$—$NR_{1-a}R_{1-b}$,
(m) —$(CH_2)_{0-4}$—CO—$NR_{1-a}R_{1-b}$,
(n) —$(CH_2)_{0-4}$—$SO_2$—($C_1$–$C_6$ alkyl), and
(o) =O,
(p) —$(CH_2)_{0-4}$—$N(R_{N-2})$—$SO_2$—
(q) —$(CH_2)_{0-4}$—$N(R_{N-2})$—C(O)—
(15) —$(CH_2)_{0-4}$—CO—$R_{N-4}$ wherein $R_{N-4}$ at each occurrence is independently selected from the group consisting of morpholinyl, thiomorpholinyl, pyrrolidinonyl, pyrrolyl, pyrazolyl, thienyl, pyridyl N-oxide, piperazinyl, piperidinyl, homomorpholinyl, homothiomorpholinyl, homothiomorpholinyl S-oxide, homothiomorpholinyl S,S-dioxide, pyrrolinyl and pyrrolidinyl where each group is optionally substituted with 1, 2, 3, or 4 groups that are independently $C_1$–$C_6$ alkyl,
(16) —$(CH_2)_{0-4}$—$CO_2$—$R_{N-5}$ where $R_{N-5}$ at each occurrence is independently selected from the group consisting of:
(a) $C_1$–$C_6$ alkyl,
(b) —$(CH_2)_{0-2}$—$(R_{1-aryl})$,
(c) $C_2$–$C_6$ alkenyl,
(d) $C_2$–$C_6$ alkynyl,
(e) $C_3$–$C_7$ cycloalkyl, and
(f) —$(CH_2)_{0-4}$—$(R_{1-heteroaryl})$,
(17) —$(CH_2)_{0-4}$—$SO_2$—$NR_{N-2}R_{N-3}$
(18) —$(CH_2)_{0-4}$—SO—($C_1$–$C_8$ alkyl),
(19) —$(CH_2)_{0-4}$—$SO_2$—($C_1$–$C_{12}$ alkyl),
(20) —$(CH_2)_{0-4}$—$SO_2$—($C_3$–$C_7$ cycloalkyl),
(21) —$(CH_2)_{0-4}$—N(H or $R_{N-5}$)—$CO_2$—$R_{N-5}$,
(22) —$(CH_2)_{0-4}$—N(H or $R_{N-5}$)—CO—$N(R_{N-5})_2$,
(23) —$(CH_2)_{0-4}$—N—CS—$N(R_{N-5})_2$,
(24) —$(CH_2)_{0-4}$—N(—H or $R_{N-5}$)—CO—$R_{N-2}$,
(25) —$(CH_2)_{0-4}$—$NR_{N-2}R_{N-3}$,
(26) —$(CH_2)_{0-4}$—$R_{N-4}$,
(27) —$(CH_2)_{0-4}$—O—CO—($C_1$–$C_6$ alkyl),
(28) —$(CH_2)_{0-4}$—O—P(O)—$(OR_{100})_2$ where $R_{100}$ is independently H or $C_1$–$C_4$ alkyl,
(29) —$(CH_2)_{0-4}$—O—CO—$N(R_{N-5})_2$,
(30) —$(CH_2)_{0-4}$—O—CS—$N(R_{N-5})_2$,
(31) —$(CH_2)_{0-4}$—O—$(R_{N-5})$,
(32) —$(CH_2)_{0-4}$—O—$(R_{N-5})$—COOH,
(33) —$(CH_2)_{0-4}$—S—$(R_{N-5})$,
(34) —$(CH_2)_{0-4}$—O—($C_1$–$C_6$ alkyl) wherein the alkyl group is optionally substituted with one, two, three, four, or five substituents independently selected from the group consisting of F, Cl, Br, and I,
(35) —$(CH_2)_{0-4}$—($C_3$–$C_8$ cycloalkyl)
(36) $C_2$–$C_6$ alkenyl optionally substituted with $C_1$–$C_3$ alkyl, halogen, —OH, —SH, —C≡N, —$CF_3$, $C_1$–$C_3$ alkoxy, or —$NR_{1-a}R_{1-b}$,
(37) $C_2$–$C_6$ alkynyl optionally substituted with $C_1$–$C_3$ alkyl, —F, —Cl, —Br, —I, —OH, —SH, —C≡N, —$CF_3$, $C_1$–$C_3$ alkoxy, or —$NR_{1-a}R_{1-b}$, and
(38) —$(CH_2)_{0-4}$—N(—H or $R_{N-5}$)—$SO_2$—$R_{N-2}$;
(IV) —$(CR_{C-x}R_{C-y})_{0-4}$—$R_{C-heteroaryl}$ wherein $R_{C-heteroaryl}$ at each occurrence is independently selected from the group consisting of pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzoisothiazolyl, benzimidazolyl, benzofuranyl, furanyl, thienyl, pyrrolyl, oxadiazolyl, thiadiazolyl, triazolyl, tetrazolyl, oxazolopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, henoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, imidazopyrazolyl, quinazolinonyl, pyrazopyridyl, benzooxadiazolyl, dihydropyrimidinonyl, dihydrobenzofuranonyl, pyridinyl-N-oxide, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, and benzothiopyranyl S,S-dioxide,
where the $R_{C-heteroaryl}$ group is bonded by any atom of the parent $R_{C-heteroaryl}$ group substituted by hydrogen such that the new bond to the $R_{C-heteroaryl}$ group replaces the hydrogen atom and its bond, where heteroaryl is optionally substituted 1, 2, 3, or 4 groups that are independently:
(1) $C_1$–$C_6$ alkyl, optionally substituted with 1, 2, or 3 groups independently selected from the group consisting of $C_1$–$C_3$ alkyl, —F, —Cl, —Br, —I, —OH, —SH, —C≡N, —$CF_3$, $C_1$–$C_3$ alkoxy, and —$NR_{1-a}R_{1-b}$,
(2) —OH,
(3) —$NO_2$,
(4) —F, —Cl, —Br, —I,
(5) —CO—OH,
(6) —C≡N,
(7) —$(CH_2)_{0-4}$—CO—$NR_{N-2}R_{N-3}$,
(8) —$(CH_2)_{0-4}$—CO—($C_1$–$C_{12}$ alkyl),
(9) —$(CH_2)_{0-4}$—CO—($C_2$–$C_{12}$ alkenyl with one, two or three double bonds),

(10) —(CH$_2$)$_{0-4}$—CO—(C$_2$–C$_{12}$ alkynyl with one, two or three triple bonds),
(11) —(CH$_2$)$_{0-4}$—CO—(C$_3$–C$_7$ cycloalkyl),
(12) —(CH$_2$)$_{0-4}$—CO—R$_{1-aryl}$ where R$_{1-aryl}$ is as defined above,
(13) —(CH$_2$)$_{0-4}$—CO—R$_{1-heteroaryl}$,
(14) —(CH$_2$)$_{0-4}$—CO—R$_{1-heterocycle}$,
(15) —(CH$_2$)$_{0-4}$—CO—R$_{N-4}$,
(16) —(CH$_2$)$_{0-4}$—CO—O—R$_{N-5}$,
(17) —(CH$_2$)$_{0-4}$—SO$_2$—NR$_{N-2}$R$_{N-3}$,
(18) —(CH$_2$)$_{0-4}$—SO—(C$_1$–C$_8$ alkyl),
(19) —(CH$_2$)$_{0-4}$—SO$_2$(C$_1$–C$_{12}$ alkyl),
(20) —(CH$_2$)$_{0-4}$—SO$_2$—(C$_3$–C$_7$ cycloalkyl),
(21) —(CH$_2$)$_{0-4}$—N(H or R$_{N-5}$)—CO—O—R$_{N-5}$,
(22) —(CH$_2$)$_{0-4}$—N(H or R$_{N-5}$)—CO—N(R$_{N-5}$)$_2$,
(23) —(CH$_2$)$_{0-4}$—N—CS—N(R$_{N-5}$)$_2$,
(24) —(CH$_2$)$_{0-4}$—N(—H or R$_{N-5}$)—CO—R$_{N-2}$,
(25) —(CH$_2$)$_{0-4}$—NR$_{N-2}$R$_{N-3}$,
(26) —(CH$_2$)$_{0-4}$—R$_{N-4}$,
(27) —(CH$_2$)$_{0-4}$—O—CO—(C$_1$–C$_6$ alkyl),
(28) —(CH$_2$)$_{0-4}$—O—P(O)—(OR$_{100}$)$_2$ where R$_{100}$ is —H or C$_1$–C$_4$ alkyl,
(29) —(CH$_2$)$_{0-4}$—O—CO—N(R$_{N-5}$)$_2$,
(30) —(CH$_2$)$_{0-4}$—O—CS—N(R$_{N-5}$)$_2$,
(31) —(CH$_2$)$_{0-4}$—O—(R$_{N-5}$),
(32) —(CH$_2$)$_{0-4}$—O—(R$_{N-5}$)—COOH,
(33) —(CH$_2$)$_{0-4}$—S—(R$_{N-5}$),
(34) —(CH$_2$)$_{0-4}$—O—(C$_1$–C$_6$ alkyl optionally substituted with one, two, three, four, or five of —F),
(35) C$_3$–C$_7$ cycloalkyl,
(36) C$_2$–C$_6$ alkenyl optionally substituted with C$_1$–C$_3$ alkyl, —F, —Cl, —Br, —I, —OH, —SH, —C≡N, —CF$_3$, C$_1$–C$_3$ alkoxy, or —NR$_{1-a}$R$_{1-b}$,
(37) C$_2$–C$_6$ alkynyl optionally substituted with C$_1$–C$_3$ alkyl, —F, —Cl, —Br, —I, —OH, —SH, —C≡N, —CF$_3$, C$_1$–C$_3$ alkoxy, or —NR$_{1-a}$R$_{1-b}$,
(38) —(CH$_2$)$_{0-4}$—N(—H or R$_{N-5}$)—SO$_2$—R$_{N-2}$,
(39) —(CH$_2$)$_{0-4}$—(C$_3$–C$_7$ cycloalkyl),
(V) —(CR$_{C-x}$R$_{C-y}$)$_{0-4}$—R$_{C-aryl}$—R$_{101}$—R$_{C-aryl}$,
(VI) —(CR$_{C-x}$R$_{C-y}$)$_{0-4}$—R$_{C-aryl}$—R$_{101}$—R$_{C-heteroaryl}$,
(VII) —(CR$_{C-x}$R$_{C-y}$)$_{0-4}$—R$_{heteroaryl}$—R$_{101}$—R$_{C-aryl}$,
(VIII) —(CR$_{C-x}$R$_{C-y}$)$_{0-4}$—R$_{C-heteroaryl}$—R$_{101}$—R$_{C-heteroaryl}$,
(IX) —(CR$_{C-x}$R$_{C-y}$)$_{0-4}$—R$_{C-aryl}$—R$_{101}$—R$_{1-heterocycle}$,
(X) —(CR$_{C-x}$R$_{C-y}$)$_{0-4}$—R$_{C-heteroaryl}$—R$_{101}$—R$_{1-heterocycle}$,
(XI) —(CR$_{C-x}$R$_{C-y}$)$_{0-4}$—R$_{1-heterocycle}$—R$_{101}$—R$_{C-aryl}$,
(XII) —(CR$_{C-x}$R$_{C-y}$)$_{0-4}$—R$_{1-heterocycle}$—R$_{101}$—R$_{C-heteroaryl}$,
(XIII) —(CR$_{C-x}$R$_{C-y}$)$_{0-4}$—R$_{1-heterocycle}$—R$_{101}$—R$_{1-heterocycle}$, wherein R$_{101}$ is a bond, (CH$_2$)$_{0-4}$, —O—, —NH—, or —N(C$_1$–C$_6$ alkyl)
(XIV) —(CR$_{C-x}$R$_{C-y}$)$_{0-4}$—R$_{1-heterocycle}$,
(XV) —[C(R$_{C-1}$)(R$_{C-2}$)]$_{1-3}$—CO—N(R$_{C-3}$)$_2$ where R$_{C-1}$ and R$_{C-2}$ are the same or different and are selected from the group consisting of:
(A) —H,
(B) —C$_1$–C$_6$ alkyl, optionally substituted with one, two or three substituents independently selected from the group consisting of C$_1$–C$_3$ alkyl, —F, —Cl, —Br, —I, —OH, —SH, —C≡N, —CF$_3$, C$_1$–C$_6$ alkoxy, —O-phenyl, and —NR$_{1-a}$R$_{1-b}$,
(C) C$_2$–C$_6$ alkenyl with one or two double bonds, optionally substituted with one, two or three substituents independently selected from the group consisting of C$_1$–C$_3$ alkyl, —F, —Cl, —Br, —I, —OH, —SH, —C≡N, —CF$_3$, C$_1$–C$_6$ alkoxy, —O-phenyl, and —NR$_{1-a}$R$_{1-b}$,
(D) C$_2$–C$_6$ alkynyl optionally substituted with one, two or three substituents independently selected from the group consisting of C$_1$–C$_3$ alkyl, —F, —Cl, —Br, —I, —OH, —SH, —C≡N, —CF$_3$, C$_1$–C$_6$ alkoxy, —O-phenyl, and —NR$_{1-a}$R$_{1-b}$,
(E) —(CH$_2$)$_{1-2}$—S(O)$_{0-2}$—(C$_1$–C$_6$ alkyl),
(F) —(CH$_2$)$_{0-4}$—C$_3$–C$_7$ cycloalkyl, optionally substituted with one, two or three substituents independently selected from the group consisting of C$_1$–C$_3$ alkyl, —F, —Cl, —Br, —I, —OH, —SH, —C≡N, —CF$_3$, C$_1$–C$_6$ alkoxy, —O-phenyl, and —NR$_{1-a}$R$_{1-b}$,
(G) —(C$_1$–C$_4$ alkyl)—R$_{1-aryl}$,
(H) —(C$_1$–C$_4$ alkyl)—R$_{C-heteroaryl}$,
(I) —(C$_1$–C$_4$ alkyl)—R$_{1-heterocycle}$,
(J) —R$_{1-heteroaryl}$,
(K) —R$_{1-heterocycle}$,
(M) —(CH$_2$)$_{1-4}$—R$_{C-4}$—(CH$_2$)$_{0-4}$—R$_{1-aryl}$ where R$_{C-4}$ is —O—, —S— or —NR(C$_1$–C$_6$ alkyl)—,
(N) —(CH$_2$)$_{1-4}$—R$_{C-4}$—(CH$_2$)$_{0-4}$—R$_{C-heteroaryl}$,
(O) —R$_{1-aryl}$, and where
R$_{C-3}$ at each occurrence is independently:
(A) —H,
(B) —C$_1$–C$_6$ alkyl optionally substituted with one, two or three substituents independently selected from the group consisting of C$_1$–C$_3$ alkyl, —F, —Cl, —Br, —I, —OH, —SH, —C≡N, —CF$_3$, C$_1$–C$_6$ alkoxy, —O-phenyl, and —NR$_{1-a}$R$_{1-b}$,
(C) C$_2$–C$_6$ alkenyl with one or two double bonds, optionally substituted with one, two or three substituents independently selected from the group consisting of C$_1$–C$_3$ alkyl, halogen, —OH, —SH, —C≡N, —CF$_3$, C$_1$–C$_6$ alkoxy, —O-phenyl, and —NR$_{1-a}$R$_{1-b}$,
(D) C$_2$–C$_6$ alkynyl with one or two triple bonds, optionally substituted with one, two or three substituents independently selected from the group consisting of C$_1$–C$_3$ alkyl, —F, —Cl, —Br, —I, —OH, —SH, —C≡N, —CF$_3$, C$_1$–C$_6$ alkoxy, —O-phenyl, and —NR$_{1-a}$R$_{1-b}$,
(E) —(CH$_2$)$_{0-4}$—C$_3$–C$_7$ cycloalkyl, optionally substituted with 1, 2, or 3 groups that are independently selected from the group consisting of C$_1$–C$_3$ alkyl, —F, —Cl, —Br, —I, —OH, —SH, —C≡N, —CF$_3$, C$_1$–C$_6$ alkoxy, —O-phenyl, and —NR$_{1-a}$R$_{1-b}$,
(F) —R$_{1-aryl}$,
(G) —R$_{C-heteroaryl}$,
(H) —R$_{1-heterocycle}$,
(I) —(C$_1$–C$_4$ alkyl)—R$_{1-aryl}$,
(J) —(C$_1$–C$_4$ alkyl)—R$_{C-heteroaryl}$,
(K) —(C$_1$–C$_4$ alkyl)—R$_{1-heterocycle}$,
(XVI) —CH(R$_{C-aryl}$)$_2$,
(XVII) —CH(R$_{C-heteroaryl}$)$_2$,
(XVIII) —CH(R$_{C-aryl}$)(R$_{C-heteroaryl}$),
(XIX) -cyclopentyl, -cyclohexyl, or -cycloheptyl ring fused to R$_{C-aryl}$ or R$_{C-heteroaryl}$ or R$_{1-heterocycle}$ where R$_{C-aryl}$ or R$_{C-heteroaryl}$ or R$_{1-heterocycle}$ are as defined above where one carbon of cyclopentyl, cyclohexyl, or -cycloheptyl is optionally replaced with NH, $NR_{N-5}$, O, $S(=O)_{0-2}$, and where cyclopentyl, cyclohexyl, or -cycloheptyl can be optionally substituted with one or two —$C_1$–$C_3$ alkyl, —F, —OH, —SH, —C≡N, —$CF_3$, $C_1$–$C_6$ alkoxy, =O, or —$NR_{1-a}R_{1-b}$, (XX) $C_2$–$C_{10}$ alkenyl optionally substituted with one, two or three substituents independently selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$, (XXI) $C_2$–$C_{10}$ alkynyl optionally substituted with one, two or three substituents independently selected from the group consisting of $C_1$–$C_3$ alkyl, —F, —Cl, —Br, —I, —OH, —SH, —C≡N, —$CF_3$, $C_1$–$C_6$ alkoxy, —O-phenyl, and —$NR_{1-a}R_{1-b}$, (XXI) —$(CH_2)_{0-1}$—$CHR_{C-6}$—$(CH_2)_{0-1}$—$R_{C-aryl}$ wherein $R_{C-6}$ is —$(CH_2)_{0-6}$—OH, (XXII) —$(CH_2)_{0-1}$—$CHR_{C-6}$—$(CH_2)_{0-1}$—$R_{C-heteroaryl}$, (XXIII) —CH(—$R_{C-aryl}$ or $R_{C-heteroaryl}$)—CO—O($C_1$–$C_4$ alkyl), (XXIV) —CH(—$CH_2OH$)—CH(OH)—($C_1$–$C_6$ alkyl)—$NO_2$, (XXV) —($C_1$–$C_6$ alkyl)—O—($C_1$–$C_6$ alkyl)—OH, (XXVII) —$CH_2$—NH—$CH_2$—CH(—O—$CH_2$—$CH_3$)$_2$, (XXVIII) —H, and (XXIX) —$(CH_2)_{0-6}$—C(=$NR_{1-a}$)($NR_{1-a}R_{1-b}$).

Additionally provided are protected compounds of formula (II)

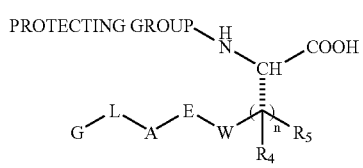

where n, $R_4$, $R_5$, G, L, A, E and W are as defined above;

where PROTECTING GROUP is a nitrogen protecting group. 1-methylcyclohexanyloxycabonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl)benzyloxycarbonyl, isobornyloxycarbonyl and 1-piperidyloxycarbonyl.

Further provided are protected compounds of formula (III)

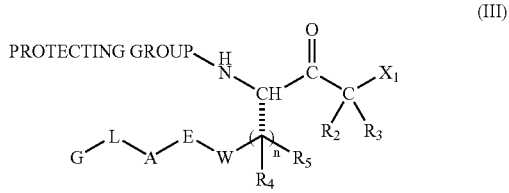

where n, $R_2$, $R_3$, $R_4$, $R_5$, $X_1$, G, L, A, E, W, and PROTECTING GROUP are as defined above;

where $X_1$ is —Cl, —Br, —I, —O-tosylate, —O-mesylate, —O-nosylate.

Further provided are alcohols of formula (IV)

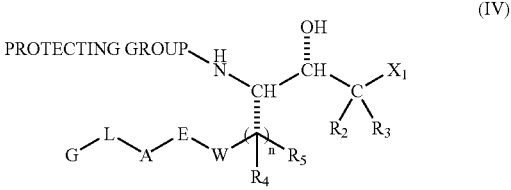

where n, $R_1$, $R_2$, $R_3$, $R_4$, $R_5$, G, L, A, E, W, $X_1$ and PROTECTING GROUP are as defined above.

Additionally provided are epoxides of formula (V)

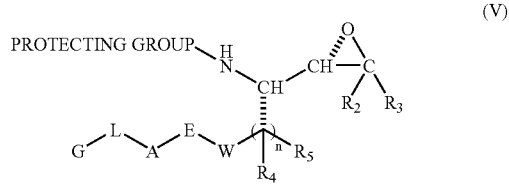

where n, $R_2$, $R_3$, $R_4$, $R_5$, G, L, A, E, W, and PROTECTING GROUP are as defined above.

Further provided are protected alcohols of formula (VII)

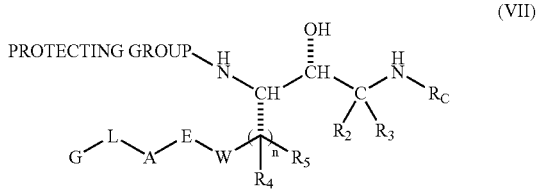

where n, $R_C$, $R_2$, $R_3$, $R_4$, $R_5$, G, L, A, E, W, and PROTECTING GROUP are as defined above and chemically acceptable salts thereof.

Also provided are amines of formula (VIII)

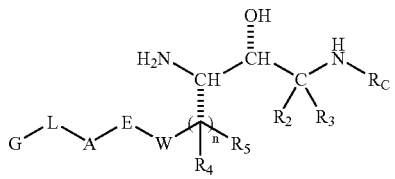

(VIII)

where n, $R_C$, $R_2$, $R_3$, $R_4$, $R_5$, G, L, A, E and W are as defined above and chemically acceptable salts thereof.

Provided are protected ketones of formula (XI)

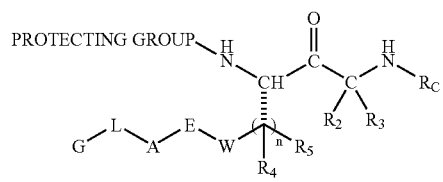

(XI)

where n, $R_C$, $R_2$, $R_3$, $R_4$, $R_5$, G, L, A, E, W, and PROTECTING GROUP are as defined above.

Also provided are protected azides of formula (XII)

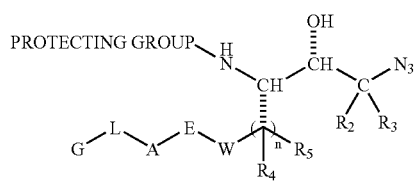

(XII)

where n, $R_2$, $R_3$, $R_4$, $R_5$, G, L, A, E, W, and PROTECTING GROUP are as defined above.

Further provided are protected amines of formula (XIII)

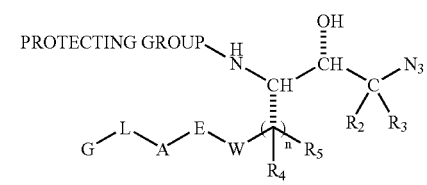

(XIII)

where n, $R_2$, $R_3$, $R_4$, $R^5$, G, L, A, E, W, and PROTECTING GROUP are as defined above.

Additionally provided are unprotected azides of formula (XIV)

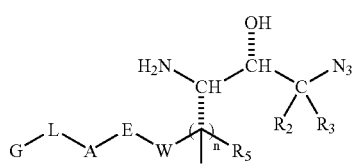

(XIV)

where n, $R_2$, $R_3$, $R_4$, $R_5$, G, L, A, E and W are as defined above for the compound (X).

Further provided are azides of formula (XV)

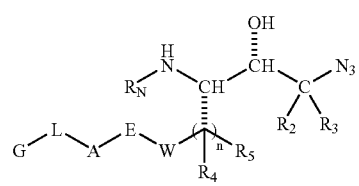

(XV)

where n, $R_N$, $R_2$, $R_3$, $R_4$, $R_5$, G, L, A, E and W are as defined above for the compound (X).

Also provided are free amines of formula (XVI)

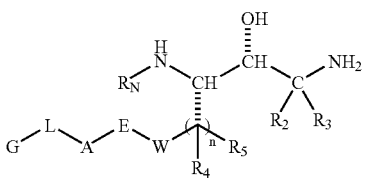

(XVI)

where n, $R_N$, $R_2$, $R_3$, $R_4$, $R_5$, G, L, A, E and W are as defined above.

The invention also provides methods for treating a patient who has, or preventing a patient from developing, a disease or condition selected from the group consisting of Alzheimer's disease, Frontotemporal dementias with parkinsonism (FTDP), for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, or diffuse Lewy body type of Alzheimer's disease and who is in need of such treatment which includes administration of a therapeutically effective amount of a compound or salt of formula (X).

In an embodiment, this method of treatment can be used where the disease is Alzheimer's disease.

In an embodiment, this method of treatment can help prevent or delay the onset of Alzheimer's disease.

In an embodiment, this method of treatment can be used where the disease is mild cognitive impairment.

In an embodiment, this method of treatment can be used where the disease is Down's syndrome.

In an embodiment, this method of treatment can be used where the disease is Hereditary Cerebral Hemorrhage with Amyloidosis of the Dutch-Type.

In an embodiment, this method of treatment can be used where the disease is cerebral amyloid angiopathy.

In an embodiment, this method of treatment can be used where the disease is degenerative dementias.

In an embodiment, this method of treatment can be used where the disease is diffuse Lewy body type of Alzheimer's disease.

In an embodiment, this method of treatment can treat an existing disease.

In an embodiment, this method of treatment can prevent a disease from developing.

The invention also includes pharmaceutical compositions comprising a compound or salt according to formula I and at least one pharmaceutically acceptable carrier, solvent, adjuvant, additive or excipient.

In an embodiment, this method of treatment can employ therapeutically effective amounts: for oral administration from about 0.1 mg/day to about 1,000 mg/day; for parenteral, sublingual, intranasal, intrathecal administration from about 0.5 to about 100 mg/day; for depo administration and implants from about 0.5 mg/day to about 50 mg/day; for topical administration from about 0.5 mg/day to about 200 mg/day; for rectal administration from about 0.5 mg to about 500 mg.

In an embodiment, this method of treatment can employ therapeutically effective amounts: for oral administration from about 1 mg/day to about 100 mg/day; and for parenteral administration from about 5 to about 50 mg daily.

In an embodiment, this method of treatment can employ therapeutically effective amounts for oral administration from about 5 mg/day to about 50 mg/day.

The invention also includes the use of a compound or salt of formula (X) for the manufacture of a medicament for use in treating a patient who has, or in preventing a patient from getting, a disease or condition selected from the group consisting of Alzheimer's disease, for helping prevent or delay the onset of Alzheimer's disease, for treating patients with mild cognitive impairment (MCI) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, diffuse Lewy body type of Alzheimer's disease and who is in need of such treatment.

In an embodiment, this use of a compound of formula (X) can be employed where the disease is Alzheimer's disease.

In an embodiment, this use of a compound of formula (X) can help prevent or delay the onset of Alzheimer's disease.

In an embodiment, this use of a compound of formula (X) can be employed where the disease is mild cognitive impairment.

In an embodiment, this use of a compound of formula (X) can be employed where the disease is Down's syndrome.

In an embodiment, this use of a compound of formula (X) can be employed where the disease is Hereditary Cerebral Hemorrhage with Amyloidosis of the Dutch-Type.

In an embodiment, this use of a compound of formula (X) can be employed where the disease is cerebral amyloid angiopathy.

In an embodiment, this use of a compound of formula (X) can be employed where the disease is degenerative dementias.

In an embodiment, this use of a compound of formula (X) can be employed where the disease is diffuse Lewy body type of Alzheimer's disease.

In an embodiment, this use of a compound employs a pharmaceutically acceptable salt selected from the group consisting of salts of the following acids hydrochloric, hydrobromic, hydroiodic, nitric, sulfuric, phosphoric, citric, methanesulfonic, $CH_3—(CH_2)_n—COOH$ where n is 0 thru 4, $HOOC—(CH_2)_n—COOH$ where n is as defined above, $HOOC—CH=CH—COOH$, and phenyl-COOH.

The present invention also includes methods for inhibiting beta-secretase activity, for inhibiting cleavage of amyloid precursor protein (APP), in a reaction mixture, at a site between Met596 and Asp597, numbered for the APP-695 amino acid isotype, or at a corresponding site of an isotype or mutant thereof; for inhibiting production of amyloid beta peptide (A beta) in a cell; for inhibiting the production of beta-amyloid plaque in an animal; and for treating or preventing a disease characterized by beta-amyloid deposits in the brain. These methods each include administration of a therapeutically effective amount of a compound or salt of formula (X).

The present invention also includes a method for inhibiting beta-secretase activity, including exposing said beta-secretase to an effective inhibitory amount of a compound or salt of formula (X).

In an embodiment, this method employs a compound that inhibits 50% of the enzyme's activity at a concentration of less than 50 micromolar.

In an embodiment, this method employs a compound that inhibits 50% of the enzyme's activity at a concentration of 10 micromolar or less.

In an embodiment, this method employs a compound that inhibits 50% of the enzyme's activity at a concentration of 1 micromolar or less.

In an embodiment, this method employs a compound that inhibits 50% of the enzyme's activity at a concentration of 10 nanomolar or less.

In an embodiment, this method includes exposing said beta-secretase to said compound in vitro.

In an embodiment, this method includes exposing said beta-secretase to said compound in a cell.

In an embodiment, this method includes exposing said beta-secretase to said compound in a cell in an animal.

In an embodiment, this method includes exposing said beta-secretase to said compound in a human.

The present invention also includes a method for inhibiting cleavage of amyloid precursor protein (APP), in a reaction mixture, at a site between Met596 and Asp597, numbered for the APP-695 amino acid isotype; or at a corresponding site of an isotype or mutant thereof, including exposing said reaction mixture to an effective inhibitory amount of a compound or salt of formula (X).

In an embodiment, this method employs a cleavage site: between Met652 and Asp653, numbered for the APP-751 isotype; between Met 671 and Asp 672, numbered for the APP-770 isotype; between Leu596 and Asp597 of the APP-695 Swedish Mutation; between Leu652 and Asp653 of the APP-751 Swedish Mutation; or between Leu671 and Asp672 of the APP-770 Swedish Mutation.

In an embodiment, this method exposes said reaction mixture in vitro.

In an embodiment, this method exposes said reaction mixture in a cell.

In an embodiment, this method exposes said reaction mixture in an animal cell.

In an embodiment, this method exposes said reaction mixture in a human cell.

The present invention also includes a method for inhibiting production of amyloid beta peptide (A beta) in a cell, including administering to said cell an effective inhibitory amount of a compound or salt of formula (X).

In an embodiment, this method includes administering to an animal.

In an embodiment, this method includes administering to a human.

The present invention also includes a method for inhibiting the production of beta-amyloid plaque in an animal, including administering to said animal an effective inhibitory amount of a compound or salt of formula (X).

In an embodiment, this method includes administering to a human.

The present invention also includes a method for treating or preventing a disease characterized by beta-amyloid deposits in the brain including administering to a patient an effective therapeutic amount of a hydroxyethylene compound or salt of formula (X).

In an embodiment, this method employs a compound that inhibits 50% of the enzyme's activity at a concentration of less than 50 micromolar.

In an embodiment, this method employs a compound that inhibits 50% of the enzyme's activity at a concentration of 10 micromolar or less.

In an embodiment, this method employs a compound that inhibits 50% of the enzyme's activity at a concentration of 1 micromolar or less.

In an embodiment, this method employs a compound that inhibits 50% of the enzyme's activity at a concentration of 10 nanomolar or less.

In an embodiment, this method employs a compound at a therapeutic amount in the range of from about 0.1 to about 1000 mg/day.

In an embodiment, this method employs a compound at a therapeutic amount in the range of from about 15 to about 1500 mg/day.

In an embodiment, this method employs a compound at a therapeutic amount in the range of from about 1 to about 100 mg/day.

In an embodiment, this method employs a compound at a therapeutic amount in the range of from about 5 to about 50 mg/day.

In an embodiment, this method can be used where said disease is Alzheimer's disease.

In an embodiment, this method can be used where said disease is Mild Cognitive Impairment, Down's Syndrome, or Hereditary Cerebral Hemorrhage with Amyloidosis of the Dutch Type.

The present invention also includes a composition or complex comprising beta-secretase complexed with a compound or salt of formula (X).

The present invention also includes a method for producing a beta-secretase complex including exposing beta-secretase to a compound or salt of formula (X) in a reaction mixture under conditions suitable for the production of said complex.

In an embodiment, this method employs exposing in vitro.

In an embodiment, this method employs a reaction mixture that is a cell.

The present invention also includes a component kit including component parts capable of being assembled, in which at least one component part includes a compound of formula I enclosed in a container.

In an embodiment, this component kit includes lyophilized compound, and at least one further component part includes a diluent.

The present invention also includes a container kit including a plurality of containers, each container including one or more unit dose of a compound or salt of formula (X).

In an embodiment, this container kit includes each container adapted for oral delivery and includes a tablet, gel, or capsule.

In an embodiment, this container kit includes each container adapted for parenteral delivery and includes a depot product, syringe, ampoule, or vial.

In an embodiment, this container kit includes each container adapted for topical delivery and includes a patch, medipad, ointment, or cream.

The present invention also includes an agent kit including a compound or salt of formula (X) and one or more therapeutic agent selected from the group consisting of an antioxidant, an anti-inflammatory, a gamma secretase inhibitor, a neurotrophic agent, an acetyl cholinesterase inhibitor, a statin, an A beta peptide, and an anti-A beta antibody.

The present invention also includes a composition including a compound or salt of formula (X) together with a pharmaceutically acceptable carrier or an inert diluent or edible carrier.

In this aspect, the carrier may be an oil, binder, excipient, disintegrating agent, lubricant, or gildant.

Alternatively, in this aspect the compound or salt may be disposed in a cream, ointment, or patch.

The present invention provides compounds, compositions, kits, and methods for inhibiting beta-secretase-mediated cleavage of amyloid precursor protein (APP). More particularly, the compounds, compositions, and methods of the invention are effective to inhibit the production of A beta peptide and to treat or prevent any human or veterinary disease or condition associated with a pathological form of A beta peptide.

The compounds, compositions, and methods of the invention are useful for treating humans who have Alzheimer's Disease (AD), for helping prevent or delay the onset of AD, for treating patients with mild cognitive impairment (MCI), and preventing or delaying the onset of AD in those patients who would otherwise be expected to progress from MCI to AD, for treating Down's syndrome, for treating Hereditary Cerebral Hemorrhage with Amyloidosis of the Dutch Type, for treating cerebral beta-amyloid angiopathy and preventing its potential consequences such as single and recurrent lobar hemorrhages, for treating other degenerative dementias, including dementias of mixed vascular and degenerative origin, for treating dementia associated with Parkinson's disease, dementia associated with progressive supranuclear palsy, dementia associated with cortical basal degeneration, and diffuse Lewy body type AD.

The compounds of the invention possess beta-secretase inhibitory activity. The inhibitory activities of the compounds of the invention are readily demonstrated, for example, using one or more of the assays described herein or known in the art.

DETAILED DESCRIPTION OF THE INVENTION

The invention encompasses compounds of Formula X above. More specifically, it encompasses such compounds that inhibit the activity of beta-secretase. These compounds are therefore useful in treating and preventing Alzheimer's disease.

The compounds of the invention may contain geometric or optical isomers as well as tautomers. Thus, the invention includes all tautomers and pure geometric isomers, such as the E and Z geometric isomers, as well as mixtures thereof. Furthermore, the invention includes pure enantiomers and diasteriomers as well as mixtures thereof, including racemic mixtures. The individual geometric isomers, enantiomers, or diasteriomers may be prepared or isolated by methods known in the art.

Compounds of the invention with the stereochemistry designated in formula X may be included in mixtures, including racemic mixtures, with other enantiomers, diasteriomers, geometric isomers or tautomers. Compounds of the invention with the stereochemistry designated in formula X are typically present in these mixtures in excess of 50 percent. Preferably, compounds of the invention with the stereochemistry designated in formula X are present in these mixtures in excess of 80 percent. Most preferably, compounds of the invention with the stereochemistry designated in formula X are present in these mixtures in excess of 90 percent.

In one aspect, the compounds of the invention have the following stereochemistry

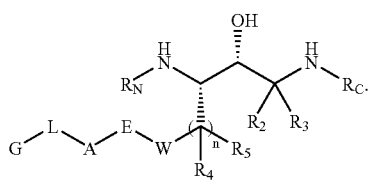

The (S,R)-compounds (X) and the compound with $R_N$ cyclized (X') are amines and as such form salts when reacted with acids. Pharmaceutically acceptable salts are preferred over the corresponding (S,R)-compounds (X) and the compounds with $R_N$ cyclized (X') since they produce compounds which are more water soluble, stable and/or more crystalline. Pharmaceutically acceptable salts are any salt which retains the activity of the parent compound and does not impart any deleterious or undesirable effect on the subject to whom it is administered and in the context in which it is administered. Pharmaceutically acceptable salts include salts of both inorganic and organic acids. The preferred pharmaceutically acceptable salts include salts of the following acids acetic, aspartic, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycollylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, succinic, sulfamic, sulfanilic, sulfonic, sulfuric, tannic, tartaric, teoclic and toluenesulfonic. For other acceptable salts, see *Int. J. Pharm.*, 33, 201–217 (1986) and *J. Pharm. Sci.*, 66(1), 1, (1977).

The present invention provides compounds, compositions, kits, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.

It is preferred that $R_C$ is:
—$C_1$–$C_8$ alkyl,
—$(CH_2)_{0-3}$—$(C_3$–$C_7)$ cycloalkyl,
—$(CR_{C-x}R_{C-y})_{0-4}$—$R_{C-aryl}$,
—$(CR_{C-x}R_{C-y})_{0-4}$—$R_{C-heteroaryl}$,
—$(CR_{C-x}R_{C-y})_{0-4}$—$R_{C-heterocycle}$,
-cyclopentyl or -cyclohexyl ring fused to $R_{C-aryl}$ or $R_{C-heteroaryl}$ or $R_{C-heterocycle}$.

It is more preferred that $R_C$ is:
—$(CH_2)_{0-3}$—$(C_3$–$C_7)$ cycloalkyl,
—$(CR_{C-x}R_{C-y})_{0-4}$—$R_{C-aryl}$,
—$(CR_{C-x}R_{C-y})_{0-4}$—$R_{C-heteroaryl}$,
—$(CR_{C-x}R_{C-y})_{0-4}$—$R_{C-heterocycle}$,
-cyclopentyl or -cyclohexyl ring fused to a $R_{C-aryl}$ or $R_{C-heteroaryl}$ or $R_{C-heterocycle}$.

It is even more preferred that $R^C$ is:
—$(CR_{C-x}R_{C-y})_{0-4}$—$R_{C-aryl}$,
—$(CR_{C-x}R_{C-y})_{0-4}$—$R_{C-heteroaryl}$,
-cyclopentyl or -cyclohexyl ring fused to a $R_{C-aryl}$ or $R_{C-heteroaryl}$ or $R_{C-heterocycle}$.

It is still more preferred that $R_C$ is selected from the group consisting of:
—$(CR_{C-x}R_{C-y})_{0-4}$—$R_{C-aryl}$ where $R_{C-aryl}$ is phenyl,
—$(CR_{C-x}R_{C-y})_{0-4}$—$R_{C-heteroaryl}$,
-cyclopentyl or -cyclohexyl ring fused to a $R_{C-aryl}$ or $R_{C-heteroaryl}$ or $R_{C-heterocycle}$. Further, it is preferred that when $R_C$ is phenyl, it is substituted in the 3-position or 3,5-positions.

In one aspect, preferred compounds of formula I are selected from

N-{(1S,2R)-1-[3-(cyclohexylmethyl)benzyl]-2-hydroxy-3-[(3-methoxybenzyl)amino]propyl}acetamide hydrochloride;

N'-{(1S,2R)-1-[3-(cyclohexylmethyl)benzyl]-2-hydroxy-3-[(3-methoxybenzyl)amino]propyl}-5-methyl-N,N-dipropylisophthalamide hydrochloride;

N-{(1S,2R)-1-[3-(cyclohexylmethyl)benzyl]-2-hydroxy-3-[(3-methoxybenzyl)amino]propyl}-3-{[(trifluoromethyl)sulfonyl]amino}benzamide hydrochloride;

tert-butyl (1S,2R)-1-[3-(cyclohexylmethyl)benzyl]-2-hydroxy-3-[(3-methoxybenzyl)amino]propylcarbamate hydrochloride;

tert-butyl (1S,2R)-1-{3-[(tert-butoxycarbonyl)amino]benzyl}-2-hydroxy-3-[(3-methoxybenzyl)amino]propylcarbamate hydrochloride;

N-{(1R,2R)-2-hydroxy-3-[(3-iodobenzyl)amino]-1-[(2-naphthylthio)methyl]propyl}-3-methylbenzamide;

N-{(1R,2S)-2-hydroxy-3-[(3-iodobenzyl)amino]-1-[(2-naphthylthio)methyl]propyl}-3-methylbenzamide;

N'-{(1R,2R)-2-hydroxy-3-[(3-iodobenzyl)amino]-1-[(2-naphthylthio)methyl]propyl}-5-methyl-N,N-dipropylisophthalamide; and (2S,3R)-3-amino-1-[(3-iodobenzyl)amino]-4-(2-naphthylthio)butan-2-ol.

In another aspect, preferred compounds of formula I have the formula I-a:

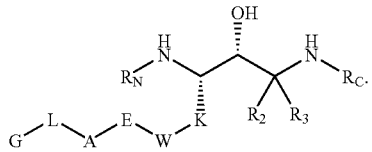

Preferred compounds of formula I and I-a include those wherein n is 0, 1 or 2;
A is phenyl, or naphthyl optionally substituted with 1, 2, or 3 substituents each independently selected from the group consisting of halogen, $C_1$–$C_6$ alkyl, —O—($C_1$–$C_6$ alkyl), and —N—($C_1$–$C_6$ alkyl)($C_1$–$C_6$ alkyl)
E is a bond or $C_1$–$C_3$ alkylene;
K is —$(CR_4R_5)_n$—, wherein
  $R_4$ and $R_5$ are independently hydrogen, halogen, $C_1$–$C_6$ alkoxy or $C_1$–$C_4$ alkyl optionally substituted with halogen, —CN, —$CF_3$, or —OH; (preferably $R_4$ is $C_1$–$C_3$ alkyl and $R_5$ is H);
L is a bond, —O—, or —N(R)— where R is hydrogen or $C_1$–$C_4$ alkyl;
G is $C_1$–$C_{10}$ alkyl, optionally substituted with up to three groups independently selected from
  (A) halogen,
  (B) —OH,
  (C) $C_1$–$C_6$ alkoxy,
  (D) $C_1$–$C_6$ haloalkyl;
$R_N$ is hydrogen, $C_1$–$C_6$ alkanoyl, —C(=O)—(CRR')$_{0-6}$ $R_{100}$, $R'_{100}$, —$SO_2R'_{100}$, or —(CRR')$_{1-6}R'_{100}$;
$R_2$ and $R_3$ are independently hydrogen, $C_1$–$C_4$ alkyl or benzyl;
$R_{100}$ and $R'_{100}$ are independently, phenyl, heteroaryl or -aryl-W-heteroaryl, where the ring portions of each are optionally substituted with 1, 2, or 3 groups independently selected from
  —OR, $C_1$–$C_6$ alkyl, —$NO_2$, halogen, —C≡N, —SR, —$SO_2R_{145}$, —C(=O)R, —$OCF_3$, —$CF_3$, —O—P(=O)(OR)(OR')—C(O)NRR, or —$(CH_2)_{0-4}$—$C_3$–$C_7$ cycloalkyl; or
$R_{100}$ is $C_1$–$C_{10}$ alkyl optionally substituted with 1, 2, or 3 $R_{115}$ groups, wherein
  $R_{115}$ at each occurrence is independently halogen, —OH, —$CO_2R$, —$C_1$–$C_6$ alkoxy or $C_1$–$C_6$ haloalkoxy;
R and R' at each occurrence are independently hydrogen; $C_1$–$C_6$ alkyl optionally substituted with 1, 2, or 3 groups that are independently F, Cl, Br, or I; or —($C_1$–$C_6$)-alkyl;
W is —$(CH_2)_{0-4}$—, —O—, —$S(O)_{0-2}$—, —$N(R_{135})$—, or —C(O)—;
$R_{135}$ is $C_1$–$C_6$ alkyl, $C_2$–$C_6$ alkenyl, $C_2$–$C_6$ alkynyl, $C_3$–$C_7$ cycloalkyl, —$(CH_2)_{0-2}$—(aryl), —$(CH_2)_{0-2}$-(heteroaryl), or —$(CH_2)_{0-2}$—(heterocyclyl);
$R_C$ is —$CH_2$-aryl, wherein the aryl is optionally substituted with 1, 2, 3, or 4 $R_{200}$, wherein
  $R_{200}$ at each occurrence is independently selected from the group consisting of $C_1$–$C_6$ alkyl optionally substituted with 1, 2, or 3 $R_{205}$ groups; OH, alkoxy, —$NO_2$; halogen; —$CO_2H$; C≡N; and —$(CH_2)_{0-4}$—$C_3$–$C_7$ cycloalkyl;
  $R_{205}$ at each occurrence is independently selected from the group consisting of $C_1$–$C_6$ alkyl, halogen, —OH, —O-phenyl, —SH, —C≡N, —$CF_3$, $C_1$–$C_6$ alkoxy, $NH_2$, $NH(C_1$–$C_6$ alkyl), and N—($C_1$–$C_6$ alkyl)($C_1$–$C_6$ alkyl).

More preferred compounds of formula I-a include those of formula I-b, i.e., compounds wherein
n is 0, 1 or 2;
A is phenyl, optionally substituted with 1, 2, or 3 substituents each independently selected from the group consisting of halogen, $C_1$–$C_6$ alkyl, —O—($C_1$–$C_6$ alkyl), and —N—($C_1$–$C_6$ alkyl)($C_1$–$C_6$ alkyl);
L is a bond, —O— or —N(R)— where R is hydrogen or $C_1$–$C_4$ alkyl;
G is $C_1$–$C_{10}$ alkyl, optionally substituted with up to three groups independently selected from
  (A) halogen,
  (B) —OH,
  (C) $C_1$–$C_6$ alkoxy,
  (D) $C_1$–$C_6$ haloalkyl;
$R_N$ is hydrogen, $C_1$–$C_6$ alkanoyl, or —C(=O)—$R_{100}$;
$R_{100}$ is heteroaryl which is selected from pyridyl, pyridazinyl, pyrimidyl, pyrazinyl, thiazolyl, isothiazolyl, oxazolyl, isoxazolyl, and imidazolyl, wherein each is optionally substituted with 1, 2, or 3 groups independently selected from —OR, —$NO_2$, halogen, —C≡N, —SR, —$SO_2R_{145}$, —C(=O)R, —$OCF_3$, —$CF_3$, —O—P(=O)(OR)(OR'), and —$N(R)(SO_2R_{145})$, or $R_{100}$ is -aryl-W-heteroaryl, wherein aryl is phenyl or naphthyl and heteroaryl is selected from pyridyl, pyridazinyl, pyrimidyl, pyrazinyl, thiazolyl, isothiazolyl, oxazolyl, isoxazolyl, and imidazolyl, wherein each is optionally substituted with 1, 2, or 3 groups independently selected from —OR, —$NO_2$, halogen, —C≡N, —SR, —$SO_2R_{145}$, —C(=O)R, —$OCF_3$, —$CF_3$, —O—P(=O)(OR)(OR'), and —$N(R)(SO_2R_{145})$, or
$R_{100}$ is $C_1$–$C_6$ alkyl optionally substituted with 1, 2, or 3 $R_{115}$ groups, wherein
  $R_{115}$ at each occurrence is independently halogen, —OH, $C_1$–$C_6$ alkoxy or $C_1$–$C_6$ haloalkoxy;
W is —$(CH_2)_{0-4}$—, —O—, —$S(O)_{0-2}$—, —$N(R_{135})$—, or —C(O)—;
$R_{145}$ is $C_1$–$C_6$ alkyl or $CF_3$;
$R_{150}$ is hydrogen, $C_3$–$C_7$ cycloalkyl, —($C_1$–$C_2$ alkyl)—($C_3$–$C_7$ cycloalkyl), $C_2$–$C_6$ alkenyl, $C_2$–$C_6$ alkynyl, $C_1$–$C_6$ alkyl with one double bond and one triple bond, —$R_{110}$, —$R_{120}$, or
$C_1$–$C_6$ alkyl optionally substituted with 1, 2, 3, or 4 groups independently selected from —OH, —$NH_2$, $C_1$–$C_3$ alkoxy, $R_{110}$, and halogen;
$R_C$ is —$CH_2$-aryl, wherein the aryl is optionally substituted with 1, 2, 3, or 4 $R_{200}$, wherein
  $R_{200}$ at each occurrence is independently selected from the group consisting of $C_1$–$C_6$ alkyl optionally substituted with 1, 2, or 3 $R_{205}$ groups; OH; alkoxy, —$NO_2$; halogen; —$CO_2H$; C≡N;
  $R_{205}$ at each occurrence is independently selected from the group consisting of $C_1$–$C_6$ alkyl, halogen, —OH, —O-phenyl, —SH, —C≡N, —$CF_3$, $C_1$–$C_6$ alkoxy, $NH_2$, $NH(C_1$–$C_6$ alkyl), and N—($C_1$–$C_6$ alkyl)($C_1$–$C_6$ alkyl); and
K is $CH_2$.

More preferred compounds of formula I-b include those of formula I-c, i.e., those compounds wherein
n is 0, 1, or 2;
A is phenyl, optionally substituted with 1, 2, or 3 substituents each independently selected from the group consisting of halogen, $C_1$–$C_6$ alkyl, —O—($C_1$–$C_6$ alkyl), and —N—($C_1$–$C_6$ alkyl)($C_1$–$C_6$ alkyl)

L is a bond or —O—;
G is $C_1$–$C_6$ alkyl, optionally substituted with up to three groups independently selected from
(A) halogen,
(B) —OH,
(C) $C_1$–$C_6$ alkoxy,
(D) $C_1$–$C_6$ haloalkyl;
$R_N$ is hydrogen, $C_1$–$C_6$ alkanoyl, or —C(=O)—$R_{100}$;
$R_{100}$ is heteroaryl which is selected from pyridyl, thiazolyl, isothiazolyl, oxazolyl, isoxazolyl, and imidazolyl, wherein each is optionally substituted with 1, 2, or 3 groups independently selected from —OR, —NO$_2$, halogen, —C≡N, —SR, —SO$_2$R$_{145}$, —C(=O)R, —OCF$_3$, —CF$_3$, —O—P(=O)(OR)(OR'), and —N(R)(SO$_2$R$_{145}$), or
$R_{100}$ is -aryl-W-heteroaryl, wherein aryl is phenyl or naphthyl and heteroaryl is selected from pyridyl, thiazolyl, isothiazolyl, oxazolyl, isoxazolyl, and imidazolyl, wherein each is optionally substituted with 1, 2, or 3 groups independently selected from —OR, —NO$_2$, halogen, —C≡N, —SR, —SO$_2$R$_{145}$, —C(=O)R, —OCF$_3$, —CF$_3$, —O—P(=O)(OR)(OR'), and —N(R)(SO$_2$R$_{145}$), or
$R_{100}$ is $C_1$–$C_6$ alkyl optionally substituted with 1, 2, or 3 $R_{115}$ groups, wherein
$R_{115}$ at each occurrence is independently halogen, —OH, $C_1$–$C_6$ alkoxy or $C_1$–$C_6$ haloalkoxy;
$R_{145}$ is $C_1$–$C_6$ alkyl or CF$_3$;
$R_C$ is —CH$_2$-aryl, wherein the aryl is phenyl or naphthyl, and is optionally substituted with 1, 2, 3, or 4 $R_{200}$, wherein
$R_{200}$ at each occurrence is independently selected from the group consisting of $C_1$–$C_6$ alkyl optionally substituted with 1, 2, or 3 $R_{205}$ groups; OH; alkoxy, —NO$_2$; halogen; —CO$_2$H; C≡N;
$R_{205}$ at each occurrence is independently selected from the group consisting of $C_1$–$C_6$ alkyl, halogen, —OH, —O-phenyl, —SH, —C≡N, —CF$_3$, $C_1$–$C_6$ alkoxy, NH$_2$, NH($C_1$–$C_6$ alkyl), and N—($C_1$–$C_6$ alkyl)($C_1$–$C_6$ alkyl).

More preferred compounds of formula I-c include those of formula I-d, i.e., those compounds wherein
n is 0, 1, or 2;
A is phenyl, optionally substituted with 1, 2, or 3 substituents each independently selected from the group consisting of halogen, $C_1$–$C_6$ alkyl, —O—($C_1$–$C_6$ alkyl), and —N—($C_1$–$C_6$ alkyl)($C_1$–$C_6$ alkyl);
L is —O—;
G is $C_1$–$C_6$ alkyl, optionally substituted with up to three groups independently selected from
(A) halogen,
(B) —OH,
(C) $C_1$–$C_6$ alkoxy,
(D) $C_1$–$C_6$ haloalkyl;
$R_N$ is hydrogen, $C_1$–$C_4$ alkanoyl, or —C(=O)—$R_{100}$;
$R_{100}$ is heteroaryl which is selected from pyridyl, thiazolyl, isothiazolyl, oxazolyl, isoxazolyl, and imidazolyl, wherein each is optionally substituted with 1, 2, or 3 groups independently selected from —OR, —NO$_2$, halogen, —C≡N, —SR, —SO$_2$R$_{145}$, —C(=O)R, —OCF$_3$, —CF$_3$, and —N(R)(SO$_2$R$_{145}$), or
$R_{100}$ is -aryl-W-heteroaryl, wherein aryl is phenyl and heteroaryl is selected from thiazolyl, isothiazolyl, oxazolyl, and isoxazolyl, wherein each is optionally substituted with 1, 2, or 3 groups independently selected from —OR, —NO$_2$, halogen, —C≡N, —SR, —SO$_2$R$_{145}$, —C(=O)R, —OCF$_3$, —CF$_3$, and —N(R)(SO$_2$R$_{145}$), or
$R_{100}$ is $C_1$–$C_6$ alkyl optionally substituted with 1, 2, or 3 $R_{115}$ groups, wherein
$R_{115}$ at each occurrence is independently halogen, —OH, —NH—SO$_2$—($C_1$–$C_6$ alkyl), $C_1$–$C_6$ alkoxy or $C_1$–$C_6$ haloalkoxy;
R is H or $C_1$–$C_4$ alkyl;
W is —(CH$_2$)$_{0-4}$—, —O—, —S(O)$_{0-2}$—, —N(R$_{135}$)—, or —C(O)
$R_{145}$ is $C_1$–$C_6$ alkyl or CF$_3$;
$R_C$ is —CH$_2$-phenyl, which is optionally substituted with 1, 2, 3, or 4 $R_{200}$, wherein
$R_{200}$ at each occurrence is independently selected from the group consisting of $C_1$–$C_6$ alkyl optionally substituted with 1, 2, or 3 $R_{205}$ groups; OH; alkoxy, —NO$_2$; halogen; —CO$_2$H; C≡N; and
$R_{205}$ at each occurrence is independently selected from the group consisting of $C_1$–$C_6$ alkyl, halogen, —OH, —O-phenyl, —SH, —C≡N, —CF$_3$, $C_1$–$C_6$ alkoxy, NH$_2$, NH($C_1$–$C_6$ alkyl), and N—($C_1$–$C_6$ alkyl)($C_1$–$C_6$ alkyl).

More preferred compounds of formula I-d include those of formula I-e, i.e., those compounds wherein
$R_C$ is benzyl substituted with at least one $R_{200}$; wherein
$R_{200}$ is $C_1$–$C_4$ alkyl, halogen, or $C_1$–$C_4$ alkoxy; or
$R_C$ is

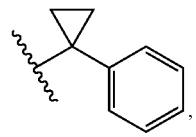

which is substituted with at least one $R_{200}$;
$R_N$ is —C(=O)—$R_{100}$; wherein
$R_{100}$ is $C_1$–$C_5$ alkyl or oxazol-4-yl optionally substituted with 1, or 2 groups independently selected from —OH, $C_1$–$C_4$ alkoxy, halogen, —C≡N, —SO$_2$R$_{145}$, and —N(R)(SO$_2$R$_{145}$); or
$R_{100}$ is -phenyl-oxazolyl or -phenyl-thiazolyl, wherein
R is H or $C_1$–$C_4$ alkyl;
$R_{145}$ is $C_1$–$C_6$ alkyl; or
$R_N$ is hydrogen or $C_1$–$C_4$ alkanoyl; and
$R_2$ and $R_3$ are both hydrogen.

More preferred compounds of formula I-e include those of formula I-f, i.e., those compounds wherein
G-L-A-E-W-K- is —CH$_2$-phenyl, wherein the phenyl is substituted with 1, 2, or 3 substituents each independently selected from the group consisting of halogen, $C_1$–$C_6$ alkyl, —O—($C_1$–$C_6$ alkyl), NH$_2$, NH($C_1$–$C_6$ alkyl), and —N—($C_1$–$C_6$ alkyl)($C_1$–$C_6$ alkyl).

More preferred compounds of formula I-f include those of formula I-g, i.e., those compounds wherein
G-L-A-E-W-K- is —CH$_2$-phenyl, and the phenyl group is substituted at the 3 or 4-position.

More preferred compounds of formula I-f and formula I-g, include those of formula I-h, i.e., those compounds wherein
G-L-A-E-W-K- is of the formula

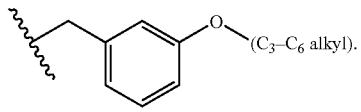

Even more preferably, the $C_3$–$C_6$ alkyl group is n-propyl, n-butyl, or n-pentyl or n-hexyl. Still more preferably, the $C_3$–$C_6$ alkyl group is n-butyl, or n-pentyl or n-hexyl.

Preferred compound of formulas I-e, I-f, I-g, and I-h include those of formula I-i, i.e., compounds wherein
$R_N$ is hydrogen, —C(O)oxazol-4-yl optionally substituted with —NRSO$_2$($C_1$–$C_4$ alkyl), phenyl substituted with oxazole, or $C_1$–$C_4$ alkanoyl; wherein
R is H or $C_1$–$C_4$ alkyl.

Preferred compound of formula I-i include those compounds wherein
$R_N$ is hydrogen.

Other preferred compound of formula I-i include those compounds wherein
$R_N$ is —C(O)oxazol-4-yl substituted at the two position of the oxazol-4-yl ring with —NRSO$_2$($C_1$–$C_4$ alkyl), wherein
R is H or $C_1$–$C_4$ alkyl.

Still other preferred compound of formula I-i include those compounds wherein
$R_N$ is phenyl substituted at the 3 position with oxazol-2-yl;

Yet still other preferred compound of formula I-i include those compounds wherein
$R_N$ is $C_2$–$C_4$ alkanoyl. More preferably, $R_N$ is $C_2$ or $C_3$ alkanoyl. Still more preferably, $R_N$ is $C_2$ alkanoyl.

Other preferred compounds of formula I-a include those of formula I-j, i.e., those wherein
A is naphthyl optionally substituted with 1, 2, or 3 substituents each independently selected from the group consisting of halogen, $C_1$–$C_6$ alkyl, —O—($C_1$–$C_6$ alkyl), and —N—($C_1$–$C_6$ alkyl)($C_1$–$C_6$ alkyl)
K is —CH$_2$—;
E is a bond;
L is a bond; and
W is selected from S, S(O), and SO$_2$.

Preferred compounds of formula I-j include those of formula I-k, i.e., compounds wherein
$R_C$ is benzyl substituted with at least one $R_{200}$; wherein
$R_{200}$ is $C_1$–$C_4$ alkyl, halogen, or $C_1$–$C_4$ alkoxy; or
$R_C$ is

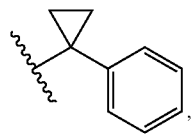

which is substituted with at least one $R_{200}$;
$R_N$ is —C(=O)—$R_{100}$; wherein
$R_{100}$ is phenyl, $C_1$–$C_5$ alkyl or oxazol-4-yl, wherein the phenyl and the oxazol-4-yl groups are optionally substituted with 1 or 2 groups independently selected from —OH, $C_1$–$C_4$ alkyl, $C_1$–$C_4$ alkoxy, halogen, —C≡N, —SO$_2$R$_{145}$, —C(O)NRR, and —N(R)(SO$_2$R$_{145}$); or
$R_{100}$ is -phenyl-oxazolyl or -phenyl-thiazolyl, wherein
R at each occurrence is independently H or $C_1$–$C_4$ alkyl;
$R_{145}$ is $C_1$–$C_6$ alkyl; or
$R_N$ is hydrogen or $C_1$–$C_4$ alkanoyl;

W is S; and
$R_2$ and $R_3$ are both hydrogen.

Preferred compounds of formula I-k include those of formula I-l, i.e., compounds wherein
$R_C$ is 3-halobenzyl; (preferably the halo group is bromo or iodo, more preferably it is iodo);
A is naphth-2-yl optionally substituted with 1, or 2 substituents each independently selected from the group consisting of halogen, $C_1$–$C_6$ alkyl, and —O—($C_1$–$C_6$ alkyl)

Preferred compounds of formula I-l include those of formula I-m, i.e., compounds wherein
$R_N$ is —C(=O)—$R_{100}$; wherein
$R_{100}$ is phenyl optionally substituted with 1 or 2 groups selected from $C_1$–$C_4$ alkyl and —C(O)NRR, wherein
R at each occurrence is independently H or $C_1$–$C_4$ alkyl.

Preferred compounds of formula I-m include those of formula I-n, i.e., compounds wherein
$R_C$ is 3-iodo benzyl;
A is naphthyl-2-yl; and
$R_{100}$ is phenyl substituted with 1 group selected from methyl, ethyl, and —C(O)NRR, wherein
R at each occurrence is independently H or $C_3$–$C_4$ alkyl.

Other preferred compounds of formula I include those of formula I-o, i.e., compounds wherein
$R_C$ is benzyl substituted with at least one $R_{200}$; wherein
$R_{200}$ is $C_1$–$C_4$ alkyl, halogen, or $C_1$–$C_4$ alkoxy; or
$R_C$ is

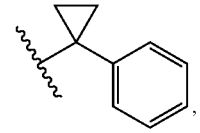

which is substituted with at least one $R_{200}$;
$R_N$ is —C(=O)—$R_{100}$; wherein
$R_{100}$ is phenyl, $C_1$–$C_5$ alkyl or oxazol-4-yl, wherein the phenyl and the oxazol-4-yl groups are optionally substituted with 1 or 2 groups independently selected from —OH, $C_1$–$C_4$ alkyl, $C_1$–$C_4$ alkoxy, halogen, —C≡N, —SO$_2$R$_{145}$, —C(O)NRR, and —N(R)(SO$_2$R$_{145}$); or
$R_{100}$ is -phenyl-oxazolyl or -phenyl-thiazolyl, wherein
R at each occurrence is independently H or $C_1$–$C_4$ alkyl;
$R_{145}$ is $C_1$–$C_6$ alkyl; or
$R_N$ is hydrogen or $C_1$–$C_4$ alkanoyl;
A is phenyl, or naphthyl each of which is optionally substituted with 1, 2, or 3 substituents each independently selected from the group consisting of halogen, $C_1$–$C_6$ alkyl, —O—($C_1$–$C_6$ alkyl), $C_3$–$C_6$ cyclolalkyl-$C_1$–$C_4$ alkyl, and —N—($C_1$–$C_6$ alkyl)($C_1$–$C_6$ alkyl)
E is a bond or $C_1$–$C_3$ alkylene;
K is —(CR$_4$R$_5$)$_n$—; wherein
n is 0, 1, or 2;
L is a bond, —O—, or —N(R)— where R is hydrogen or $C_1$–$C_4$ alkyl;
G is $C_1$–$C_{10}$ alkyl, optionally substituted with up to three groups independently selected from
(A) halogen,
(B) —OH,
(C) $C_1$–$C_6$ alkoxy,
(D) $C_1$–$C_6$ haloalkyl; and
W is —(CH$_2$)$_{0-4}$—, —O—, —S(O)$_{0-2}$—, —N(R$_{135}$)—, or —C(O)—.

Preferred compounds of formulas I-n and I-o include those of formula I-p, i.e., compounds wherein
$R_K$ is H; and
$R_C$ is 3-methoxybenzyl.
Preferred compounds of formula I-p include those of formula I-q, i.e., compounds wherein
G-L-A-E-W is of the formula

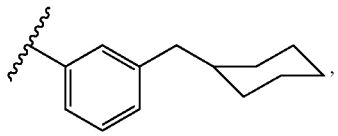

wherein the phenyl ring is optionally substituted with 1, 2, or 3 substituents each independently selected from the group consisting of halogen, $C_1$–$C_4$ alkyl, —O—($C_1$–$C_4$ alkyl), and —N—($C_1$–$C_4$ alkyl)($C_1$–$C_4$ alkyl); and
$R_J$ and $R_K$ are both H.
Preferred compounds of formula I-q include those of formula I-r, i.e., compounds wherein
$R_N$ is $C_2$–$C_4$ alkanoyl.
Other preferred compounds of formula I-q include those of formula I-s, i.e., compounds wherein
$R_N$ is —C(=O)—$R_{100}$; wherein
$R_{100}$ is phenyl, optionally substituted with 1 or 2 groups independently selected from $C_1$–$C_4$ alkyl, $C_1$–$C_4$ alkoxy, halogen, —C(O)NRR, —N(R)($SO_2CF_3$), and —N(R)($SO_2R_{145}$);
$R_{145}$ is $C_1$–$C_6$ alkyl; and
R is H or $C_1$–$C_4$ alkyl.
Preferred compounds of formula I-s include those of formula I-t, i.e., compounds wherein
$R_{100}$ is phenyl substituted with 1 or 2 groups that are independently methyl, ethyl, —C(O)NRR, and —N(R)($SO_2CF_3$);
wherein R is H or $C_1$–$C_4$ alkyl.
Preferred compounds of formula I-t include those of formula I-u, i.e., compounds wherein
$R_{100}$ is of the formula

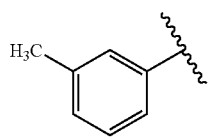

and is optionally further substituted with —C(O)NRR, wherein R is $C_1$–$C_4$ alkyl. Preferably both R groups are the same. More preferably, R is $C_3$ or $C_4$ alkyl. Still more preferably R is $C_3$ alkyl.
Other preferred compounds of formula I are selected from
(2R,3S)-3-amino-4-(2-butoxyphenyl)-1-[(3-ethylbenzyl)amino]butan-2-ol,
(2R,3S)-3-amino-4-(3-butoxyphenyl)-1-[(3-ethylbenzyl)amino]butan-2-ol,
(2R,3S)-3-amino-4-(4-butoxyphenyl)-1-[(3-ethylbenzyl)amino]butan-2-ol,
(2R,3S)-3-amino-1-[(3-ethylbenzyl)amino]-4-[2-(hexyloxy)phenyl]butan-2-ol,
(2R,3S)-3-amino-1-[(3-ethylbenzyl)amino]-4-[3-(hexyloxy)phenyl]butan-2-ol,
(2R,3S)-3-amino-1-[(3-ethylbenzyl)amino]-4-[4-(hexyloxy)phenyl]butan-2-ol, N-{(1S,2R)-1-(2-butoxybenzyl)-3-[(3-ethylbenzyl)amino]-2-hydroxypropyl}acetamide,
N-{(1S,2R)-1-(3-butoxybenzyl)-3-[(3-ethylbenzyl)amino]-2-hydroxypropyl}acetamide,
N-{(1S,2R)-1-(4-butoxybenzyl)-3-[(3-ethylbenzyl)amino]-2-hydroxypropyl}acetamide,
N-{(1S,2R)-3-[(3-ethylbenzyl)amino]-1-[2-(hexyloxy)benzyl]-2-hydroxypropyl}acetamide,
N-{(1S,2R)-3-[(3-ethylbenzyl)amino]-1-[3-(hexyloxy)benzyl]-2-hydroxypropyl}acetamide,
N-{(1S,2R)-3-[(3-ethylbenzyl)amino]-1-[4-(hexyloxy)benzyl]-2-hydroxypropyl}acetamide,
N-{(1S,2R)-1-(2-butoxybenzyl)-3-[(3-ethylbenzyl)amino]-2-hydroxypropyl}-2-[(methylsulfonyl)amino]-1,3-oxazole-4-carboxamide,
N-{(1S,2R)-1-(3-butoxybenzyl)-3-[(3-ethylbenzyl)amino]-2-hydroxypropyl}-2-[(methylsulfonyl)amino]-1,3-oxazole-4-carboxamide,
N-{(1S,2R)-1-(4-butoxybenzyl)-3-[(3-ethylbenzyl)amino]-2-hydroxypropyl}-2-[(methylsulfonyl)amino]-1,3-oxazole-4-carboxamide,
N-{(1S,2R)-3-[(3-ethylbenzyl)amino]-1-[2-(hexyloxy)benzyl]-2-hydroxypropyl}-2-[(methylsulfonyl)amino]-1,3-oxazole-4-carboxamide,
N-{(1S,2R)-3-[(3-ethylbenzyl)amino]-1-[3-(hexyloxy)benzyl]-2-hydroxypropyl}-2-[(methylsulfonyl)amino]-1,3-oxazole-4-carboxamide,
N-{(1S,2R)-3-[(3-ethylbenzyl)amino]-1-[4-(hexyloxy)benzyl]-2-hydroxypropyl}-2-[(methylsulfonyl)amino]-1,3-oxazole-4-carboxamide,
N-{(1S,2R)-3-[(3-ethylbenzyl)amino]-1-[2-(hexyloxy)benzyl]-2-hydroxypropyl}-3-(1,3-oxazol-2-yl)benzamide
N-{(1S,2R)-3-[(3-ethylbenzyl)amino]-1-[3-(hexyloxy)benzyl]-2-hydroxypropyl}-3-(1,3-oxazol-2-yl)benzamide, and
N-{(1S,2R)-3-[(3-ethylbenzyl)amino]-1-[4-(hexyloxy)benzyl]-2-hydroxypropyl}-3-(1,3-oxazol-2-yl)benzamide.
Other preferred compounds of the invention include those of formula XXA

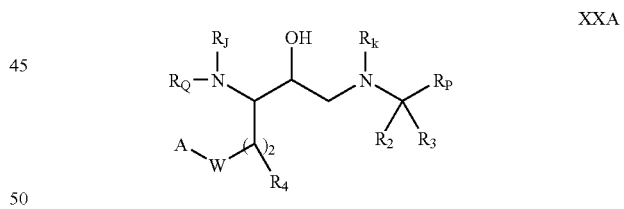

or a pharmaceutically acceptable salt thereof, wherein
A is phenyl, optionally substituted with 1, 2, or 3 substituents each independently selected from the group consisting of halogen, $C_1$–$C_6$ alkyl, —O—($C_1$–$C_6$ alkyl), $C_3$–$C_6$ cycloalkyl $C_1$–$C_4$ alkyl, and —N—($C_1$–$C_6$ alkyl)($C_1$–$C_6$ alkyl) or $C_1$–$C_6$ haloalkyl;
$R_Q$ is H or $C_1$–$C_6$ alkyl optionally substituted with 1, 2, or 3 groups that are independently F, Cl, Br, I, —CN, —$CF_3$, or —OH;
W is —$(CH_2)_{0-4}$—;
$R_P$ is phenyl, optionally substituted with 1, 2, 3, or 4 $R_{200}$, wherein
$R_{200}$ is halogen, $C_1$–$C_4$ alkoxy, or $C_1$–$C_4$ alkyl optionally substituted with 1, 2, or 3 groups that are independently F, Cl, Br, I, —CN, —$CF_3$, or —OH;

$R_2$ and $R_3$ at each occurrence are independently selected from the group consisting of H or $C_1$–$C_4$ alkyl; or $R_2$ and $R_3$ are taken together with the carbon to which they are attached to form a carbocycle of 3–6 carbon atoms;

$R_J$ is H, $C_1$–$C_4$ alkoxycarbonyl, or benzyloxycarbonyl;

$R_K$ is H, or $C_1$–$C_4$ alkoxycarbonyl;

$R_4$ at each occurrence is independently H or $C_1$–$C_3$ alkyl optionally substituted with 1, 2, or 3 groups that are independently F, Cl, Br, I, —CN, —$CF_3$, or —OH.

Preferred compounds of formula XXA include those of formula XXA-a, i.e., those wherein A is phenyl, optionally substituted with 1 or 2 substituents each independently selected from the group consisting of halogen, $C_1$–$C_6$ alkyl, —O—($C_1$–$C_6$ alkyl), and —N—($C_1$–$C_6$ alkyl)($C_1$–$C_6$ alkyl) or $C_1$–$C_6$ haloalkyl;

$R_Q$ is $C_1$–$C_4$ alkyl optionally substituted with 1, 2, or 3 groups that are independently F, Cl, Br, I, —CN, —$CF_3$, or —OH;

W is —$(CH_2)_{0-2}$—;

$R_P$ is phenyl, optionally substituted with 1 or 2 $R_{200}$, wherein $R_{200}$ is $C_1$–$C_6$ alkyl optionally substituted with 1, 2, or 3 groups that are independently F, Cl, Br, I, —CN, —$CF_3$, or —OH;

$R_2$ and $R_3$ at each occurrence are independently selected from the group consisting of H or $C_1$–$C_4$ alkyl; or $R_2$ and $R_3$ are taken together with the carbon to which they are attached to form a carbocycle of 3 or 4 carbon atoms;

$R_4$ is $C_1$–$C_2$ alkyl optionally substituted with 1, 2, or 3 groups that are independently F, Cl, Br, I, —CN, $CF_3$, or OH.

Preferred compounds of formula XXA-a include those of formula XXA-b, i.e., those wherein A is phenyl, optionally substituted with 1 substituent selected from the group consisting of halogen, $C_1$–$C_6$ alkyl, —O—($C_1$–$C_6$ alkyl), and —N—($C_1$–$C_6$ alkyl)($C_1$–$C_6$ alkyl) or $C_1$–$C_6$ haloalkyl.

Preferred compounds of formula XXA-b include those of formula XXA-c, i.e., those wherein $R_Q$ is methyl, optionally substituted with 1, 2, or 3 groups that are independently F, Cl, Br, I, —CN, —$CF_3$, or —OH.

Preferred compounds of formula XXA-c include those of formula XXA-d, i.e., those wherein W is —$CH_2$— or —$CH_2CH_2$—.

Preferred compounds of formula XXA-d include those of formula XXA-e, i.e., those wherein $R_P$ is 3-halophenyl.

Other preferred compounds of formula XXA-b include those of formula XXA-f, i.e., those wherein $R_P$ is 3-methoxybenzyl;

$R_K$ is H or $C_4$ alkoxycarbonyl; and $R_J$ is H, $C_4$ alkoxycarbonyl, or benzyloxycarbonyl.

Preferred compounds of formula XXA-f include those of formula XXA-g, i.e., those wherein $R_Q$ is H; and A is 3-halophenyl.

Other Preferred compounds of formula XXA-f include those of formula XXA-h, i.e., those wherein A is phenyl substituted with —$CH_2$-cyclohexyl;

$R_Q$ and $R_J$ are both H.

Still other Preferred compounds of formula XXA-f include those of formula XXA-i, i.e., those wherein $R_2$ and $R_3$ at each occurrence are independently selected from the group consisting of H or methyl.

Yet still other Preferred compounds of formula XXA-f include those of formula XXA-j, i.e., those wherein $R_2$ and $R_3$ are taken together with the carbon to which they are attached to form a carbocycle of 3 carbon atoms.

Preferred compounds of formulas XXA-i and XXA-j include those of formula XXA-k, i.e., those wherein $R_4$ is $C_1$–$C_2$ alkyl;

$R_J$ is H; and $R_K$ is H.

Preferred compounds of formula XXA-k include those of formula XXA-l, i.e., those wherein $R_4$ is methyl.

Another preferred compound of formula I is exemplified by N-[(1S)-1-((1R)-2-{[1-(3-bromophenyl)cyclopropyl]amino}-1-hydroxyethyl)-3-methyl-4-phenylbutyl]acetamide.

Other preferred compounds of the invention include those of formula XXAV

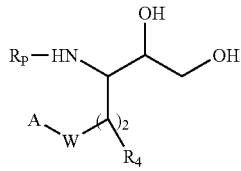

XXAV or a pharmaceutically acceptable salt thereof, wherein

A is phenyl, optionally substituted with 1, 2, or 3 substituents each independently selected from the group consisting of halogen, $C_1$–$C_6$ alkyl, —O—($C_1$–$C_6$ alkyl), and —N—($C_1$–$C_6$ alkyl)($C_1$–$C_6$ alkyl) or $C_1$–$C_6$ haloalkyl;

W is —$(CH_2)_{0-4}$—;

$R_4$ at each occurrence is independently H or $C_1$–$C_3$ alkyl optionally substituted with 1, 2, or 3 groups that are independently F, Cl, Br, I, —CN, —$CF_3$, or —OH; (more preferably, R4 is H or $C_1$–$C_3$ alkyl)

$R_P$ is an amine protecting group selected from the group consisting of t-butyloxycarbonyl (Boc), benzyloxycarbonyl(Cbz), t-butyl-dimethylsilyl (TBDMS).

Yet other preferred compounds of the invention include those of formula XXAVI

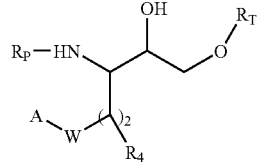

XXAVI or a pharmaceutically acceptable salt thereof, wherein

A is phenyl, optionally substituted with 1, 2, or 3 substituents each independently selected from the group consisting of halogen, $C_1$–$C_6$ alkyl, —O—($C_1$–$C_6$ alkyl), and —N—($C_1$–$C_6$ alkyl)($C_1$–$C_6$ alkyl) or $C_1$–$C_6$ haloalkyl;

W is —$(CH_2)_{0-4}$—;

$R_4$ at each occurrence is independently H or $C_1$–$C_3$ alkyl optionally substituted with 1, 2, or 3 groups that are independently F, Cl, Br, I, —CN, —$CF_3$, or —OH;

$R_P$ is an amine protecting group selected from the group consisting of t-butyloxycarbonyl (Boc), benzyloxycarbonyl(Cbz), t-butyl-dimethylsilyl (TBDMS);

$R_T$ is selected from the group consisting of tosylate, mesylate, triflate, and brosylate.

Still yet other preferred compounds of formulas I, XXA, XXAV and XXAVI are exemplified by N-[(1S)-1-((1S)-2-[(4-methylphenyl)sulfonate]-1-hydroxyethyl)-3-methyl-4-phenylbutyl]-t-butylcarbamate; and N-[(1S)-1-((1S)-2-hydroxy-1-hydroxyethyl)-3-methyl-4-phenylbutyl]-t-butylcarbamate.

Still other preferred compounds of the invention include those of the formula XXAVII

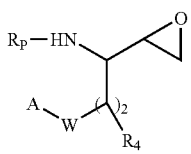

XXAVII or a pharmaceutically acceptable salt thereof, wherein

A is phenyl, optionally substituted with 1, 2, or 3 substituents each independently selected from the group consisting of halogen, $C_1$-$C_6$ alkyl, —O—($C_1$-$C_6$ alkyl), and —N—($C_1$-$C_6$ alkyl)($C_1$-$C_6$ alkyl) or $C_1$-$C_6$ haloalkyl;

W is —$(CH_2)_{0-4}$—;

$R_4$ at each occurrence is independently H or $C_1$-$C_3$ alkyl optionally substituted with 1, 2, or 3 groups that are independently F, Cl, Br, I, —CN, —$CF_3$, or —OH; $R_P$ is an amine protecting group selected from the group consisting of t-butyloxycarbonyl (Boc), benzyloxycarbonyl(Cbz), t-butyl-dimethylsilyl (TBDMS).

A preferred compound of formula XXAVII is exemplified by N-[(1S)-1-((1S)-oxiran-1-yl)-3-methyl-4-phenylbutyl]-t-butylcarbamate.

Methods of the Invention

The compounds of the invention, or a pharmaceutically acceptable salt thereof, are useful for treating humans or animals suffering from a condition characterized by a pathological form of beta-amyloid peptide, such as beta-amyloid plaques, and for helping to prevent or delay the onset of such a condition. For example, the compounds are useful for treating Alzheimer's disease, for helping prevent or delay the onset of Alzheimer's disease, for treating patients with MCI (mild cognitive impairment) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e. single and recurrent lobal hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type Alzheimer's disease. The compounds and compositions of the invention are particularly useful for treating or preventing Alzheimer's disease. When treating or preventing these diseases, the compounds of the invention can either be used individually or in combination, as is best for the patient.

As used herein, the term "treating" means that the compounds of the invention can be used in humans with at least a tentative diagnosis of disease. The compounds of the invention will delay or slow the progression of the disease thereby giving the individual a more useful life span.

The term "preventing" means that the compounds of the present invention are useful when administered to a patient who has not been diagnosed as possibly having the disease at the time of administration, but who would normally be expected to develop the disease or be at increased risk for the disease. The compounds of the invention will slow the development of disease symptoms, delay the onset of the disease, or prevent the individual from developing the disease at all. Preventing also includes administration of the compounds of the invention to those individuals thought to be predisposed to the disease due to age, familial history, genetic or chromosomal abnormalities, and/or due to the presence of one or more biological markers for the disease, such as a known genetic mutation of APP or APP cleavage products in brain tissues or fluids.

In treating or preventing the above diseases, the compounds of the invention are administered in a therapeutically effective amount. The therapeutically effective amount will vary depending on the particular compound used and the route of administration, as is known to those skilled in the art.

In treating a patient displaying any of the diagnosed above conditions a physician may administer a compound of the invention immediately and continue administration indefinitely, as needed. In treating patients who are not diagnosed as having Alzheimer's disease, but who are believed to be at substantial risk for Alzheimer's disease, the physician should preferably start treatment when the patient first experiences early pre-Alzheimer's symptoms such as, memory or cognitive problems associated with aging. In addition, there are some patients who may be determined to be at risk for developing Alzheimer's through the detection of a genetic marker such as APOE4 or other biological indicators that are predictive for Alzheimer's disease. In these situations, even though the patient does not have symptoms of the disease, administration of the compounds of the invention may be started before symptoms appear, and treatment may be continued indefinitely to prevent or delay the outset of the disease.

Dosage Forms and Amounts

The compounds of the invention can be administered orally, parenternally, (IV, IM, depo-IM, SQ, and depo SQ), sublingually, intranasally (inhalation), intrathecally, topically, or rectally. Dosage forms known to those of skill in the art are suitable for delivery of the compounds of the invention.

Compositions are provided that contain therapeutically effective amounts of the compounds of the invention. The compounds are preferably formulated into suitable pharmaceutical preparations such as tablets, capsules, or elixirs for oral administration or in sterile solutions or suspensions for parenternal administration. Typically the compounds described above are formulated into pharmaceutical compositions using techniques and procedures well known in the art.

About 1 to 500 mg of a compound or mixture of compounds of the invention or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 2 to about 100 mg, more preferably about 10 to about 30 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, one or more compounds of the invention are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered. Typically, the compositions are formulated for single dosage administration.

The compounds of the invention may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampules, vials, and the like for parenternal administration; and patches, medipads, creams, and the like for topical administration.

The concentration of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered orally, parenternally (IV, IM, depo-IM, SQ, and depo-SQ), sublingually, intranasally (inhalation), intrathecally, topically, or rectally. Dosage forms known to those skilled in the art are suitable for delivery of the compounds of the invention.

Compounds of the invention may be administered enterally or parenternally. When administered orally, compounds of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The oral dosage forms are administered to the patient 1, 2, 3, or 4 times daily. It is preferred that the compounds of the invention be administered either three or fewer times, more preferably once or twice daily. Hence, it is preferred that the compounds of the invention be administered in oral dosage form. It is preferred that whatever oral dosage form is used, that it be designed so as to protect the compounds of the invention from the acidic environment of the stomach. Enteric coated tablets are well known to those skilled in the art. In addition, capsules filled with small spheres each coated to protect from the acidic stomach, are also well known to those skilled in the art.

When administered orally, an administered amount therapeutically effective to inhibit beta-secretase activity, to inhibit A beta production, to inhibit A beta deposition, or to treat or prevent AD is from about 0.1 mg/day to about 1,000 mg/day. It is preferred that the oral dosage is from about 1 mg/day to about 100 mg/day. It is more preferred that the oral dosage is from about 5 mg/day to about 50 mg/day. It is understood that while a patient may be started at one dose, that dose may be varied over time as the patient's condition changes.

Compounds of the invention may also be advantageously delivered in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

The compounds of the invention can be administered parenterally, for example, by IV, IM, depo-IM, SC, or depo-SC. When administered parenterally, a therapeutically effective amount of about 0.5 to about 100 mg/day, preferably from about 5 to about 50 mg daily should be delivered. When a depot formulation is used for injection once a month or once every two weeks, the dose should be about 0.5 mg/day to about 50 mg/day, or a monthly dose of from about 15 mg to about 1,500 mg. In part because of the forgetfulness of the patients with Alzheimer's disease, it is preferred that the parenteral dosage form be a depo formulation.

The compounds of the invention can be administered sublingually. When given sublingually, the compounds of the invention should be given one to four times daily in the amounts described above for IM administration.

The compounds of the invention can be administered intranasally. When given by this route, the appropriate dosage forms are a nasal spray or dry powder, as is known to those skilled in the art. The dosage of the compounds of the invention for intranasal administration is the amount described above for IM administration.

The compounds of the invention can be administered intrathecally. When given by this route the appropriate dosage form can be a parenternal dosage form as is known to those skilled in the art. The dosage of the compounds of the invention for intrathecal administration is the amount described above for IM administration.

The compounds of the invention can be administered topically. When given by this route, the appropriate dosage form is a cream, ointment, or patch. Because of the amount of the compounds of the invention to be administered, the patch is preferred. When administered topically, the dosage is from about 0.5 mg/day to about 200 mg/day. Because the amount that can be delivered by a patch is limited, two or more patches may be used. The number and size of the patch is not important, what is important is that a therapeutically effective amount of the compounds of the invention be delivered as is known to those skilled in the art. The compounds of the invention can be administered rectally by suppository as is known to those skilled in the art. When administered by suppository, the therapeutically effective amount is from about 0.5 mg to about 500 mg.

The compounds of the invention can be administered by implants as is known to those skilled in the art. When administering a compound of the invention by implant, the therapeutically effective amount is the amount described above for depot administration.

The invention here is the new compounds of the invention and new methods of using the compounds of the invention. Given a particular compound of the invention and a desired dosage form, one skilled in the art would know how to prepare and administer the appropriate dosage form.

The compounds of the invention are used in the same manner, by the same routes of administration, using the same pharmaceutical dosage forms, and at the same dosing schedule as described above, for preventing disease or treating patients with MCI (mild cognitive impairment) and preventing or delaying the onset of Alzheimer's disease in those who would progress from MCI to AD, for treating or preventing Down's syndrome, for treating humans who have Hereditary Cerebral Hemorrhage with Amyloidosis of the Dutch-Type, for treating cerebral amyloid angiopathy and preventing its potential consequences, i.e. single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type of Alzheimer's disease.

The compounds of the invention can be used in combination, with each other or with other therapeutic agents or approaches used to treat or prevent the conditions listed above. Such agents or approaches include: acetylcholine esterase inhibitors such as tacrine (tetrahydroaminoacridine, marketed as COGNEX®), donepezil hydrochloride, (marketed as Aricept® and rivastigmine (marketed as Exelon®); gamma-secretase inhibitors; anti-inflammatory agents such as cyclooxygenase II inhibitors; anti-oxidants such as Vitamin E and ginkolides; immunological approaches, such as, for example, immunization with A beta peptide or administration of anti-A beta peptide antibodies; statins; and direct or indirect neurotropic agents such as Cerebrolysin®, AIT-082 (Emilieu, 2000, *Arch. Neurol.* 57:454), and other neurotropic agents of the future.

In addition, the compounds of the present invention can also be used with inhibitors of P-glycoproten (P-gp). The use of P-gp inhibitors is known to those skilled in the art. See for example, *Cancer Research,* 53, 4595–4602 (1993), *Clin. Cancer Res.,* 2, 7–12 (1996), *Cancer Research,* 56, 4171–4179 (1996), International Publications WO99/64001 and WO01/10387. The important thing is that the blood level of the P-gp inhibitor be such that it exerts its effect in inhibiting P-gp from decreasing brain blood levels of the compounds of the present invention. To that end the P-gp inhibitor and the compounds of the present invention can be administered at the same time, by the same or different route of administration, or at different times. The important thing is not the time of administration but having an effective blood level of the P-gp inhibitor.

Suitable P-gp inhibitors include cyclosporin A, verapamil, tamoxifen, quinidine, Vitamin E-TGPS, ritonavir, megestrol acetate, progesterone, rapamycin, 10,11-methanodibenzosuberane, phenothiazines, acridine derivatives such as GF120918, FK506, VX-710, LY335979, PSC-833, GF-102, 918 and other steroids. It is to be understood that additional agents will be found that do the same function and are also considered to be useful.

The P-gp inhibitors can be administered orally, parenterally, (IV, IM, IM-depo, SQ, SQ-depo), topically, sublingually, rectally, intranasally, intrathecally and by implant.

The therapeutically effective amount of the P-gp inhibitors is from about 0.1 to about 300 mg/kg/day, preferably about 0.1 to about 150 mg/kg daily. It is understood that while a patient may be started on one dose, that dose may have to be varied over time as the patient's condition changes.

When administered orally, the P-gp inhibitors can be administered in usual dosage forms for oral administration as is known to those skilled in the art. These dosage forms include the usual solid unit dosage forms of tablets and capsules as well as liquid dosage forms such as solutions, suspensions and elixirs. When the solid dosage forms are used, it is preferred that they be of the sustained release type so that the P-gp inhibitors need to be administered only once or twice daily. The oral dosage forms are administered to the patient one thru four times daily. It is preferred that the P-gp inhibitors be administered either three or fewer times a day, more preferably once or twice daily. Hence, it is preferred that the P-gp inhibitors be administered in solid dosage form and further it is preferred that the solid dosage form be a sustained release form which permits once or twice daily dosing. It is preferred that what ever dosage form is used, that it be designed so as to protect the P-gp inhibitors from the acidic environment of the stomach. Enteric coated tablets are well known to those skilled in the art. In addition, capsules filled with small spheres each coated to protect from the acidic stomach, are also well known to those skilled in the art.

In addition, the P-gp inhibitors can be administered parenterally. When administered parenterally they can be administered IV, IM, depo-IM, SQ or depo-SQ.

The P-gp inhibitors can be given sublingually. When given sublingually, the P-gp inhibitors should be given one thru four times daily in the same amount as for IM administration.

The P-gp inhibitors can be given intranasally. When given by this route of administration, the appropriate dosage forms are a nasal spray or dry powder as is known to those skilled in the art. The dosage of the P-gp inhibitors for intranasal administration is the same as for IM administration.

The P-gp inhibitors can be given intrathecally. When given by this route of administration the appropriate dosage form can be a parenteral dosage form as is known to those skilled in the art.

The P-gp inhibitors can be given topically. When given by this route of administration, the appropriate dosage form is a cream, ointment or patch. Because of the amount of the P-gp inhibitors needed to be administered the patch is preferred. However, the amount that can be delivered by a patch is limited. Therefore, two or more patches may be required. The number and size of the patch is not important, what is important is that a therapeutically effective amount of the P-gp inhibitors be delivered as is known to those skilled in the art.

The P-gp inhibitors can be administered rectally by suppository as is known to those skilled in the art.

The P-gp inhibitors can be administered by implants as is known to those skilled in the art.

There is nothing novel about the route of administration nor the dosage forms for administering the P-gp inhibitors. Given a particular P-gp inhibitor, and a desired dosage form, one skilled in the art would know how to prepare the appropriate dosage form for the P-gp inhibitor.

It should be apparent to one skilled in the art that the exact dosage and frequency of administration will depend on the particular compounds of the invention administered, the particular condition being treated, the severity of the condition being treated, the age, weight, general physical condition of the particular patient, and other medication the individual may be taking as is well known to administering physicians who are skilled in this art.

The compounds of the present invention are also useful to inhibit beta-secretase and reduce or inhibit the formation of plaque.

Inhibition of APP Cleavage

The compounds of the invention inhibit cleavage of APP between Met595 and Asp596 numbered for the APP695 isoform, or a mutant thereof, or at a corresponding site of a different isoform, such as APP751 or APP770, or a mutant thereof (sometimes referred to as the "beta secretase site"). While not wishing to be bound by a particular theory, inhibition of beta-secretase activity is thought to inhibit production of beta amyloid peptide (A beta). Inhibitory activity is demonstrated in one of a variety of inhibition assays, whereby cleavage of an APP substrate in the presence of a beta-secretase enzyme is analyzed in the presence of the inhibitory compound, under conditions normally sufficient to result in cleavage at the beta-secretase cleavage site. Reduction of APP cleavage at the beta-secretase cleavage site compared with an untreated or inactive control is correlated with inhibitory activity. Assay systems that can be used to demonstrate efficacy of the compound inhibitors of the invention are known. Representative assay systems are described, for example, in U.S. Pat. Nos. 5,942,400, 5,744,346, as well as in the Examples below.

The enzymatic activity of beta-secretase and the production of A beta can be analyzed in vitro or in vivo, using natural, mutated, and/or synthetic APP substrates, natural, mutated, and/or synthetic enzyme, and the test compound. The analysis may involve primary or secondary cells expressing native, mutant, and/or synthetic APP and enzyme, animal models expressing native APP and enzyme, or may utilize transgenic animal models expressing the substrate and enzyme. Detection of enzymatic activity can be by analysis of one or more of the cleavage products, for example, by immunoassay, flurometric or chromogenic assay, HPLC, or other means of detection. Inhibitory compounds are determined as those having the ability to decrease the amount of beta-secretase cleavage product produced in comparison to a control, where beta-secretase mediated cleavage in the reaction system is observed and measured in the absence of inhibitory compounds.

Beta-secretase

Various forms of beta-secretase enzyme are known, and are available and useful for assay of enzyme activity and inhibition of enzyme activity. These include native, recombinant, and synthetic forms of the enzyme. Human beta-secretase is known as Beta Site APP Cleaving Enzyme (BACE), Asp2, and memapsin 2, and has been characterized, for example, in U.S. Pat. No. 5,744,346 and published PCT patent applications WO98/22597, WO00/03819, WO01/23533, and WO00/17369, as well as in literature publications (Hussain et.al., 1999, *Mol. Cell. Neurosci.* 14:419–427; Vassar et.al., 1999, *Science* 286:735–741; Yan et.al., 1999, *Nature* 402:533–537; Sinha et.al., 1999, *Nature* 40:537–540; and Lin et.al., 2000, *PNAS USA* 97:1456–1460). Synthetic forms of the enzyme have also been described (WO98/22597 and WO00/17369). Beta-secretase can be extracted and purified from human brain tissue and can be produced in cells, for example mammalian cells expressing recombinant enzyme.

Preferred compounds are effective to inhibit 50% of beta-secretase enzymatic activity at a concentration of less than about 50 micromolar, preferably at a concentration of less than about 10 micromolar, more preferably less than about 1 micromolar, and most preferably less than about 10 nanomolar.

APP Substrate

Assays that demonstrate inhibition of beta-secretase-mediated cleavage of APP can utilize any of the known forms of APP, including the 695 amino acid "normal" isotype described by Kang et.al., 1987, *Nature* 325:733–6, the 770 amino acid isotype described by Kitaguchi et. al., 1981, *Nature* 331:530–532, and variants such as the Swedish Mutation (KM670-1NL) (APP-SW), the London Mutation (V7176F), and others. See, for example, U.S. Pat. No. 5,766,846 and also Hardy, 1992, *Nature Genet.* 1:233–234, for a review of known variant mutations. Additional useful substrates include the dibasic amino acid modification, APP-KK disclosed, for example, in WO 00/17369, fragments of APP, and synthetic peptides containing the beta-secretase cleavage site, wild type (WT) or mutated form, e.g., SW, as described, for example, in U.S. Pat. No. 5,942,400 and WO00/03819.

The APP substrate contains the beta-secretase cleavage site of APP (KM-DA or NL-DA) for example, a complete APP peptide or variant, an APP fragment, a recombinant or synthetic APP, or a fusion peptide. Preferably, the fusion peptide includes the beta-secretase cleavage site fused to a peptide having a moiety useful for enzymatic assay, for example, having isolation and/or detection properties. A useful moiety may be an antigenic epitope for antibody binding, a label or other detection moiety, a binding substrate, and the like.

Antibodies

Products characteristic of APP cleavage can be measured by immunoassay using various antibodies, as described, for example, in Pirttila et.al., 1999, *Neuro.Lett.* 249:21–4, and in U.S. Pat. No. 5,612,486. Useful antibodies to detect A beta include, for example, the monoclonal antibody 6E10 (Senetek, St. Louis, Mo.) that specifically recognizes an epitope on amino acids 1–16 of the A beta peptide; antibodies 162 and 164 (New York State Institute for Basic Research, Staten Island, N.Y.) that are specific for human A beta 1–40 and 1–42, respectively; and antibodies that recognize the junction region of beta-amyloid peptide, the site between residues 16 and 17, as described in U.S. Pat. No. 5,593,846. Antibodies raised against a synthetic peptide of residues 591 to 596 of APP and SW192 antibody raised against 590–596 of the Swedish mutation are also useful in immunoassay of APP and its cleavage products, as described in U.S. Pat. Nos. 5,604,102 and 5,721,130.

Assay Systems

Assays for determining APP cleavage at the beta-secretase cleavage site are well known in the art. Exemplary assays, are described, for example, in U.S. Pat. Nos. 5,744,346 and 5,942,400, and described in the Examples below.

Cell Free Assays

Exemplary assays that can be used to demonstrate the inhibitory activity of the compounds of the invention are described, for example, in WO00/17369, WO 00/03819, and U.S. Pat. Nos. 5,942,400 and 5,744,346. Such assays can be performed in cell-free incubations or in cellular incubations using cells expressing a beta-secretase and an APP substrate having a beta-secretase cleavage site.

An APP substrate containing the beat-secretase cleavage site of APP, for example, a complete APP or variant, an APP fragment, or a recombinant or synthetic APP substrate containing the amino acid sequence: KM-DA or NL-DA, is incubated in the presence of beta-secretase enzyme, a fragment thereof, or a synthetic or recombinant polypeptide variant having beta-secretase activity and effective to cleave the beta-secretase cleavage site of APP, under incubation conditions suitable for the cleavage activity of the enzyme. Suitable substrates optionally include derivatives that may be fusion proteins or peptides that contain the substrate peptide and a modification useful to facilitate the purification or detection of the peptide or its beta-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example: approximately 200 nanomolar to 10 micromolar substrate, approximately 10 to 200 picomolar enzyme, and approximately 0.1 nanomolar to 10 micromolar inhibitor compound, in aqueous solution, at an approximate pH of 4–7, at approximately 37 degrees C., for a time period of approximately 10 minutes to 3 hours. These incubation conditions are exemplary only, and can be varied as required for the particular assay components and/or desired measurement system. Optimization of the incubation conditions for the particular assay components should account for the specific beta-secretase enzyme used and its pH optimum, any additional enzymes and/or markers that might be used in the assay, and the like. Such optimization is routine and will not require undue experimentation.

One useful assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of beta-secretase results in cleavage of the substrate at the beta-secretase cleavage site. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assay

Numerous cell-based assays can be used to analyze beta-secretase activity and/or processing of APP to release A beta. Contact of an APP substrate with a beta-secretase enzyme within the cell and in the presence or absence of a compound inhibitor of the invention can be used to demonstrate beta-secretase inhibitory activity of the compound. Preferably, assay in the presence of a useful inhibitory compound provides at least about 30%, most preferably at least about 50% inhibition of the enzymatic activity, as compared with a non-inhibited control.

In one embodiment, cells that naturally express beta-secretase are used. Alternatively, cells are modified to express a recombinant beta-secretase or synthetic variant enzyme as discussed above. The APP substrate may be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the beta-secretase APP cleavage site can be used, provided that the expressed APP is permitted to contact the enzyme and enzymatic cleavage activity can be analyzed.

Human cell lines that normally process A beta from APP provide a useful means to assay inhibitory activities of the compounds of the invention. Production and release of A beta and/or other cleavage products into the culture medium can be measured, for example by immunoassay, such as Western blot or enzyme-linked immunoassay (EIA) such as by ELISA.

Cells expressing an APP substrate and an active beta-secretase can be incubated in the presence of a compound inhibitor to demonstrate inhibition of enzymatic activity as compared with a control. Activity of beta-secretase can be measured by analysis of one or more cleavage products of the APP substrate. For example, inhibition of beta-secretase activity against the substrate APP would be expected to decrease release of specific beta-secretase induced APP cleavage products such as A beta.

Although both neural and non-neural cells process and release A beta, levels of endogenous beta-secretase activity are low and often difficult to detect by EIA. The use of cell types known to have enhanced beta-secretase activity, enhanced processing of APP to A beta, and/or enhanced production of A beta are therefore preferred. For example, transfection of cells with the Swedish Mutant form of APP (APP-SW); with APP-KK; or with APP-SW-KK provides cells having enhanced beta-secretase activity and producing amounts of A beta that can be readily measured.

In such assays, for example, the cells expressing APP and beta-secretase are incubated in a culture medium under conditions suitable for beta-secretase enzymatic activity at its cleavage site on the APP substrate. On exposure of the cells to the compound inhibitor, the amount of A beta released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of beta-secretase activity include primary human neuronal cells, primary transgenic animal neuronal cells where the transgene is APP, and other cells such as those of a stable 293 cell line expressing APP, for example, APP-SW.

In vivo Assays: Animal Models

Various animal models can be used to analyze beta-secretase activity and/or processing of APP to release A beta, as described above. For example, transgenic animals expressing APP substrate and beta-secretase enzyme can be used to demonstrate inhibitory activity of the compounds of the invention. Certain transgenic animal models have been described, for example, in U.S. Pat. Nos. 5,877,399; 5,612,486; 5,387,742; 5,720,936; 5,850,003; 5,877,015, and 5,811,633, and in Ganes et. al., 1995, *Nature* 373:523. Preferred are animals that exhibit characteristics associated with the pathophysiology of AD. Administration of the compound inhibitors of the invention to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

Inhibition of beta-secretase mediated cleavage of APP at the beta-secretase cleavage site and of A beta release can be analyzed in these animals by measure of cleavage fragments in the animal's body fluids such as cerebral fluid or tissues. Analysis of brain tissues for A beta deposits or plaques is preferred.

On contacting an APP substrate with a beta-secretase enzyme in the presence of an inhibitory compound of the invention and under conditions sufficient to permit enzymatic mediated cleavage of APP and/or release of A beta from the substrate, the compounds of the invention are effective to reduce beta-secretase-mediated cleavage of APP at the beta-secretase cleavage site and/or effective to reduce released amounts of A beta. Where such contacting is the administration of the inhibitory compounds of the invention to an animal model, for example, as described above, the compounds are effective to reduce A beta deposition in brain tissues of the animal, and to reduce the number and/or size of beta amyloid plaques. Where such administration is to a human subject, the compounds are effective to inhibit or slow the progression of disease characterized by enhanced amounts of A beta, to slow the progression of AD in the, and/or to prevent onset or development of AD in a patient at risk for the disease.

Unless defined otherwise, all scientific and technical terms used herein have the same meaning as commonly understood by one of skill in the art to which this invention belongs. All patents and publications referred to herein are hereby incorporated by reference for all purposes.

Definitions and Conventions

The definitions and explanations below are for the terms as used throughout this entire document including both the specification and the claims.

Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$Ri$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(=Z_1)$H. Groups $R_i$ and $R_j$ would represent monovalent variable substituents if attached to the formula $CH_3$—$CH_2$—$C(R_i)(R_j)H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=C($R_1$)—O—$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

It is understood that when two or more adjacent variables are simultaneously a bond, that said adjacent bonds are to be treated as a single bond.

Chemical formulas of cyclic (ring) compounds or molecular fragments can be represented in a linear fashion. Thus, the compound 4-chloro-2-methylpyridine can be represented in linear fashion by N*=C($CH_3$)—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—($CH_2$)$_2$—N($C_2H_5$)—$CH_2$—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —$C(X_1)(X_2)$— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha configuration and is identified by a broken, dashed or dotted line attachment to the carbon atom, i.e., by the symbol "- - -" or ". . .". The corresponding substituent attached "above" ($X_2$) the other ($X_1$) is identified as being in the beta configuration and is indicated by an unbroken line attachment to the carbon atom.

When a variable substituent is bivalent, the valences may be taken together or separately or both in the definition of the variable. For example, a variable $R_i$ attached to a carbon atom as —$C(=R_i)$— might be bivalent and be defined as oxo or keto (thus forming a carbonyl group (—CO—) or as two separately attached monovalent variable substituents alpha-$R_{i\text{-}j}$ and beta-$R_{i\text{-}k}$. When a bivalent variable, $R_i$, is defined to consist of two monovalent variable substituents, the convention used to define the bivalent variable is of the form "alpha-$R_{i\text{-}j}$:beta-$R_{i\text{-}k}$" or some variant thereof. In such a case both alpha-$R_{i\text{-}j}$ and beta-$R_{i\text{-}k}$ are attached to the carbon atom to give —C(alpha-$R_{i\text{-}j}$)(beta-$R_{i\text{-}k}$)—. For example, when the bivalent variable $R_6$, —C(=$R_6$)— is defined to consist of two monovalent variable substituents, the two monovalent variable substituents are alpha-$R_{6\text{-}1}$:beta-$R_{6\text{-}2}$, . . . alpha-$R_{6\text{-}9}$:beta-$R_{6\text{-}10}$, etc, giving —C(alpha-$R_{6\text{-}1}$)(beta-$R_{6\text{-}2}$)—, . . . —C(alpha-$R_{6\text{-}9}$)(beta-$R_{6\text{-}10}$)—, etc. Likewise, for the bivalent variable $R_{11}$, —C(=$R_{11}$)—, two monovalent variable substituents are alpha-$R_{11\text{-}1}$:beta-$R_{11\text{-}2}$. For a ring substituent for which separate alpha and beta orientations do not exist (e.g. due to the presence of a carbon carbon double bond in the ring), and for a substituent bonded to a carbon atom which is not part of a ring the above convention is still used, but the alpha and beta designations are omitted.

Just as a bivalent variable may be defined as two separate monovalent variable substituents, two separate monovalent variable substituents may be defined to be taken together to form a bivalent variable. For example, in the formula —$C_1(R_i)$H—$C_2(R_j)$H— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide.

When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation " . . . $R_i$ and $R_j$ are taken together to form —$CH_2$—$CH_2$—O—CO— . . . " means a lactone in which the carbonyl is bonded to $C_2$. However, when designated " . . . $R_j$ and $R_i$ are taken together to form —CO—O—$CH_2$—$CH_2$— the convention means a lactone in which the carbonyl is bonded to $C_1$.

The carbon atom content of variable substituents is indicated in one of two ways. The first method uses a prefix to the entire name of the variable such as "$C_1$–$C_4$", where both "1" and "41" are integers representing the minimum and maximum number of carbon atoms in the variable. The prefix is separated from the variable by a space. For example, "$C_1$–$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$–$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$–$C_j$" designation in parentheses and placing it immediately (no intervening space) before the portion of the definition being defined. By this optional convention $(C_1$–$C_3)$alkoxycarbonyl has the same meaning as $C_2$–$C_4$ alkoxycarbonyl because the "$C_1$–$C_3$" refers only to the carbon atom content of the alkoxy group. Similarly while both $C_2$–$C_6$ alkoxyalkyl and $(C_1$–$C_3)$alkoxy$(C_1$–$C_3)$alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the SCHEMES which will also set forth the chemical structural formula of that particular substituent.

As used herein, the term "aryl" embraces aromatic carbocyclic ring systems having one or two rings. Examples include phenyl, naphthyl, indanyl, indenyl, dihydronaphthyl, tetrahydronaphthyl, and tetralinyl. The aryl groups herein are unsubstituted or, as specified, substituted in one or more substitutable positions with various groups. For example, such aryl groups may be optionally substituted with, for example, $C_1$–$C_6$ alkyl, $C_1$–$C_6$ alkoxy, halogen, hydroxy, cyano, nitro, amino, mono($C_1$–$C_6$)alkylamino, di($C_1$–$C_6$)alkylamino, $C_2$–$C_6$alkenyl, $C_2$–$C_6$alkynyl, $C_1$–$C_6$ haloalkyl, $C_1$–$C_6$ haloalkoxy, amino($C_1$–$C_6$)alkyl, mono $(C_1$–$C_6)$alkylamino$(C_1$–$C_6)$alkyl or di $(C_1$–$C_6)$ alkylamino $(C_1$–$C_6)$ alkyl.

As used herein, the term "cycloalkyl" refers to saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. Preferred cycloalkyl groups are cyclopentyl, cyclohexyl, and cycloheptyl. The cycloalkyl groups herein are unsubstituted or, as specified, substituted in one or more substitutable positions with various groups. For example, such cycloalkyl groups may be optionally substituted with, for example, $C_1$–$C_6$ alkyl, $C_1$–$C_6$ alkoxy, halogen, hydroxy, cyano, nitro, amino, mono($C_1$–$C_6$)alkylamino, di $(C_1$–$C_6)$alkylamino, $C_2$–$C_6$alkenyl, $C_2$–$C_6$alkynyl, $C_1$–$C_6$ haloalkyl, $C_1$–$C_6$ haloalkoxy, amino $(C_1$–$C_6)$ alkyl, mono$(C_1$–$C_6)$alkylamino$(C_1$–$C_6)$alkyl or di$(C_1$–$C_6)$ alkylamino $(C_1$–$C_6)$ alkyl.

As used herein, "heteroaryl" embraces heterocyclic ring systems having at least one ring containing one or more hetero atoms and at least one aromatic ring. The hetero atoms are selected from oxygen, nitrogen, and sulfur. The term, therefore, embraces groups having a carbocyclic ring, e.g., cyclohexyl or cyclopentyl, fused with a heterocyclic aromatic ring. Examples include 5,6,7,8-tetrahydroisoquinolinyl, 4,5,6,7-tetrahydrobenzoimidazolyl, 4,5,6,7-tetrahydroindolyl, and 6,7-dihydropyrindinyl. The term also embraces groups having a carbocyclic ring, e.g., benzo, fused with a heterocyclic non-aromatic ring. Examples of this type of heteroary group include 1,2,3,4-tetrahydroisoquinolinyl, 2,3-dihydroindolyl, 2,3-dihydrobenzoxazolyl, and 2,3-dihydrobenzofuranyl. The heteroaryl groups herein are unsubstituted or, as specified, substituted in one or more substitutable positions with various groups. For example, such heteroaryl groups may be optionally substituted with, for example, $C_1$–$C_6$ alkyl, $C_1$–$C_6$ alkoxy, halogen, hydroxy, cyano, nitro, amino, mono $(C_1$–$C_6)$ alkylamino, di $(C_1$–$C_6)$ alkylamino, $C_2$–$C_6$alkenyl, $C_2$–$C_6$alkynyl, $C_1$–$C_6$ haloalkyl, $C_1$–$C_6$ haloalkoxy, amino $(C_1$–$C_6)$ alkyl, mono$(C_1$–$C_6)$alkylamino$(C_1$–$C_6)$alkyl or di$(C_1$–$C_6)$ alkylamino $(C_1$–$C_6)$ alkyl.

Preferred heteroaryl groups include

| | |
|---|---|
| A) | pyridinyl, |
| B) | pyrimidinyl, |
| C) | quinolinyl, |
| D) | imidazothiazolyl |
| E) | dihydrobenzisoxazinyl |
| F) | benzothiophenyl, |
| G) | indolyl, |
| H) | indolinyl, |
| I) | pryidazinyl, |
| J) | pyrazinyl, |
| K) | isoindolyl, |
| L) | isoquinolyl, |
| M) | quinazolinyl, |
| N) | quinoxalinyl, |
| O) | phthalazinyl, |
| P) | imidazolyl, |
| Q) | isoxazolyl, |
| R) | pyrazolyl, |
| S) | oxazolyl, |
| T) | thiazolyl, |
| U) | indolizinyl, |
| V) | indazolyl, |
| W) | benzothiazolyl, |
| X) | benzimidazolyl, |
| Y) | benzofuranyl, |
| Z) | furanyl, |
| AA) | thienyl, |
| BB) | pyrrolyl, |
| CC) | oxadiazolyl, |
| DD) | thiadiazolyl, |
| EE) | triazolyl, |
| FF) | tetrazolyl, |
| GG) | oxazolyl, |
| HH) | thiazolyl, |
| II) | oxazolo [4,5-b]pyridinyl, |
| JJ) | imidazo [1,2-a]pyridinyl, |
| KK) | isothiazolyl, |
| LL) | naphthyridinyl, |
| MM) | cinnolinyl, |
| NN) | carbazolyl, |
| OO) | beta-carbolinyl, |
| PP) | isochromanyl, |
| QQ) | chromanyl, |
| RR) | furazanyl, |
| SS) | tetrahydroisoquinoline, |

-continued

| | |
|---|---|
| TT) | isoindolinyl, |
| UU) | isobenzotetrahydrofuranyl, |
| VV) | isobenzotetrahydrothienyl, |
| WW) | isobenzothiophenyl, |
| XX) | benzoxazolyl, |
| YY) | pyrido[3,4-b]pyridinyl, |
| ZZ) | pyrido[3,2-b]pyridinyl, |
| AAA) | pyrido [4, 3-b]pyridinyl, |
| BBB) | purinyl, and |
| CCC) | 1,3-benzodioxole |

As used herein, the term "heterocycle" refers to monocyclic, bicyclic and tricyclic non-aromatic heterocyclic ring systems having from 3–9 ring members, where at least one of the members is selected from oxygen, nitrogen and sulfur. Examples of such groups include (A) morpholinyl, (B) thiomorpholinyl, (C) thiomorpholinyl S-oxide, (D) thiomorpholinyl S,S-dioxide, (E) piperazinyl,(F) homopiperazinyl, (G) pyrrolidinyl,(H) pyrrolinyl, (I) tetrahydropyranyl, (J) piperidinyl, (K) tetrahydrofuranyl, and(L) tetrahythiophenyl. These heterocyclic groups may be substituted as provided herein.

The compounds (X) are made by methods well known to those skilled in the art from starting materials that are commercially available, known or that can be prepared using literature methods. Similarly, the processes and transformations for making the compounds are known to those skilled in the art. Representative routes suitable for the preparation of compounds of Formula I are set forth in the following Schemes. To the extent any transformations shown in these schemes are not discussed in detail herein, those skilled in the art will appreciate appropriate reaction conditions and reagents for achieving the desired transformation. Further, the variables on the structures carry the same definitions as set forth above with respect to Formula X, unless specifically stated otherwise. Stereochemistry is generally shown in the following schemes for exemplary purposes only and is not meant to limit the scope of the invention. The invention is not limited to any particular stereochemical configuration about the chiral centers present in the compounds of Formula X.

SCHEME A

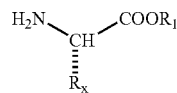

(I)

↓

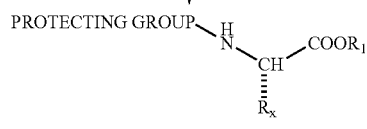

(Ia)

↓

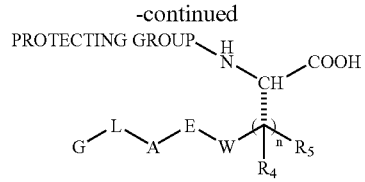

(II)

↓

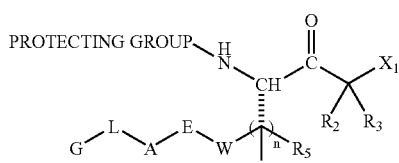

(III)

↓

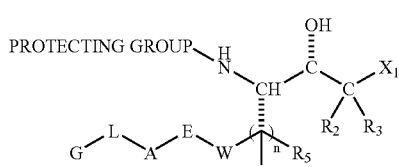

(IV)

↓

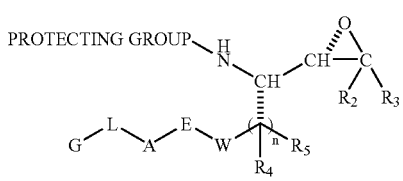

(V)

+

$R_C$—$NH_2$ (VI)

↓

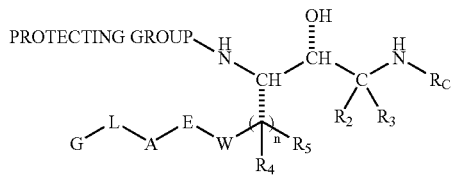

(VII)

↓

-continued
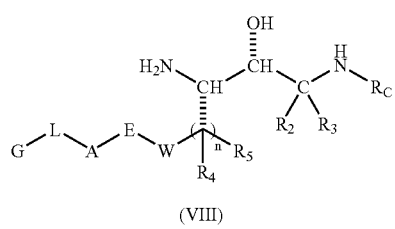
(VIII)
+
(R_{N-1}-X_N—)_2O   or   R_{N-1}-X_N-X_2   or   R_{N-1}-X_N-OH
(IX)
↓
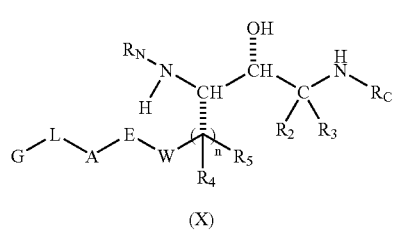
(X)
SCHEME B
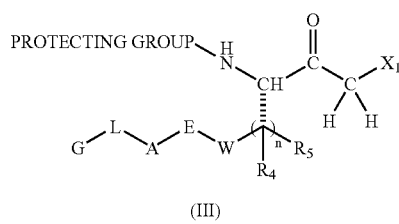
(III)
↓
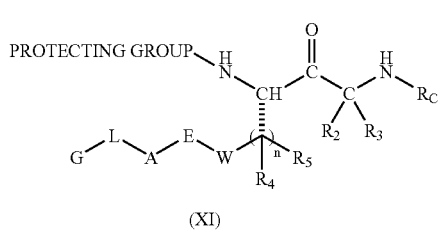
(XI)
↓
-continued
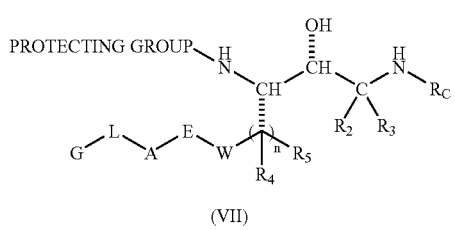
(VII)
SCHEME C
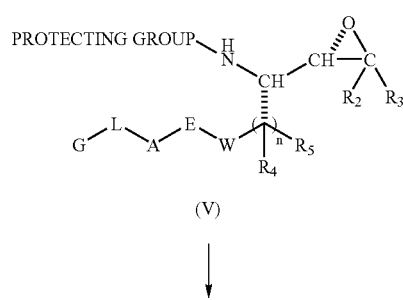
(V)
↓
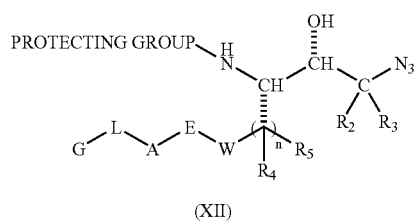
(XII)
↓
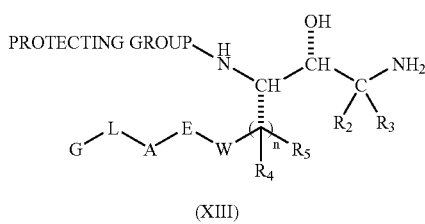
(XIII)
↓

-continued
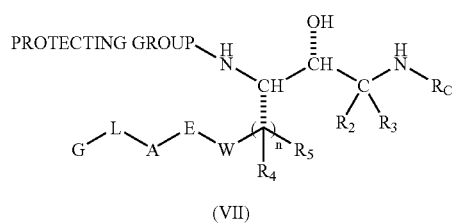
(VII)
SCHEME D
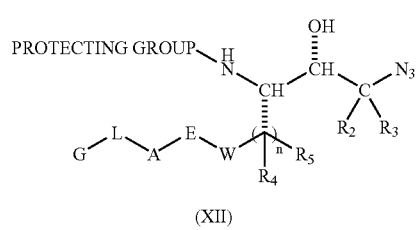
(XII)
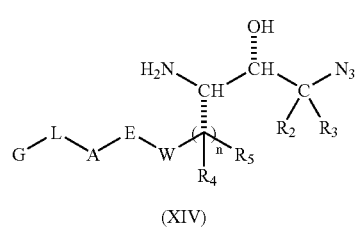
(XIV)
-continued
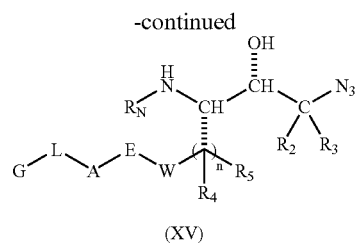
(XV)
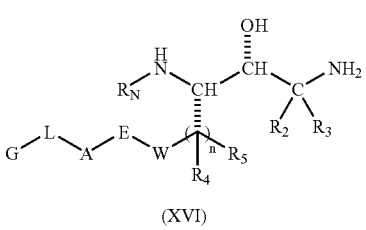
(XVI)
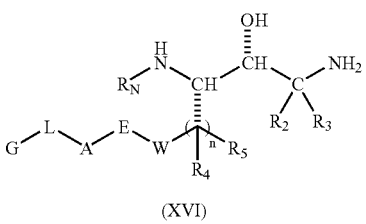
(XVI)
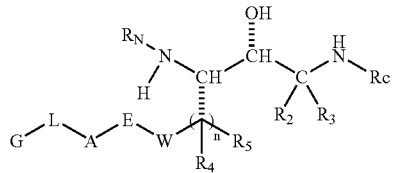
(X)
SCHEME E
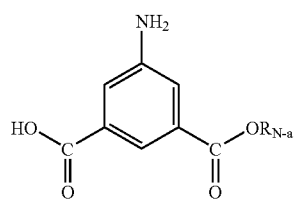
(XVII)

-continued
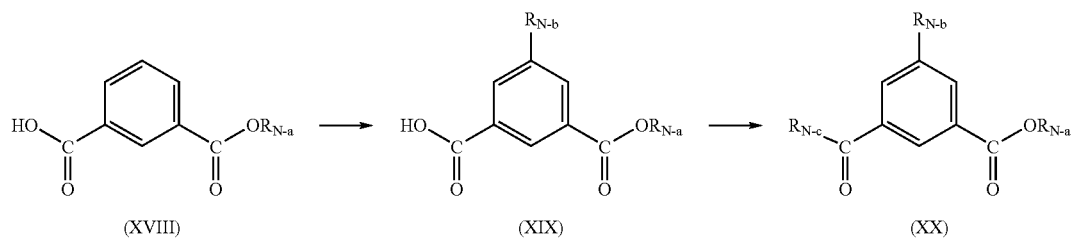
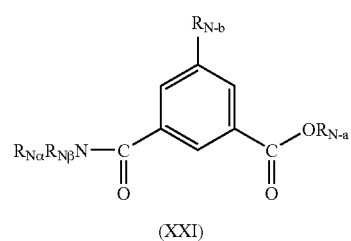
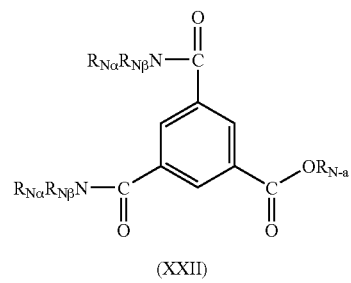
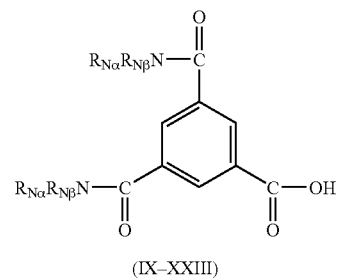

SCHEME F
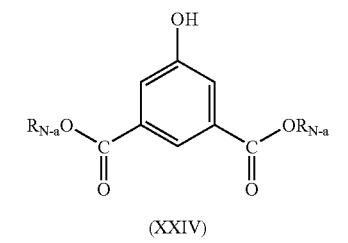
(XXIV)
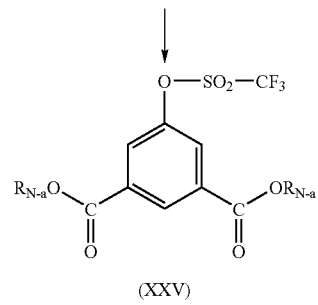
(XXV)
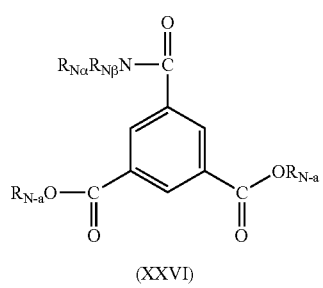
(XXVI)
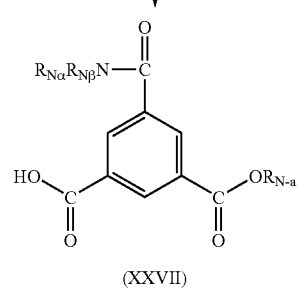
(XXVII)
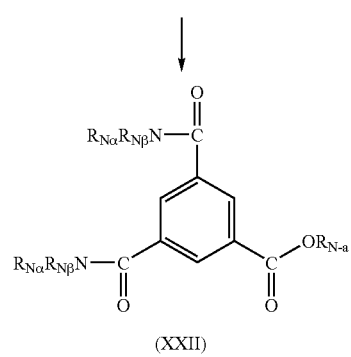
(XXII)
SCHEME G
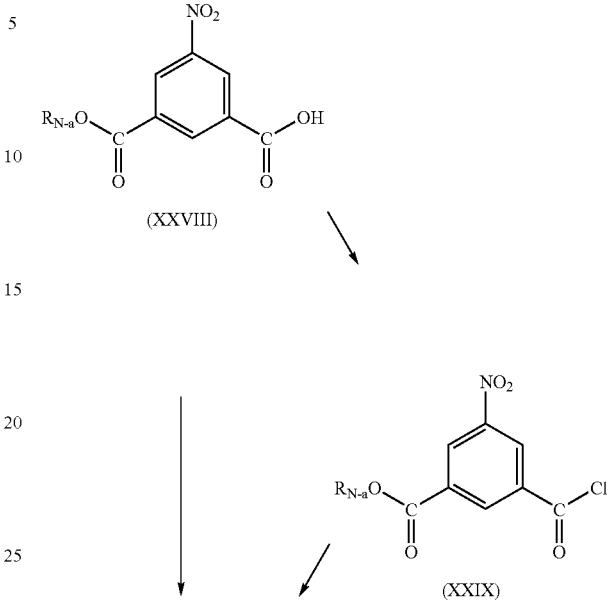
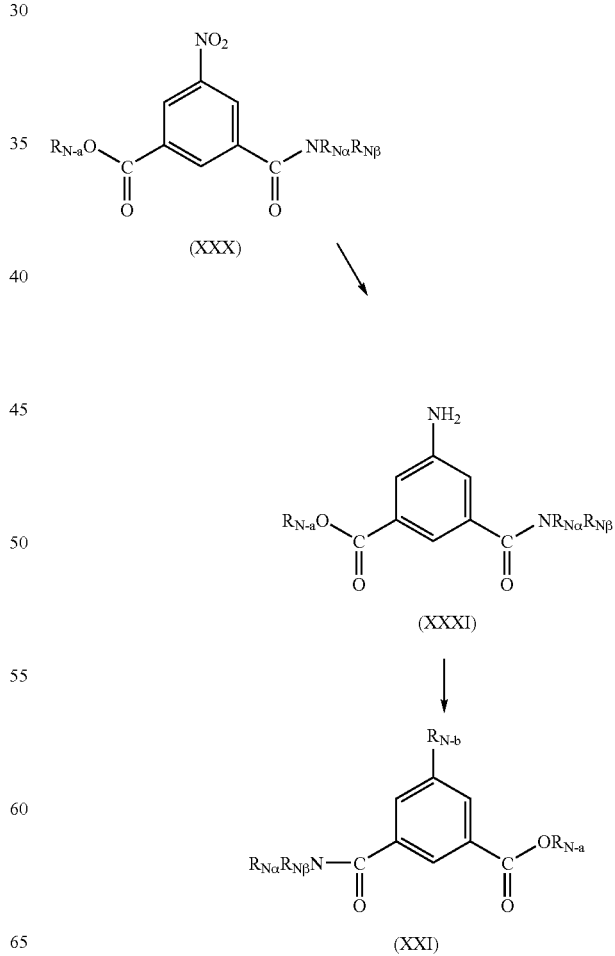

SCHEME H
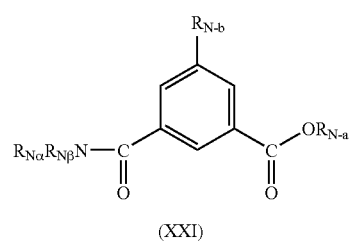
(XXI)
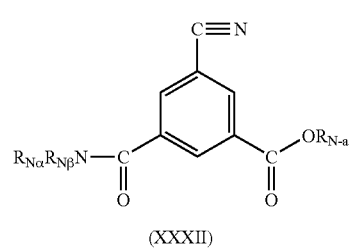
(XXXII)
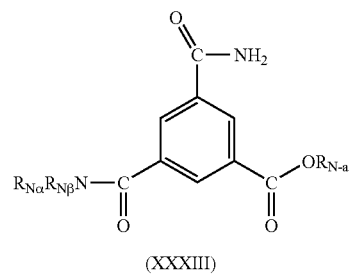
(XXXIII)
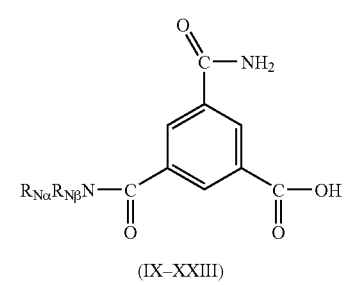
(IX–XXIII)
SCHEME I
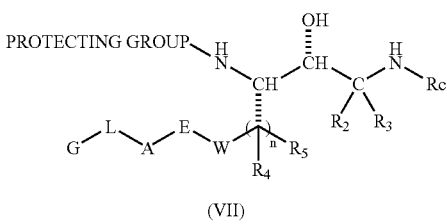
(VII)
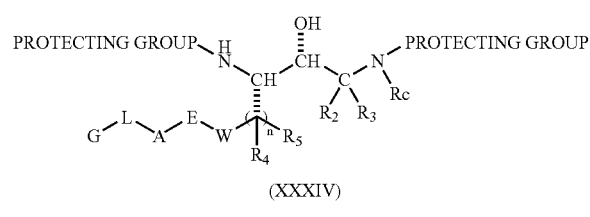
(XXXIV)
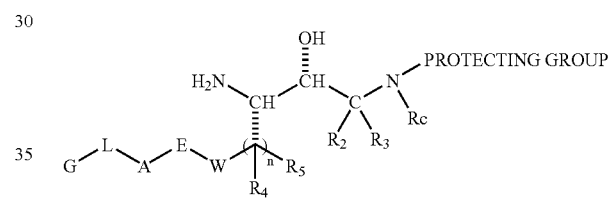
(XXXV)
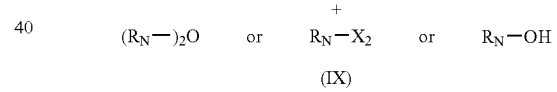
$(R_N-)_2O$ or $R_N-X_2$ or $R_N-OH$
(IX)
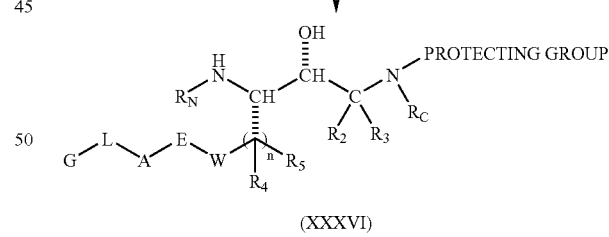
(XXXVI)
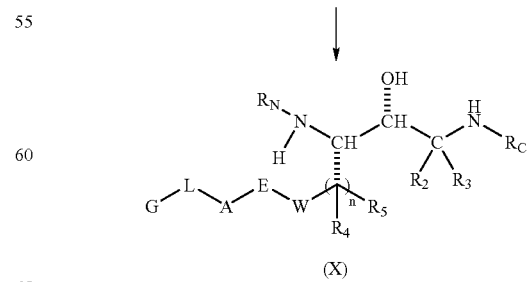
(X)

SCHEME J
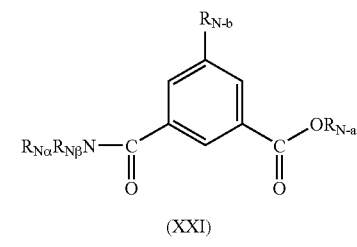
(XXI)
↓
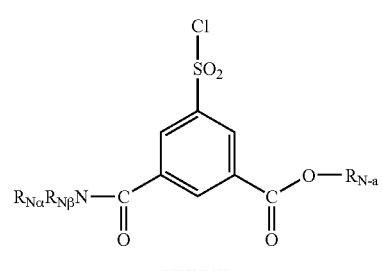
(XXXVII)
↓
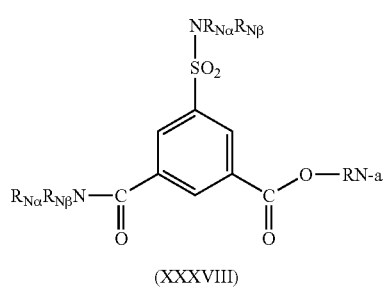
(XXXVIII)
↓
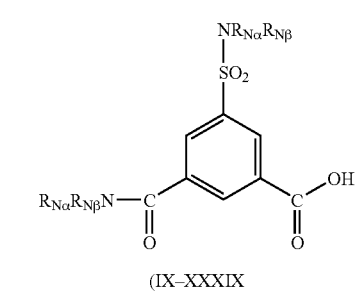
(IX–XXXIX)
SCHEME K
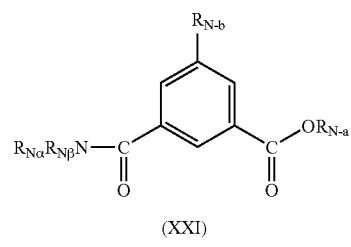
(XXI)
↓
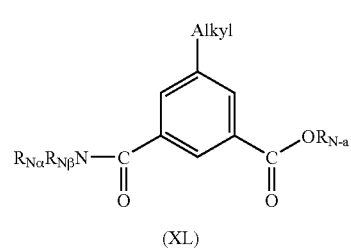
(XL)
↓
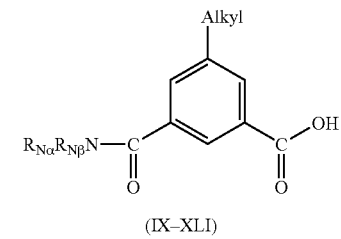
(IX–XLI)
SCHEME L
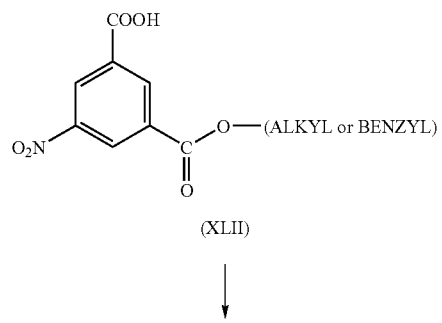
(XLII)
↓

71
-continued
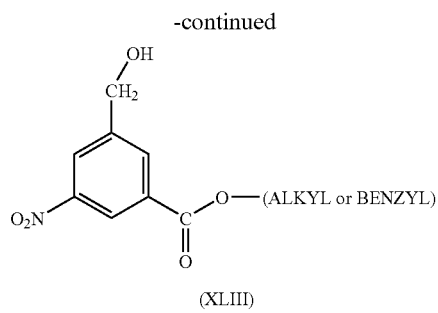
(XLIII)
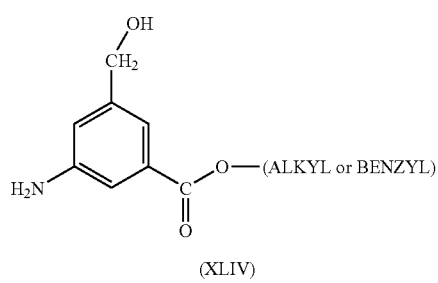
(XLIV)
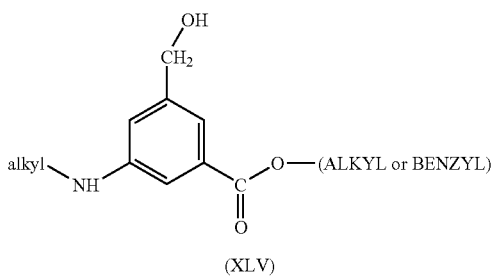
(XLV)
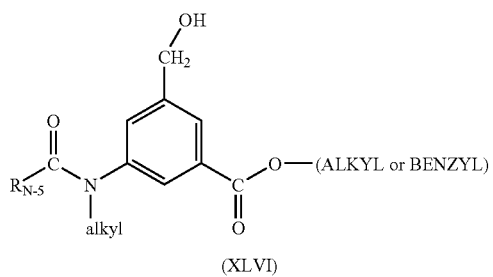
(XLVI)
72
-continued
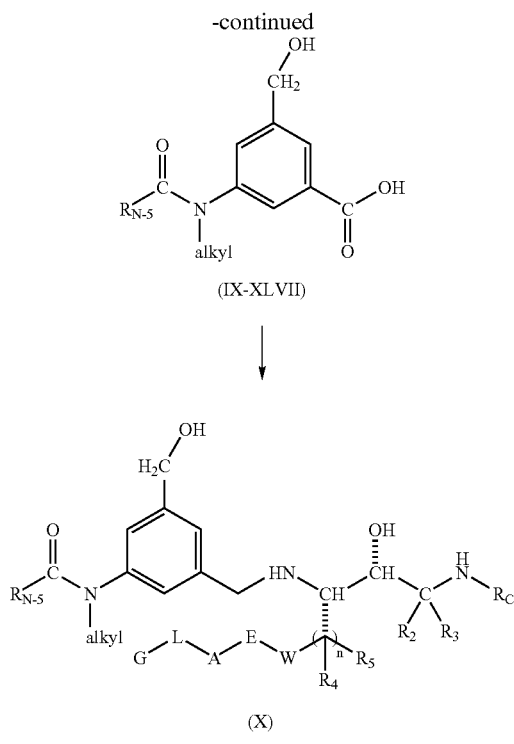
(IX-XLVII)
(X)
(X)
SCHEME M
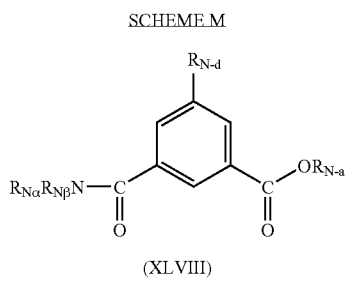
(XLVIII)
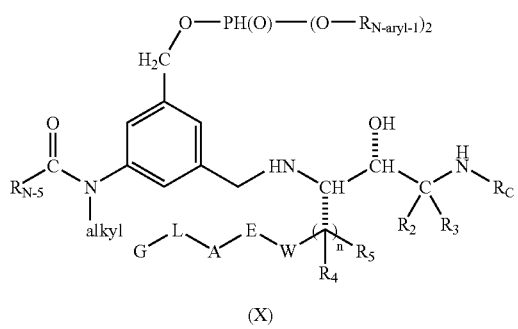

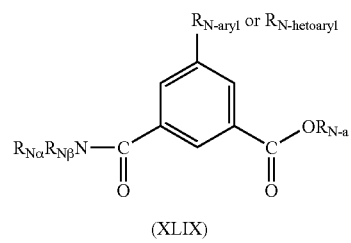
(XLIX)
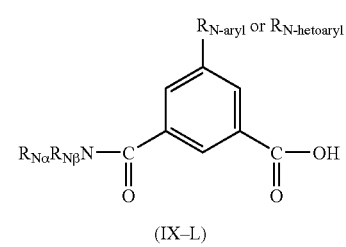
(IX–L)
SCHEME N
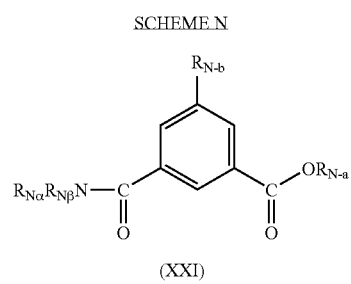
(XXI)
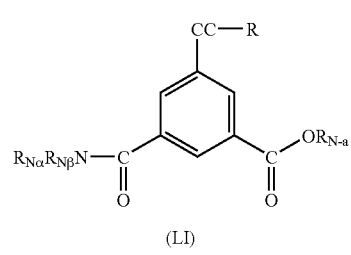
(LI)
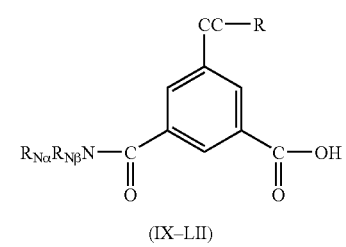
(IX–LII)
SCHEME O
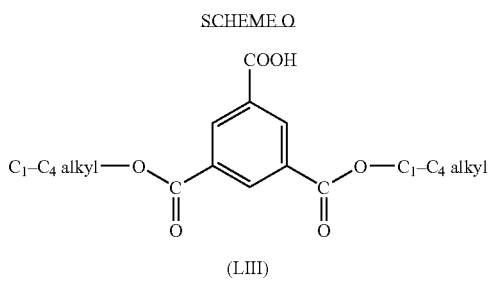
(LIII)
(LIV)
(LV)
(LVI)

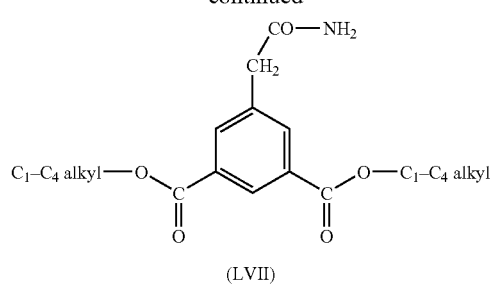
(LVII)
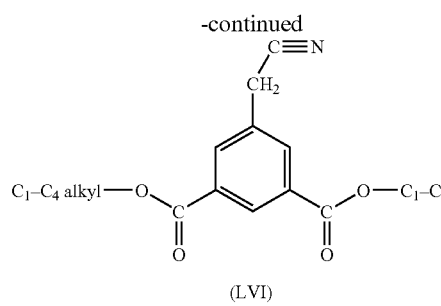
(LVI)
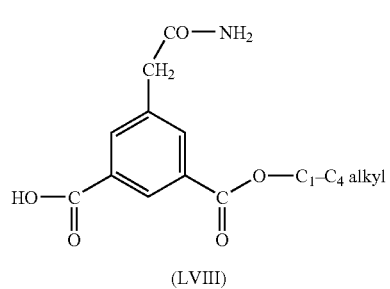
(LVIII)
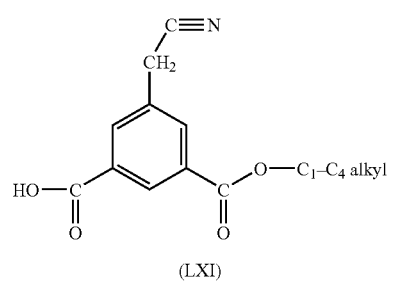
(LXI)
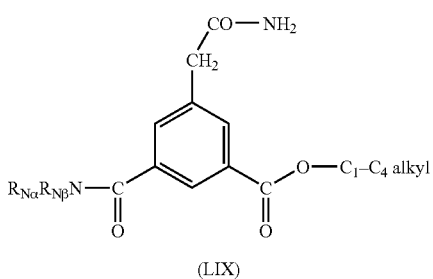
(LIX)
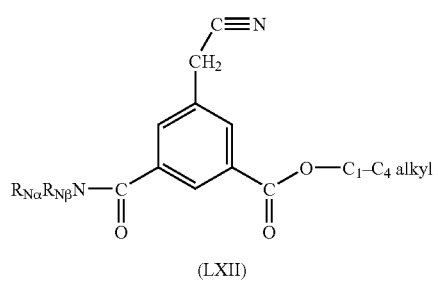
(LXII)
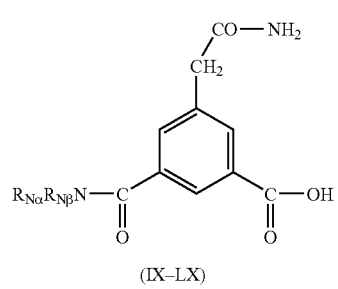
(IX–LX)
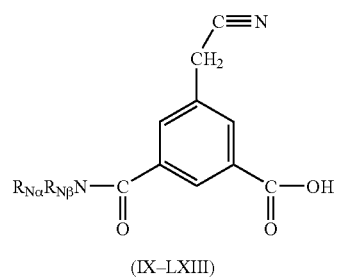
(IX–LXIII)

SCHEME P
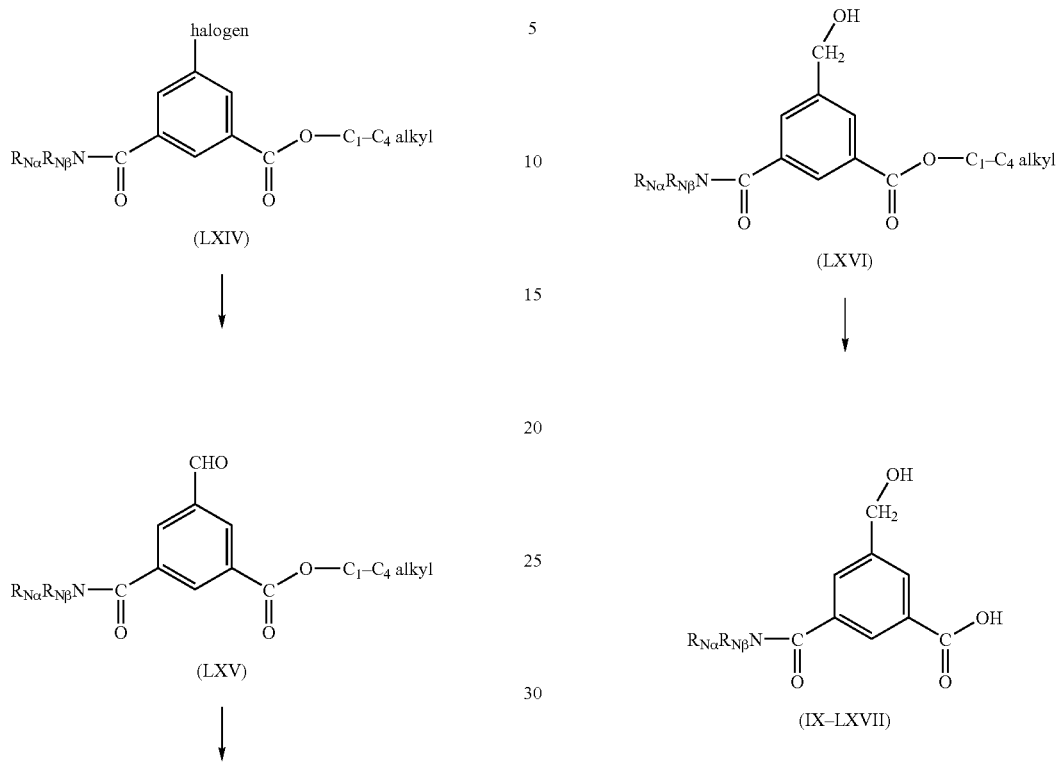
SCHEME Q
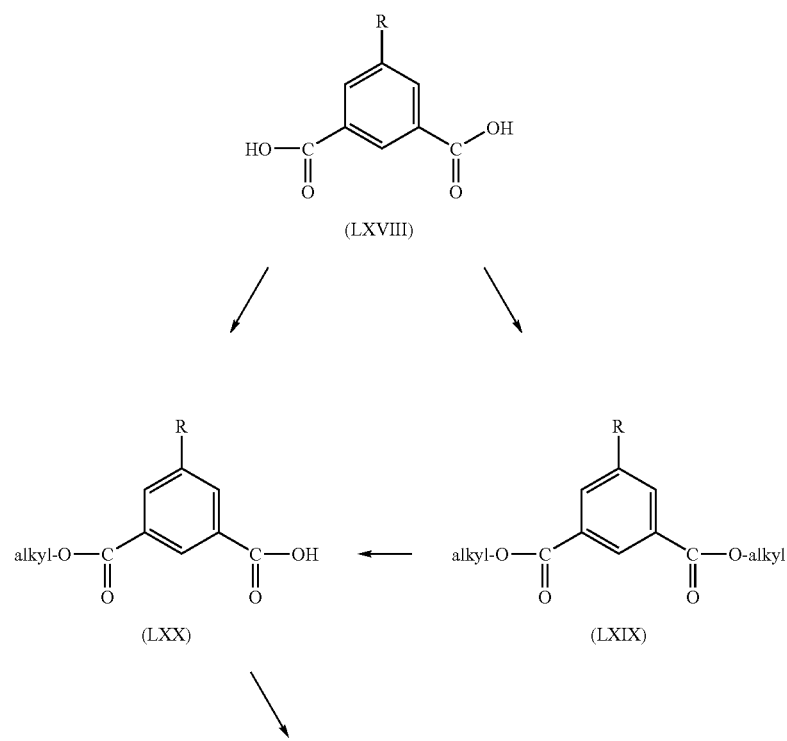

-continued
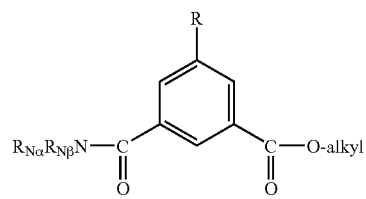
(LXXI)
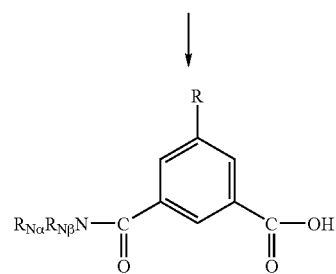
(IX–LXXII)
SCHEME R
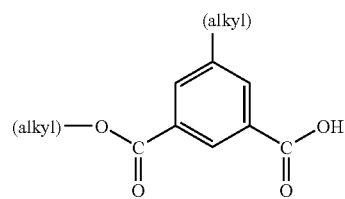
(LXXIII)
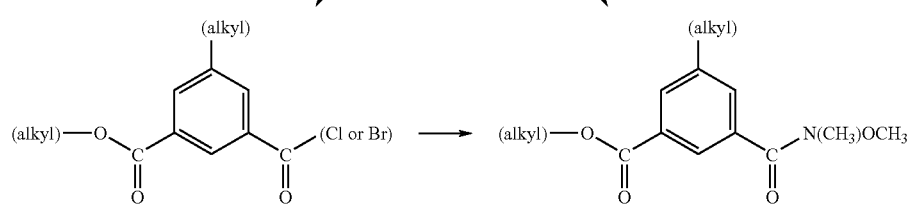
(LXXIV)    (LXXV)
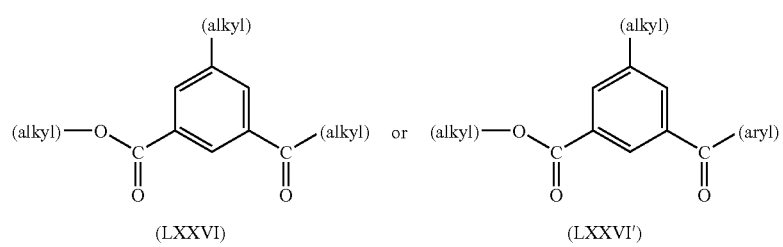
(LXXVI)    (LXXVI')

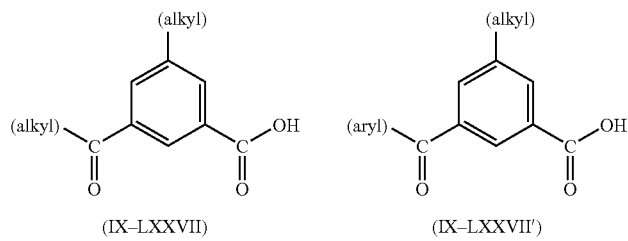
(IX–LXXVII)  (IX–LXXVII')
SCHEME 8
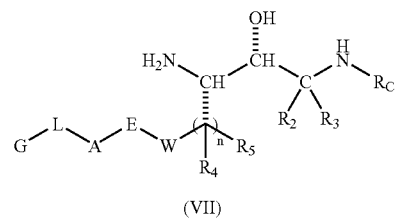
(VII)
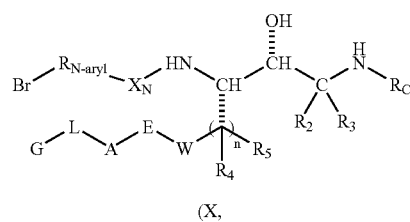
(X, $R_N = Br-R_{N\text{-aryl}}-X_N$)
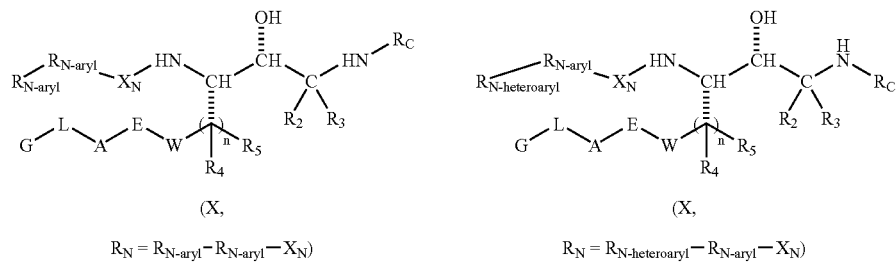
(X, $R_N = R_{N\text{-aryl}}-R_{N\text{-aryl}}-X_N$)　　(X, $R_N = R_{N\text{-heteroaryl}}-R_{N\text{-aryl}}-X_N$)

SCHEME T
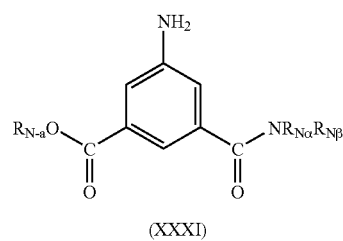
(XXXI)
↓
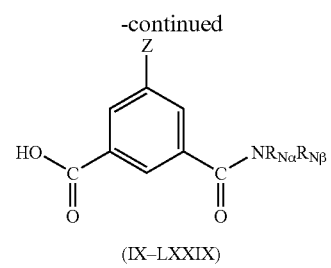
(LXXVIII)
↓
-continued
(IX–LXXIX)
Scheme U
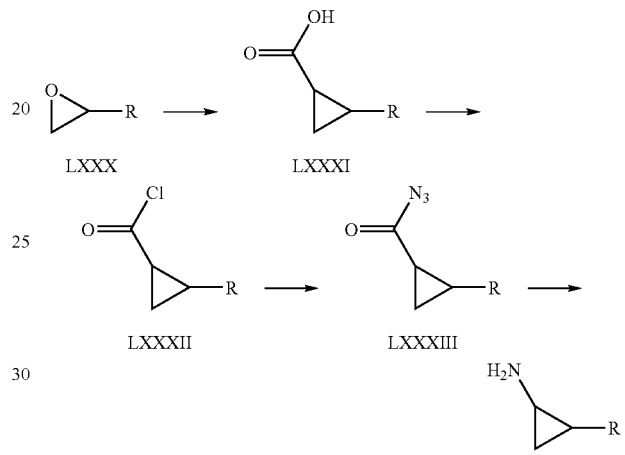
Scheme V
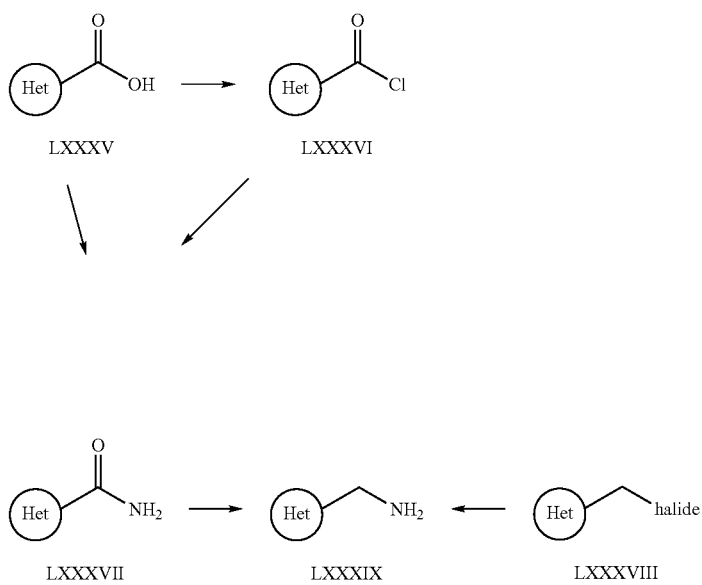

Scheme W
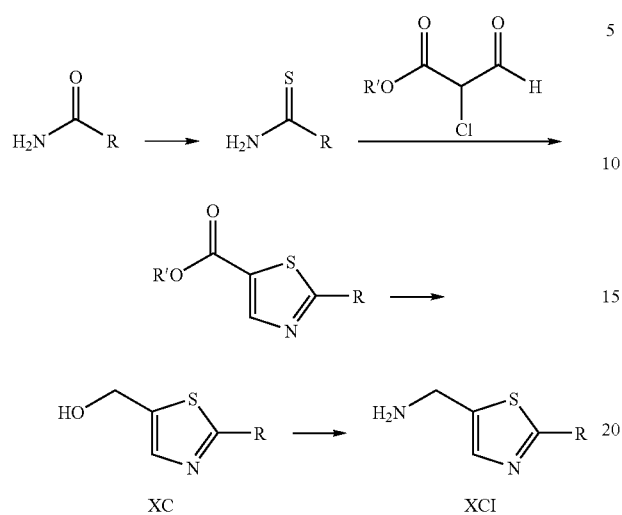
Scheme X
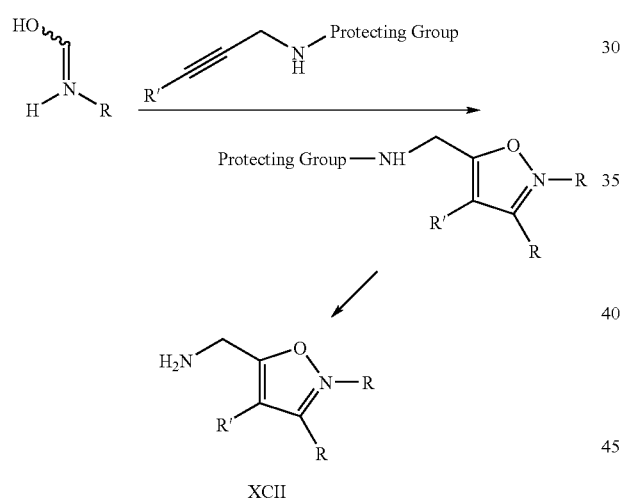
SCHEME Y
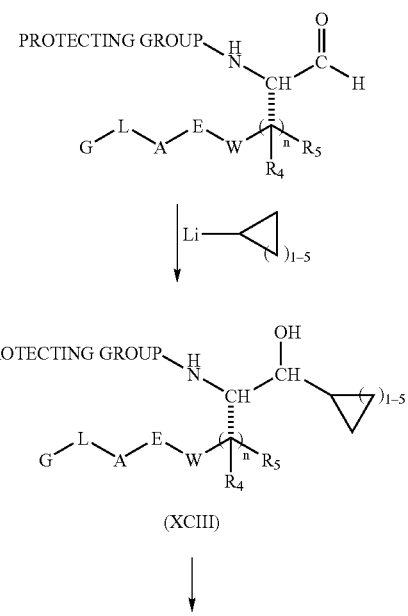
SCHEME Z
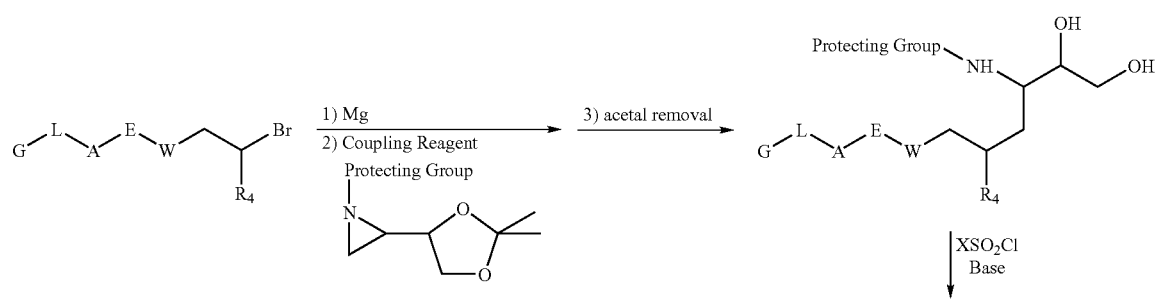

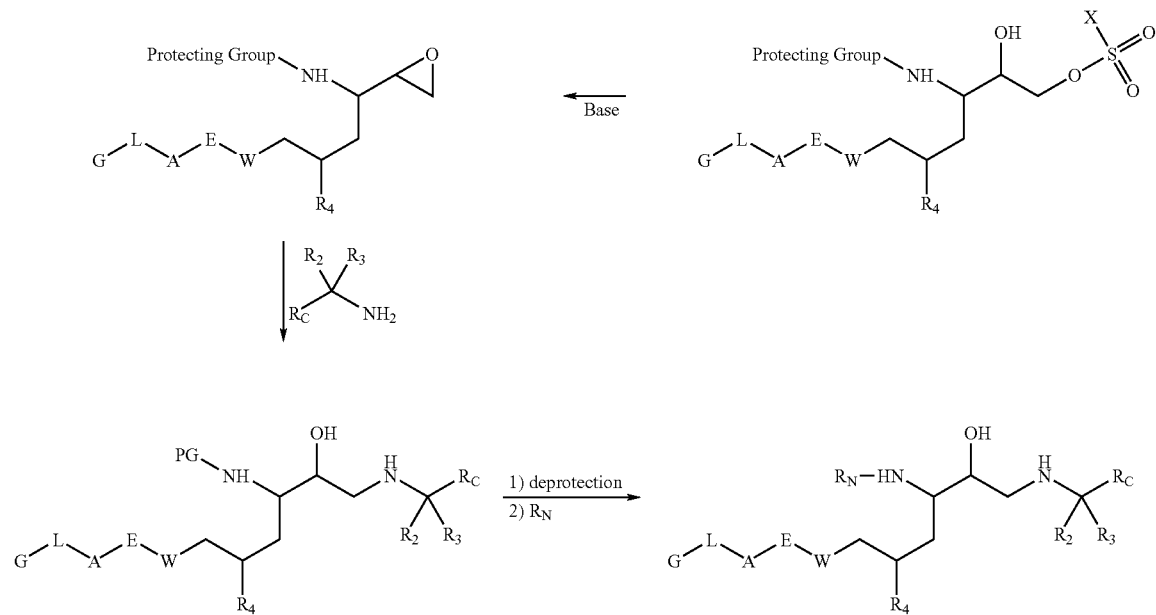
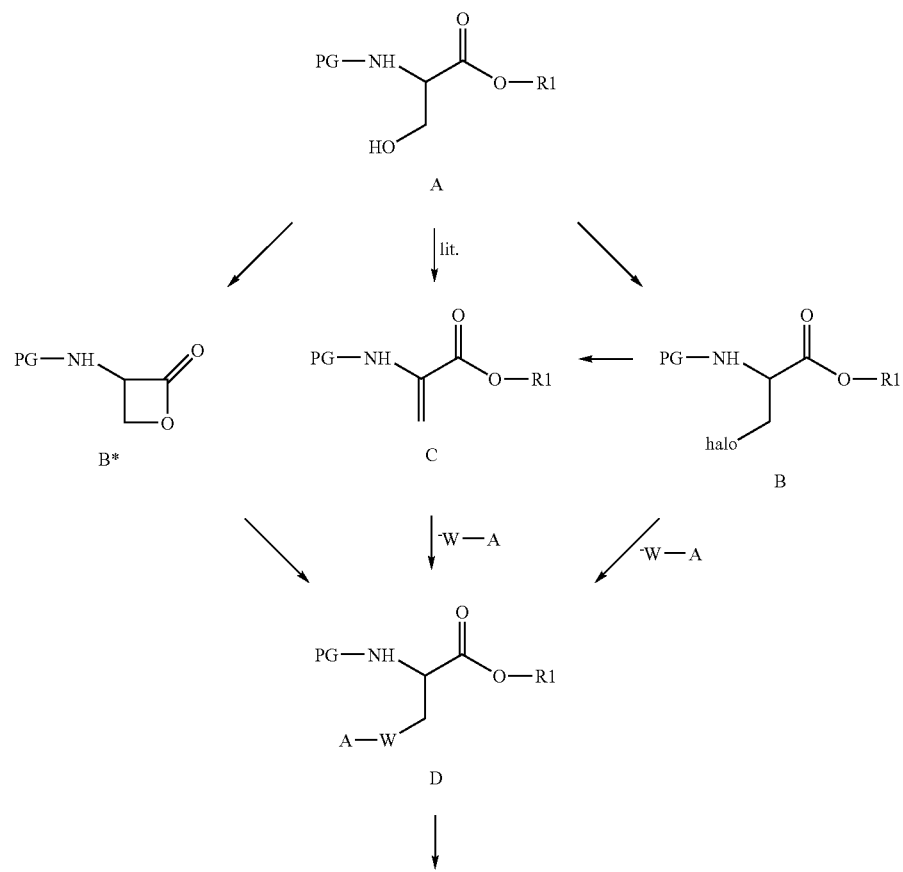
SCHEME AA

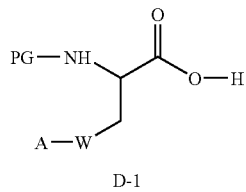
D-1
SCHEME BB
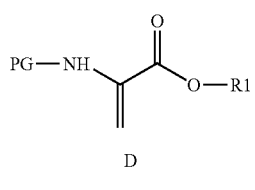
D
+
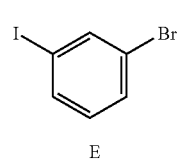
E
↓
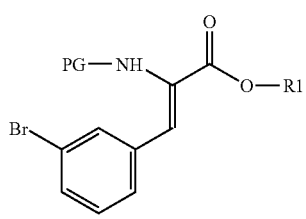
F
↓
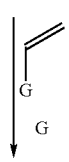
-continued
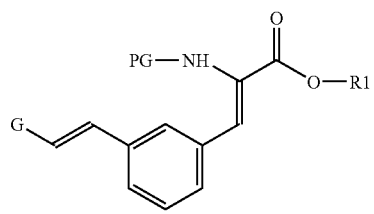
H
↓
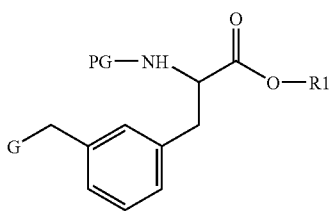
I
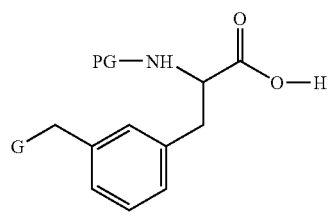
I-1

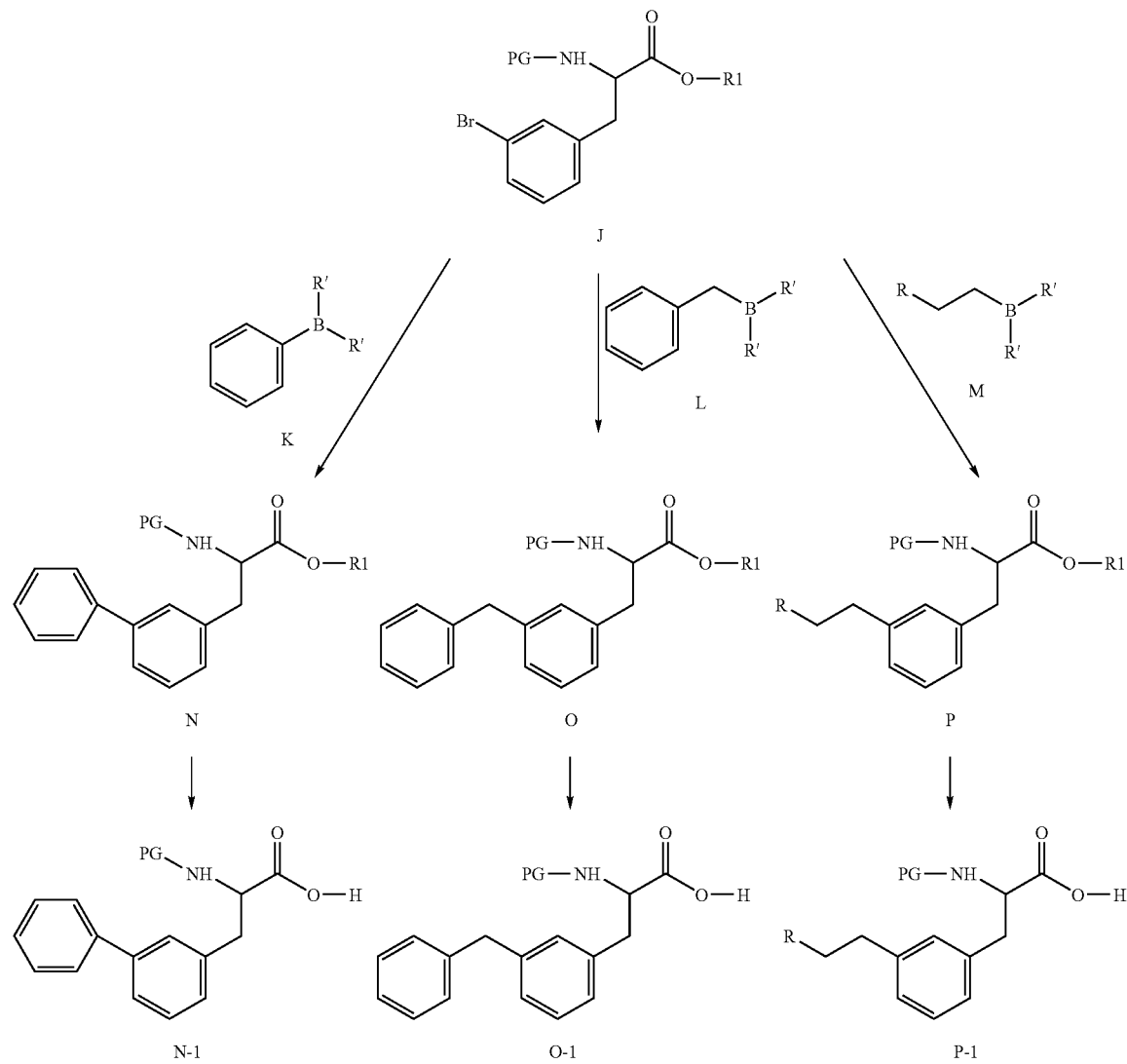
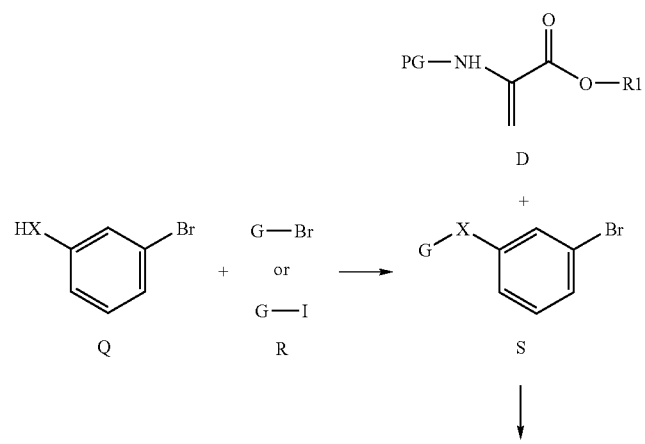

-continued
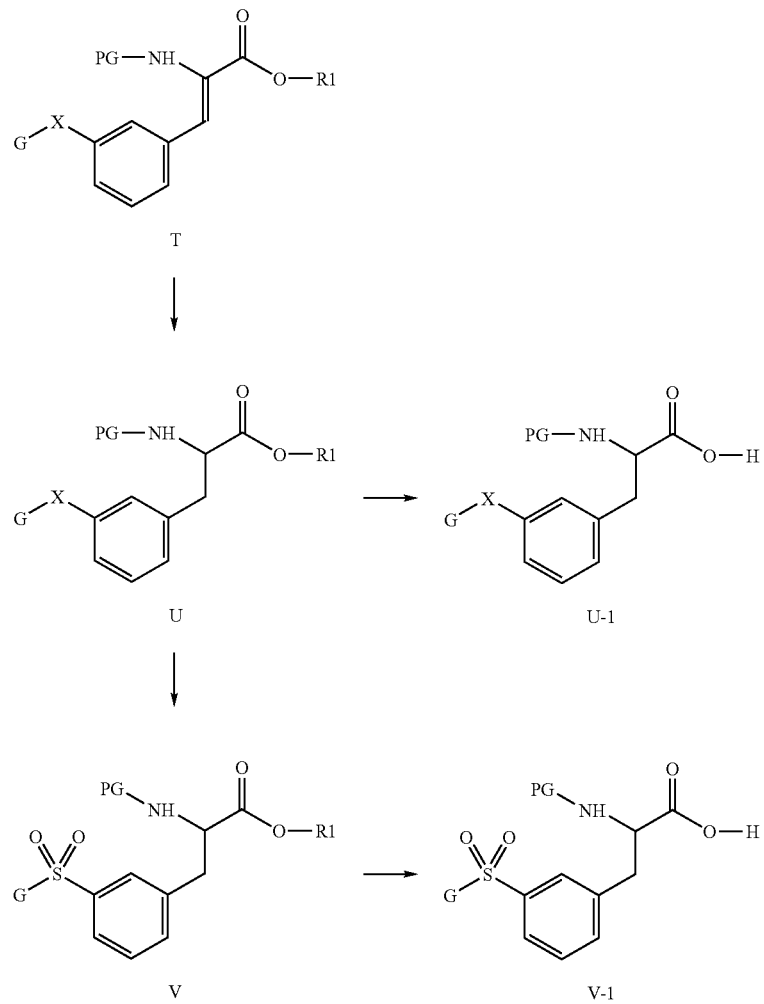
SCHEME EE
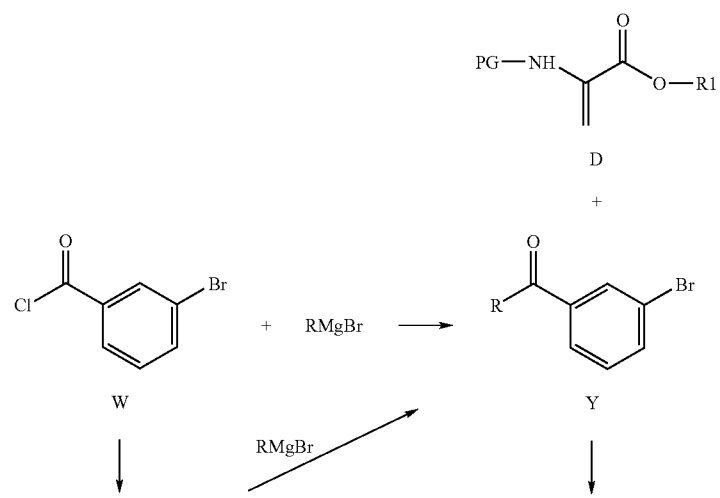

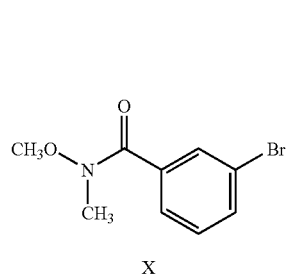

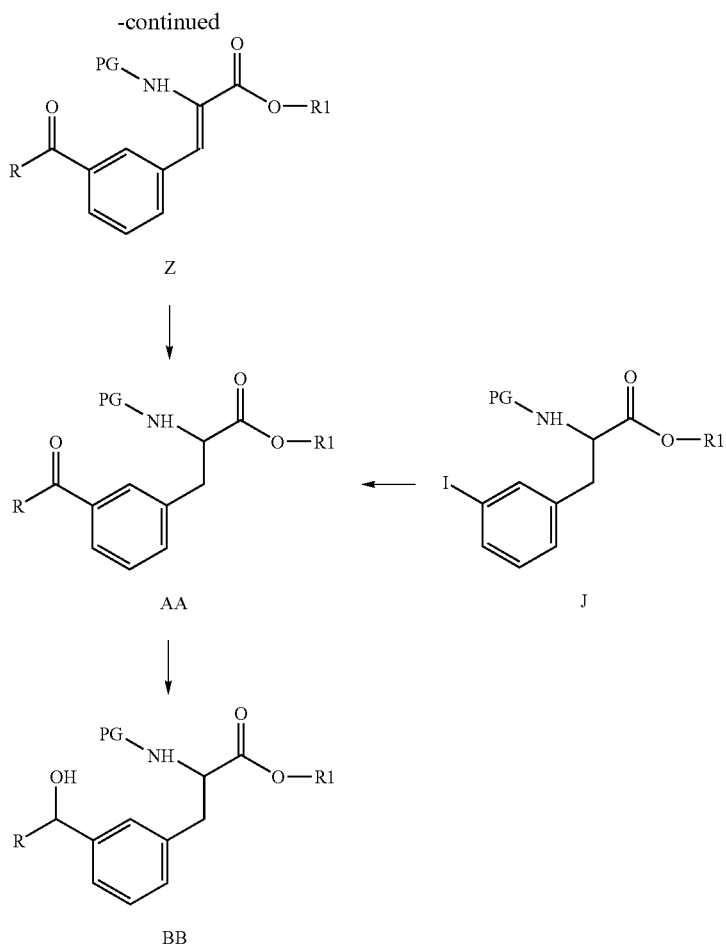

The most general process to prepare the compounds (X) of the present invention is set forth in SCHEME A. The chemistry is straight forward and in summary involves the steps of N-protecting an amino acid (I) starting material to produce protected amino acid (Ia). Protected amino acid (Ia) is reacted to produce the a corresponding protected amino acid (II), reaction of the protected amino acid (II) with diazomethane followed by work-up to add a carbon atom to produce the corresponding protected compound (III), reduction of the protected compound (III) to the corresponding alcohol (IV), formation of the corresponding epoxide (V), opening of the epoxide (V) with a C-terminal amine, Rc-NH$_2$ (VI) to produce the corresponding protected alcohol (VII) which then has the nitrogen protecting group removed to produce the corresponding amine (VIII), which is then reacted with an amide forming agent of the formula (R$_{N-1}$—X$_N$)$_2$O or R$_{N-1}$—X$_N$—X$_2$ or R$_{N-1}$—X$_N$—OH (IX) to produce the compound (X). One skilled in the art will appreciate that these are all well known reactions in organic chemistry. A chemist skilled in the art, knowing the chemical structure of the biologically active compound end product (X) of the invention would be able to prepare them by known methods from known starting materials without any additional information. The explanation below therefore is not necessary but is deemed helpful to those skilled in the art who desire to make the compounds of the present invention.

The backbone of the compounds of the present invention is a hydroxyethylamine moiety, —NH—CH(R)—CH (OH)—. It can be readily prepared by methods disclosed in the literature and known to those skilled in the art. For example, J. Med. Chem., 36, 288–291 (1992), Tetrahedron Letters, 28, 5569–5572 (1987), J. Med. Chem., 38, 581–584 (1994) and Tetrahedron Letters, 38, 619–620 (1997) all disclose processes to prepare hydroxyethylamine type compounds.

SCHEME A sets forth a general method used in the present invention to prepare appropriately compounds of formula X. Compounds of Formula X are prepared by starting with the corresponding amino acid (I), where R$_1$ is —H, C$_1$–C$_4$ alkyl, or benzyl. The amino acids (I) are well known to those skilled in the art or can be readily prepared from known compounds by methods well known to those skilled in the art. The compounds (X) of the present invention have at least two enantiomeric centers, which give four enantiomers. The first of these enantiomeric centers derives from the amino acid starting material (I). It is preferred to commercially obtain or produce the desired enantiomer (S) rather than produce an enantiomerically impure mixture and then have to separate out the desired enantiomer (S). It is preferred to start the process with enantiomerically pure (S)-amino acid (I) of the same configuration as that of the desired final product. For the amino acids (I), R$_X$ is bonded with a single or double bond and is, for example, —(CH$_2$)$_{1-6}$—OH, —Cl, —Br, —I, —O-tosylate, —O-mesylate, —O-triflate, or methylene.

The first step of the process is to protect the free amino group of the (S)-amino acid (I) with an amino protecting group to produce the (S)-protected amino acid (Ia) by methods well known to those skilled in the art. Amino protecting groups are well known to those skilled in the art. See for example, "Protecting Groups in Organic Synthesis", John Wiley and sons, New York, N.Y., 1981, Chapter 7; "Protecting Groups in Organic Chemistry", Plenum Press, New York, N.Y., 1973, Chapter 2. The function of the amino protecting group is to protect the free amino functionality (—$NH_2$) during subsequent reactions on the (S)-amino acid (I) which would not proceed well either because the amino group would react and be functionalized in a way that is inconsistent with its need to be free for subsequent reactions or the free amino group would interfere in the reaction. When the amino protecting group is no longer needed, it is removed by methods well known to those skilled in the art.

By definition the amino protecting group must be readily removable as is known to those skilled in the art by methods well known to those skilled in the art. Suitable amino PROTECTING GROUPs are selected from the group consisting of t-butoxycarbonyl, benzyloxycarbonyl, formyl, trityl, acetyl, trichloroacetyl, dichloroacetyl, chloroacetyl, trifluoroacetyl, difluoroacetyl, fluoroacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycabonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl)benzyloxycarbonyl, isobornyloxycarbonyl and 1-piperidyloxycarbonyl, 9-fluorenylmethyl carbonate, —CH—CH═$CH_2$ and phenyl-C(═N—)—H.

It is preferred that the protecting group be t-butoxycarbonyl (BOC) and benzyloxycarbony (CBZ), it is more preferred that the protecting group be t-butoxycarbonyl. One skilled in the art will understand the preferred methods of introducing a t-butoxycarbonyl or benzyloxycarbonyl protecting group and may additionally consult T. W. Green and P. G. M. Wuts in "Protective Groups in Organic Chemistry," John Wiley and Sons, 1991 for guidance.

Numerous preparations of amino acids, both natural and non-natural, are found in the literature and are known to those well-versed in the art. For example, several methods are described and/or reviewed in *Angew. Chem. Int. Ed.*, 38, 2873 (1999); *Aldrichimica Acta*, 32, 18 (1999); *Angew. Chem. Int. Ed.*, 39, 1010 (1999), and *Aldrichimica Acta*, 34, 3 (2001). Protected amino acid (Ia) can be reacted to form amino acids (II).

Several examples of preparations of unnatural amino acids that form compounds of formula (II) from compounds of formula (Ia) are discussed here for illustration but are not meant to be limiting.

CHART A sets forth a general method used in the present invention to prepare the appropriately compounds (X). The anti-Alzheimer compounds (X) of the present invention are prepared by starting with the corresponding amino acid (I). The amino acids (I) are well known to those skilled in the art or can be readily prepared from known compounds by methods well known to those skilled in the art. The compounds (X) of the invention have at least two chiral centers which give four stereoisomers. The first of these chiral centers derives from the amino acid starting material (I). When, for example, (S) stereochemistry is ultimately desired, it is preferred to commercially obtain or produce the desired pure starting (S) stereisomer rather than produce an racemic mixture and later separate out the desired products. Generally, it is preferred to start the process with enantiomerically pure (S)-amino acid (I) of the same configuration as that of the desired product of Formula X.

The first step of the process is to protect the free amino group of the (S)-amino acid (I) with an amino protecting group to produce the (S)-protected amino acid (II) by methods well known to those skilled in the art. Amino protecting groups are well known to those skilled in the art. See for example, "Protecting Groups in Organic Synthesis", John Wiley and sons, New York, N.Y., 1981, Chapter 7; "Protecting Groups in Organic Chemistry", Plenum Press, New York, N.Y., 1973, Chapter 2. The function of the amino protecting group is to protect the free amino functionality (—$NH_2$) during subsequent reactions on the (S)-amino acid (I) which would not proceed well, either because the amino group would react and be functionalized in a way that is inconsistent with its need to be free for subsequent reactions, or the free amino group would interfere in the reaction. When the amino protecting group is no longer needed, it is removed by methods well known to those skilled in the art. By definition the amino protecting group must be readily removable as is known to those skilled in the art by methods well known to those skilled in the art. Suitable amino PROTECTING GROUP is selected from the group consisting of t-butoxycarbonyl, benzyloxycarbonyl, formyl, trityl, acetyl, trichloroacetyl, dichloroacetyl, chloroacetyl, trifluoroacetyl, difluoroacetyl, fluoroacetyl, 4-phenylbenzyloxycarbonyl, 2-methylbenzyloxycarbonyl, 4-ethoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycabonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl, 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxyl)benzyloxycarbonyl, isobornyloxycarbonyl and 1-piperidyloxycarbonyl, 9-fluorenylmethyl carbonate, —CH—CH═$CH_2$ and phenyl-C(═N—)—H. It is preferred that the protecting group be t-butoxycarbonyl (BOC) and benzyloxycarbonyl (CBZ), it is more preferred that the protecting group be t-butoxycarbonyl. One skilled in the art will understand the preferred methods of introducing a t-butoxycarbonyl or benzyloxycarbonyl protecting group and may additionally consult T. W. Green and P. G. M. Wuts in "Protective Groups in Organic Chemistry," John Wiley and Sons, 1991 for guidance.

The (S)-protected amino acid (II) is transformed to the corresponding (S)-protected compound (III) by two different methods depending on the nature of $R_2$ and $R_3$. $R_2$ and $R_3$ are independently selected from the group consisting of:

(I) —H,
(II) $C_1$–$C_6$ alkyl, optionally substituted with one, two or three substituents selected from the group consisting of $C_1$–$C_3$ alkyl, —F, —Cl, —Br, —I, —OH, —SH, —C≡N, —CF$_3$, $C_1$–$C_3$ alkoxy, —NR$_{1-a}$R$_{1-b}$ where $R_{1-a}$ and $R_{1-b}$ are as defined above,
(III) —(CH$_2$)$_{0-4}$—R$_{2-1}$ where $R_{2-1}$ is $R_{1-aryl}$ or $R_{1-heteroaryl}$ where $R_{1-aryl}$ and $R_{1-heteroaryl}$ are as defined above;
(IV) $C_2$–$C_6$ alkenyl with one or two double bonds,
(V) $C_2$–$C_6$ alkynyl with one or two triple bonds,
(VI) —(CH$_2$)$_{0-4}$—$C_3$–$C_7$ cycloalkyl, optionally substituted with one, two or three substituents selected from the group consisting of —F, —Cl, —OH, —SH, —C≡N, —CF$_3$, $C_1$–$C_3$ alkoxy, —NR$_{1-a}$R$_{1-b}$ where $R_{1-a}$ and $R_{1-b}$ are —H or $C_1$–$C_6$ alkyl, and where $R_2$ and $R_3$ are taken together with the carbon to which they are attached to form a carbocycle of three, four, five, six, and seven carbon atoms, optionally where one carbon atom is replaced by a heteroatom selected from the group consisting of —O—, —S—, —SO$_2$—, —NR$_{N-2}$—, where $R_{N-2}$ is as defined below. It is preferred that $R_2$ and $R_3$ both be —H. If $R_2$ and $R_3$ are not the same, an additional enantiomeric center is added to the molecule. If it is desired that both $R_2$ and $R_3$ are —H, then the (S)-protected amino acid (II) is reacted with diazomethane, as is well known to those skilled in the art, followed by reaction with a compound of the formula H—$X_1$ to produce the (S)-protected compound (III). $X_1$ includes —Cl, —Br, —I, —O-tosylate, —O-mesylate, —O-nosylate; it is preferred that —$X_1$ be —Br or —Cl. Suitable reaction conditions include running the reaction in inert solvents, such as but not limited to ether, tetrahydrofuran and the like. The reactions from the (S)-protected amino acid (II) to the (S)-protected compound (III) are carried out for a period of time between 10 minutes and 1 day and at temperatures ranging from −78 degrees to 20–25 degrees C. It is preferred to conduct the reactions for a period of time between 1–4 hours and at temperatures between −30 degrees to −10 degrees C. This process adds one methylene group.

Alternatively, the (S)-protected compounds of formula (III) can be prepared by first converting the (S)-protected amino acid (II) to a corresponding methyl or ethyl ester, according to methods well established in the art, followed by treatment with a reagent of formula $X_1$—C(R$_2$)(R$_3$)—$X_1$ and a strong metal base. The base serves to affect a halogen-metal exchange, where the —$X_1$ undergoing exchange is a halogen selected from chlorine, bromine or iodine. The nucleophilic addition to the ester derivative gives directly the (S)-protected compound (III). Suitable bases include, but are not limited to the alkyllithiums including, for example, sec-butyllithium, n-butyllithium, and t-butyllithium. The reactions are preferably conducted at low temperature, such as −78 degrees C. Suitable reaction conditions include running the reaction in inert solvents, such as but not limited to, ether, tetrahydrofuran and the like. Where $R_2$ and $R_3$ are both hydrogen, then examples of $X_1$—C(R$_2$)(R$_3$)—$X_1$ include dibromomethane, diiodomethane, chloroiodomethane, bromoiodomethane and bromochloromethane. One skilled in the art knows the preferred conditions required to conduct this reaction. Furthermore, if $R_2$ and/or $R_3$ are not —H, then by the addition of —C(R$_2$)(R$_3$)—$X_1$ to esters of the (S)-protected amino acid (II) to produce the (S)-protected compound (III), an additional chiral center will be incorporated into the product, provided that $R_2$ and $R_3$ are not the same.

The (S)-protected compound (III) is then reduced by means well known to those skilled in the art for reduction of a ketone to the corresponding secondary alcohol affording the corresponding alcohol (IV). The means and reaction conditions for reducing the (S)-protected compound (III) to the corresponding alcohol (IV) include, for example, sodium borohydride, lithium borohydride, borane, diisobutylaluminum hydride, and lithium aluminium hydride. Sodium borohydride is the preferred reducing agent. The reductions are carried out for a period of time between 1 hour and 3 days at temperatures ranging from −78 degrees C. to elevated temperature up to the reflux point of the solvent employed. It is preferred to conduct the reduction between −78 degrees C. and 0 degrees C. If borane is used, it may be employed as a complex, for example, borane-methyl sulfide complex, borane-piperidine complex, or borane-tetrahydrofuran complex. The preferred combination of reducing agents and reaction conditions needed are known to those skilled in the art, see for example, Larock, R. C. in Comprehensive Organic Transformations, VCH Publishers, 1989. The reduction of the (S)-protected compound (III) to the corresponding alcohol (IV) produces the second chiral center (third chiral center if $R_2$ and $R_3$ are not the same). The reduction of the (S)-protected compound (III) produces a mixture of enantiomers at the second center, (S, R/S)-alcohol (IV). This enantiomeric mixture is then separated by means known to those skilled in the art such as selective low-temperature recrystallization or chromatographic separation, for example by HPLC, employing commercially available chiral columns. The enantiomer that is used in the remainder of the process of CHART A is the (S,S)-alcohol (IV) since this enantiomer will give the desired biologically active anti-Alzheimer (S,R)-compound (X).

The (S,S)-alcohol (IV) is transformed to the corresponding epoxide (V) by means known to those skilled in the art. The stereochemistry of the (S)—(IV) center is maintained in forming the epoxide (V). A preferred means is by reaction with base, for example, but not limited to, hydroxide ion generated from sodium hydroxide, potassium hydroxide, lithium hydroxide and the like. Reaction conditions include the use of $C_1$–$C_6$ alcohol solvents; ethanol is preferred. A common co-solvent, such as for example, ethyl acetate may also be employed. Reactions are conducted at temperatures ranging from −45 degrees C. up to the reflux temperature of the alcohol employed; preferred temperature ranges are between −20 degrees C. and 20–25 degrees C.

The epoxide (V) is then reacted with the appropriately substituted C-terminal amine, R$_C$—NH$_2$ (VI) by means known to those skilled in the art that opens the epoxide to produce the desired corresponding enantiomerically pure (S,R)-protected alcohol (VII). The substituted C-terminal amines, R$_C$—NH$_2$ (VI) of this invention are commercially available or are known to those skilled in the art and can be readily prepared from known compounds.

Suitable reaction conditions for opening the epoxide (V) include running the reaction in a wide range of common and inert solvents. $C_1$–$C_6$ alcohol solvents are preferred and isopropyl alcohol most preferred. The reactions can be run at temperatures ranging from 20–25 degrees C. up to the reflux temperature of the alcohol employed. The preferred temperature range for conducting the reaction is between 50 degrees C. up to the reflux temperature of the alcohol employed. When the substituted C-terminal amine (VI) is a 1-amino-3,5-cis-dimethyl cyclohexyldicarboxylate it is preferably prepared as follows. To dimethyl-5-aminoisophthalate in acetic acid and methanol, is added rhodium in alumina in a high-pressure bottle. The bottle is saturated with hydrogen at 55 psi and shaken for one week of time. The mixture is then filtered through a layer of diatomaceous earth and rinsed with methanol three times, the solvents are removed under reduced pressure (with heat) to give a concentrate. The concentrate is triturated with ether and filtered again to give the desired C-terminal amine (VI). When the substituted C-terminal amine (VI) is 1-amino-3,5-cis-dimethoxy cyclohexane it is prepared by following the general procedure above and making non-critical variations but starting with 3,5-dimethoxyaniline. When the substituted C-terminal amine (VI) is an aminomethyl group where the substituent on the methyl group is an aryl group, for example $NH_2$—$CH_2$-$R_{C-aryl}$, and $NH_2$—$CH_2$—$R_{C-aryl}$ is not commercially available it is preferrably prepared as follows. A suitable starting material is the (appropriately substituted) aralkyl compound. The first step is bromination of the alkyl substitutent via methods known to those skilled in the art, see for example R. C. Larock in Comprehensive Organic Transformations, VCH Publishers, 1989, p. 313. Next the alkyl halide is reacted with azide to produce the aryl-(alkyl)-azide. Last the azide is reduced to the corresponding amine by hydrogen/catalyst to give the C-terminal amine (VI) of formula $NH_2$—$CH_2$—$R_{C-aryl}$. The suitably functionalized C-terminal amines (VI) may readily be prepared by one skilled in the art via known methods in the literature, making non-significant modifications. Select literature references include 1) Calderwood, et al., *Tet. Lett.*, 1997, 38, 1241, 2) Ciganek, *J. Org. Chem.*, 1992, 57, 4521, 3) Thurkauf, et al., *J. Med. Chem.*, 1990, 33, 1452, 4) Werner, et al., *Org. Syn., Coll. Vol.* 5, 273, 5) *J. Med. Chem.*, 1999, 42, 4193, 6) *Chem. Rev.* 1995, 95, 2457, 7) *J. Am. Chem. Soc.*, 1986, 3150, 8) Felman et al., *J. Med. Chem.*, 1992, 35, 1183, 9) *J. Am. Chem. Soc.* 1970, 92, 3700, 10) *J. Med. Chem.*, 1997, 40, 2323.

As set forth in SCHEME AA, alcohol A, a protected form of serine, is converted to halide B by the methods, for example, of Bajgrowicz et al., *Tetrahedron Letters*, 2759 (1984) and Bajgrowicz et al., *Tetrahedron Letters*, 1833 (1985), or by treatment of alcohol A with thionyl bromide or thionyl chloride in the presence of a catalytic amount of DMF and in non-reactive solvents such as THF, dichloromethane, and cyclohexane. Other methods for the conversion of alcohol A to halide B include contact with carbon tetrabromide and triphenylphosphine in a non-reactive solvent such as dichloromethane. Other halogenating reagents include, but are not limited to, trimethylsilylchloride, trimethylsilylbromide, and trimethylsilyliodide, and tosyl chloride followed by NaI. Halide B then may be allowed to react with various amines, alcohols, and thiols in the presence of bases such as, but not limited to, alkaline earth metal carbonates, alkali metal hydrides (preferably sodium or potassium hydride), alkaline earth metal hydrides, alkali metal dialkylamides (preferably lithium diisopropylamide), alkali metal bis(trialkylsilyl)amides, trialkyl amines (preferably triethylamine and diisopropylethylamine) or aromatic amines (preferably pyridine), in non-reactive solvents such as acetonitrile, THF, DMF, dichloromethane and the like to give amide D.

In SCHEME AA, PG is PROTECTING GROUP as described above; A and W are as described above; $R_1$ is $C_1$-$C_4$ alkyl or benzyl; halo is Cl, Br, or I. In place of halo can be any suitable leaving group, such as, —O-tosylate, —O-mesylate, or —O-triflate.

Treatment of halide B with base in non-reactive solvents such as THF or acetonitrile gives acrylate C. Acrylate C may be prepared directly from alcohol A by converting the alcohol to a leaving group with reagents such as haloacetyl chlorides, mesyl chlorides, oxalyl chloride, diethyl chloridophosphate, N-phenylditriflamide, and CDI, DCC, and the like in the presence of a copper halide, followed by a base such as, but not limited to, alkaline earth metal carbonates, alkali metal hydroxides, alkali metal hydrides (preferably sodium or potassium hydride), alkali metal alkoxides (preferably sodium methoxide or sodium ethoxide), alkaline earth metal hydrides, alkali metal dialkylamides (preferably litium diisopropylamide), alkali metal bis(trialkylsilyl)amides, trialkyl amines (preferably triethylamine and diisopropylethylamine) or aromatic amines (preferably pyridine).

Alternatively, alcohol A may be treated under Mitsunobu conditions with dialkyl azodicarboxylate, preferably diethyl diazodicarboxylate and triphenyl phosphine in solvents such as THF to give cyclic amine B*, which is then treated in situ with amines, alcohols, and thiols in the presence of bases such as, but not limited to, alkaline earth metal carbonates, alkali metal hydroxides, alkali metal hydrides (preferably sodium or potassium hydride), alkaline earth metal hydrides, alkali metal dialkylamides (preferably litium diisopropylamide), alkali metal bis(trialkylsilyl)amides, trialkyl amines (preferably triethylamine and diisopropylethylamine) or aromatic amines (preferably pyridine) give amide D.

Acrylate C is also an item of commerce. It is well known to those versed in the art how to add or remove or exchange one protecting group for another as may be necessary depending upon the particular reaction intended. Treatment of acrylate C or halide B with amines, alcohols, and thiols in the presence of bases such as, but not limited to, alkaline earth metal carbonates, alkali metal hydroxides, alkali metal hydrides (preferably sodium or potassium hydride), alkaline earth metal hydrides, alkali metal dialkylamides (preferably lithium diisopropylamide), alkali metal bis(trialkylsilyl)amides, trialkyl amines (preferably triethylamine and diisopropylethylamine) or aromatic amines (preferably pyridine) in solvents such as THF or DMF at temperatures ranging from room temperature to reflux temperature of the solvent give amide D.

Amide D is hydrolyzed, preferably using alkali metal hydroxide such as lithium hydroxide, sodium hydroxide, or potassium hydroxide, followed by acidification, to give acid D-1, compounds of formula (II).

As set forth in SCHEME BB, the treatment of amide D with bromoiodobenzene (E) under conditions of the Heck reaction by means well-known to those versed in the art such as a palladium catalyst (preferably palladium acetate), an alkyl ammonium halide such as tetra-n-butylammonium chloride, aq. base (preferably sodium bicarbonate or sodium carbonate), and solvents such as DMF, N-methylpyrrolidinone, N-methylacetamide, and the like at temperatures ranging from room temperature to the boiling point of the solvent, to give styrene F. Styrene F is further treated with alkene G under conditions of the Heck reaction by means well-known to those versed in the art. One such example of Heck reaction conditions are a palladium catalyst (preferably palladium acetate), an alkyl ammonium halide such as tetra-n-butylammonium chloride, aq. base (preferably sodium bicarbonate or sodium carbonate), and solvents such as DMF, N-methylpyrrolidinone, N-methylacetamide, and the like at temperatures ranging from room temperature to the boiling point of the solvent, to give dialkene H. Dialkene H is then reduced with hydrogen to alkane I using various catalysts and chiral ligands well known to those versed in the art to give the desired protected (S) amino acid I. One such catalyst and ligand is (but is not limited to) Rh(COD)[(S,S)-Et-DuPHOS]$^+$OTf$^-$. In SCHEME BB, PG is PROTECTING GROUP as described above; G is as described above; $R_1$ is $C_1$–$C_4$ alkyl or benzyl.

Protected amino acid (I) is hydrolyzed, preferably using alkali metal hydroxide such as lithium hydroxide, sodium hydroxide, or potassium hydroxide, followed by acidification, to give acid I-1, compounds of formula (II).

As set forth in SCHEME CC, Aryl halide J, which is available as an item of commerce, is reacted with borane reagents under conditions of the Suzuki reaction by methods well known to those versed in the art. In SCHEME CC, PG is PROTECTING GROUP as described above; G is as described above; $R_1$ is $C_1$–$C_4$ alkyl or benzyl.

Thus aryl halide J is treated with borane reagents K, L, and M where R' and R" are, for example, OH, or OR where R is a lower alkyl, or where R' and R" are $C_1$–$C_8$ alkyl or when taken together are $C_8$ cycloalkyl, in the presence of a metal catalyst such as the salts or phosphine complexes of Cu, Pd, and Ni. Preferred are palladium catalysts such as PdCl$_2$(PPh$_3$)$_2$, PdCl$_2$(dppf), and Pd(OAc)$_2$ with or without added base, in solvents such as THF, acetone, acetonitrile, dialkyl ethers, DMF, NMP, N,N-dialkylacetamides, and so forth, from about 50 degrees C. to reflux temperature, to afford biphenyl N, benzylphenyl O, and alkyl phenyl P. A wide range of organoborane reagents can be made for use in this derivatization by the hydroboration of alkenes with 9-BBN (*J. Am. Chem. Soc.*, 314 (1989)), or by the methods described in *Tetrahedron*, 50, 979 (1994).

Biphenyl N, benzylphenyl O, and alkyl phenyl P are hydrolyzed, preferably using alkali metal hydroxide such as lithium hydroxide, sodium hydroxide, or potassium hydroxide, followed by acidification, to give acids N-1, O-1, and P-1, compounds of formula (II).

As set forth in SCHEME DD, halobenzene S is prepared from commercially available benzene Q, a base, and alkyl halide G using methods well known to those versed in the art. When G is desired to be aryl, then aryl iodides are reacted with phenol Q or thiophenol Q using palladium catalysts as described in *J. Am. Chem. Soc.*, 4369 (1999) and *J. Am. Chem. Soc.*, 10539 (1997). Another method is combining thiophenol Q and aryl iodide R in the presence of a palladium catalyst such as Pd(PPh$_3$)$_4$ and sodium tert-butoxide and ethanol give halobenzene S. When X is desired to be nitrogen, aniline Q is reacted with iodobenzene R in the presence of potassium or sodium tert-butoxide, Pd$_2$(dba)$_3$, BINAP, and toluene to give halobenzene S. In SCHEME DD, PG is PROTECTING GROUP as described above; G is as described above; $R_1$ is $C_1$–$C_4$ alkyl or benzyl.

The Heck reaction for the addition of halobenzene S to amide D to give alkene T is as described in SCHEME BB. Reduction of alkene T as described in SCHEME BB gives amine U. When X is sulfur, it may be desired to oxidize the sulfur to sulfone using m-chloroperoxybenzoic acid or hydrogen peroxide or other oxidizing agents, using methods well known to those versed in the art, to give sulfone V.

Amine U and sulfone V are hydrolyzed, preferably using alkali metal hydroxide such as lithium hydroxide, sodium hydroxide, or potassium hydroxide, followed by acidification, to give acids U-1 and V-1, compounds of the formula (II).

SCHEME EE, Scheme E sets forth a route for the preparation of benzophenone AA and benzyl alcohol BB. In SCHEME EE, PG is PROTECTING GROUP as described above; G is as described above; $R_1$ is $C_1$–$C_4$ alkyl or benzyl.

Acetophenone Y is prepared from acid halide W (which, if not commercially available, is prepared by numerous methods well known to those skilled in the art, using commercially available benzoic acids). Acid halide W is reacted with a Grignard reagent (which is commercially available or prepared from available alkyl and aryl halides by methods well known to those versed in the art) in solvents such as THF and at temperatures ranging from −78 degrees C. to room temperature to produce acetophenone Y. Alternatively, contacting HN(Me)(OMe) with acid halide W in neutral solvents such as THF, acetonitrile, or dichloromethane in the presence of a base gives Weinreb amide X, which upon addition of a Grignard reagent in solvents such as THF at temperatures ranging from −78 degrees C. to room temperature to give acetophone Y. Acetophenone Y and amide D are then reacted under the conditions of the Heck reaction discussed in SCHEME BB to give alkene Z. Alkene Z is reduced to ketone AA and benzyl alcohol BB using H$_2$ and metal catalysts such as palladium on carbon in solvents such as alcohols, preferably $C_1$–$C_4$ alcohols, or RuCl$_2$ in the presence of a phosphine ligand and potassium tert-butoxide in solvents such as isopropanol, or using conditions of the Heck reaction as described in SCHEME BB. Benzyl alcohol BB may be oxidized using oxidizing agents well known to those versed in the art, for example with activated manganese dioxide in non-reactive solvents such as chloroform to give ketone AA. Alternatively, ketone AA may be produced by reacting aryl halide J with a palladium catalyst, preferably PdCl$_2$(PPh$_3$)$_2$, carbon monoxide, Ph(n-butyl)$_3$Sn, and DMF according to the method of *Bioorg. Med. Chem. Lett.*, 10, 1815 (2000).

Ketone AA and alcohol BB are hydrolyzed, preferably using alkali metal hydroxide such as lithium hydroxide, sodium hydroxide, or potassium hydroxide, followed by acidification, to give acids AA-1 and BB-1, compounds of the formula (II).

As set forth in Scheme 1, protected amino acids of general type 3, where PG is PROTECTING GROUP as described above, can be prepared by the Heck reaction of compound 1 or its iodo-analog, in the presence of a Pd(0)–Pd(II) catalyst system (for example, PdOAc$_2$, Bu$_4$NCl, NaHCO$_3$, DMF, 85 degrees C., 18 hours) with a suitable alkene, such as methylenecyclohexane, followed by hydrogenation of the alkene double bonds. Use of a chiral ligand such as (S,S) Et-DuPHOS with a rhodium hydrogenation catalyst affords one enantiomer in high excess. Racemic amino acid derivatives obtained from nonchiral hydrogenations can be resolved by procedures well established in the art. Alternatively, 1 can be hydrogenated to 3b, and subjected to Heck coupling to give 3c.

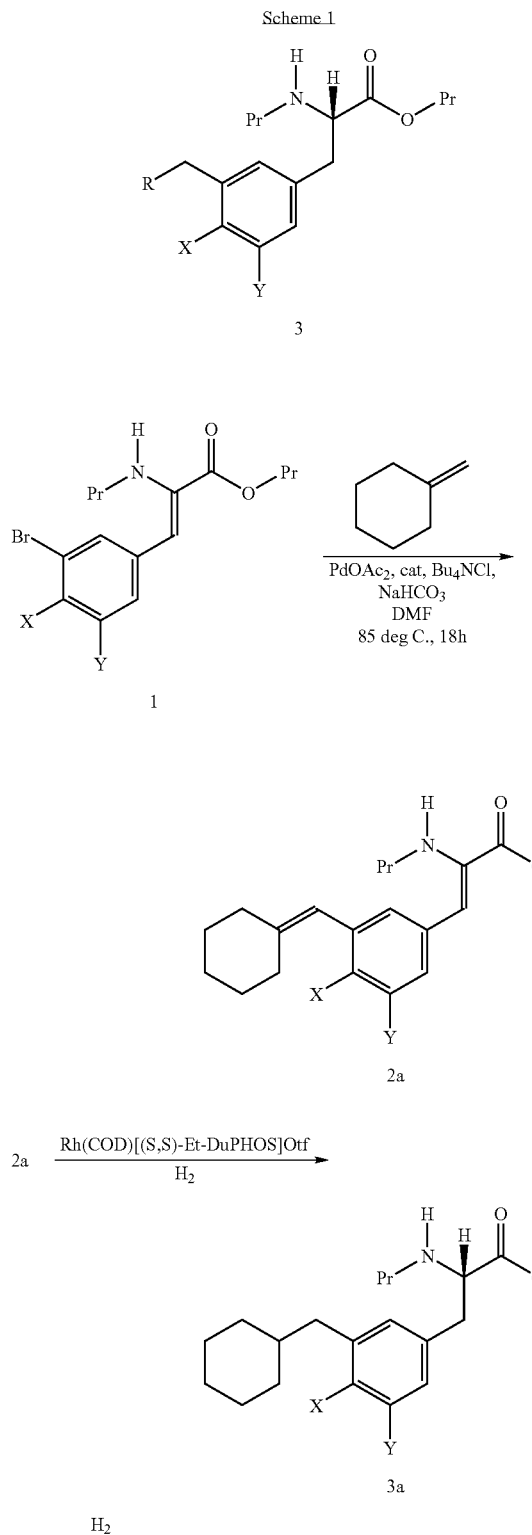

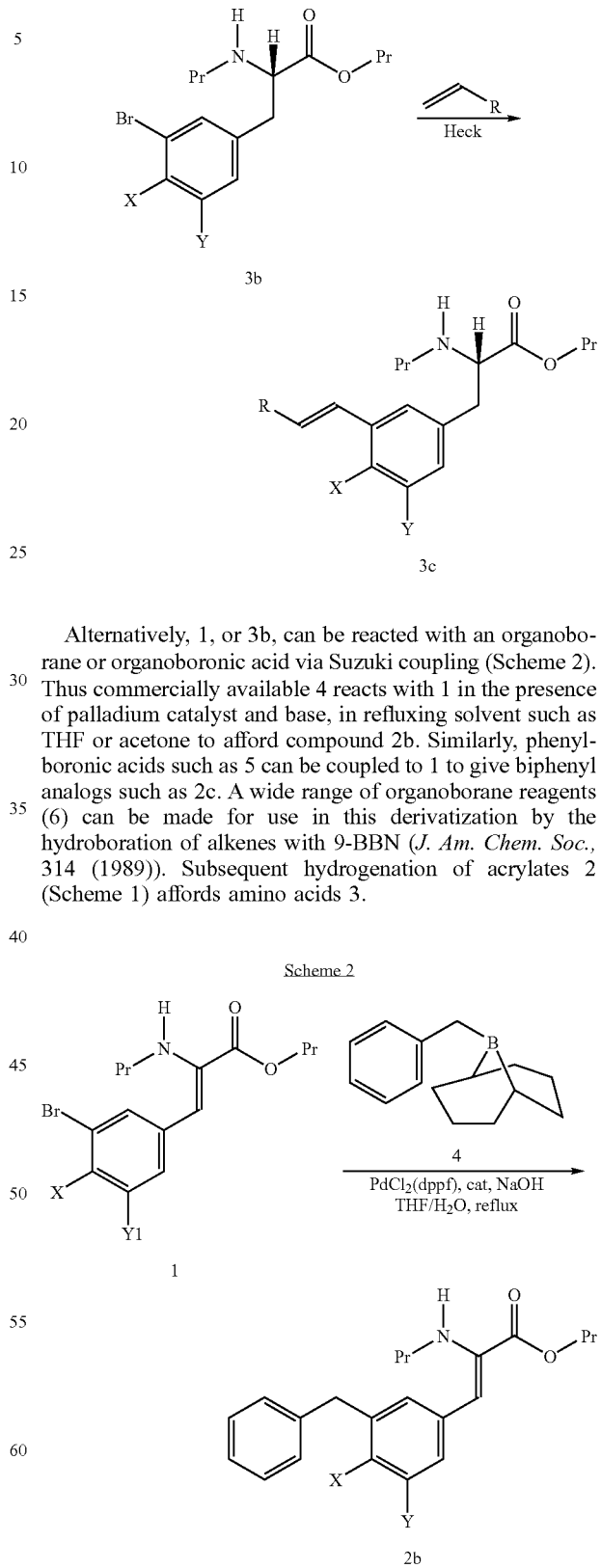

Alternatively, 1, or 3b, can be reacted with an organoborane or organoboronic acid via Suzuki coupling (Scheme 2). Thus commercially available 4 reacts with 1 in the presence of palladium catalyst and base, in refluxing solvent such as THF or acetone to afford compound 2b. Similarly, phenylboronic acids such as 5 can be coupled to 1 to give biphenyl analogs such as 2c. A wide range of organoborane reagents (6) can be made for use in this derivatization by the hydroboration of alkenes with 9-BBN (*J. Am. Chem. Soc.*, 314 (1989)). Subsequent hydrogenation of acrylates 2 (Scheme 1) affords amino acids 3.

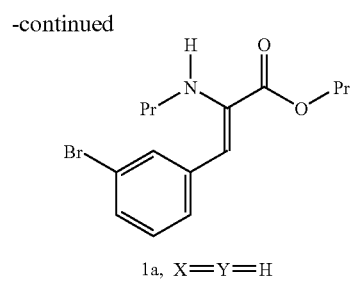

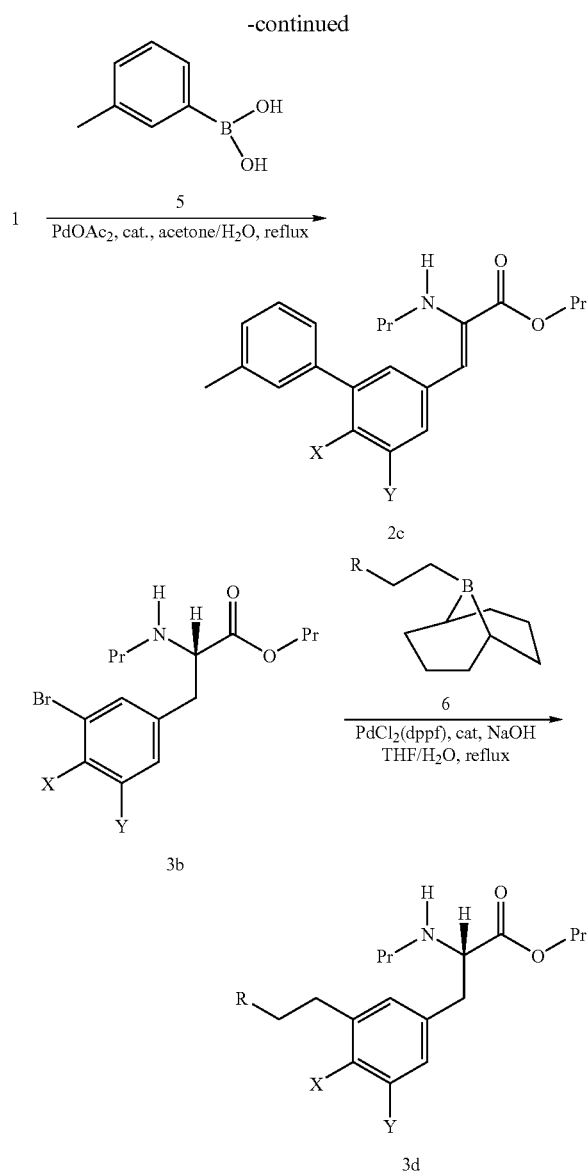

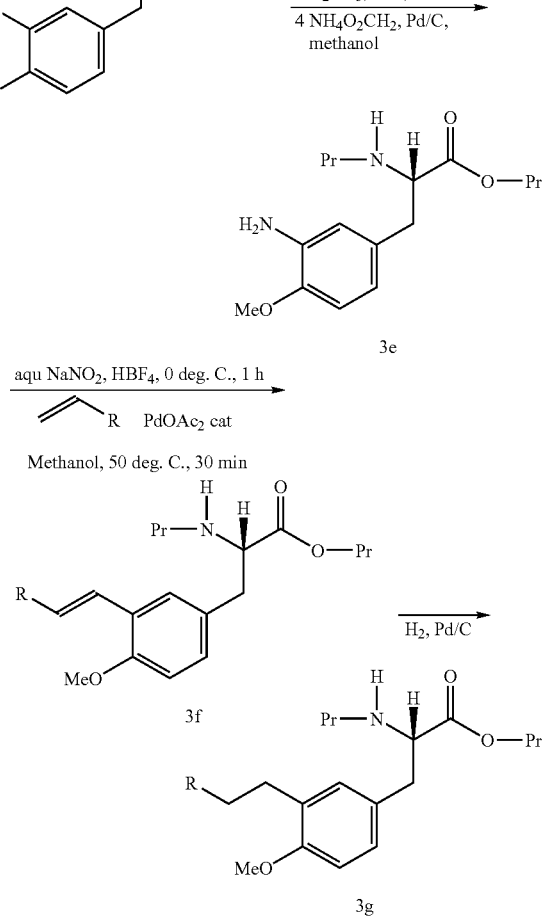

Alternatively, commercially available amino acid derivatives such as 3-nitrotyrosine can be converted to 3f (X=OMe, Y=H) by a sequence of known steps (Scheme 4) involving protection, reduction and diazotization, and finally an in situ aqueous Heck reaction on the diazonium salt. Compound 3f can also be hydrogenated to 3g by standard procedures.

Compound 1 can be prepared (Scheme 3) by a selective Heck reaction of the protected aminoacrylate 7 (derived from serine by literature procedures) with a commercially available bromoiodobenzene (JCS Perkin I, 3419 (1998)).

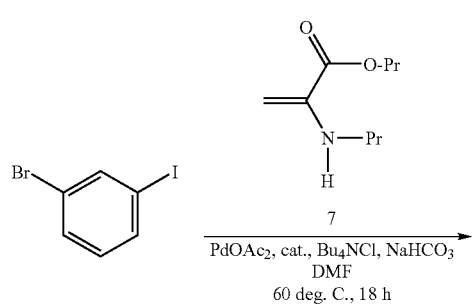

The reactions in Schemes 1–4 are equally applicable to derivatized amino acids of general formula 8, shown below with the reactive halogen or nitro group of the starting material residing in the para, vs. meta, position.

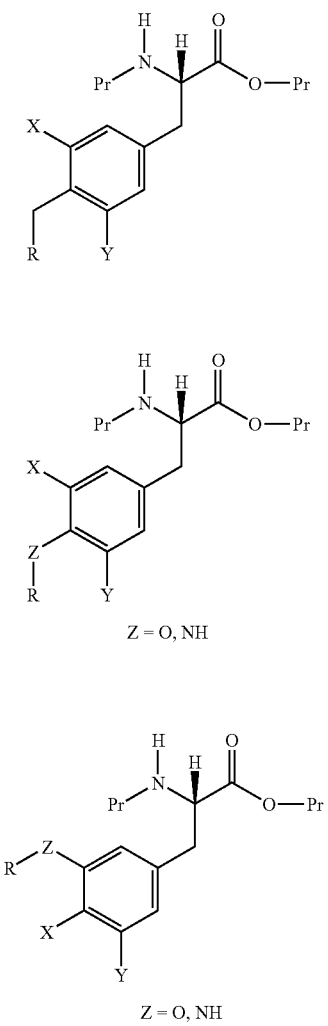

Amino acids of general formula 9, shown above, are accessible from commercially available tyrosine (Z=O) or from p-aminophenylalanine (Z=N), which is obtained by nitration and reduction of phenylalanine. Alkylation is affected by reaction of the protected amino acid derivative with an alkyl halide or mesylate in a solvent such as DMF, in the presence of a base such as potassium carbonate or triethyamine. Alternatively the ether or amino linkage can be formed by Mitsunobu reaction with an appropriate alcohol using diethylazodicarboxylate and triphenylphosphine in THF at low temperature.

Amino acids of general formula 10 may be obtained from the meta-bromo- or iodo-phenol or aniline, as illustrated in Scheme 5 for meta-bromophenol.

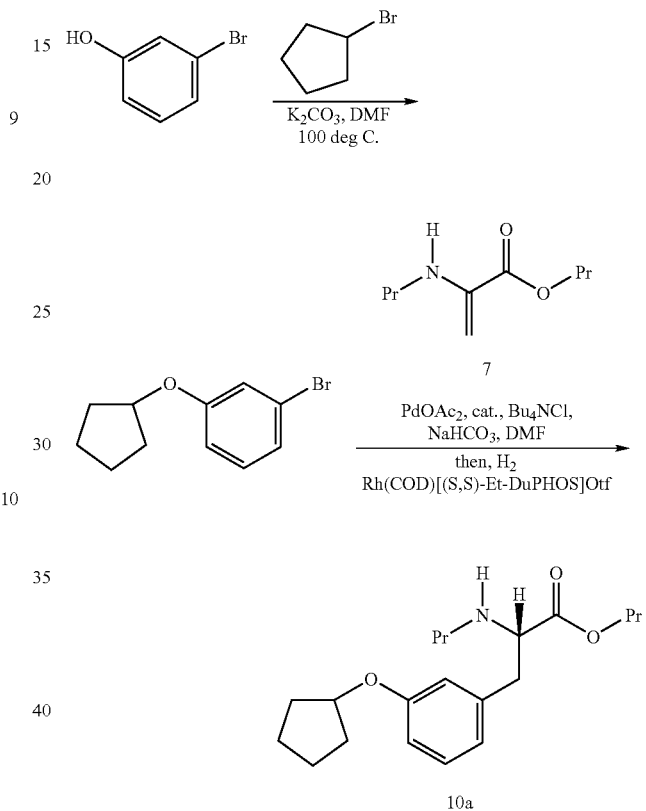

Amino acids of general formula 11 may be obtained from phenylacetic acids, as illustrated in Scheme 6, via esterification, reaction with an organometallic carbon nucleofile, bromination and reaction of the product aziridine derivative 2.

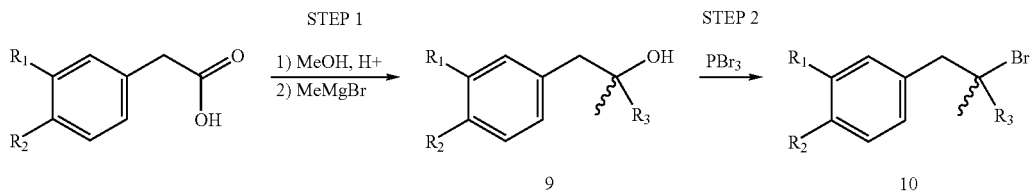

-continued

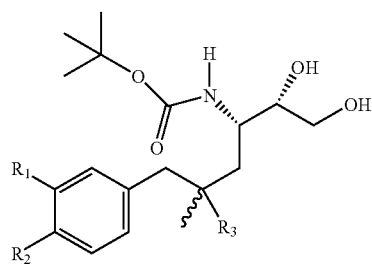

11

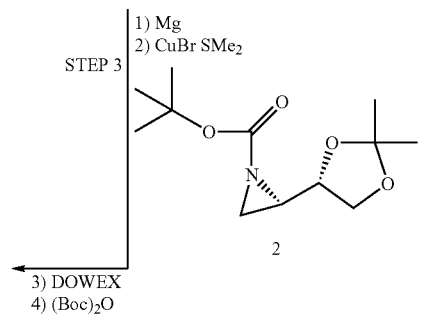

2

STEP 3
1) Mg
2) CuBr SMe$_2$
3) DOWEX
4) (Boc)$_2$O

The (S)-protected amino acid (II) is transformed to the corresponding (S)-protected compound (III) by two different methods depending on nature of R$_2$ and R$_3$. R$_2$ and R$_3$ carry the definitions set forth above for formula X. It is preferred that R$_2$ and R$_3$ both be —H. If R$_2$ and R$_3$ are not the same, an additional enantiomeric center is present in the molecule. To obtain compounds where R$_2$ and R$_3$ are —H, then the (S)-protected amino acid (II) is reacted with diazomethane, as is well known to those skilled in the art, followed by reaction with a compound of the formula H-X$_1$ to produce the (S)-protected compound (III). X$_1$ includes —Cl, —Br, —I, —O-tosylate, —O-mesylate, or —O-nosylate; it is preferred that —X$_1$ be —Br or —Cl. Suitable reaction conditions include running the reaction in inert solvents, such as, but not limited to, ether, tetrahydrofuran and the like. The reactions from the (S)-protected amino acid (II) to the (S)-protected compound (III) are carried out for a period of time between 10 minutes and 1 day and at temperatures ranging from −78 degrees to 20–25 degrees C. It is preferred to conduct the reactions for a period of time between 1–4 hours and at temperatures between −30 degrees to −10 degrees C. This process adds one methylene group.

Alternatively, the (S)-protected compounds of formula (III) can be prepared by first converting the (S)-protected amino acid (II) to a corresponding methyl or ethyl ester, according to methods well established in the art, followed by treatment with a reagent of formula X$_1$—C(R$_2$)(R$_3$)—X$_1$ and a strong metal base. The base serves to affect a halogen-metal exchange, where the -X$_1$ undergoing exchange is a halogen selected from chlorine, bromine or iodine. The nucleophilic addition to the ester derivative gives directly the (S)-protected compound (III). Suitable bases include, but are not limited to the alkyllithiums including, for example, sec-butyllithium, n-butyllithium, and t-butyllithium. The reactions are preferably conducted at low temperature, such as −78 degrees C. Suitable reaction conditions include running the reaction in inert solvents, such as but not limited to, ether, tetrahydrofuran and the like. Where R$_2$ and R$_3$ are both hydrogen, then examples of X$_1$—C(R$_2$)(R$_3$)—X$_1$ include dibromomethane, diiodomethane, chloroiodomethane, bromoiodomethane and bromochloromethane. One skilled in the art will recognize suitable conditions for this reaction. Furthermore, if R$_2$ and/or R$_3$ are not —H, then by the addition of —C(R$_2$)(R$_3$)—X$_1$ to esters of the (S)-protected amino acid (II) to produce the (S)-protected compound (III), an additional chiral center will be incorporated into the product, provided that R$_2$ and R$_3$ are not the same.

The (S)-protected compound (III) is then reduced by means well known to those skilled in the art for reduction of a ketone to the corresponding secondary alcohol affording the corresponding alcohol (IV). The means and reaction conditions for reducing the (S)-protected compound (III) to the corresponding alcohol (IV) include, for example, sodium borohydride, lithium borohydride, borane, diisobutylaluminum hydride, and lithium aluminium hydride. Sodium borohydride is the preferred reducing agent. The reductions are carried out for a period of time between 1 hour and 3 days at temperatures ranging from −78 degrees C. to elevated temperature up to the reflux point of the solvent employed. It is preferred to conduct the reduction between −78 degrees C. and 0 degrees C. If borane is used, it may be employed as a complex, for example, borane-methyl sulfide complex, borane-piperidine complex, or borane-tetrahydrofuran complex. The preferred combination of reducing agents and reaction conditions needed are known to those skilled in the art, see for example, Larock, R. C. in Comprehensive Organic Transformations, VCH Publishers, 1989. The reduction of the (S)-protected compound (III) to the corresponding alcohol (IV) produces the second chiral center (third chiral center if R$_2$ and R$_3$ are not the same). The reduction of the (S)-protected compound (III) produces a mixture of enantiomers at the second center, (S, R/S)-alcohol (IV). This enantiomeric mixture is then separated by means known to those skilled in the art such as selective low-temperature recrystallization or chromatographic separation, for example by HPLC, employing commercially available chiral columns. The enantiomer that is used in the remainder of the process of SCHEME A is the (S,S)-alcohol (IV) since this enantiomer will give the desired biologically active anti-Alzheimer (S,R)-compound (X).

The (S,S)-alcohol (IV) is transformed to the corresponding epoxide (V) by means known to those skilled in the art. The stereochemistry of the (S)—(IV) center is maintained in forming the epoxide (V). A preferred means is by reaction with base, for example, but not limited to, hydroxide ion generated from sodium hydroxide, potassium hydroxide, lithium hydroxide and the like. Reaction conditions include the use of C$_1$–C$_6$ alcohol solvents; ethanol is preferred. A common co-solvent, such as for example, ethyl acetate may also be employed. Reactions are conducted at temperatures ranging from −45 degrees C. up to the reflux temperature of the alcohol employed; preferred temperature ranges are between −20 degrees C. and 20–25 degrees C.

The epoxide (V) is then reacted with the appropriately substituted C-terminal amine, R$_C$—NH$_2$ (VI) by means known to those skilled in the art which opens the epoxide to produce the desired corresponding enantiomerically pure (S,R)-protected alcohol (VII). The substituted C-terminal amines, $R_C$—$NH_2$ (VI) of this invention are commercially available or are known to those skilled in the art and can be readily prepared from known compounds.

Preferably, $R_C$ is:
—$C_1$–$C_8$ alkyl,
—$(CH_2)_{0-3}$—$(C_3$–$C_7)$ cycloalkyl,
—$(CR_{C-x}R_{C-y})_{0-4}$—$R_{C-aryl}$,
—$(CR_{C-x}R_{C-y})_{0-4}$—$R_{C-heteroaryl}$,
—$(CR_{C-x}R_{C-y})_{0-4}$—$R_{C-heterocycle}$, or
-cyclopentyl or -cyclohexyl ring fused to $R_{C-aryl}$ or $R_{C-heteroaryl}$ or $R_{C-heterocycle}$.

More preferably $R_C$ is:
—$(CH_2)_{0-3}$—$(C_3$–$C_7)$ cycloalkyl,
—$(CR_{C-x}R_{C-y})_{0-4}$—$R_{C-aryl}$,
—$(CR_{C-x}R_{C-y})_{0-4}$—$R_{C-heteroaryl}$,
—$(CR_{C-x}R_{C-y})_{0-4}$—$R_{C-heterocycle}$, or
-cyclopentyl or -cyclohexyl ring fused to a $R_{C-aryl}$ or $R_{C-heteroaryl}$ or $R_{C-heterocycle}$.

Other more preferred $R_C$ groups are
—$(CR_{C-x}R_{C-y})_{0-4}$—$R_{C-aryl}$,
—$(CR_{C-x}R_{C-y})_{0-4}$—$R_{C-heteroaryl}$, and
-cyclopentyl or -cyclohexyl ring fused to a $R_{C-aryl}$ or $R_{C-heteroaryl}$ or $R_{C-heterocycle}$.

Particularly preferred $R_C$ groups are selected from the group consisting of:
—$(CR_{C-x}R_{C-y})_{0-4}$—$R_{C-aryl}$ where $R_{C-aryl}$ is phenyl,
—$(CR_{C-x}R_{C-y})_{0-4}$—$R_{C-heteroaryl}$, and
-cyclopentyl or -cyclohexyl ring fused to a $R_{C-aryl}$ or $R_{C-heteroaryl}$ or $R_{C-heterocycle}$.

Further, it is preferred that when $R_C$ is phenyl, it is substituted in the 3-position or 3,5-positions.

Suitable reaction conditions for opening the epoxide (V) include running the reaction in a wide range of common and inert solvents. $C_1$–$C_6$ alcohol solvents are preferred and isopropyl alcohol most preferred. The reactions can be run at temperatures ranging from 20–25 degrees C. up to the reflux temperature of the alcohol employed. The preferred temperature range for conducting the reaction is between 50 degrees C. up to the reflux temperature of the alcohol employed. When the substituted C-terminal amine (VI) is a 1-amino-3,5-cis-dimethyl cyclohexyldicarboxylate it is preferably prepared as follows. To dimethyl-5-aminoisophthalate in acetic acid and methanol, is added rhodium in alumina in a high-pressure bottle. The bottle is saturated with hydrogen at 55 psi and shaken for one week of time. The mixture is then filtered through a layer of diatomaceous earth and rinsed with methanol three times, the solvents are removed under reduced pressure (with heat) to give a concentrate. The concentrate is triturated with ether and filtered again to give the desired C-terminal amine (VI). When the substituted C-terminal amine (VI) is 1-amino-3,5-cis-dimethoxy cyclohexane it is preferably following the general procedure above and making non-critical variations but starting with 3,5-dimethoxyaniline. When the substituted C-terminal amine (VI) is an aminomethyl group where the substituent on the methyl group is an aryl group, for example $NH_2$-$CH_2$-$R_{C-aryl}$, and $NH_2$—$CH_2$—$R_{C-aryl}$ is not commercially available it is preferably prepared as follows.

A suitable starting material is the (appropriately substituted) aralkyl compound. The first step is bromination of the alkyl substituent via methods known to those skilled in the art, see for example R. C. Larock in Comprehensive Organic Transformations, VCH Publishers, 1989, p. 313. Next the alkyl halide is reacted with azide to produce the aryl-(alkyl)-azide. Last the azide is reduced to the corresponding amine by hydrogen/catalyst to give the C-terminal amine (VI) of formula $NH_2$—$CH_2$—$R_{C-aryl}$. The suitably functionalized C-terminal amines (VI) may readily be prepared by one skilled in the art via known methods in the literature, making non-significant modifications. Select literature references include 1) Calderwood, et al., *Tet. Lett.*, 1997, 38, 1241, 2) Ciganek, *J. Org. Chem.*, 1992, 57, 4521, 3) Thurkauf, et al., *J. Med. Chem.*, 1990, 33, 1452, 4) Werner, et al., *Org. Syn., Coll. Vol.* 5, 273, 5) *J. Med. Chem.*, 1999, 42, 4193, 6) *Chem. Rev.* 1995, 95, 2457, 7) *J. Am. Chem. Soc.*, 1986, 3150, 8) Felman et al., *J. Med. Chem.*, 1992, 35, 1183, 9) *J. Am. Chem. Soc.* 1970, 92, 3700, and 10) *J. Med. Chem.*, 1997, 40, 2323.

SCHEME B discloses an alternative process for production of the enantiomerically pure (S,R)-protected alcohol (VII) from the (S)-protected compound (III). In the alternative process, the (S)-protected compound (III) is first reacted with the appropriately substituted C-terminal amine $R_C$—$NH_2$ (VI) using the preferred conditions described above to produce the corresponding (S)-protected ketone (XI) which is then reduced using the preferred conditions described above to produce the corresponding (S,R)-protected alcohol (VII).

SCHEME C discloses another alternative process for production of enantiomerically pure (S,R)-protected alcohol (VII) but this time from the epoxide (V). In the process of SCHEME C, the epoxide (V) is reacted with azide to produce the corresponding enantiomerically pure (S,R)-protected azide (XII). Conditions to conduct the azide mediated epoxide opening are known to those skilled in the art, see for example, J. March, Advanced Organic Chemistry, $3^{rd}$ Edition, John Wiley & Sons Publishers, 1985, p. 380. Next, the (S,R)-protected azide (XII) is reduced to the corresponding protected amine (XIII) by methods known to those skilled in the art. Preferred reducing conditions to reduce the (S,R)-protected azide (XII) in the presence of a t-butoxycarbonyl N-protecting group include catalytic hydrogenation, the conditions for which are known to those skilled in the art. Alternative reducing conditions which may be used to avoid N-deprotection with protecting groups other than t-butoxycarbonyl are known to those skilled in the art, see for example, R. C. Larock in Comprehensive Organic Transformations, VCH Publishers, 1989, p. 409.

The (S,R)-protected alcohol (VII) is deprotected to the corresponding (S,R)-amine (VIII) by means known to those skilled in the art for removal of amine protecting group. Suitable means for removal of the amine protecting group depends on the nature of the protecting group. Those skilled in the art, knowing the nature of a specific protecting group, know which reagent is preferable for its removal. For example, it is preferred to remove the preferred protecting group, BOC, by dissolving the (S,R)-protected alcohol (VII) in a trifluoroacetic acid/dichloromethane mixture. When complete, the solvents are removed under reduced pressure to give the corresponding (S,R)-amine (as the corresponding salt, i.e. trifluoroacetic acid salt) which is used without further purification. However, if desired, the (S,R)-amine can be purified further by means well known to those skilled in the art, such as for example, recrystallization. Further, if the non-salt form is desired that also can be obtained by means known to those skilled in the art, such as for example, preparing the free base amine via treatment of the salt with mild basic conditions. Additional BOC deprotection conditions and deprotection conditions for other protecting groups can be found in T. W. Green and P. G. M. Wuts in "Protective Groups in Organic Chemistry," John Wiley and Sons, 1991, p. 309. Typical chemically suitable salts include trifluoroacetate, and the anion of mineral acids such as chloride, sulfate, phosphate; preferred is trifluoroacetate and chloride.

The (S,R)-amine (VIII) is then reacted with an appropriately substituted amide forming agent (IX) such as anhydride, acyl halide, or acid of the formula $(R_{N-1}-X_N)_2O$ or $R_{N-1}-X_N-X_2$ or $R_{N-1}-X_N-OH$ (IX) by nitrogen-acylation means known to those skilled in the art to produce the corresponding (S,R)-compound (X). Nitrogen acylation conditions for reaction of the (S,R)-amine (VIII) with an amide forming agent (IX) to produce the corresponding (S,R)-compound (X) are known to those skilled in the art and can be found in R. C. Larock in Comprehensive Organic Transformations, VCH Publishers, 1989, p. 981, 979, and 972.

Preferably, $R_N$ is selected from the group consisting of:
$R_{N-1}-X_N-$, where $X_N$ is $-CO-$, where $R_{N-1}$ is $R_{N-aryl}$ or $R_{N-heteroaryl}$ where $R_{N-aryl}$ is phenyl where the substitution on phenyl is 1,3-, and where $R_{N-aryl}$ or $R_{N-heteroary}$ are substituted with one $-CO-NR_{N-2}R_{N-3}$, $R_{N-1}-X_N-$, where $X_N$ is $-CO-$, where $R_{N-1}$ is $R_{N-aryl}$ or $R_{N-heteroaryl}$ where $R_{N-aryl}$ is phenyl substituted with one $C_1$ alkyl, where the substitution on the phenyl is 1,3,5-, and where $R_{N-aryl}$ or $R_{N-heteroaryl}$ are substituted with one $-CO-NR_{N-2}R_{N-3}$, and $R_{N-1}-X_N-$, where $X_N$ is $-CO-$, where $R_{N-1}$ is $R_{N-heteroaryl}$ where $R_{N-heteroaryl}$ is substituted with one $-CO-NR_{N-2}R_{N-3}$, It is further preferred that $R_{N-2}$ and $R_{N-3}$ are the same and are $C_3$ alkyl. It is further preferred that:

$R_{N-1}-X_N-$, where $X_N$ is $-CO-$, where $R_{N-1}$ is $R_N$ aryl where $R_{N-aryl}$ is phenyl substituted with one $-CO-NR_{N-2}R_{N-3}$ where the substitution on phenyl is 1,3-, and $R_{N-1}-X_N-$, where $X_N$ is $-CO-$, where $R_{N-1}$ is $R_{N-aryl}$ where $R_{N-aryl}$ is phenyl substituted with one $C_1$ alkyl and with one $-CO-NR_{N-2}R_{N-3}$ where the substitution on the phenyl is 1,3,5-. It is preferred that $X_N$ is (A) $-CO-$ and (B) $-SO_2-$; it is more preferred that $X_N$ be $-CO-$. $X_2$ includes $-Cl$, $-Br$; it is preferred that $X_2$ is $-Cl$.

The nitrogen-acylation of primary amines to produce secondary amides is one of the oldest known reactions. The amide forming agents, $(R_{N-1}-X_N)_2O$ or $R_{N-1}-X_N-X_2$ or $R_{N-1}-X_N-OH$ (IX) are known to those skilled in the art and are commercially available or can be readily prepared from known starting materials by methods known in the literature. It is preferred to use an isophthalic acid acylating agent (IX) of the formula $R_{N-2}R_{N-3}N-CO$-phenyl-$CO-$ or a methylisophthalic acid acylating agent (IX) $R_{N-2}R_{N-3}N-CO-(CH_3-)$phenyl-$CO-$ where the substitution is 5-methyl-1,3-isophthalic acid. The more preferred 5-methyl-1,3-isophthalic acid is 3-[(N,N-dipropylamino)carbonyl]-5-methylbenzoic acid (IX). These compounds are preferably prepared as follows.

An ester, preferably the monomethyl ester of isophthalic acid or methyl 5-methyl-1,3-isophthalate is dissolved in a THF/DMF mixture. 1,1'-Carbonyldiimidazole is added at 20–25 degrees C. Next the desired amine (H—$NR_{N-2}R_{N-3}$) is added. After 3–24 hours of stirring at 20 degrees C. to the reflux temperature of the solvent, the reaction mixture is partitioned between saturated aqueous ammonium chloride and a water immiscible organic solvent such as ethyl acetate. The aqueous layer is separated and extracted twice more with the organic solvent (ethyl acetate). The organic extracts are combined and then washed with saturated aqueous solutions of bicarbonate and saline and dried over anhydrous sodium sulfate or magnesium sulfate. Filtration of the drying agent and removal of solvents by reduced pressure gives the methyl ester of the desired $R_{N-2}R_{N-3}N-CO$-phenyl-$CO-O-CH_3$ or a methylisophthalic acid acylating agent (IX) $R_{N-2}R_{N-3}N-CO-(CH_3-)$phenyl-$CO-O-CH_3$. Purification of the (methyl) ester can be achieved via chromatography on silica gel eluting with ethyl acetate in hexanes. The isophthalate ester or methylisophthalate ester of the monoalkyl or di-alkyl amide is then treated with an aqueous solution of base such as lithium hydroxide in a minimum amount of THF/methanol/water and stirred 3–24 hours at 20 degrees C. to the reflux temperature of the solvent.

The solvents are then removed under reduced pressure and subsequently partitioned between water and a water immiscible solvent such as ethyl acetate, for example. If emulsions prohibit separation of the two phases, a small amount of saline is added to aid in separation. The aqueous phase is separated and extracted once more with a water immiscible solvent such as ethyl acetate, for example. The aqueous phase is then acidified with concentrated acid, preferably hydrochloric until $pH \leq 3$. The mixture obtained is then extracted three times with a water immiscible solvent such as ethyl acetate, for example. These combined organic extracts are dried over anhydrous sodium or magnesium sulfate. The drying agent is removed by filtration and the organic solvent is removed under reduced pressure to give product. The mono- or di-alkyl amide isophthalate/methylisophthalate is used as such in the next reaction with the (S,R)-amine (VIII) to produce the (S,R)-compound (X).

When it is desired to produce a primary amide, $R_{N-2}$ and $R_{N-3}$ are both —H, the following procedure is preferred. An ester, preferably the methyl ester of isophthalate or methyl 5-methyl-1,3-isophthalate is dissolved in a THF/DMF mixture. CDI is added at 20–25 degrees C. After five to thirty minutes, ammonia gas is bubbled into the mixture through a syringe needle for 1 hour. The mixture is cooled to 0 degrees C. for the duration of the hour. The reaction is left stirring under a balloon of ammonia overnight at 20–25 degrees C., after which time the reaction mixture is partitioned between saturated aqueous ammonium chloride and a water immiscible solvent such as ethyl acetate, for example. The phases are separated and the aqueous phase is extracted twice more with ethyl acetate. The organic extracts are washed with saturated aqueous solutions of bicarbonate and saline and dried over anhydrous sodium or magnesium sulfate. Filtration of the drying agent and removal of solvents under reduced pressure gives the ester of the desired isophthalic acid or the isophthalic acid acylating agent (IX). Purification of the (methyl) ester can be achieved via chromatography on silica gel eluting with isopropanol/chloroform. The isophthalate ester or methylisophthalate ester of the primary amide is then treated with an aqueous solution of base such as lithium hydroxide in a minimum amount of THF/methanol/water and stirred overnight at 20–25 degrees C. after which time the solvents are removed under reduced pressure and subsequently partitioned between water and a water immiscible solvent such as ethyl acetate, for example.

If emulsions prohibit separation of the two phases, a small amount of saline is added to aid in separation. The aqueous phase is separated and extracted once more with a water immiscible solvent such as ethyl acetate, for example. The aqueous phase is then acidified with concentrated acid, preferably hydrochloric until $pH \leq 3$. The mixture obtained is then extracted three times with ethyl acetate. These combined organic extracts are dried over anhydrous sodium or magnesium sulfate. The drying agent is removed by filtration and the organic solvent removed under reduced pressure to give product. The amide isophthalic acid is used as such in the next reaction with (VIII) to produce (X).

When it is desired that the amine be cyclized to be a group such as morpholinyl, piperazinyl, piperidinyl, and pyrrolidinyl, etc. the following procedure can be followed. An ester, preferably the methyl ester of isophthalic acid or methyl 5-methyl-1,3-isophthalate is dissolved in dry methylene chloride and three drops of DMF are added. The mixture is cooled to 0 degrees C. and then oxalyl chloride is added. The mixture is stirred at 0 degrees C. for 30 minutes to two hours after which the solvents are removed under reduced pressure. The acid chloride is left under vacuum overnight. The crude acid chloride is dissolved in dry methylene and cooled to 0 degrees C. before the addition of the cyclic amine and a tertiary amine base such as N-methyl piperidine, for example. The reaction mixture is stirred at 0 degrees C. for 1 to 6 hours before the solvents are removed under reduced pressure. The residue is diluted with water and a water immiscible solvent such as ethyl acetate, for example, and the phases are separated. The aqueous phase is extracted twice more with a water immiscible solvent such as ethyl acetate, for example, and the combined organic extracts are washed with saturated aqueous bicarbonate and dried over anhydrous sodium or magnesium sulfate. Filtration of the drying agent and removal of solvents under reduced pressure gives the product cyclic amide. The cyclic amide is then treated with an aqueous base such as lithium hydroxide in a minimum amount of THF/methanol/water and stirred overnight at 20–25 degrees C., after which time the solvents are removed under reduced pressure and the residue is subsequently partitioned between water and a water immiscible solvent such as ethyl acetate, for example. The aqueous phase is extracted once more with ethyl acetate. Removal of water from the aqueous phase under reduced pressure gives the desired cyclic amide product (IX).

When it is desired that $R_{N-1}$ is carbocycle, for example but not limited to, cyclohexane, one may then start with a suitably functionalized dimethyl isophthalate. Via methods taught in the literature (Meyers, A. I., Org. Syn., 1971, 51, 103) one may reduce the six-membered ring with reducing agents such as rhodium (5%) on alumina in the presence of acetic acid and methanol under a hydrogen atmosphere to afford the corresponding dimethyl cyclohexane dicarboxylate.

SCHEME D sets forth an alternative processes for production of the (S,R)-compound (X) from the (S,R)-protected azide (XII), which is produced from the corresponding epoxide (V) in SCHEME C. The amino protecting group is removed to produce the corresponding unprotected azide (XIV) by methods previously described in SCHEME A for the conversion of (S,R)-protected alcohol (VII) to the corresponding (S,R)-amine (VIII). The (S,R)-unprotected azide (XIV) is then acylated on nitrogen to produce the corresponding (S,R)-azide (XV). Next, the azide functionality is reduced as previously discussed for the conversion of the (S,R)-protected azide (XII) to the corresponding (S,R)-protected amine (XIII) to give the (S,R)-free amine (XVI). Last, the (S,R)-free amine (XVI) is transformed to the corresponding (S,R)-compound (X) by nitrogen alkylation with a compound of the formula $R_C$—$X_3$ to give the corresponding (S,R)-compound (X). X3 is an appropriate leaving group, such as but not limited to, —Cl, —Br, —I, —O-mesylate, —O-tosylate, O-triflate, etc. $X_3$ may also be an aldehyde; the corresponding coupling with (XVI) via the well known reductive amination procedure gives the (S,R)-compound (X).

Carbocylic amide forming agents (IX) are also provided for by the invention. For example, the carbocyclic amide forming agents of the formula R'—CH—C(R")(R"')—CH—$X_N$—OH (IX) are readily prepared from known starting materials by methods disclosed in the literature and known to those skilled in the art, for example, J. Med. Chem. 1998, 41, 1581, J. Org. Chem. 2000, 65, 1305. It is also understood that instead of the carboxylic acid, one may readily employ an acyl halide, where the halide is preferably chloride, or a suitable group to produce a mixed anhydride; these methods are taught by SCHEME A. For additional guidance on the formation of carbocyles and preferably cyclopropanes, one may consult M. P. Doyle; M. A. McKervery; T. Ye in *Modern Catalytic Methods for Organic Synthesis with Diazo Compounds From Cyclopropanes to Ylides*, Wiley-Interscience, 1998, pp. 163–279.

SCHEMES E, F, G, and H disclose various methods to produce the $R_N$ portion of the compound (X) where the phenyl ring of the $R_N$ 1,3-disubstituted moiety, —CO-phenyl-CO—, is further substituted in the 5-position with various groups such as amides, nitrites, halides, and amines. These compounds are prepared by methods known to those skilled in the art. The process chemistry of each reaction is known to those skilled in the art. What is novel here is the order of each process step and/or the specific reactants used. One skilled in the art knowing the desired product would know at least one method to prepare the desired product by using known starting materials. Hence, the following discussion is not necessary but is set forth to further aid those interested in preparing the compounds of the invention.

SCHEME E discloses alternate processes for the transformation of the aniline (XVII) or acid ester (XVIII) to the corresponding acid (IX-XXIII). One process begins with the commercially available aniline (XVII) where $R_{N-a}$ is preferably —H, $C_1$–$C_4$ alkyl or benzyl. The aniline (XVII) is treated with a diazotizing reagent such as sodium or potassium nitrite in mineral acid, followed by a halogen source such as copper (II) halide or alkali metal halide, or by an organic diazotizing reagent such as an alkyl nitrite in a strong acid such as acetic acid or trifluoroacetic acid, followed by a halide source such as copper (II) halide or alkali metal halide to give the halo acid ester (XIX) where $R_{N-b}$ is —Cl, —Br or —I. Alternatively, the acid ester (XVIII) is treated with N-halosuccinimide and trifluoromethanesulfonic acid to give the halo acid ester (XIX).

The halo acid ester (XIX) is then converted to the ester amide (XXI) using a primary or secondary amine of the formula H-$NR_{Nalpha}R_{Nbeta}$ (AMINE) where $R_{Nalpha}$ and $R_{Nbeta}$ are the same or different or can be cyclized. These groups, $R_{Nalpha}$ and $R_{Nbeta}$, become part of the compound (X) and are included in the definition of $R_N$. $R_N$ includes $R_{N-1}$—$X_N$— where the linker, —$X_N$—, includes (A) —CO— and $R_{N-1}$ includes $R_{N-aryl}$. $R_{N-aryl}$ is defined to include phenyl (-phenyl) optionally substituted with two amides:

—CO—$NR_{N-2}R_{N-3}$ and —CO—$R_{N-4}$.

$R_{Nalpha}$ and $R_{Nbeta}$ include both the non-cyclic amides, —CO—$NR_{N-2}R_{N-3}$ and the cyclic amides-CO—$R_{N-4}$ where $R_{N-2}$, $R_{N-3}$ and $R_{N-4}$ are as defined in the claims. Alternatively, the halo acid ester (XIX) is converted to the dihalo ester (XX) by methods known to those skilled in the art. $R_{N-C}$ includes —Cl and —F. The dihalo ester (XX) is treated with a primary or secondary amine of the formula H—$NR_{Nalpha}R_{Nbeta}$ (AMINE) to give the ester amide (XXI). The ester amide (XXI) is then reacted with an AMINE in a carbon monoxide atmosphere in the presence of a palladium catalyst using methods such as those reviewed by Heck, (Palladium Reagents in Organic Synthesis, 1985 pp. 342–365). to give the diamide (XXII). Hydrolysis of the ester portion of the diamide (XXII) using methods well known to those skilled in the art gives the diamide acid (XXIII).

In Scheme F, an alternate route to intermediate diamide (XXII) is shown starting from commercially available phenol (XXIV). The phenol (XXIV) is treated with a trifluoromethanesulfonating reagent such as trifluoromethanesulfonic anhydride to give triflate (XXV). The triflate (XXV) is reacted under the conditions of palladium catalysis in the presence of carbon monoxide and an amine of the formula H—NR$_{Nalpha}$R$_{Nbeta}$ (AMINE) as for the conversion of the ester amide (XXI) to the corresponding diamide (XXII) in SCHEME E to give the diester (XXVI). The diester (XXVI) is hydrolyzed using methods known to those skilled in the art to give the monoacid (XXVII). The monoacid (XXVII) is then converted to the diamide (XXII) using conditions such as for the conversion of the halo acid ester (XIX) to the ester amide (XXI) in SCHEME E.

Scheme G discloses another route to prepare the ester amide (XXI). The reaction starts with commercially available nitro compound (XXVIII) which is condensed with an (AMINE) using coupling methods known to those skilled in the art to give the nitro amide (XXX). The nitro amide (XXX) can also be prepared by first treating the nitro compound (XXVIII) with reagents such as thionyl chloride, or DMF and oxalyl chloride, or other methods known to those skilled in the art to give the acid chloride (XXIX), which upon treatment with the (AMINE) gives the nitro amide (XXX). Reduction of the nitro amide (XXX) using methods known to those skilled in the art (see, for example, Smith and March, Advanced Organic Chemistry, 5$^{th}$ ed.) gives amide aniline (XXXI). The amide aniline (XXXI) is then treated with diazotizing reagents such as sodium or potassium nitrite in mineral acid, followed by a halogen source such as copper (II) halide or alkali metal halide, or by an organic diazotizing reagent such as an alkyl nitrite in a strong acid such as acetic acid or trifluoroacetic acid, followed by a halide source such as copper (II) halide or alkali metal halide to give the ester amide (XXI).

Scheme H discloses a process to prepare the diamide acid (IX-XXIII) from the ester amide (XXI), where one of the amides is unsubstituted and is —CO—NH$_2$. This process starts from either the ester or the acid, for example the ester amide (XXI) is treated with copper (I) cyanide (CuCN) in N-methylpyrrolidinone or DMF, preferably N-methylpyrrolidinone, to give the nitrile (XXXII). The nitrile (XXXII) is converted to the primary amide (XXXIII) using urea-hydrogen peroxide complex (see *Synth. Commun*. (1993) 3149) or the methods of Synth. Commun. (1990) 1445, *Synth. Commun*. (1997) 3119, *J. Org. Chem*. (1992) 2521, *Tet. Lett*. (1996) 6555, *Ind. J. Chem*., Sect. B, (1999) 974, *Tet. Lett*. (1995) 3469, *Tet. Lett*. (1998) 3005, or others. When the ester amide (XXI) is in the form of an ester, an additional hydrolysis step using lithium hydroxide, sodium hydroxide, potassium hydroxide, barium hydroxide, or other hydrolysis methods known to those skilled in the art is used to convert the diamide ester (XXXIII) to the diamide acid (IX–XXIII).

SCHEME I discloses an alternate synthetic route from the protected alcohol (VII) to the compound (X) which uses a diprotected intermediate (XXXIV) whereby the nitrogen atom attached to the R$_C$ substituent is protected. Using the process of SCHEME I, the mono protected alcohol (VII) is reacted with a new protecting group to form the orthogonally protected (XXXIV). This is a common strategy employed in traditional peptide chemistry by those skilled in the art, see M. Bodansky, Principles of Peptide Chemistry. When the mono protected alcohol (VII) is protected with CBZ one skilled in the art could react it with either (BOC)$_2$O in methylene chloride or similar organic solvent or FMOC-Cl in methylene chloride or similar organic solvent to prepare orthogonally protected (XXXIV).

Then the CBZ group is removed by hydrogenation in the presence of a catalytic amount of palladium on carbon in an alcoholic solvent, such as methanol, or ethyl acetate, or with catalytic palladium on carbon in alcoholic solvents in the presence of ammonium formate as is known to those skilled in the art. This gives the R$_C$—N protected (XXXV).

Similarly, when the mono protected alcohol (VII) is protected as a BOC it can be reacted with CBZ-Cl under Schotten-Bauman conditions or CBZ-OSu in THF to prepare the reversed (XXXIV). Then the BOC group can be cleaved with hydrochloric acid (4 N) in methanol, ethanol or dioxane or with trifluoroacetic acid in methylene chloride or by other methods such as those described in The Peptides, Analysis, Synthesis, Biology, Vol. 3, Ed. E. Gross and J. Meienhofer (1981) to liberate the CBZ R$_C$—N protected (XXXV). This functional group manipulation gives various permutations in the sequence (VII) to (XXXIV) to (XXXV) as is apparent to one skilled in the art.

When the appropriately R$_C$—N protected compound (XXXV) is reacted with the amide forming agent (IX), in acid form, under standard peptide coupling conditions, for example, EDC/HOBt in methylene chloride or DMF or a previously activated acid, (R$_N$)$_2$O gives the corresponding R$_N$-substituted R$_C$—N protected (XXXVI). Simple de-protection of the R$_N$-substituted R$_C$—N protected (XXXVI) then gives the desired compound (X). Thus when the R$_N$-substituted R$_C$—N protected (XXXVI) is protected with BOC, treatment with hydrochloric acid (4N) in dioxane or the other reagents discussed above gives the compound (X). When the R$_N$-substituted R$_C$—N protected (XXXVI) is protected with CBZ, treatment with hydrogen from 10–50 psi in alcoholic solvents, such as methanol with a catalytic amount of palladium on carbon will give, after work-up, the desired compound (X). Similarly when the R$_N$-substituted R$_C$—N protected (XXXVI) is protected with FMOC, treatment with a secondary amine, preferably either piperidine (10%) or diethylamine (10%) in an inert solvent such as, for example, methylene chloride will give after work up the desired compound (X).

SCHEME J discloses a process to prepare compounds where the phenyl ring of the R$_N$ substituent of —CO-phenyl-CO— is substituted with a sulfonamide group in the 5-position. The process starts with the halo amide ester (XXI, SCHEME E) which is reacted with sodium nitrite, sulfur dioxide, copper chloride (II) and acetic acid by the method disclosed in *J. Med. Chem.*, 42, 3797 (1999) to prepare the sulfonyl chloride (XXXVII). The sulfonyl chloride (XXXVII) is then reacted with AMINE, as defined above, by methods known to those skilled in the art to produce the corresponding sulfonamide (XXXVIII). Last the sulfonamide (XXXVIII) is transformed to the corresponding sulfonamide acid (XXXIX) by methods known to those skilled in the art such as using lithium hydroxide, sodium hydroxide, potassium hydroxide, barium hydroxide, or other hydrolysis methods known to those skilled in the art.

SCHEME K discloses how to prepare the R$_N$ substituents where R$_N$ is R$_{N-1}$—X$_N$—, where X$_N$ is —CO— and R$_{N-1}$ is R$_{N-aryl}$ where R$_{N-aryl}$ is phenyl substituted with one alkyl group and one —CO—NR$_{N-2}$R$_{N-3}$ or —CO—R$_{N-4}$. See the discussion above for SCHEME E regarding the amine, H—NR$_{Nalpha}$R$_{Nbeta}$ (AMINE), used to form the amide R$_N$ substituents. The process starts with the halo amide ester (XXI) which is then reacted with an alkyl boronic acid having the desired alkyl group in the presence of a palladium catalyst such as Pd(PPh$_3$)Cl$_2$ using the general method described in *J. Med. Chem.*, 4288 (2000). The alkyl boronic acids are commercially available or can be prepared by the process described in *J. Am. Chem. Soc.*, 60, 105 (1938). It is preferred that R$_N$ b is bromo. This step produces the alkyl ester (XL) which is then hydrolyzed by means known to those skilled in the art to produce the desired alkyl acid (XLI).

SCHEME L discloses a process to prepare the amide forming agent (IX-XLVII) where the R$_N$ substituent is R$_{N-1}$—X$_N$—, where the linker, —X$_N$— is —CO—, where R$_{N-1}$ is R$_{N-aryl}$ and where R$_{N-aryl}$ is phenyl (-phenyl) substituted with groups: C$_1$–C$_6$ alkyl, optionally substituted with one, two or three substituents selected from the group consisting of C$_1$–C$_3$ alkyl, —F, —Cl, —Br, —I, —OH, —SH, —C≡N, —CF$_3$, C$_1$–C$_3$ alkoxy, and —NR$_{1-a}$R$_{1-b}$, where R$_{1-a}$ and R$_{1-b}$ are as defined above, and —N(—H and C$_1$–C$_3$ alkyl)—CO—R$_{N-5}$.

This specific amide forming agent, (IX-XLVII) is prepared by starting with the phenyl nitro compound (XLII) which is reduced to the corresponding phenyl nitro hydroxy compound (XLIII) using borane-methyl sulfide or borane in THF. The phenyl nitro hydroxy compound (XLIII) is reduced to the corresponding phenyl amino hydroxy compound (XLIV) using hydrogen and palladium catalyst as is known to those skilled in the art. The phenyl amino hydroxy compound (XLIV) is reacted with an aldehyde in the presence of a reducing agent such as sodium cyanoborohydride or sodium triacetoxyborohydride to give the phenyl substituted amino hydroxy compound (XLV). The phenyl substituted amino hydroxy compound (XLV) is acylated with an acid chloride or acid anhydride by methods known to those skilled in the art to give the phenyl disubstituted amino hydroxy compound (XLVI). The phenyl disubstituted amino hydroxy compound (XLVI) is hydrolyzed using an alkali hydroxide, followed by acidification, to give the amide forming agent (IX-XLVII). The amide forming agent (XLVII) is then coupled with amine (VIII) using methods known to those skilled in the art and methods previously discussed, such as with diethyl cyanophosphonate, to give the compound (X). Further treatment of the compound (X) with diethyl cyanophosphonate gives the compound where the hydroxyalkyl substituent on the phenyl ring has a phosphate substituent.

SCHEME M discloses a process to prepare amide forming agents (IX-L) where the where the R$_N$ substituent is R$_{N-1}$—X$_N$—, where the linker, —X$_N$— is —CO—, where R$_{N-1}$ is R$_{N-aryl}$, and where R$_{N-aryl}$ is phenyl (-phenyl) substituted with two groups. The first substituent at what is usually identified as position "5-" can be either:

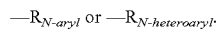

The second substituent at what is usually identified as position "3-" can be either:

—CO—NR$_{N-2}$R$_{N-3}$ or —CO—R$_{N-4}$.

R$_{Nalpha}$ and R$_{Nbeta}$ include both the non-cyclic amides, —CO—NR$_{N-2}$R$_{N-3}$, and the cyclic amides, —CO—R$_{N-4}$, where R$_{N-2}$, R$_{N-3}$ and R$_{N-4}$ are as defined in the claims. The process starts with the trisubstituted phenyl compound (XLVIII) where R$_{N-d}$ is —Cl, —Br, —I or —O-triflate. Treatment with an aryl or heteroaryl boronic acid or heteroaryl or aryl boronic acid ester such as (aryl or heteroaryl)—B(OH)$_2$ or (aryl or heteroaryl)—B(OR$^a$)(OR$^b$) (where R$^a$ and R$^b$ are lower alkyl, ie. C$_1$–C$_6$, or taken together, R$^a$ and R$^b$ are lower alkylene, ie. C$_2$–C$_{12}$) in the presence of a metal catalyst with or without a base in an inert solvent yields (XLIX).

Metal catalysts in these transformations include, but are not limited to, salts or phosphine complexes of Cu, Pd, or Ni (eg. Cu(OAc)$_2$, PdCl$_2$(PPh$_3$)$_2$, NiCl$_2$(PPh$_3$)$_2$).

Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (preferably sodium methoxide or sodium ethoxide), alkaline earth metal hydrides, alkali metal dialkylamides (preferably lithium diisopropylamide), alkali metal bis(trialkylsilyl)amides (preferably sodium bis(trimethylsilyl)amide), trialkyl amines (preferably diisopropylethylamine or triethylamine) or aromatic amines (preferably pyridine).

Inert solvents may include, but are not limited to, acetonitrile, dialkyl ethers (preferably diethyl ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloalkanes (preferably methylene chloride).

Preferred reaction temperatures range from room temperature up to the boiling point of the solvent employed. The reactions may be run in conventional glassware or in one of many commercially available parallel synthesizer units. Non-commercially available boronic acids or boronic acid esters may be obtained from the corresponding optionally substituted aryl halide as described in *Tetrahedron*, 50, 979–988 (1994). Intermediate (XLIX) is then hydrolyzed using alkali metal hydroxide, for example lithium, sodium or potassium hydroxide, followed by acidification, to give aryl or heteroaryl coupled acids (IX-L). Alternatively, as described in *Tetrahedron*, 50, 979–988 (1994), one may convert the R$_{N-d}$ to the corresponding boronic acid or boronic acid ester (OH)$_2$B— or (OR$^a$)(OR$^b$)B— and obtain the same products set forth above by treating with a suitable aryl or heteroaryl halide or triflate SCHEME N discloses a process to prepare amide forming agents (IX-LII) where the where the R$_N$ substituent is R$_{N-1}$—X$_N$— where the linker, —X$_N$— is —CO—, where R$_{N-1}$ is R$_{N-aryl}$ and where R$_{N-aryl}$ is phenyl. The first substituent at what is usually identified as position "5-" is —C≡C—R. The second substituent at what is usually identified as position "3-" can be either —CO—NR$_{N-2}$R$_{N-3}$ or —CO—R$_{N-4}$. The halo ester (XXI) is treated with a mixture of PdCl$_2$(Pphenyl$_3$)$_2$ and trimethylsilyl acetylene, using methods known to those skilled in the art, to give acetylene ester (LI). Acetylene ester (LI) is then hydrolyzed using alkali metal hydroxide, followed by acidification, to give acetylene acid (IX-LII).

SCHEMES O and O' disclose processes to prepare amide forming agents (IX-LX) and (IX-LXIII) with an extended methylene group where the R$_N$ substituent is R$_{N-1}$—X$_N$— where the linker, —X$_N$— is —CO—, where R$_{N-1}$ is R$_{N-aryl}$ and where R$_{N-aryl}$ is phenyl (-phenyl) substituted with two groups. The substituent at what is usually identified as position "3-" can be either —CO—NR$_{N-2}$R$_{N-3}$ or —CO—R$_{N-4}$. In the process of SCHEME O, the substituent at the 5-position is —CH$_2$CO—NH$_2$ and in the process of SCHEME O', the substituent at the 5-position is —$CH_2C \equiv N$. The starting diester acid (LIII) is reduced with borane in solvents such as THF to give the corresponding diester alcohol (LIV). The diester alcohol (LIV) is converted to the corresponding diester bromo compound (LV) using a brominating agent such as $PBr_3$, $CBr_4$, or other halogenating agent such as are known to those skilled in the art. The bromine of the diester bromo compound (LV) is then displaced with cyanide to give the corresponding nitrile (LVI). In SCHEME O', the nitrile (LVI) is then hydrolyzed to the corresponding cyano ester (LXI). The cyano ester (LXI) is then coupled with H—$NR_{N\alpha}R_{N\beta}$ (AMINE), as previously described using methods known to those skilled in the art to give the corresponding cyano amide (LXII). The cyano amide (LXII) is then hydrolyzed to the corresponding cyano acid (IX-LXIII) which is in turn coupled with amine (VIII) to give the compound (X). When the substituent on the extended methyl group is —CO—$NH_2$, the process of SCHEME O is used. There the nitrile (LVI) is converted to the corresponding diester amine (LVII) by methods known to those skilled in the art. The next steps are the same as for SCHEME O' where the diester amide (LVII) is hydrolyzed to the corresponding ester amine (LVIII) which is then converted to the corresponding diamide ester (LIX) which is hydrolyzed to the corresponding diamide acid (IX-LX). The diamide acid (IX-XL) is then coupled with the appropriate amine (VIII) to produce the desired substituted amide (X).

SCHEME P discloses a process to prepare amide forming agents (IX-LXVII) with an extended hydroxymethylene group where the $R_N$ substituent is $R_{N-1}$—$X_N$— where the linker, —$X_N$— is —CO—, where the $R_{N-1}$ is $R_{N-aryl}$, where $R_{N-aryl}$ is phenyl (-phenyl) substituted with two groups. The substituent at what is usually identified as position "3-" can be either -CO—$NR_{N-2}R_{N-3}$ or —CO—$R_{N-4}$. The process begins with a halo amide (LXIV), preferably iodo, which is converted to the corresponding aldehyde (LXV) and then to the corresponding alcohol (LXVI) by the method described in Synth. Commun. 28, 4270 (1998), optionally with variations known to those skilled in the art. Hydrolysis of the alcohol (LXVI) using alkali hydroxides, followed by acidification, gives the desired hydroxy acid (IX-LXVII). The hydroxy acid (IX-LXVII) is then coupled with the appropriate amine (VIII) to give the desired compound (X).

SCHEME Q discloses a process to prepare amide forming agents (IX-LXXII) with an alkyl group or a halogen atom or an amino group at the 5-position where the $R_N$ substituent is $R_{N-1}$—$X_N$— where the linker, —$X_N$— is —CO—, where the $R_{N-1}$ is $R_{N-aryl}$, where $R_{N-aryl}$ is phenyl (-phenyl) substituted with two groups. The substituent at what is usually identified as position "3-" can be either —CO—$NR_{N-2}R_{N-3}$ or —CO—$R_{N-4}$. The process begins with an appropriately 5-substituted diacid (LXVIII) which is esterified by methods known to those skilled in the art to give the corresponding diester (LXIX). The diester (LXIX) is then hydrolyzed using alkali hydroxides, followed by acidification, to give the corresponding monoacid (LXX). Alternatively, the monoacid (LXX) can be produced directly from the diacid (LXVIII) by known methods. The monoacid (LXX) is then coupled with H—$NR_{Nalpha}R_{Nbeta}$ (AMINE) to give the corresponding amide ester (LXXI). The amide ester (LXXI) is then hydrolyzed using alkali hydroxides, followed by acidification, to give the corresponding acid amide (IX-LXXII).

SCHEME R discloses a general process to prepare the amide forming agents (IX-LXXVII) which, for example, have an alkyl group at what is known as the 5-position and a ketone at the 3-position. These acids (IX-LXXVII) are formed by starting with the acid (LXXIII) which is converted to the corresponding acid halide (LXXIV) using methods known to those skilled in the art. The acid halide (LXXIV) is preferrably the acid chloride. The acid halide (LXXIV) in the presence of copper (I) bromide and tetrahydrofuran and at temperatures ranging from −78 degrees C. to 0 degrees C. is treated with a Grignard reagent (aryl-Mg—X, or alkyl-Mg—X, where X is —Cl or —Br) to give the ketone esters (LXXVI and LXXVI'). Many Grignard reagents are available for purchase; others are prepared by methods known to those skilled in the art. An alternative method for preparing the ketone esters (LXXVI, LXXVI') is to prepare the Weinreb amide (LXXV), either from the acid (LXXIII) directly or by way of acid halide (LXXIV) followed by treatment with N,O-dimethylhydroxylamine to give Weinreb amide (LXXV) and then treating the Weinreb amide (LXXV) with a Grignard reagent, by methods known to those skilled in the art. The ketone esters (LXXVI, LXXVI') are then hydrolyzed using alkali hydroxides, followed by acidification, to give the ketone acids (LXXVII, LXXVII').

SCHEME S discloses various methods to modify the $R_N$ portion of the compound (X) where the phenyl ring of the $R_N$ moiety is further substituted in the 3-position with various groups such as aryl and heteroaryl. These compounds are prepared by methods known to those skilled in the art. The process chemistry of each reaction is known to those skilled in the art. What is novel here is the order of each process step and/or the specific reactants used. One skilled in the art knowing the desired product would know at least one method to prepare the desired product by using known starting materials. Hence, the following discussion is not necessary but is set forth to further aid those interested in preparing the compounds of the invention.

SCHEME S sets forth a general method used in the present invention to prepare the compounds (X) where $R_N = R_{N-aryl} - R_{N-aryl} - X_N$ or $R_{N-heteroaryl} - R_{N-aryl} - X_N$. Treatment of the (S,R)-amine (VIII) with amide forming agents (IX) according to the methods set forth above where for SCHEME S, $R_{N-1}$ is Br—$R_{N-aryl}$ generates the corresponding (S,R)-compound (X) where $R_N$ is Br—$N_{R-aryl}$—$X_N$. Further treatment with an aryl boronic acid or aryl boronic acid ester such as (aryl or heteroaryl)—$B(OH)_2$ or (aryl or heteroaryl)—$B(OR^a)(OR^b)$ (where $R^a$ and $R^b$ are lower alkyl, ie. $C_1$–$C_6$, or taken together, $R^a$ and $R^b$ are lower alkylene, ie. $C_2$–$C_{12}$) in the presence of a metal catalyst with or without a base in an inert solvent yields the (S,R)-compound (X) where $R_N$ is $N_{R-aryl} - N_{R-aryl} - X_N$ or $R_{N-heteroaryl} - R_{N-aryl} - X_N$.

Metal catalysts in these transformations include, but are not limited to, salts or phosphine complexes of Cu, Pd, or Ni (eg. $Cu(OAc)_2$, $PdCl_2 (PPh_3)_2$, $NiCl_2 (PPh_3)_2$).

Bases may include, but are not limited to, alkaline earth metal carbonates, alkaline earth metal bicarbonates, alkaline earth metal hydroxides, alkali metal carbonates, alkali metal bicarbonates, alkali metal hydroxides, alkali metal hydrides (preferably sodium hydride), alkali metal alkoxides (preferably sodium methoxide or sodium ethoxide), alkaline earth metal hydrides, alkali metal dialkylamides (preferably lithium diisopropylamide), alkali metal bis(trialkylsilyl)amides (preferably sodium bis(trimethylsilyl)amide), trialkyl amines (preferably diisopropylethylamine or triethylamine) or aromatic amines (preferably pyridine).

Inert solvents may include, but are not limited to, acetonitrile, dialkyl ethers (preferably diethyl ether), cyclic ethers (preferably tetrahydrofuran or 1,4-dioxane), N,N-dialkylacetamides (preferably dimethylacetamide), N,N-dialkylformamides (preferably dimethylformamide), dialkylsulfoxides (preferably dimethylsulfoxide), aromatic hydrocarbons (preferably benzene or toluene) or haloalkanes (preferably methylene chloride).

Preferred reaction temperatures range from room temperature up to the boiling point of the solvent employed. The reactions may be run in conventional glassware or in one of many commercially available parallel synthesizer units. Non-commercially available boronic acids or boronic acid esters may be obtained from the corresponding optionally substituted aryl halide as described in *Tetrahedron*, 50, 979–988 (1994).

Where the above chemistry is incompatible with other functionality present in the (S,R)-compound (X) where $R_N$ is Br—$N_{R\text{-}aryl}$—$X_N$, then one skilled in the art will readily understand that an alternative sequence of coupling steps is required. For example, treatment of an appropriately substituted amide forming agent (IX) $R_{N\text{-}1}$—$X_N$—OH where $R_{N\text{-}1}$ is Br—$R_{N\text{-}aryl}$ with a boronic acid or boronic acid ester under the conditions described above will afford the appropriately substituted amide forming agent (IX) where $R_{N\text{-}1}$ is $N_{R\text{-}aryl}$—$N_{R\text{-}aryl}$ or $R_{N\text{-}heteroaryl}$—$R_{N\text{-}aryl}$. When the amide forming agent (IX) where $R_{N\text{-}1}$ is $N_{R\text{-}aryl}$—$N_{aryl}$ or $R_{N\text{-}heteroaryl}$—$R_{N\text{-}aryl}$ is treated with the (S,R)-amine (VIII), one then obtains the same compounds (X) set forth in SCHEME S.

The above examples for SCHEME S are not meant to limit the scope of the chemistry. In addition to bromine, a suitable group may include iodine or triflate. Alternatively, as described in *Tetrahedron*, 50, 979–988 (1994), one may convert the Br—$R_{N\text{-}aryl}$ to the corresponding boronic acid or boronic acid ester $(OH)_2B$—$R_{N\text{-}aryl}$ or $(OR^a)(OR^b)B$—$R_{N\text{-}aryl}$ and obtain the same products set forth above by treating with a suitable aryl or heteroaryl halide or triflate. Additionally, each —$R_{N\text{-}aryl}$ and —$R_{N\text{-}heteroaryl}$ are interchangeable at each occurrence in the chemistry described above.

SCHEME T discloses a process to prepare amide forming agents (IX-LXXIX) where the $R_N$ substituent is $R_{N\text{-}1}$—$X_N$—, where the linker, —$X_N$— is —CO—, where $R_{N\text{-}1}$ is $R_{N\text{-}aryl}$ and where $R_{N\text{-}aryl}$ is phenyl substituted with —CO—$NR_{Nalpha}R_{Nbeta}$ (AMINE) and with an amide of the formulas:

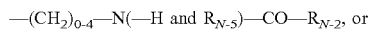

—$(CH_2)_{0\text{-}4}$—N(—H and $R_{N\text{-}5}$)—CO—$R_{N\text{-}2}$, or

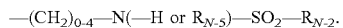

—$(CH_2)_{0\text{-}4}$—N(—H or $R_{N\text{-}5}$)—$SO_2$—$R_{N\text{-}2}$.

The process begins with the amide aniline (XXXI) which is reacted with the corresponding acid halide or sulfonyl halide, or acid anhydride or sulfonyl anhydride to produce the corresponding amide ester (LXXVIII). Suitable solvents include THF or dichloromethane at temperatures ranging from −78 degrees to 100 degrees C. The amide ester (LXXVIII) is then hydrolyzed to the corresponding amide acid (IX-LXXIX) by methods known to those skilled in the art. When the amide forming agent (IX-LXXIX) is reacted with the appropriate amine (VIII), the desired compound (X) is obtained.

SCHEME U discloses a general method for preparing various C-terminal amines (VI) as represented by the preparation of C-terminal amine (LXXXIV). Methods to prepare amines of this type are well understood using methods known to those skilled in the art, or one may consult the references: 1) *JACS*, 1970, 92, 3700, and 2) U.S. Pat. No. 4,351,842.

SCHEME V further discloses general methods for preparing various C-terminal amines (VI) as represented by the preparation of C-terminal amines (LXXXIX). Multiple examples of the heterocyclic carboxylic acids or acid chlorides are commercially available. Optionally, the carboxylic acid (LXXXV) may be converted to the acid chloride (LXXXVI) with reagents such as, but not limited to, thionyl chloride. Displacement with ammonia generates the common intermediate amides (LXXXVII) which are readily reduced to amines (VI-LXXXIX) using a variety of methods detailed previously. Alternatively, other heteroaryls are commercially available as the methyl halide (LXXXVIII) which are treated with ammonia to yield the title C-terminal amines (VI-LXXXVIII).

SCHEME W discloses general methods for preparing thiazolyl containing C-terminal amines as represented by the preparation of C-terminal amines (LXXXXI). The synthesis of the thiazoles is outlined in SCHEME W; these procedures are amply taught in the literature and are modified from the procedures outlined in: Mashraqui, SH; Keehn, P M. *J. Am. Chem. Soc.* 1982, 104, 4461–4465. The synthesis of substituted 5-aminomethylthiazoles (XCI) was achieved from 5-hydroxymethylthiazole (XC) by the procedure described in: Alterman et al. *J. Med. Chem.* 1998, 41, 3782–3792. All other thiazole analogs were transformed to the hydroxymethyl derivative using SCHEME W, and converted to the aminomethyl derivative by the Alterman procedure without notable changes.

SCHEME X discloses general methods for preparing isoxazolyl containing C-terminal amines as represented by the preparation of C-terminal amines (XCII). The synthesis of isoxazole derivatives was modified from the procedure in: Felman, S W et al. *J. Med. Chem.* 1992, 35, 1183–1190 and is readily understood by those skilled in the art making non-notable changes to achieve the title compounds. The substituted hydroxylamine precursors were synthesized using the procedure taught by Bousquet, E W. *Org. Synth. Coll. Vol II*, 313–315. Commercially available propargylamine may be protected using any number of methods known in the art (see: Greene, T W; Wuts, P G M. *Protective Groups in Organic Synthesis*, 3rd Ed. New York: John Wiley, 1999. Chapter 7.), preferred is a BOC protecting group. Substituted propargyl amines may be obtained by a number of methods commonly known in the art.

SCHEME Y discloses a general route to prepare hydroxyethylamines where one carbon atom of the peptide backbone, along with $R_2$ and $R_3$ form a ring. It is understood the present invention also allows for a heteroatom to be incorporated into the ring. In summary, the synthesis of compounds where $R_2$ and $R_3$ may form a ring proceeds from a suitably protected amino acid aldehyde and cycloalkyllithium species, both of which are commercially available or where known procedures for making such compounds are known in the art. The general procedure involved is also precedent in the literature, for example, see Klumpp, et al., *J. Am. Chem. Soc.*, 1979, 101, 7065, and it is intended that making non-critical variations, one may obtain the title compounds provided for by SCHEME Y. Treatment of a suitably protected amino acid aldehyde and cycloalkyllithium species affords alcohol (XCIII). These reactions are carried out in an inert solvent such as, for example, tetrahydrofuran or diethyl ether. Optimally the reactions are conducted at low temperatures, for example below 0° C. Carbonylation via the Klumpp procedure yields the acid (XCIV) which when exposed to Curtius or related procedures well known to those skilled in the art generates the primary amine (XCV). The primary amines (XCV) may be capped C-terminally via the conditions set forth in SCHEME C & D followed by nitrogen deprotection and capping N-terminally via the conditions set forth in SCHEME A.

SCHEME Z discloses a general route for preparing hydroxyethylamines wherein n=2. A metalloorganic nucleophilic halogenoethane derivative, for example the Grignard reagent of a bromoethane, is coupled to an aziridine derivative via a coupling reagent, for example cuprous bromide dimethyl sulfode, wherein the aziridine derivative has the ring nitrogen atom substituted with one of the protecting groups known to those skilled in the art, for example tBOC, and one of the ring carbon atoms substituted with an optionally substituted 1,3-dioxolan. The product is isolated with one of the methods known in the art, for example via absorption on DOWEX resin, and the acetal moiety of the dioxolan is removed. If the step of acetal group removal results in the deprotection of the nitrogen atom originally present on the aziridine ring, the nitrogen atom is re-.protected. The resulting dihydroxy-substituted product is reacted with one equivalent of a chlorosulfide derivative, for example tosyl chloride, yielding a monotosylated derivative that cyclizes to the epoxide derivative when treated with a base. The epoxide is then reacted according to one of the procedures outlined above to yield the desired product. Those skilled in the art will recognize that this synthesis may be carried out in a stereospecific or a racemate-yielding fashion.

Compounds of formula X where W is sulfur can be prepared according to the procedures outlined in Scheme FF below.

Scheme FF

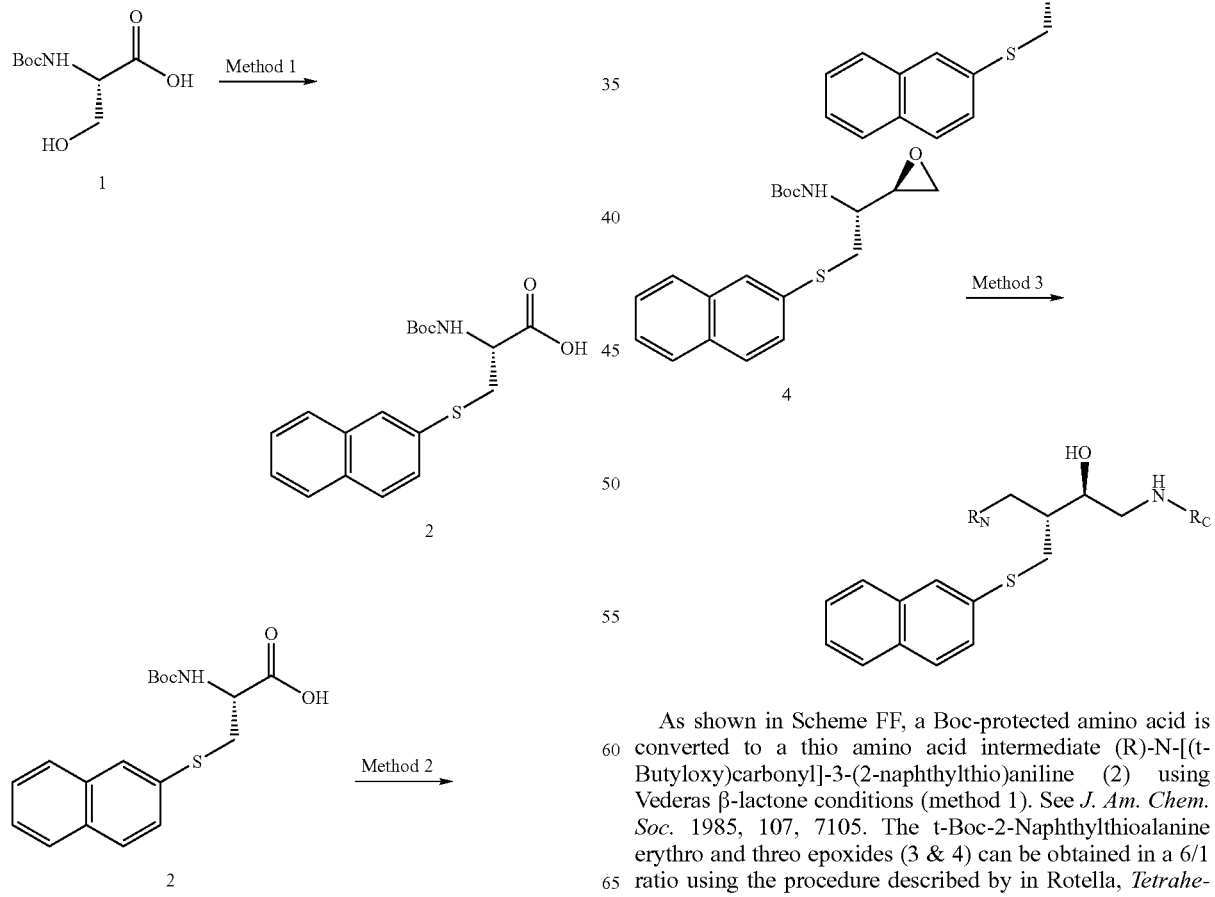

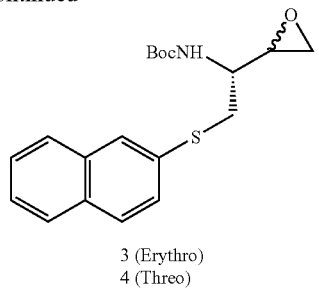

3 (Erythro)
4 (Threo)

Scheme GG

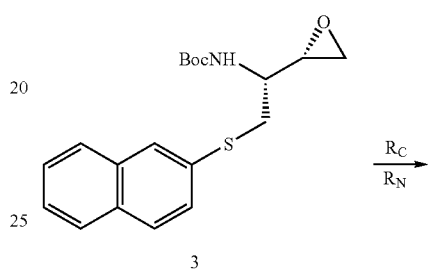

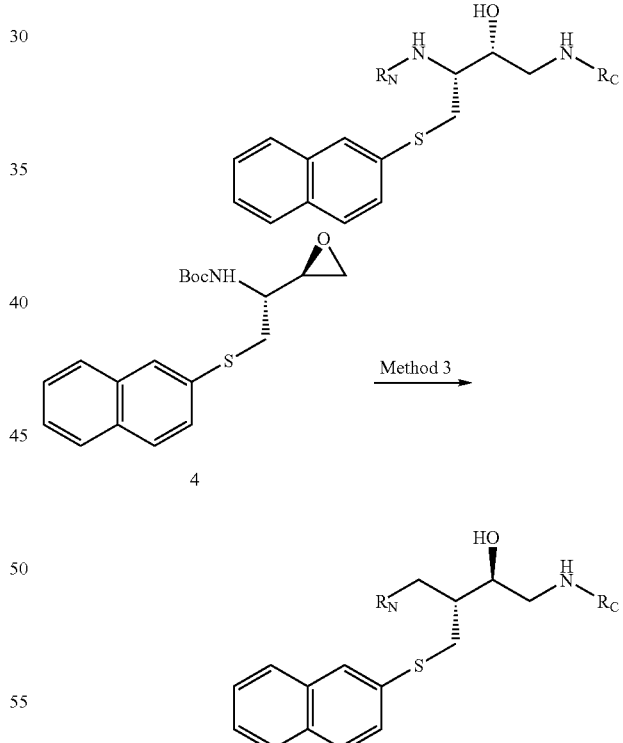

As shown in Scheme FF, a Boc-protected amino acid is converted to a thio amino acid intermediate (R)-N-[(t-Butyloxy)carbonyl]-3-(2-naphthylthio)aniline (2) using Vederas β-lactone conditions (method 1). See *J. Am. Chem. Soc.* 1985, 107, 7105. The t-Boc-2-Naphthylthioalanine erythro and threo epoxides (3 & 4) can be obtained in a 6/1 ratio using the procedure described by in Rotella, *Tetrahedron Letters* 1995, 36, 5453–5456 for the synthesis of Boc-phenylalanine erythro epoxides (method 2).

Subsequent epoxide opening (Scheme GG) with, for example, m-iodobenzylamine, followed by cleavage of the Boc protecting group and subsequent coupling of resulting acid as discussed elswhere herein produce desired compounds of Formula X where W is sulfur.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

A therapeutically effective amount is defined as an amount effective to reduce or lessen at least one symptom of the disease being treated or to reduce or delay onset of one or more clinical markers or symptoms of the disease.

The present invention provides compounds, compositions, and methods for inhibiting beta-secretase enzyme activity and A beta peptide production. Inhibition of beta-secretase enzyme activity halts or reduces the production of A beta from APP and reduces or eliminates the formation of beta-amyloid deposits in the brain.

The present invention may be better understood with reference to the following examples. These examples are intended to be representative of specific embodiments of the invention, and are not intended as limiting the scope of the invention.

EXAMPLES

The following detailed examples describe how to prepare the various compounds and/or perform the various processes of the invention and are to be construed as merely illustrative, and not limitations of the preceding disclosure in any way whatsoever. Those skilled in the art will recognize appropriate variations from the procedures both as to reactants and as to reaction conditions and techniques.

These compounds described herein are named using IUPAC Name Batch 4.5, commercially available from Advanced Chemistry Development Inc.

Definitions

All temperatures are in degrees Celsius.
TLC refers to thin-layer chromatography.
psi refers to pounds/in$^2$.
HPLC refers to high pressure liquid chromatography.
THF refers to tetrahydrofuran.
DMF refers to dimethylformamide.
EDC refers to ethyl-1-(3-dimethylaminopropyl)carbodiimide or 1-(3-dimethylaminopropyl)-3-ethylcarbodiimide hydrochloride.
HOBt refers to 1-hydroxy benzotriazole hydrate.
NMM refers to N-methylmorpholine.
NBS refers to N-bromosuccinimide.
TEA refers to triethylamine.
BOC refers to 1,1-dimethylethoxy carbonyl or t-butoxycarbonyl, —CO—O—C(CH$_3$)$_3$.
CBZ refers to benzyloxycarbonyl, —CO—O—CH$_2$-ϕ.
FMOC refers to 9-fluorenylmethyl carbonate.
TFA refers to trifluoroacetic acid, CF$_3$—COOH.
CDI refers to 1,1'-carbonyldiimidazole.
Saline refers to an aqueous saturated sodium chloride solution.
Chromatography (column and flash chromatography) refers to purification/separation of compounds expressed as (support, eluent). It is understood that the appropriate fractions are pooled and concentrated to give the desired compound(s).

CMR refers to C-13 magnetic resonance spectroscopy, chemical shifts are reported in ppm (δ) downfield from TMS.
NMR refers to nuclear (proton) magnetic resonance spectroscopy, chemical shifts are reported in ppm (d) downfield from TMS.
IR refers to infrared spectroscopy.
-phenyl refers to phenyl (C$_6$H$_5$).
MS refers to mass spectrometry expressed as m/e, m/z or mass/charge unit. MH$^+$ refers to the positive ion of a parent plus a hydrogen atom. EI refers to electron impact. CI refers to chemical ionization. FAB refers to fast atom bombardment.
HRMS refers to high resolution mass spectrometry.
Ether refers to diethyl ether.
When solvent pairs are used, the ratios of solvents used are volume/volume (v/v).
When the solubility of a solid in a solvent is used the ratio of the solid to the solvent is weight/volume (wt/v).
BOP refers to benzotriazol-1-yloxy-tris(dimethylamino) phosphonium hexafluorophosphate.
TBDMSCl refers to t-butyldimethylsilyl chloride.
TBDMSOTf refers to t-butyldimethylsilyl trifluosulfonic acid ester.
Trisomy 21 refers to Down's Syndrome.
DBU refers to 1,8-diazabicyclo[5.4.0]undec-7-ene.
EDC refers to 1-[3-(dimethylamino)propyl]-3-ethyl carbodiimide.
DIPMAP refers to (R,R)-1,2-bis[(o-methoxyphenyl)-phenylphosphinp]ethane.
MeDuPhos refers to 1,2-bis ((2S,5S)-2,5-dimethylphospholano)benzene.
EtDuPhos refers to 1,2-bis ((2S,5S)-2,5-dimethylphospholano)benzene.
Binaphane refers to (S,S)-1,2-Bis{S)-4,5-dihydro-3H-dinaphtho[2,1-c:1',2'-e]phosphepino}benzene.
f-Binaphane refers to (R,R)-1,1'-Bis{R)-4,5-dihydro-3H-dinaphtho[2,1-c:1',2'-e]phosphepino}ferrocene.
Me-KetalPhos refers to 1,2-Bis-[(2S,3S,4S,5S)-3,4-O-isopropylidene-3,4-dihydroxy-2,5-dimethyl]benzene.
Me-f-KetalPhos refers to 1,1'-Bis-[(2S,3S,4S,5S)-2,5-dimethyl-3,4-O-isopropylidene-3,4-dihydroxyphospholanyl]ferrocene.
Et-f-KetalPhos refers to 1,1'-Bis-[(2S,3S,4S,5S)-2,5-diethyl-3,4-O-isopropylidene-3,4-dihydroxyphospholanyl] ferrocene
BINAP refers to R-2,2'-bis(diphenylphosphino)-1,1'binaphthyl.
DIOP refers to (R,R)-2,3-O-isopropylidene-2,3-dihydroxy-1,4-bis(diphenylphosphino)-butane.
BPPFA refers to R-1-[(S)-1'2-bisdiphenylphospino)ferrocenyl]-ethyldimethylamine.
BPPM refers to (2S,4S)-1-tert-butoxycarbonyl-4diphenylphosphino-2-(diphenylphosphijomethyl)pyrrolidine.
CHIRAPHOS refers to (S,S)-2,3-bis(diphenylphosphino) butane.
PROPHOS refers to (S)-1,2-bis(diphenylphosphino)propane.
NORPHOS refers to (R,R)-5,6-bis(diphenylphosphino)-2-norbornene.
CYCLOPHOS refers to R-1-cyclohexyl-1,2-bis(diphenylphosphino)ethane.
BDPP refers to (2S,4S)-bis(diphenylphosphine) pentane.
DEGPHOS refers to 1-substituted (S,S)-3,4-bis-(diphenylphosphino)-pyrrolidine.
PNNP refers to N,N'-bis(diphenylphosphino)-N,N'-bis [(R)-1-phenyl]ethylenediamine.

"PHTH" refers to $(CH_3—CH_2—CH_2—)_2N—CO$-phenyl-CO—OH where the attachment to the -phenyl-ring is 1,3-;

"5-Me-PHTH" refers to $(CH_3—CH_2—CH_2—)_2N—CO—(CH_3—)$ phenyl —CO—OH where the attachment to the -phenyl-ring is 1,3- for the carbonyl groups and 5- for the methyl group;

"3,5-pyridinyl" refers to $(CH_3—CH_2—CH_2—)_2N—CO—(pyridinyl)—CO—OH$ where the attachment to the -pyridinyl-ring is 3,5- for the carbonyl groups;

"—$SO_2$—" refers to $(CH_3—CH_2—CH_2—)_2CH—SO_2$—phenyl —CO—OH where the attachment to the -phenyl-ring is 1,3-;

"5-OMe-PHTH" refers to $(CH_3—CH_2—CH_2—)_2N—CO—(CH_3—O—)$ phenyl —CO—OH where the attachment to the -phenyl-ring is 1,3- for the carbonyl groups and 5- for the methoxy group;

"5-Cl-PHTH" refers to $(CH_3—CH_2—CH_2—)_2N—CO—(Cl—)$phenyl-CO—OH where the attachment to the -phenyl-ring is 1,3- for the carbonyl groups and 5- for the chlorine atom;

"5-F—PHTH" refers to $(CH_3—CH_2—CH_2—)_2N—CO—(F—)$phenyl-CO—OH where the attachment to the -phenyl-ring is 1,3- for the carbonyl groups and 5- for the fluorine atom;

"thienyl" refers to $(CH_3—CH_2—CH_2—)_2N—CO$-thienyl-CO—OH where the attachment to the thiophene ring is -2,5;

"2,4-pyridinyl" refers to $(CH_3—CH_2—CH_2—)_2N—CO—(pyridinyl)—CO—OH$ where the attachment to the -pyridinyl-ring is 2,4- for the carbonyl groups;

"4,6-pyrimidinyl" refers to $(CH_3—CH_2—CH_2—)_2N—CO—(pyrimidinyl-)$phenyl-CO—OH where the attachment to the -pyrimidinyl ring is 4,6- for the carbonyl groups;

"morpholinyl" refers to morpholinyl-CO-phenyl-CO—OH where the attachment to the -phenyl-ring is 1,3 for the carbonyl groups.

APP, amyloid precursor protein, is defined as any APP polypeptide, including APP variants, mutations, and isoforms, for example, as disclosed in U.S. Pat. No. 5,766,846.

A beta, amyloid beta peptide, is defined as any peptide resulting from beta-secretase mediated cleavage of APP, including peptides of 39, 40, 41, 42, and 43 amino acids, and extending from the beta-secretase cleavage site to amino acids 39, 40, 41, 42, or 43.

Beta-secretase (BACE1, Asp2, Memapsin 2) is an aspartyl protease that mediates cleavage of APP at the amino-terminal edge of A beta. Human beta-secretase is described, for example, in WO00/17369.

Preparation 1

Cyclohexylmethyl boronic acid

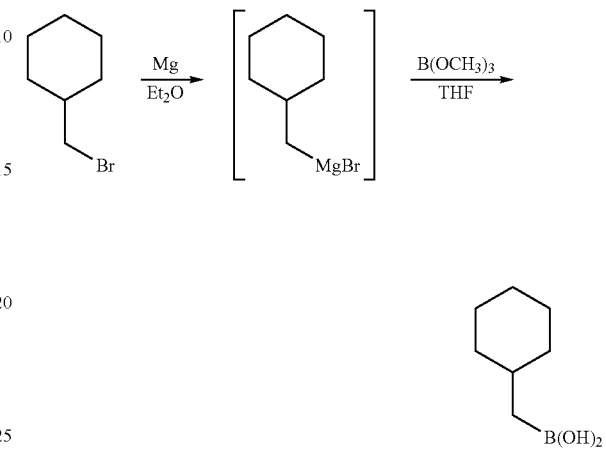

Magnesium turnings (0.66 g, 27 mmol) were flame dried in a 3-neck round bottom flask, fitted with a reflux condensor and purged with nitrogen. Once cooled to ambient temperature, 30 mL of ether was added, followed by the slow addition of cyclohexylmethyl bromide. This was heated to gentle reflux until the reaction began, at which time it was self-refluxing. The reaction mixture was then heated to reflux for an additional hour and finally cooled over ice. This was then slowly added to a solution of trimethyl borate (5.0 mL, 45 mmol) in 25 mL dry THF under nitrogen at −78° C. The resulting white mixture was stirred at −78° C. for 2 hours, warmed to ambient temperature and stirred overnight. The reaction mixture was placed over ice and 50 mL of 10% HCl was added, the phases separated, and the organic phase was washed with water and extracted with 10% NaOH. The basic extracts were combined, washed with ether, acidified with 10% HCl, and extracted with ether. These final ether extracts were dried over $Na_2SO_4$ and concentrated to afford the boronic acid as a white solid, (1.8 g, 13 mmol, 59%).

Preparation 2

3-(3-Amino-phenyl)-2-tert-butoxycarbonylamine-acrylic acid methyl ester

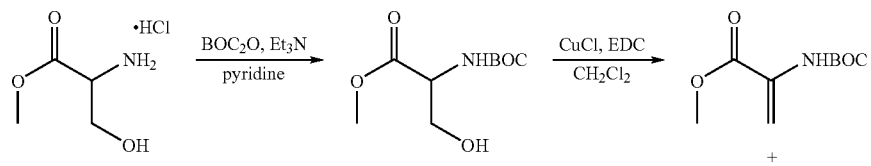

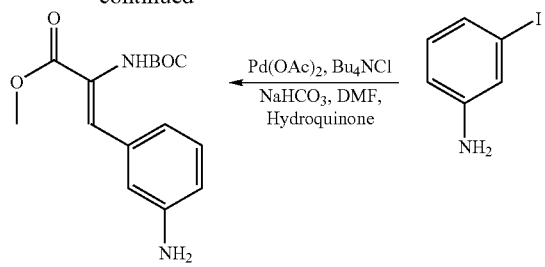

Serine methyl ester hydrochloride (4.0 g, 26 mmol) and di-tert-butyldicarbonate (6.5 g, 30 mmol) were combined to form a slurry in 40 mL of methylene chloride. Pyridine (2 mL, 25 mmol) was added and the resulting mixture was allowed to stir 10 min before the addition of Et₃N (3.8 mL, 27 mmol). This was then allowed to stir at ambient temperature overnight. The resulting slurry was partitioned between water and CH₂Cl₂. The organic phase was washed twice with water, once with 1 M KH₂PO₄, dried over Na₂SO₄, and concentrated to afford 4.8 g, 22 mmol (85%) of the BOC-protected compound as a pale yellow oil. This oil was then dissolved in 50 mL of CH₂Cl₂. EDC (5.9 g, 31 mmol) was then added, followed by CuCl (0.25 g, 2.5 mmol). The resulting pale green mixture stirred overnight under nitrogen at ambient temperature. In the morning the reaction mixture was concentrated and the residue was partitioned between EtOAc and 10% HCl. The organic phase was separated and the aqueous extracted twice with EtOAc. The combined organic extracts were dried over Na₂SO₄, run through a plug of silica gel eluting with EtOAc, to remove the green color, and concentrated to give 4.0 g (20 mmol, 92%) of the dehydrated serine as a colorless oil. The dehydrated serine (1.0 g, 5 mmol) was placed in a sealed tube under nitrogen in 4 mL of DMF. To this solution was added Pd(OAc)₂ (0.14 g, 15 mol %), Bu₄NCl (1.16 g, 4.2 mmol), 3-iodo-aniline (0.5 mL, 4.2 mmol), NaHCO₃ (0.87 g, 10 mmol), and hydroquinone (a couple of crystals). The resulting orange-red mixture was heated below 70° C. over the weekend in the sealed tube. The reaction mixture was then cooled to ambient temperature and partitioned between EtOAc and water. The EtOAc phase was washed several times with water to remove the DMF. It was then dried over Na₂SO₄, concentrated and the desired compound was isolated as an orange oil (1.0 g, 3.4 mmol, 83%) by column chromatography, eluting with 4:1 and 1:1 heptane:ethyl acetate.

Preparation 3

Methyl 2-{[(benzyloxy)carbonyl]amino}-3-(2-bromophenyl)acrylate

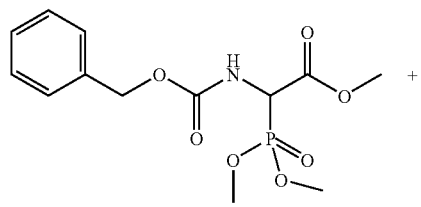

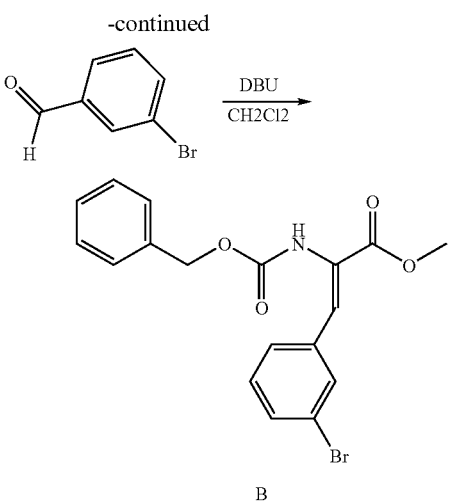

The DBU (5 mL, 33 mmol) was added to a solution of A (10.0 g, 30 mmol) and m-bromobenzaldehyde (3.9 mL, 33 mmol) in methylene chloride (50 mL) under nitrogen. The resulting solution was stirred at ambient temperature for 6 hrs, concentrated in vacuo, taken up in EtOAc 50 mL, and washed two times each with 1M NaHCO₃ and brine. The organic solution was then dried over Na₂SO₄, filtered, and crystallized from 4:1 heptane:EtOAc to afford 8.7 g (22 mmol, 74%) of an off-white solid as B (MS: M+H: 391.1).

Preparation 4

Methyl N-[(benzyloxy)carbonyl]-3-bromo-L-phenylalaninate

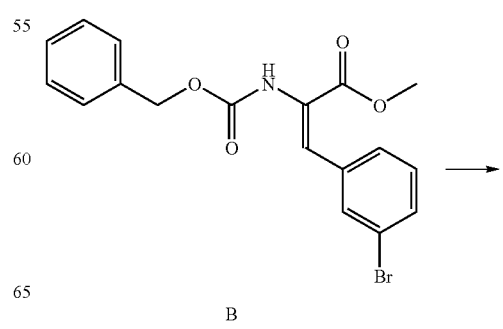

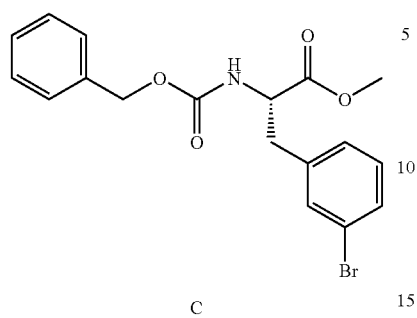

C

B (8.7 g, 22 mmol) was combined with [Rh(COD)(S,S)-Et-Duphos]⁺OTf⁻ (0.32 g, 0.44 mmol) in 100 ml of methanol in a parr vessel and placed under 40 psi of hydrogen for 6 hours. The reaction solution was then concentrated, taken up in ethyl acetate and run through a plug of silica gel to remove the catalyst. C was obtained in quantitative yield as an orange oil upon concentration.

Preparation 5

Tert-Butyl (2R,3S)-3-{[(benzyloxy)carbonyl]amino}-4-(3-bromophenyl)-2-hydroxybutyl(3-methoxybenzyl)carbamate

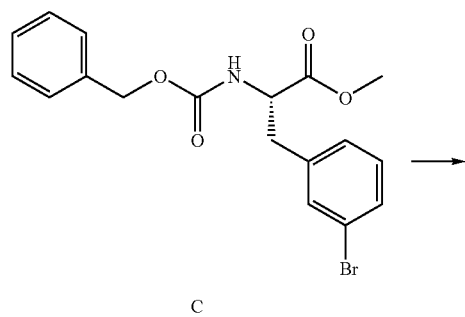

C

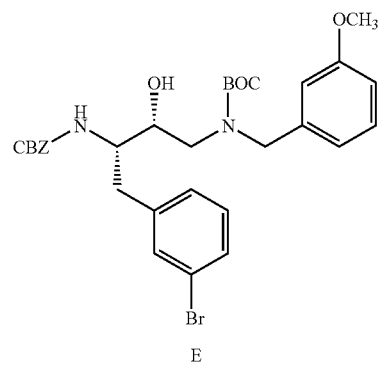

E

Epoxide D can be conveniently prepared from ester C using procedures appreciated by those skilled in the art (4.5 g, 12 mmol, 50%) (MS;M+H: 378.0) from 9.4 g, 24 mmol of C). Alternatively, epoxide D can be prepared from a precursor alcohol according to the procedures outlined in Scheme A and the discussion associated therewith. Epoxide D (2.9 g, 7.8 mmol) can be opened using procedures recognized by those skilled in the art to produce the free amine of E (4 g, 7.8 mmol). This was dissolved in 30 mL of THF and 5 mL of methanol and triethylamine (1.2 mL, 8.6 mmol) and BOC₂O (1.9 g, 8.7 mmol) were added. The resulting mixture is stirred overnight at ambient temperature. The mixture was then concentrated, partitioned between EtOAc and brine, and the organic phase was separated. This was further extracted with 1M KH₂PO₄ and brine, dried over Na₂SO₄, and concentrated to give E (4.4 g, 7.2 mmol, 93%) as a yellow oil (MS; M+H: 514.9 (-BOC).

Preparation 6

Tert-Butyl (2R,3S)-3-{[(benzyloxy)carbonyl]amino}-4-[3-(cyclohexylmethyl)phenyl]-2-hydroxybutyl(3-methoxybenzyl)carbamate

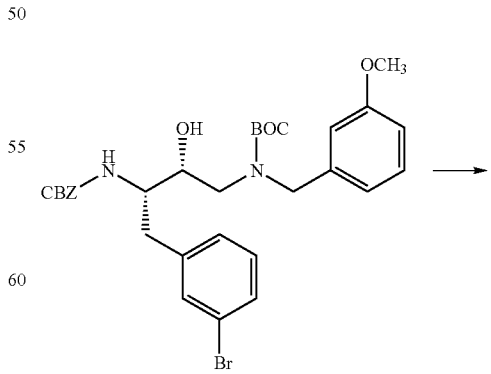

E

-continued

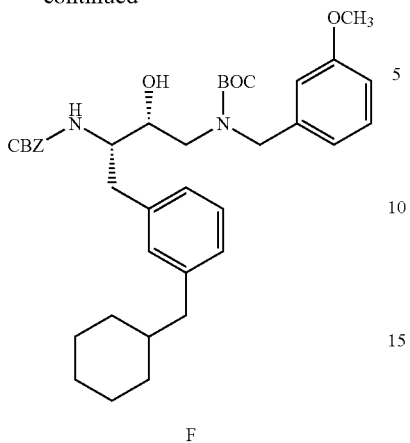

F

The methylenecyclohexane (0.86 mL, 7.2 mmol) was added to a nitrogen filled, oven dried round bottom flask and diluted with 10 mL of dry THF. This solution was then placed over ice and 9-BBN (14 mL, 0.5 M in THF, 7.0 mmol) was added slowly via syringe. The resulting solution remained over ice an additional hour before warming to ambient temperature and stirring for four hours. Then a solution of E (0.10 g, 0.16 mmol) in 5 mL of dry DMF was added to the reaction mixture, followed by $PdCl_2(dppf) \cdot CH_2Cl_2$ (0.007 g, 0.009 mmol) and solid $K_2CO_3$ (0.045 g, 0.33 mmol). This final mixture was then heated overnight to 70° C. The cooled reaction mixture was then partitioned between ethyl acetate and water, the layers were separated and the organic was washed several times with water. The aqueous washes were then back extracted with ethyl acetate and the organic phases combined. They were dried over $Na_2SO_4$ and concentrated to a smaller volume and run through a plug of silica gel to remove the catalyst. A column was run on the concentrated material eluting with 4:1 then 1:1 heptane: EtOAc to afford (0.05 g, 0.08 mmol, 50%) F as a yellow oil (MS: M+H: 631.2).

Preparation 7

Tert-Butyl (2R,3S)-3-amino-4-[3-(cyclohexylmethyl)phenyl]-2-hydroxybutyl(3-methoxybenzyl) carbamate

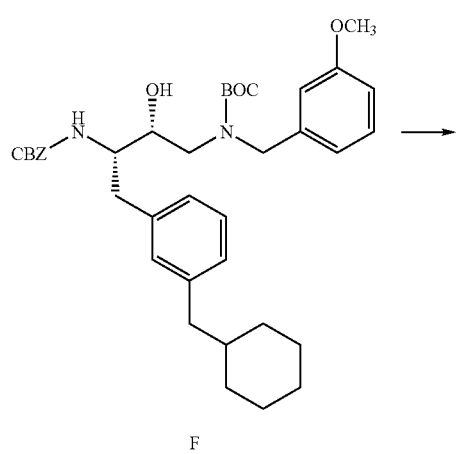

F

-continued

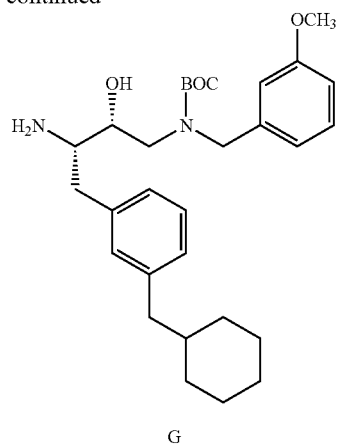

G

To a solution of F (0.40 g, 0.63 mmol) in 10 mL of methanol was added ammonium formate (0.08 g, 1.3 mmol) and 10% palladium on activated carbon (0.02 g, 5 wt %). The resulting mixture was heated to reflux under nitrogen overnight. The cooled reaction mixture was then filtered, concentrated, redissolved in ethyl acetate, and washed two times with saturated $NaHCO_3$. The solution was then dried over $Na_2SO_4$ and concentrated to give G as a pale yellow oil (0.33 g, 0.66 mmol, 79%) (MS;M+H: 497.1).

Example 1

N-{(1S,2R)-1-[3-(cyclohexylmethyl)benzyl]-2-hydroxy-3-[(3-methoxybenzyl)amino] propyl}acetamide hydrocloride

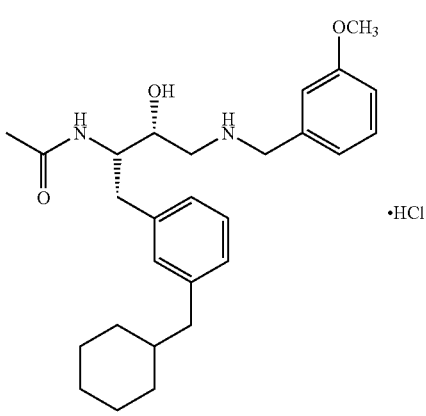

H

To a solution of G (0.09 g, 0.18 mmol) in 5 mL of $CH_2Cl_2$ under nitrogen was added triethylamine (0.03 g, 0.22 mmol) and acetyl chloride (0.03 mL, 0.42 mmol). The resulting solution stirred at ambient temperature for 3 hrs at which time tlc showed no starting amine, G. The reaction solution was then extracted twice with saturated $NaHCO_3$, twice with 1 M $KH_2PO_4$, and twice with brine before drying over $Na_2SO_4$ and concentration to afford a mixture of acylated products. To an ice cold solution of this mixture in 3 mL of CH$_2$Cl$_2$ was added 3 mL of TFA. After stirring for 2 hours at ambient temperature the solution was turned basic by the addition of 5 mL of 1M NaOH and diluted with EtOAc. The phases were separated and the organic was washed 2× with 1M NaOH, dried over Na$_2$SO$_4$, and concentrated to give a yellow oil. This oil was further dissolved in 5 mL of MeOH, 1 pellet of KOH was added, and the mixture was heated to reflux for three hours. The cooled reaction mixture was then concentrated, diluted with EtOAc, washed 3× with brine, dried over Na$_2$SO$_4$, and concentrated to a yellow oil which was partially purified by flash chromatography eluting with 10% MeOH in CH$_2$Cl$_2$. Final purification was accomplished by reverse phase prep hplc to give 0.002 g of H as the free base (MS;M+H: 439.3). The HCl salt was obtained in quantitative yield by adding 1 mL of 7N methanolic HCl to a solution of the free base in 1 mL of methanol. Concentration of the final solution followed by trituaration with EtOAc and heptane and concentration gave the HCl salt.

Example 2

N'-{(1S,2R)-1-[3-(cyclohexylmethyl)benzyl]-2-hydroxy-3-[(3-methoxybenzyl)amino]propyl}-5-methyl-N,N-dipropylisophthalamide Hydrochloride

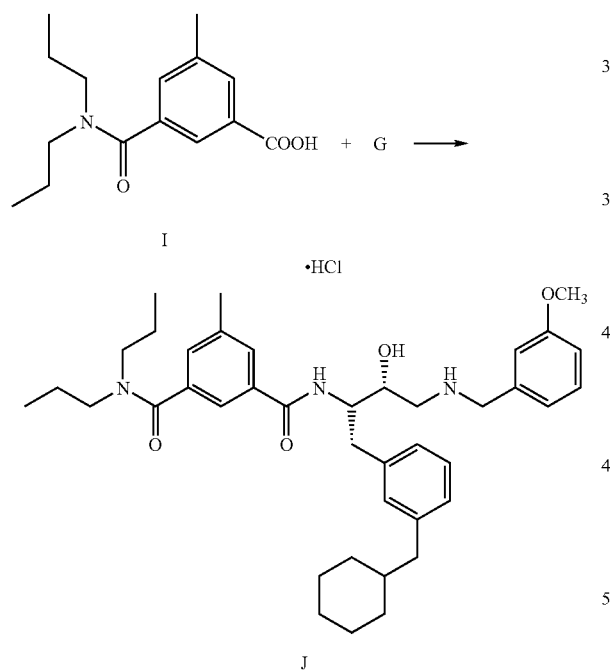

HOBT (0.018 g, 0.13 mmol), EDC (0.025 g, 0.13 mmol) and I (0.033 g, 0.12 mmol) were combined in 5 mL of CH$_2$Cl$_2$ and 3 mL of DMF under nitrogen and stirred over ice for a half hour prior to the addition of a solution of G (0.05 g, 0.10 mmol) and triethylamine (0.018 mL, 0.13 mmol) in 2 mL of CH$_2$Cl$_2$. The resulting reaction solution was warmed to ambient temperature and stirred overnight. The solution was then concentrated, redissolved in ethyl acetate, and washed 3×saturated NaHCO$_3$, 3×1M KH$_2$PO$_4$, and 3× brine. The solution was then dried over Na$_2$SO$_4$, concentrated, and purified by flash chromatography on silica gel eluting with 1:1 heptane:EtOAc to afford I as a yellow oil. This oil was dissolved in 2 mL of CH$_2$Cl$_2$ and 2 mL of TFA was added over ice. The resulting solution stirred overnight at ambient temperature. The solution was then concentrated, taken-up in EtOAc, washed 2× with saturated NaHCO$_3$ and 2× with brine, dried over Na$_2$SO$_4$, and concentrated to a yellow oil as J (MS;M+H: 642.6). The HCl salt was prepared by dissolving the free base in 1 mL of methanol, adding 2 mL of 7 N methanolic HCl, and concentration of the solution to afford 10 mg of the HCl salt.

Example 3

N-{(1S,2R)-1-[3-(cyclohexylmethyl)benzyl]-2-hydroxy-3-[(3-methoxybenzyl)amino]propyl}-3-{[(trifluoromethyl)sulfonyl]amino}benzamide hydrochloride

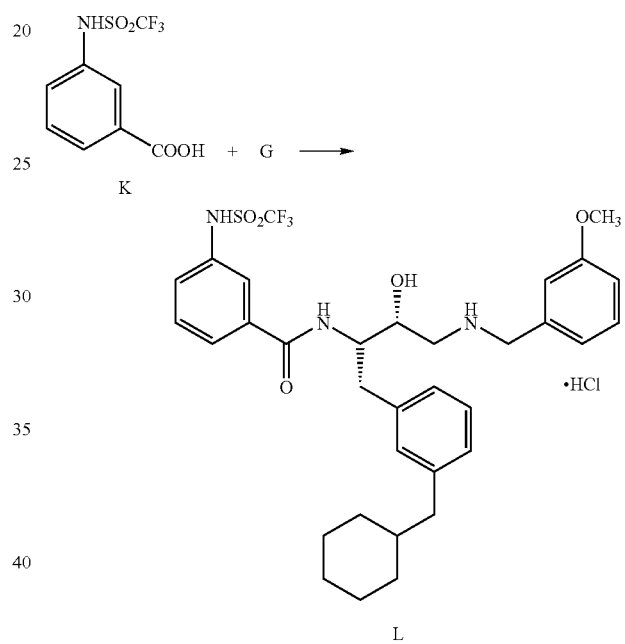

HOBT (0.018 g, 0.13 mmol), EDC (0.025 g, 0.13 mmol) and K (0.033 g, 0.12 mmol) were combined in 5 mL of CH$_2$Cl$_2$ and 3 mL of DMF under nitrogen and stirred over ice for a half hour prior to the addition of a solution of G (0.05 g, 0.10 mmol) and triethylamine (0.018 mL, 0.13 mmol) in 2 mL of CH$_2$Cl$_2$. The resulting reaction solution was warmed to ambient temperature and stirred overnight. The solution was then concentrated, redissolved in ethyl acetate, and washed 3×saturated NaHCO$_3$, 3×1M KH$_2$PO$_4$, and 3× brine. The solution was then dried over Na$_2$SO$_4$, concentrated, and purified by flash chromatography on silica gel eluting with 1:1 heptane:EtOAc to afford L (BOC protected) as a yellow oil. This oil was dissolved in 2 mL of CH$_2$Cl$_2$ and 2 mL of TFA was added over ice. The resulting solution stirred overnight at ambient temperature. The solution was then concentrated, taken-up in EtOAc, washed 2× with saturated NaHCO$_3$ and 2× with brine, dried over Na$_2$SO$_4$, and concentrated to afford L as the free base (MS;M+H: 648.3). The HCl salt was prepared by dissolving the free base in 1 mL of methanol, adding 2 mL of 7 N methanolic HCl, and concentration of the solution to afford 15 mg of the HCl salt.

Preparation 8

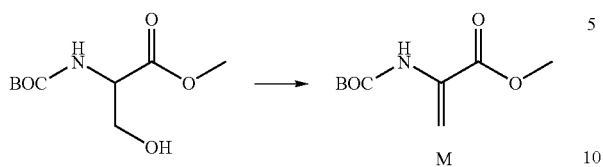

To an ice cold solution of serine hydrochloride (4.0 g, 26 mmol) and BOC20 (6.5 g, 30 mmol) in 40 mL of CH$_2$Cl$_2$ was added pyridine (2 mL, 25 mmol) and triethylamine (3.8 mL, 27 mmol). The resultant mixture stirred overnight at ambient temperature. The mixture was then partitioned between brine and CH$_2$Cl$_2$ and the phases were separated. The organic phase was extracted 3× with 1M KH$_2$PO$_4$, 3× with saturated NaHCO$_3$, and 3× with brine, dried over Na$_2$SO$_4$, and concentrated to give the boc protected amino acid. This was dissolved in 50 mL of CH$_2$Cl$_2$, combined with EDC (5.9 g, 31 mmol) and CuCl (0.25 g, 2.5 mmol), and stirred overnight at ambient temperature. The solution was then partitioned between CH$_2$Cl$_2$ and 1 M HCl. The phases were separated and the organic phase was further extracted with 1M HCl and run through a plug of silica gel to remove the last traces of copper. Upon drying over Na$_2$SO$_4$ and concentration, M was obtained as a colorless oil (4.0 g, 20 mmol, 78%) (MS;M+H: 202.1). This was stored as a cold solution in EtOAc with 5 mg of hydroquinone.

Preparation 9

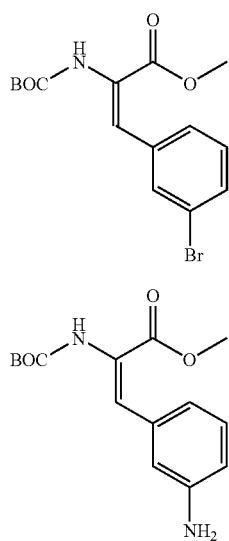

Into 12 mL of dry DMF in an oven dried, nitrogen filled tube was placed M (3.0 g, 15 mmol), 1-iodo-3-bromobenzene (1.6 mL, 13 mmol), palladium(II)acetate (0.42 g, 1.9 mmol), tetrabutylammoniumchloride (3.5 g, 13 mmol), and solid NaHCO$_3$ (2.6 g, 31 mmol). The tube was sealed and heated to 80° C. for 16 hours. The cooled reaction mixture was diluted with EtOAc, passed through a small plug of silica gel to remove the catalyst, and extracted 2× with brine. The solution was then dried over Na$_2$SO$_4$, concentrated, and purified by flash chromatography eluting with 2:1 and 1:1 heptane: EtOAc to afford N (1.8 g, 5 mmol, 40%) (MS;M+H: 356.1, 358.1). Likewise N' was formed (0.92 g, 3.1 mmol, 77%) (MS;M+H: 293.2) from M (1.0 g, 5 mmol), 3-iodoaniline (0.5 mL, 4.2 mmol), Pd(OAc)$_2$ (0.14 g, 0.62 mmol), Bu$_4$NCl (1.16 g, 4.2 mmol), and NaHCO$_3$ (0.87 g, 10 mmol) in 4 mL of dry DMF.

Preparation 10

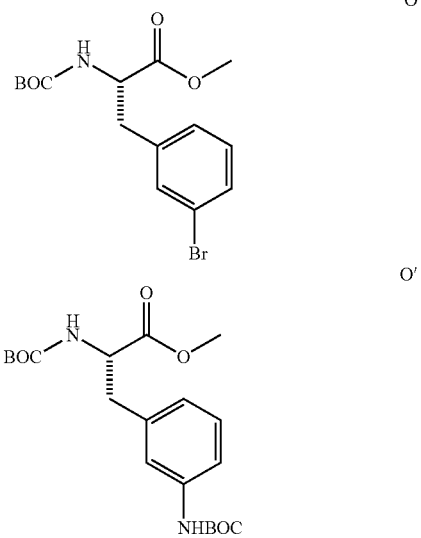

A parr vessel was loaded with N (1.4 g, 3.9 mmol), [Rh(COD) (S,S)-Et-Duphos]$^+$OTf$^-$ (0.03 g, 0.042 mmol), and 20 mL of methanol and placed under 40 psi of H$_2$ for 6 hours. The reaction solution was filtered through a plug of silica gel and concentrated to afford O in quantitative yield (MS;M+H: 358.1, 360.1). Likewise O' was prepared in quantitative yield (MS;M+H: 395.3) from the boc protected N' (1.0 g, 2.5 mmol), [Rh(COD) (S,S)-Et-Duphos]$^+$OTf$^-$ (0.02 g, 0.028 mmol), and 25 psi of H$_2$ in 13 mL of methanol.

Example 4

Tert-Butyl (1S,2R)-1-[3-(cyclohexylmethyl)benzyl]-2-hydroxy-3-[(3-methoxybenzyl)amino]propylcarbamate hydrochloride

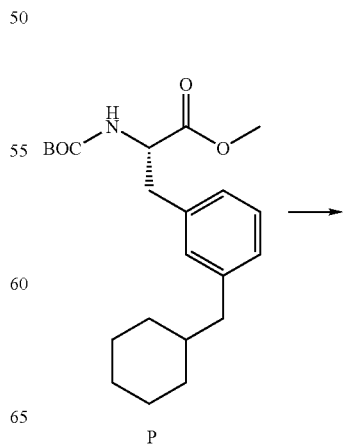

-continued

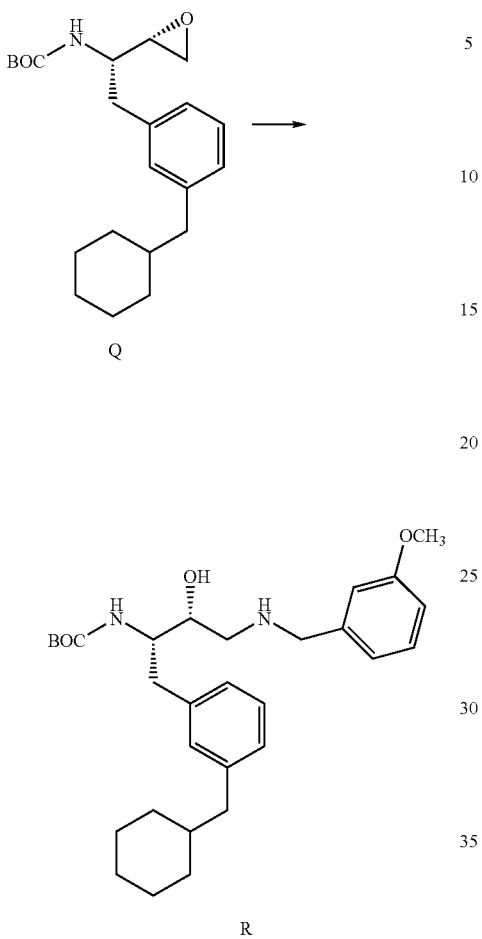

Q

R

To an ice cold solution of methylene cyclohexane (0.19 mL, 1.6 mmol) in 2 mL of dry DMF was added 9-BBN (3.1 mL, 0.5 M in THF, 1.6 mmol) slowly via syringe. The resulting solution stirred an additional hour over ice, then four hours at ambient temperature. Then a solution of O (0.5 g, 1.4 mmol) in 5 mL of dry DMF was added followed by PdCl$_2$(dppf).CH$_2$Cl$_2$ (0.06 g, 0.07 mmol) and solid K$_2$CO$_3$ (0.39 g, 2.8 mmol). The resultant mixture was heated to 70° C. for 16 hours. The reaction mixture was then diluted with EtOAc, passed through a small plug of silica gel, washed 5× with brine, dried over Na$_2$SO$_4$, concentrated, and purified by flash chromatography eluting with 4:1 heptane:EtOAc to afford P (0.48 g, 1.3 mmol, 90%) (MS;M+H: 376.3). Ester P (0.47 g, 1.3 mmol) is then converted to epoxide Q (0.2 g, 0.56 mmol, 44%) (MS;M−H: 358.3) in a fashion similar to that set forth above for the conversion of ester C to epoxide D. Alternatively, epoxide Q can be prepared according to the procedures outlined in Scheme A and the discussion associated therewith. Epoxide Q, (0.13 g, 0.36 mmol) can be opened using procedures that will be recognized by those in the art to afford R (0.05 g, 0.10 mmol, 28%) (MS;M+H: 497.6).

Example 5

Tert-Butyl (1S,2R)-1-{3-[(tert-butoxycarbonyl)amino]benzyl}-2-hydroxy-3-[(3-methoxybenzyl)amino]propylcarbamate hydrochloride

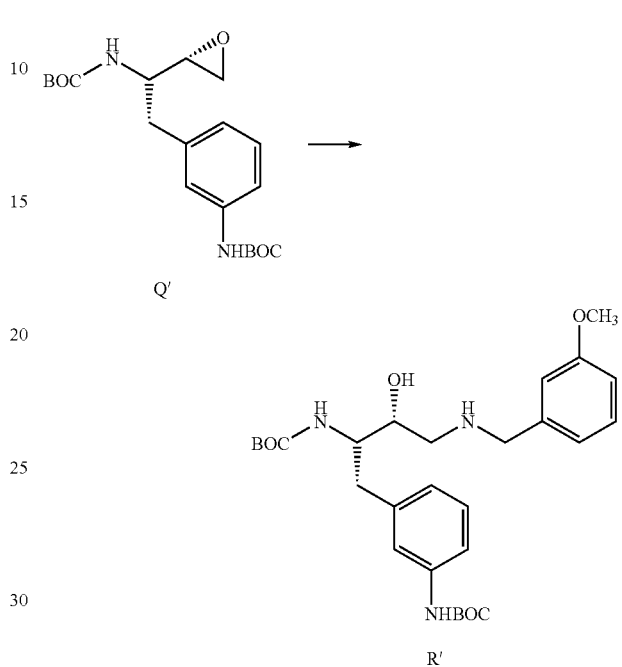

Q'

R'

O' (0.96 g, 2.4 mmol) was converted to the epoxide, Q', (0.3 g, 0.79 mmol, 33%) (MS;M+H: 379.3), and opened up to form R' (0.10 g, 0.19 mmol, 23%) (MS;M+H: 516.5) by the methods mentioned above.

Example 6

The following compounds are prepared essentially according to the procedures set forth in the schemes shown above in view of the discussion associated therewith. See in particular, Schemes FF and GG.

Example 6A

N-{(1R,2R)-2-hydroxy-3-[(3-iodobenzyl)amino]-1-[(2-naphthylthio)methyl]propyl}-3-methylbenzamide

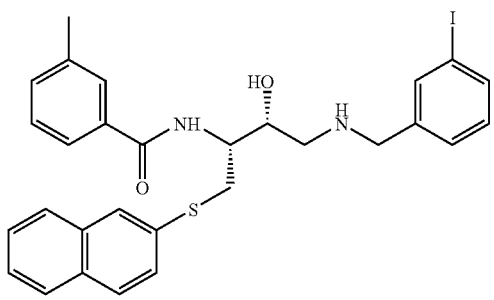

Example 6B

N-{(1R,2S)-2-hydroxy-3-[(3-iodobenzyl)amino]-1-[(2-naphthylthio)methyl]propyl}-3-methylbenzamide

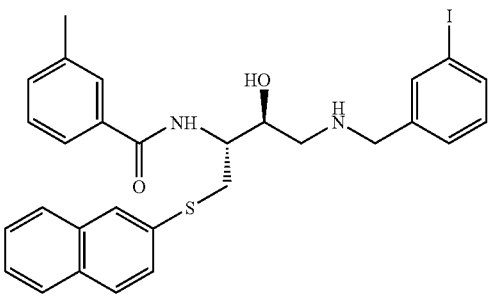

Example 6C

N'-{(1R,2R)-2-hydroxy-3-[(3-iodobenzyl)amino]-1-[(2-naphthylthio)methyl]propyl}-5-methyl-N,N-dipropylisophthalamide

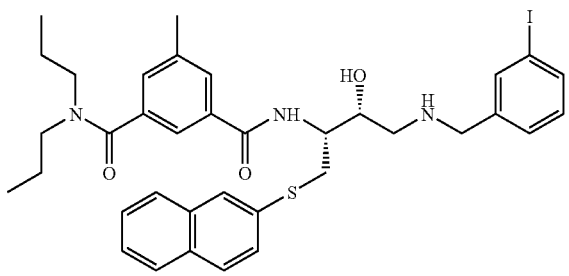

Example 6D (2S,3R)-3-amino-1-[(3-iodobenzyl)amino]-4-(2-naphthylthio)butan-2-ol

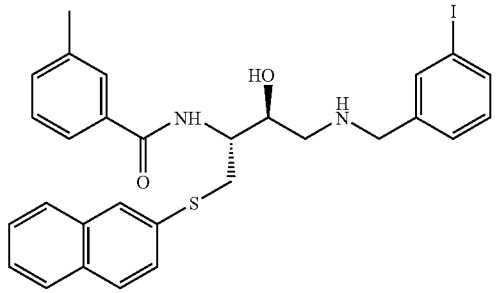

Example 7

(2R,3S)-3-amino-4-(2-butoxyphenyl)-1-[(3-ethylbenzyl)amino]butan-2-ol,
(2R,3S)-3-amino-4-(3-butoxyphenyl)-1-[(3-ethylbenzyl)amino]butan-2-ol,
(2R,3S)-3-amino-4-(4-butoxyphenyl)-1-[(3-ethylbenzyl)amino]butan-2-ol,
(2R,3S)-3-amino-1-[(3-ethylbenzyl)amino]-4-[2-(hexyloxy)phenyl]butan-2-ol,
(2R,3S)-3-amino-1-[(3-ethylbenzyl)amino]-4-[3-(hexyloxy)phenyl]butan-2-ol,
(2R,3S)-3-amino-1-[(3-ethylbenzyl)amino]-4-[4-(hexyloxy)phenyl]butan-2-ol,
N-{(1S,2R)-1-(2-butoxybenzyl)-3-[(3-ethylbenzyl)amino]-2-hydroxypropyl}acetamide,
N-{(1S,2R)-1-(3-butoxybenzyl)-3-[(3-ethylbenzyl)amino]-2-hydroxypropyl}acetamide,
N-{(1S,2R)-1-(4-butoxybenzyl)-3-[(3-ethylbenzyl)amino]-2-hydroxypropyl}acetamide,
N-{(1S,2R)-3-[(3-ethylbenzyl)amino]-1-[2-(hexyloxy)benzyl]-2-hydroxypropyl}acetamide,
N-{(1S,2R)-3-[(3-ethylbenzyl)amino]-1-[3-(hexyloxy)benzyl]-2-hydroxypropyl}acetamide,
N-{(1S,2R)-3-[(3-ethylbenzyl)amino]-1-[4-(hexyloxy)benzyl]-2-hydroxypropyl}acetamide,
N-{(1S,2R)-1-(2-butoxybenzyl)-3-[(3-ethylbenzyl)amino]-2-hydroxypropyl}-2-[(methylsulfonyl)amino]-1,3-oxazole-4-carboxamide,
N-{(1S,2R)-1-(3-butoxybenzyl)-3-[(3-ethylbenzyl)amino]-2-hydroxypropyl}-2-[(methylsulfonyl)amino]-1,3-oxazole-4-carboxamide,
N-{(1S,2R)-1-(4-butoxybenzyl)-3-[(3-ethylbenzyl)amino]-2-hydroxypropyl}-2-[(methylsulfonyl)amino]-1,3-oxazole-4-carboxamide,
N-{(1S,2R)-3-[(3-ethylbenzyl)amino]-1-[2-(hexyloxy)benzyl]-2-hydroxypropyl}-2-[(methylsulfonyl)amino]-1,3-oxazole-4-carboxamide,
N-{(1S,2R)-3-[(3-ethylbenzyl)amino]-1-[3-(hexyloxy)benzyl]-2-hydroxypropyl}-2-[(methylsulfonyl)amino]-1,3-oxazole-4-carboxamide,
N-{(1S,2R)-3-[(3-ethylbenzyl)amino]-1-[4-(hexyloxy)benzyl]-2-hydroxypropyl}-2-[(methylsulfonyl)amino]-1,3-oxazole-4-carboxamide,
N-{(1S,2R)-3-[(3-ethylbenzyl)amino]-1-[2-(hexyloxy)benzyl]-2-hydroxypropyl}-3-(1,3-oxazol-2-yl)benzamide
N-{(1S,2R)-3-[(3-ethylbenzyl)amino]-1-[3-(hexyloxy)benzyl]-2-hydroxypropyl}-3-(1,3-oxazol-2-yl)benzamide, and
N-{(1S,2R)-3-[(3-ethylbenzyl)amino]-1-[4-(hexyloxy)benzyl]-2-hydroxypropyl}-3-(1,3-oxazol-2-yl)benzamide Scheme 1 illustrates the synthesis of intermediates 89A and 89B which may be used in the synthesis of compounds of the example. On of skill in the art will appreciate that various R groups may be used and structures 89A and 89B are merely exemplary.

Scheme 1.

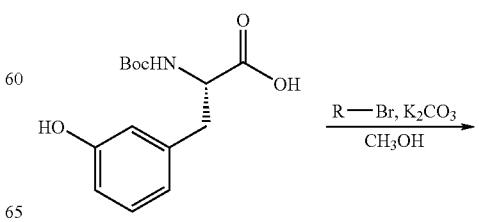

86

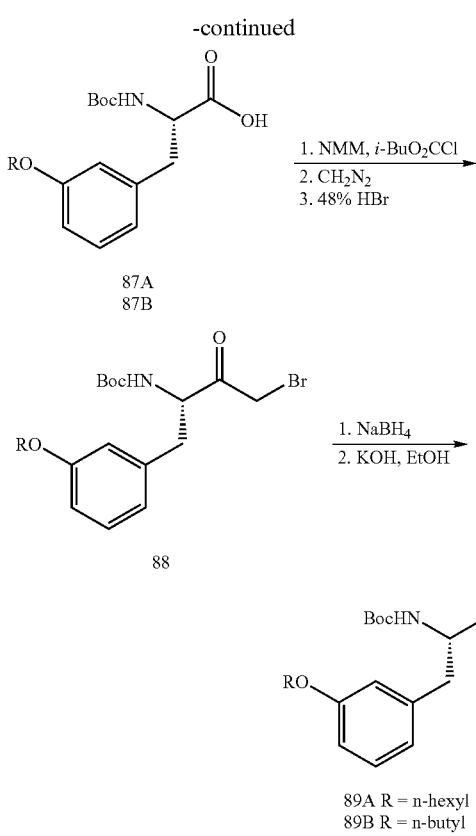

87A
87B

88

89A R = n-hexyl
89B R = n-butyl

Synthesis of 89A

Step 1: To a stirred solution at reflux of potassium carbonate (4.4 g, 32 mmol) in methanol (50 mL) was added hexyl bromide (1.5 mL, 11 mmol) and Boc-L-m-tyrosine (86) (2 g, 7.1 mmol). The reaction mixture was heated at reflux for 18 h, cooled to room temperature, and concentrated under reduced pressure to yield an off-white solid. The crude product was partitioned between ethyl acetate and water. The aqueous phase was acidified with 1 N hydrochloride and extracted with ethyl acetate. The organic layer was washed with saturated sodium chloride, dried (magnesium sulfate), filtered, and concentrated under reduced pressure to afford a brown oil. Purification by flash column chromatography (silica, gradient 8:2:0.01 to 1:1:0.01 hexanes/ethyl acetate/acetic acid) yielded the ether 87A (1.63 g): $^1$H NMR (300 MHz, CDCl$_3$) δ 7.24–7.19 (m, 1H), 6.81–6.72 (m, 3H), 4.92 (br s, 1H), 4.56 (br s, 1H), 3.93 (t, J=6 Hz, 2H), 3.20–3.01 (m, 2H), 1.82–1.72 (m, 2H), 1.42 (s, 9H), 1.42–1.33 (m, 6H), 0.93–0.88 (m, 3H).

Step 2: To a −78° C., stirred solution of 87A from step 1 (1.98 g, 5.42 mmol) in tetrahydrofuran (10 mL) was added N-methylmorpholine (630 μL, 5.70 mmol) and isobutyl chloroformate (740 μL, 5.70 mmol). The cold bath was removed, and the reaction mixture was stirred for 1 h, and then filtered. The filtrate was kept cold and used in the next step.

Step 3: To an ice-cold, stirred solution of ethyl ether (25 mL) and 40% potassium hydroxide (10 mL) in an Erlenmeyer flask was slowly added 1-methyl-3-nitro-1-nitrosoguanidine (1.70 g, 11.4 mmol). The reaction mixture was stirred until gas evolution ended. The organic layer was slowly added to an ice-cold, stirred solution of the filtrate from step 2. After the reaction mixture was stirred for 1 h, nitrogen was bubbled into the solution for 10 min. The reaction mixture was concentrated under reduced pressure, diluted with ethyl ether (200 mL), and washed with water (100 mL). The organic layer was washed with saturated sodium bicarbonate, and saturated sodium chloride, dried (sodium sulfate), filtered, and concentrated under reduced pressure to give the diazoketone, which was carried on without purification or characterization.

Step 4: To an ice-cold, stirred solution of diazoketone from step 3 in ethyl ether (20 mL) was added 48% hydrobromic acid (820 μL, 15 mmol). The cold bath was removed, the reaction mixture stirred for 30 min, and then partitioned between ethyl ether and water. The organic layer was washed with saturated sodium bicarbonate, and saturated sodium chloride, dried (sodium sulfate), filtered, and concentrated under reduced pressure to give bromoketone as a white solid, which was carried on without purification or characterization.

Step 5: To an ice-cold, stirred solution of bromoketone from step 4 in dichloromethane (50 mL) was slowly added aluminum tri-sec-butoxide (2.10 mL, 8.13 mmol). After the reaction mixture was stirred for 18 h, the reaction mixture was cooled and 1 N hydrochloric acid (50 mL) was added. The reaction mixture was warmed to room temperature and then partitioned between ether and water. The ethereal layer was dried (sodium sulfate), filtered, and concentrated under reduced pressure to give a crude white solid, which was carried on without purification or characterization.

Step 6: To an ice-cold, stirred solution of bromohydrin from step 5 in ethanol (20 mL) and ethyl acetate (15 ml) was added potassium hydroxide (395 mg, 7.05 mmol). The cold bath was removed and the reaction mixture was stirred for 30 min. The reaction mixture was partitioned between methylene chloride and water. The organic layer was washed with saturated sodium chloride, filtered, and concentrated under reduced pressure to give 89A (1.21 g): mp 43–45° C.; $^1$H NMR (500 MHz, CDCl$_3$) δ 7.27–7.18 (m, 1H), 6.79–6.72 (m, 3H), 4.58–4.56 (m, 1H), 3.93 (t, J=6 Hz, 2H), 3.68 (br s, 1H), 2.95–2.76 (m, 5H), 1.78–1.74 (m, 2H), 1.47–1.32 (m, 6H), 1.39 (s, 9H), 0.92–0.89 (m, 3H); APCI MS m/z 364 [M+H]$^+$.

Synthesis of 89B

Step 1: To a stirred solution at reflux of potassium carbonate (5.0 g, 36 mmol) in methanol (50 mL) was added butyl bromide (1.3 mL, 12 mmol) and Boc-L-m-tyrosine (86) (2.25 g, 8.0 mmol). The reaction mixture was heated at reflux for 18 h, cooled to room temperature, and concentrated under reduced pressure to yield an off-white solid. The crude product was partitioned between ethyl acetate and water. The aqueous phase was acidified with 1 N hydrochloric acid and extracted with ethyl acetate. The organic layer was washed with saturated sodium chloride, dried (magnesium sulfate), filtered, and concentrated under reduced pressure to afford a brown oil. Purification by flash column chromatography (silica, gradient 8:2:0.01 to 1:1: 0.01 hexanes/ethyl acetate/acetic acid) yielded the ether 87B (1.0 g): $^1$H NMR (300 MHz, CDCl$_3$) δ 7.24–7.19 (m, 1H), 6.81–6.72 (m, 3H), 4.92 (br s, 1H), 4.57 (br s, 1H), 3.94 (t, J=6 Hz, 2H), 3.20–3.07 (m, 2H), 1.81–1.70 (m, 2H), 1.53–1.42 (m, 2H), 1.42 (s, 9H), 0.98 (t, J=6 Hz, 3H).

Step 2: To a −78° C., stirred solution of 87B from step 1 (1.82 g, 5.43 mmol) in tetrahydrofuran (10 mL) was added N-methylmorpholine (630 μL, 5.70 mmol) and isobutyl chloroformate (740 μL, 5.70 mmol). The cold bath was removed, and the reaction mixture was stirred for 1 h, and then filtered. The filtrate was kept cold and used in the next step.

Step 3: To an ice-cold, stirred solution of ethyl ether (25 mL) and 40% potassium hydroxide (10 mL) in an Erlenmeyer flask was slowly added 1-methyl-3-nitro-1-nitrosoguanidine (1.70 g, 11.4 mmol). The reaction mixture was stirred until gas evolution ended. The organic layer was slowly added to an ice-cold, stirred solution of the filtrate from step 2. After the reaction mixture was stirred for 1 h, nitrogen was bubbled into the solution for 10 min. The reaction mixture was concentrated under reduced pressure, diluted with ethyl ether (200 mL), and washed with water (100 mL). The organic layer was washed with saturated sodium bicarbonate, and saturated sodium chloride, dried (sodium sulfate), filtered, and concentrated under reduced pressure to give the diazoketone, which was carried on without purification or characterization.

Step 4: To an ice-cold, stirred solution of diazoketone from step 3 in ethyl ether (20 mL) was added 48% hydrobromic acid (800 μL, 15 mmol). The cold bath was removed, the reaction mixture stirred for 30 min, and then partitioned between ethyl ether and water. The organic layer was washed with saturated sodium bicarbonate, and saturated sodium chloride, dried (sodium sulfate), filtered, and concentrated under reduced pressure to give bromoketone as a white solid, which was carried on without purification or characterization.

Step 5: To an ice-cold, stirred solution of bromoketone from step 4 in dichloromethane (50 mL) was slowly added aluminum tri-sec-butoxide (2.10 mL, 8.13 mmol). After the reaction mixture was stirred for 18 h, the reaction mixture was cooled and 1 N hydrochloric acid (50 mL) was added. The reaction mixture was warmed to room temperature and then partitioned between ether and water. The ethereal layer was dried (sodium sulfate), filtered, and concentrated under reduced pressure to give a crude white solid, which was carried on without purification or characterization.

Step 6: To an ice-cold, stirred solution of bromohydrin from step 5 in ethanol (20 mL) and ethyl acetate (15 ml) was added potassium hydroxide (395 mg, 7.05 mmol). The cold bath was removed and the reaction mixture was stirred for 30 min. The reaction mixture was then partitioned between methylene chloride and water. The organic layer was washed with saturated sodium chloride, filtered, and concentrated under reduced pressure to give 89B (1.03 g): mp 40–43° C.; $^1$H NMR (300 MHz, CDCl$_3$) δ 7.21–7.16 (m, 1H), 6.79–6.75 (m, 3H), 4.75–4.72 (m, 1H), 3.93 (t, J=6 Hz, 2H), 3.67 (br s, 1H), 2.95–2.74 (m, 5H), 1.79–1.70 (m, 2H), 1.54–1.42 (m, 2H), 1.38 (s, 9H), 0.97 (t, J=6 Hz, 3H); APCI MS m/z 336 [M+H]$^+$.

The following compounds of the example can be prepared as shown below. One of skill in the art may appreciate that the order of the reactions may be varied without deviating from the scope of the invention.

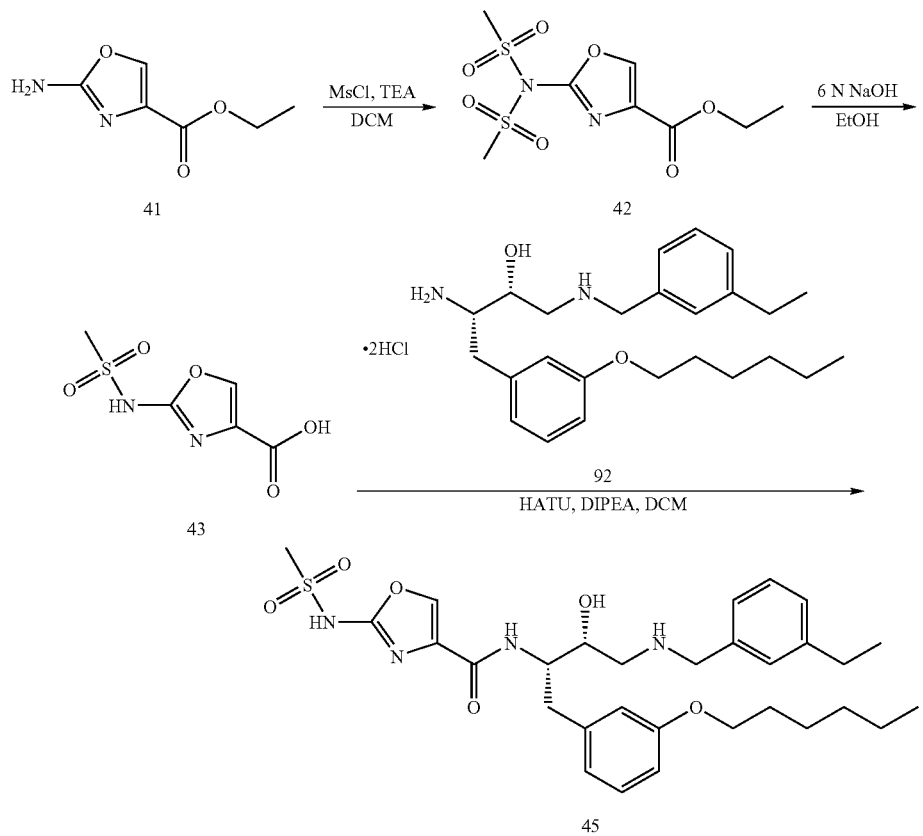

Synthesis of 45

N-{(1S,2R)-3-[(3-ethylbenzyl)amino]-1-[3-(hexyloxy)benzyl]-2-hydroxypropyl}-2-[(methylsulfonyl)amino]-1,3-oxazole-4-carboxamide Step 1: To an ice-cold, stirred solution of ethyl 2-amino-1,3-oxazole-4-carboxylate (41) (750 mg, 4.8 mmol) and triethylamine (2 mL, 14 mmol) in methylene chloride (10 mL) was added mesyl chloride (890 μL, 12 mmol). The reaction mixture was stirred for 35 min and then partitioned between methylene chloride and water. The organic layer was washed with 1 N hydrochloric acid, and saturated sodium bicarbonate, dried (sodium sulfate), and concentrated under reduced pressure to afford mesylate 42: $^1$H NMR (300 MHz, CDCl$_3$) δ 8.24 (s, 1H), 4.41 (q, J=7 Hz, 2H), 3.59 (s, 6H), 1.39 (t, J=7 Hz, 3H)

Step 2: To a solution of mesylate 42 (4.8 mmol) in ethanol (10 mL) was added a solution of 6 N sodium hydroxide (10 mL, 60 mmol) and the resulting reaction mixture stirred at room temperature for 18 h. The reaction mixture was concentrated under reduced pressure and then partitioned between water and ethyl ether. The aqueous layer was washed twice with ether and acidified to pH 1 with 6 M hydrochloric acid. The resulting aqueous layer was extracted with ethyl acetate, dried (sodium sulfate), and concentrated under reduced pressure to afford acid 43 (220 mg): $^1$H NMR (300 MHz, CD$_3$OD) δ 8.05 (s, 1H), 3.09 (s, 3H).

Step 3: To a stirred solution of acid 43 (81 mg, 0.4 mmol) and HATU (150 mg, 0.4 mmol) in methylene chloride (3 mL) was added N,N-diisopropylethylamine (100 μL, 0.6 mmol). In a separate flask, N,N-diisopropylethylamine (140 μL, 0.8 mmol) was added to (2R,3S)-3-amino-1-[(3-ethylbenzyl)amino]-4-[3-(hexyloxy)phenyl]butan-2-ol dihydrochloride (92) (185 mg, 0.39 mmol) in methylene chloride (2 mL). This solution was added to the above solution containing the acid and the resulting reaction mixture was stirred at room temperature for 18 h. The reaction mixture was partitioned between methylene chloride and water. The organic layer was washed with water, dried (sodium sulfate), filtered, and concentrated under reduced pressure to afford a crude oil. Purification by flash column chromatography (silica, gradient 93:7 to 90:10 methylene chloride/methanol) provided N-{(1S,2R)-3-[(3-ethylbenzyl)amino]-1-[3-(hexyloxy)benzyl]-2-hydroxypropyl}-2-[(methylsulfonyl)amino]-1,3-oxazole-4-carboxamide (45) (18 mg): mp 85–90° C.; IR (KBr) 2925, 1602, 1583, 1453, 1257 cm$^{-1}$; $^1$H NMR (500 MHz, CD$_3$OD) δ 7.71 (s, 1H), 7.34–7.09 (m, 5H), 6.83–6.68 (m, 3H), 4.13–3.83 (m, 6H), 3.21–3.10 (m, 2H), 2.99 (s, 3H), 2.99–2.98 (m, 1H), 2.80–2.60 (m, 3H), 1.70–1.66 (m, 2H), 1.42–1.31 (m, 6H), 1.25–1.20 (m, 3H), 0.92–0.90 (m, 3H); ESI-MS m/z 587 [M+H]$^+$.

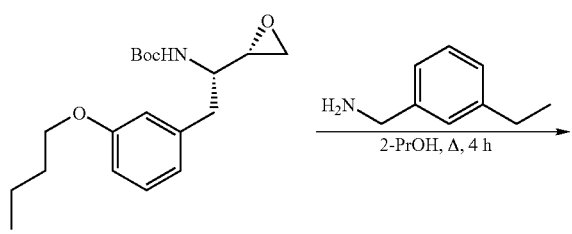

89B

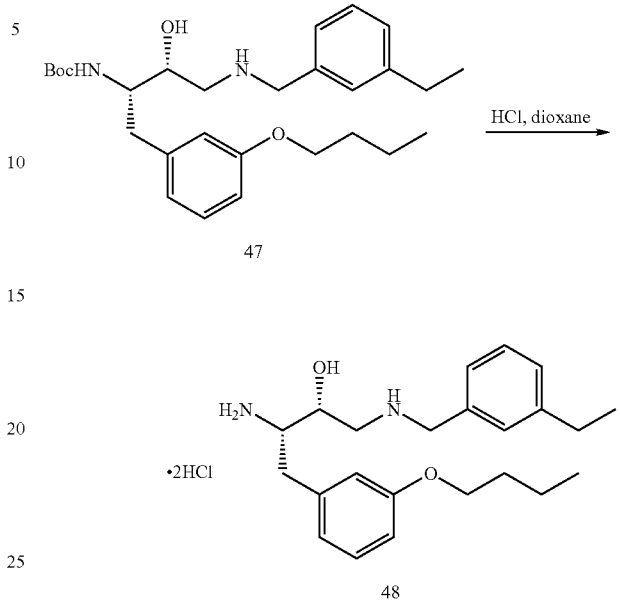

47

48

Synthesis of 48

(2R,3S)-3-amino-4-(3-butoxyphenyl)-1-[(3-ethylbenzyl)amino]butan-2-ol dihydrochloride Step 1: A mixture of Boc-L-Tyr(OBu)-epoxide (89B) (640 mg, 1.9 mmol) and 3-ethylbenzylamine (260 mg, 1.9 mmol) in 2-propanol (20 mL) was heated to 90° C. for 4 h. Upon cooling to room temperature, the reaction mixture was concentrated under reduced pressure. Purification by flash column chromatography (silica, 96:4 methylene chloride/methanol) yielded Boc-protected amino alcohol 47 (495 mg): $^1$H NMR (300 MHz, CDCl$_3$): δ 7.26–7.09 (m, 5H), 6.79–6.71 (m, 3H), 4.71–4.68 (m, 1H), 3.95–3.91 (m, 2H), 3.82–3.76 (m, 2H), 3.53–3.50 (m, 1H), 2.91–2.61 (m, 6H), 1.80–1.71 (m, 2H), 1.52–1.47 (m, 2H), 1.36 (s, 9H), 1.26–1.21 (m, 3H), 1.01–0.95 (m, 3H).

Step 2: Boc-protected amino alcohol 47 (495 mg, 1.1 mmol) in dioxane (1 mL) was treated with hydrochloric acid (3 mL, 4.0 M dioxane, 12 mmol) for 18 h. The mixture was concentrated to a clear solid. The resulting residue was then sonicated in diethyl ether and filtered to afford (2R,3S)-3-amino-4-(3-butoxyphenyl)-1-[(3-ethylbenzyl)amino]butan-2-ol dihydrochloride (48) as the hydrochloric acid salt (350 mg): mp 197–199° C.; IR (KBr) 2959, 1599, 1490, 1450, 1262 cm$^{-1}$; $^1$H NMR (300 MHz, CD$_3$OD) δ 7.38–7.25 (m, 5H), 6.89–6.83 (m, 3H), 4.29–4.23 (m, 3H), 3.98 (t, J=6 Hz, 2H), 3.73–3.70 (m, 1H), 3.22–3.19 (m, 1H), 3.08–2.90 (m, 3H), 2.71 (q, J=8 Hz, 2H), 1.78–1.73 (m, 2H), 1.54–1.47 (m, 2H), 1.26 (t, J=8 Hz, 3H), 0.99 (t, J=8 Hz, 3H); ESI-MS (m/z): 371 [M+H]$^+$.

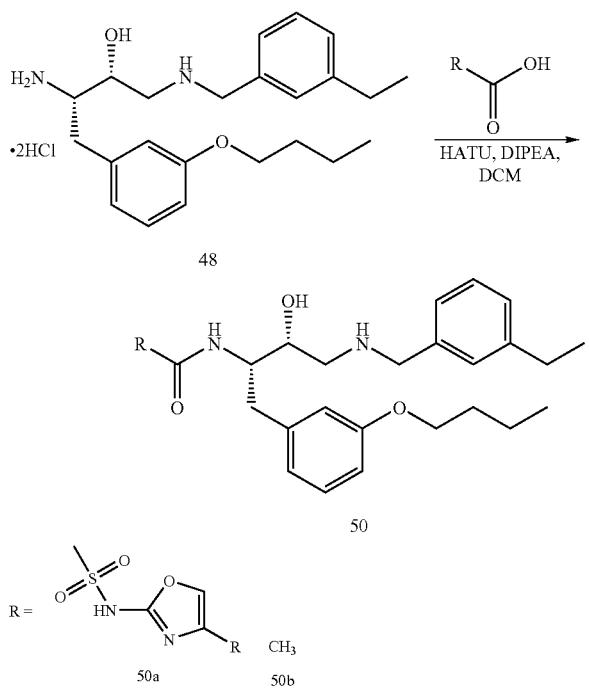

Synthesis of 50a

N-{(1S,2R)-1-(3-butoxybenzyl)-3-[(3-ethylbenzyl)amino]-2-hydroxypropyl}-2-[(methylsulfonyl)amino]-1,3-oxazole-4-carboxamide Step 1: To a stirred solution of 2-[(methylsulfonyl)amino]-1,3-oxazole-4-carboxylic acid (43) (100 mg, 0.5 mmol) and HATU (180 mg, 0.5 mmol) in methylene chloride (3 mL) was added N,N-diisopropylethylamine (100 μL, 0.6 mmol). In a separate flask, N,N-diisopropylethylamine (200 μL, 1.2 mmol) was added to amine 48 (135 mg, 0.3 mmol) in methylene chloride (2 mL). This solution was added to the above solution containing the acid and the resulting reaction mixture was stirred at room temperature for 18 h. The reaction mixture was partitioned between methylene chloride and water. The organic layer was washed with water, dried (sodium sulfate), filtered, and concentrated under reduced pressure to afford a crude oil. Purification by flash column chromatography (silica, gradient 93:7 to 90:10 methylene chloride/methanol) provided N-{(1S,2R)-1-(3-butoxybenzyl)-3-[(3-ethylbenzyl)amino]-2-hydroxypropyl}-2-[(methylsulfonyl)amino]-1,3-oxazole-4-carboxamide (50a) (10 mg): mp 78–80° C.; IR (KBr) 2960, 1602, 1581, 1490, 1450 cm$^{-1}$; $^1$H NMR (500 MHz, CD$_3$OD) δ 7.67 (s, 1H), 7.34–7.09 (m, 5H), 6.82–6.68 (m, 3H), 4.18 (s, 2H), 4.07–4.05 (m, 1H), 3.90–3.84 (m, 3H), 3.23–3.16 (m, 2H), 3.04 (s, 3H), 3.04–3.01 (m, 1H), 2.75–2.64 (m, 3H), 1.69–1.66 (m, 2H), 1.46–1.42 (m, 2H), 1.21 (t, J=8 Hz, 3H), 0.94 (t, J=8 Hz, 3H); ESI-MS m/z 559 [M+H]$^+$.

Synthesis of 50b

N-{(1S,2R)-1-(3-butoxybenzyl)-3-[(3-ethylbenzyl)amino]-2-hydroxypropyl}acetamide Step 1: To a stirred solution of acetic acid (20 μl, 0.3 mmol) and HATU (120 mg, 0.3 mmol) in methylene chloride (3 mL) was added N,N-diisopropylethylamine (100 μL, 0.6 mmol). In a separate flask, N,N-diisopropylethylamine (90 μL, 0.6 mmol) was added to amine 49 (135 mg, 0.3 mmol) in methylene chloride (2 mL). This solution was added to the above solution containing the acid and the resulting reaction mixture was stirred at room temperature for 18 h. The reaction mixture was partitioned between methylene chloride and water. The organic layer was washed with water, dried (sodium sulfate), filtered, and concentrated under reduced pressure to afford a crude oil. Purification by flash column chromatography (silica, gradient 93:7 to 90:10 methylene chloride/methanol) provided N-{(1S,2R)-1-(3-butoxybenzyl)-3-[(3-ethylbenzyl)amino]-2-hydroxypropyl}acetamide (50b) (35 mg): mp 112–114° C.; IR (KBr) 3292, 2960, 1648, 1601, 1547 cm$^{-1}$; $^1$H NMR (500 MHz, CD$_3$OD) δ 7.27–7.12 (m, 5H), 6.76–6.71 (m, 3H), 4.08–4.05 (m, 1H), 3.94–3.92 (m, 2H), 3.89–3.82 (m, 2H), 3.68–3.67 (m, 1H), 3.08–3.03 (m, 1H), 2.80–2.79 (m, 1H), 2.72–2.57 (m, 4H), 1.79 (s, 3H), 1.75–1.71 (m, 2H), 1.51–1.47 (m, 2H), 1.23 (t, J=8 Hz, 3H), 0.98 (t, J=8 Hz, 3H); ESI-MS m/z 413 [M+H]$^+$.

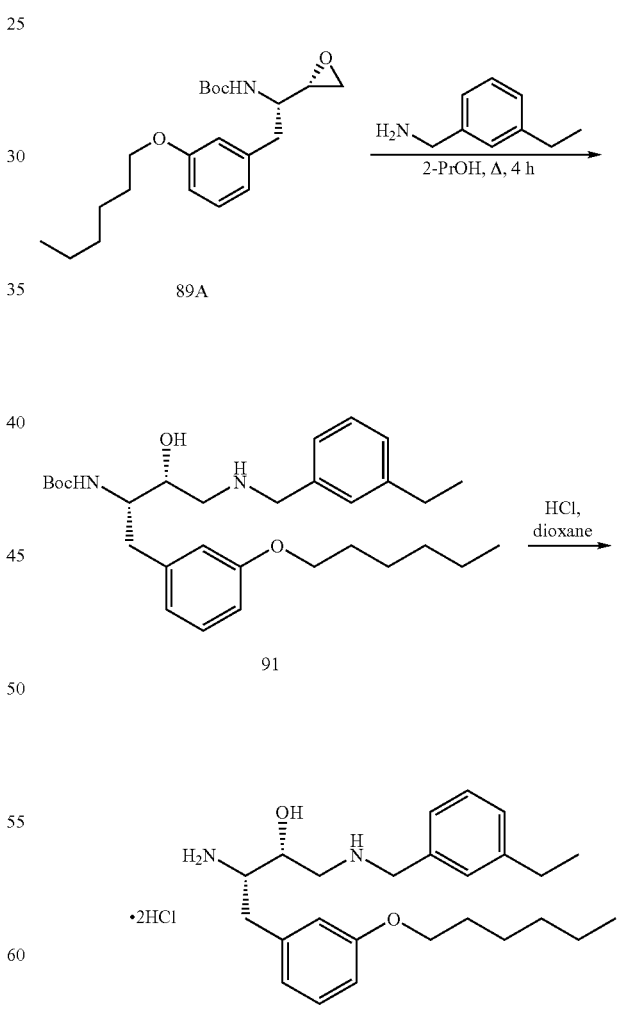

Synthesis of 92

(2R,3S)-3-amino-1-[(3-ethylbenzyl)amino]-4-[3-(hexyloxy)phenyl]butan-2-ol dihydrochloride Step 1: A mixture of Boc-L-Tyr(OBn)-epoxide (89A) (700 mg, 1.9 mmol) and 3-ethylbenzylamine (290 µL, 2.1 mmol) in 2-propanol (20 mL) was heated to 90° C. for 4 h. Upon cooling to room temperature, the reaction mixture was concentrated under reduced pressure. Purification by flash column chromatography (silica, gradient 96:4 to 93:7 methylene chloride/methanol) yielded Boc-protected amino alcohol 91 (570 mg): $^1$H NMR (300 MHz, CDCl$_3$): δ 7.31–7.09 (m, 5H), 6.81–6.74 (m, 3H), 4.71–4.68 (m, 1H), 3.95–3.77 (m, 4H), 3.53–3.51 (m, 1H), 2.91–2.61 (m, 6H), 1.81–1.74 (m, 2H), 1.47–1.21 (m, 18H), 0.93–0.90 (m, 3H)

Step 2: Boc-Protected amino alcohol 91 (460 mg, 0.9 mmol) in dioxane (3 mL) was treated with hydrochloric acid (3 mL of a 4.0 M solution in dioxane, 12 mmol) for 18 h. The reaction mixture was concentrated to an off-white solid, which was partitioned between methylene chloride and 50% aqueous ammonium hydroxide. The methylene chloride layer was collected, dried (sodium sulfate), and concentrated to afford a clear oil. Purification by flash column chromatography (silica, 94:5:1 methylene chloride/methanol/ammonium hydroxide) and subsequent reaction with 1 M hydrochloric acid in diethyl ether yielded (2R,3S)-3-amino-1-[(3-ethylbenzyl)amino]-4-[3-(hexyloxy)phenyl]butan-2-ol dihydrochloride (92) (290 mg): $^1$H NMR (300 MHz, CD$_3$OD): δ 7.38–7.22 (m, 5H), 6.90–6.84 (m, 3H), 4.30–4.23 (m, 3H), 3.97 (t, J=6 Hz, 2H), 3.73–3.70 (m, 1H), 3.34–3.22 (m, 1H), 3.05–2.87 (m, 3H), 2.71 (q, J=8 Hz, 2H), 1.79–1.74 (m, 2H), 1.48–1.23 (m, 9H), 0.95–0.93 (m, 3H); ESI MS (m/z): 399 [M+H]$^+$.

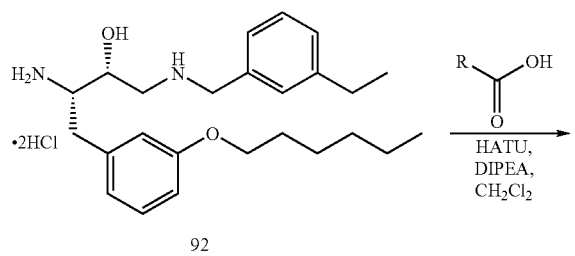

92

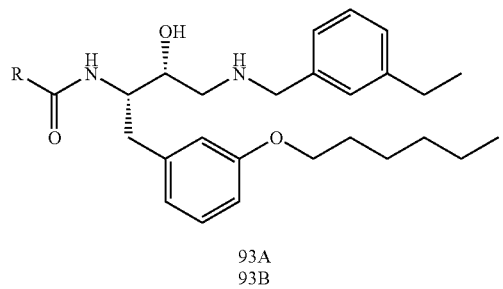

93A
93B

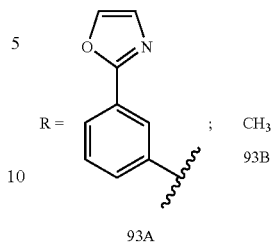

R = 93A ; 93B CH$_3$

Synthesis of 93A

N-{(1S,2R)-3-[(3-ethylbenzyl)amino]-1-[3-(hexyloxy)benzyl]-2-hydroxypropyl}-3-(1,3-oxazol-2-yl)benzamide To a stirred solution of acid (40 mg, 0.2 mmol), amine 92 (100 mg, 0.2 mmol), and HATU (80 mg, 0.2 mmol) in methylene chloride (3 mL) was added N,N-diisopropylethylamine (130 µL, 0.7 mmol). The reaction mixture was stirred at room temperature for 18 h. The reaction mixture was partitioned between methylene chloride and water. The organic layer was washed with water, dried (sodium sulfate), filtered, and concentrated under reduced pressure to afford a crude oil. Purification by flash column chromatography (silica, gradient 95:5 to 93:7 methylene chloride/methanol) provided N-{(1S,2R)-3-[(3-ethylbenzyl)amino]-1-[3-(hexyloxy)benzyl]-2-hydroxypropyl}-3-(1,3-oxazol-2-yl)benzamide 93A (42 mg): mp 117–120° C.; IR (KBr) 3298, 2931, 1637, 1501, 1537 cm$^{-1}$; $^1$H NMR (500 MHz, CD$_3$OD) δ 8.30–8.29 (m, 1H), 8.14–8.13 (m, 1H), 8.02 (s, 1H), 7.72–7.70 (m, 1H), 7.54–7.51 (m, 1H), 7.34 (s, 1H), 7.20–7.04 (m, 5H), 6.83–6.67 (m, 3H), 4.27–4.26 (m, 1H), 3.84–3.74 (m, 5H), 3.20–3.12 (m, 1H), 2.83–2.76 (m, 3H), 2.56 (q, J=8 Hz, 2H), 1.65–1.62 (m, 2H), 1.34–1.24 (m, 6H), 1.15 (t, J=8 Hz, 3H), 0.87 (t, J=7 Hz, 3H); ESI MS m/z 570 [M+H]$^+$.

Synthesis of 93B

N-{(1S,2R)-3-[(3-ethylbenzyl)amino]-1-[3-(hexyloxy)benzyl]-2-hydroxypropyl}acetamide To a stirred solution of acetic acid (15 pg, 0.2 mmol), amine 92 (100 mg, 0.2 mmol), and HATU (80 mg, 0.2 mmol) in methylene chloride (3 mL) was added N,N-diisopropylethylamine (130 µL, 0.7 mmol). The reaction mixture was stirred at room temperature for 18 h. The reaction mixture was partitioned between methylene chloride and water. The organic layer was washed with water, dried (sodium sulfate), filtered, and concentrated under reduced pressure to afford a crude oil. Purification by flash column chromatography (silica, gradient 95:5 to 90:10 methylene chloride/methanol) provided N-{(1S,2R)-3-[(3-ethylbenzyl)amino]-1-[3-(hexyloxy)benzyl]-2-hydroxypropyl}acetamide 93B (20 mg): mp 102–105° C.; IR (KBr) 3304, 2929, 1637, 1603, 1550 cm$^{-1}$; $^1$H NMR (500 MHz, CD$_3$OD) δ 7.26–7.11 (m, 5H), 6.75–6.70 (m, 3H), 4.03–3.60 (m, 6H), 3.10–3.05 (m, 1H), 2.80–2.55 (m, 5H), 1.78–1.72 (m, 2H), 1.78 (s, 3H), 1.46–1.44 (m, 2H), 1.36–1.33 (m, 4H), 1.24–1.21 (m, 3H), 0.93–0.91 (m, 3H); ESI MS m/z 441 [M+H]$^+$.

Example 8

N-[(1S)-1-((1R)-2-{[1-(3-bromophenyl)cyclopropyl]amino}-1-hydroxyethyl)-3-methyl-4-phenylbutyl] acetamide hydrochloride

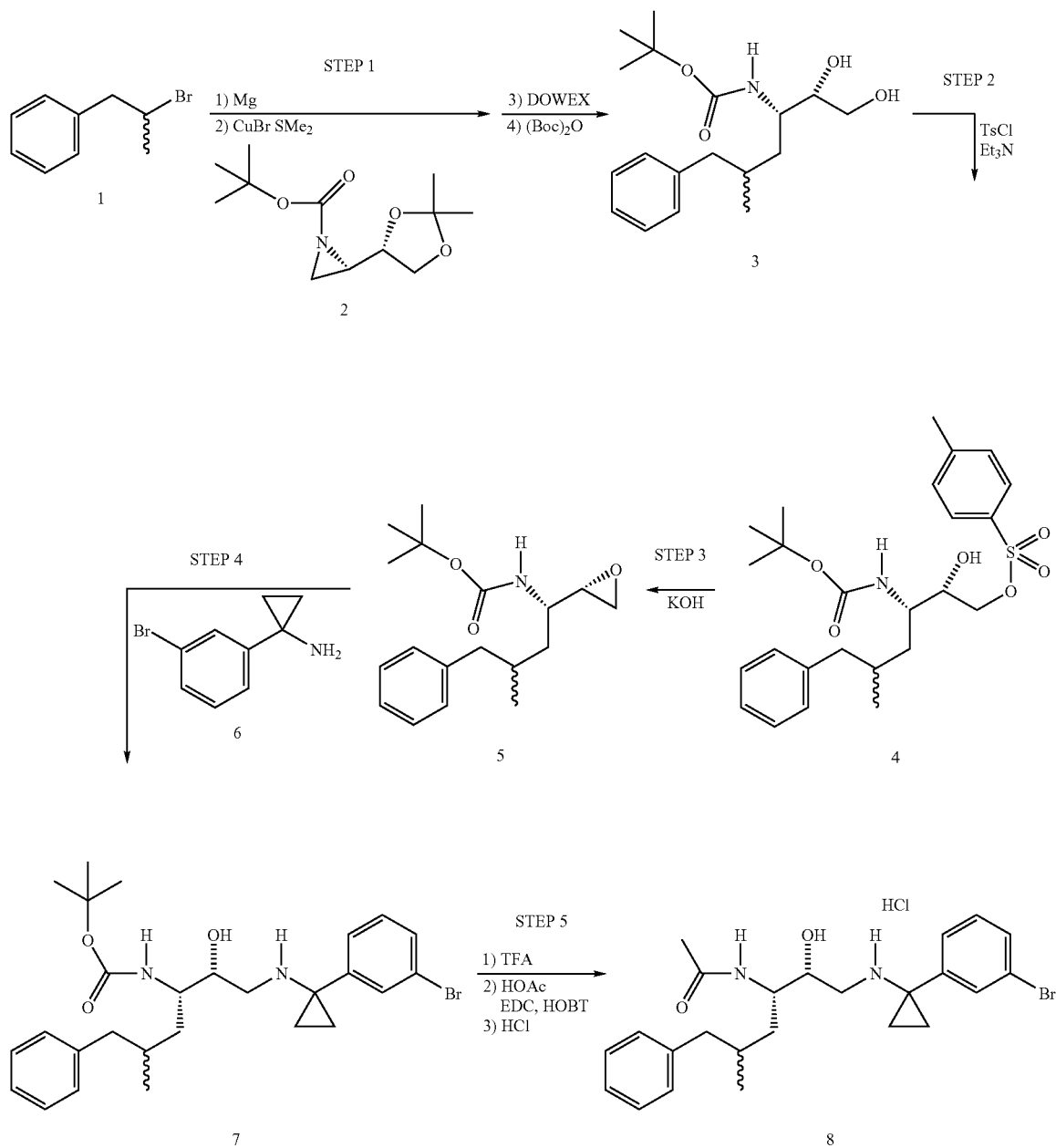

Scheme 1

Step 1: To magnesium turnings (1.94 g, 80 mmol) in 15 mL of dry tetrahydrofuran (THF) under nitrogen was added a crystal of iodine, followed by dropwise addition, over 45 min, of a solution of 2-bromo-1-phenylpropane (6.2 mL, 40 mmol) in 25 mL of dry THF. During the addition the mixture was heated to reflux in a 70° C. water bath. After addition the mixture was refluxed a further 45 min, and then allowed to cool. The resulting Grignard reagent was transferred via syringe to a flask containing 0.6 g (2.92 mmol) of cuprous bromide-dimethylsulfide complex in 15 mL of dry THF, under nitrogen, cooled to −25° C. The mixture was stirred 15–20 min, and then a solution of tert-butyl (2R)-2-[(4S)-2,2-dimethyl-1,3-dioxolan-4-yl]aziridine-1-carboxylate, 2 (2.65 g, 10.9 mmol) in 10 mL of THF was added over several minutes. After 2 h the cold bath was removed and the reaction was allowed to stir at ambient temperature ca. 40 h. It was quenched with saturated NH$_4$Cl and diluted with ether. The organic phase was washed with saturated NH$_4$Cl, 1 N NaHCO$_3$, and brine, and dried over Na$_2$SO$_4$. Filtration and concentration afforded 7.1 g of a pale yellow oil. The oil was dissolved in 100 mL of methanol. Dowex 50WX2-400 (15 g, washed with water, methanol, and dichloromethane) was added and the mixture was stirred in a 50° C. water bath for ca. 3 h. The mixture was filtered and the resin was washed extensively with methanol and dichloromethane. The resin was then washed, using a clean receiver flask, with a solution of 12% ammonium hydroxide, 48% methanol, and 40% dichloromethane. The filtrate was concentrated to 1.8 g of a pale yellow oil. This was dissolved in 40 mL of dry THF, under nitrogen, maintained at 17° C. in a cool water bath. The solution was stirred and di-t-butyl-dicarbonate (1.8 g, 8.3 mmol) was added. After ca. 15 h, the mixture was concentrated, dissolved in ether, and the ether phase was washed with 1 N KH$_2$PO$_4$ (2×) and with brine. The solution was dried (Na$_2$SO$_4$), concentrated, and chromatographed over silica gel, eluting with 50% ethyl acetate in heptane, to afford N-[(1S)-1-((1S)-2-hydroxy-1-hydroxyethyl)-3-methyl-4-phenylbutyl]-t-butylcarbamate 3 as a nearly colorless, viscous syrup (2 g, 6 mmol, 55%). $^1$H NMR (CDCl$_3$) δ 7.0–7.12 (m, 5H), 4.65 (d, 0.5H), 4.37 (d, 0.5H), 3.78–3.55 (m, 3H), 3.33 (m, 0.5H), 3.20 (m, 0.5H), 3.06 (br, 2H), 2.81 (dd, 0.5H), 2.54 (m, 1H), 2.24 (dd, 0.5H), 1.84 (m, 1.5H), 1.66 (m, 0.5H), 1.47 (s, 4.5H), 1.43 (s, 4.5H), 1.36–1.26 (m, 1H), 0.93 (d, 1.5H), 0.87 (d, 1.5H), as a mixture of diastereomers.

Step 2: To a solution of N-[(1S)-1-((1S)-2-hydroxy-1-hydroxyethyl)-3-methyl-4-phenylbutyl]-t-butylcarbamate 3 (6.4 mmol) in 14 mL of dichloromethane at 0° C. was added 1.07 mL (7.68 mmol) of triethylamine and 40 mg of 4-dimethylaminopyridine, followed by 1.24 g (6.5 mmol) of toluenesulfonyl chloride. After 1 h the cold bath was removed and the mixture was allowed to stir at ambient temperature for 20 h. Water and ether were added, and the mixture was stirred vigorously for 1.5 h. The organic phase was washed with 1 N NaHCO$_3$, 10% HCl, water, and brine, and dried (Na$_2$SO$_4$). Chromatography over silica gel, eluting with 1% to 5% of methanol in chloroform afforded 1.53 g (3.2 mmol, 50%) of N-[(1S)-1-((1S)-2-[(4-methylphenyl)sulfonate]-1-hydroxyethyl)-3-methyl-4-phenylbutyl]-t-butylcarbamate 4 as a colorless gum. $^1$H NMR (CDCl$_3$) δ 7.78 (m, 2H), 7.36–7.10 (m, 7H), 4.59 (d, 0.5H), 4.39 (d, 0.5H), 4.04 (m, 1H), 3.96 (m, 1H), 3.83 (m, 1.5H), 3.69 (m, 0.5H), 2.77 (dd, 0.5H), 2.59 (m, 1H), 2.50 (m, 1H), 2.45 (s, 3H), 2.20 (dd, 0.5H), 1.78 (m, 1H), 1.44 (s, 4.5H), 1.40 (s, 4.5H), 1.49–1.28 (m, 2H), 0.88 (d, 1.5H), 0.85 (d, 1.5H), as a mixture of diastereomers.

Step 3: N-[(1S)-1-((1S)-2-[(4-methylphenyl)sulfonate]-1-hydroxyethyl)-3-methyl-4-phenylbutyl]-t-butylcarbamate 4 (1.53 g, 3.2 mmol) was dissolved in 7 mL of methanol and 3 mL of dry THF, under nitrogen, cooled to 0° C. To the vigorously stirred solution was added 0.27 g (4.8 mmol) of freshly crushed KOH in 2 mL of methanol. After 20 min the reaction mixture was applied to a small column of silica gel packed in 10% methanol in ether, and eluted with that solvent mixture. The eluant was concentrated to 1 g of an oil, which was rechromatographed on silica gel, eluting with 15% ethyl acetate in heptane, to afford 725 mg (2.36 mmol, 74%) of N-[(1S)-1-((1S)-oxiran-1-yl)-3-methyl-4-phenylbutyl]-t-butylcarbamate 5 as a colorless syrup. $^1$H NMR (CDCl$_3$) δ 7.30–7.13 (m, 5H), 4.42 (d, 0.5H), 4.24 (d, 0.5H), 3.66 (m, 0.5H), 3.52 (m, 0.5H), 2.8–2.73 (m, 3.5H), 2.53 (m, 1H), 2.31 (dd, 0.5H), 1.91 (m, 1H), 1.6 (m, 0.5H), 1.46 (s, 4.5H), 1.44 (s, 4.5H), 1.4–1.32 (m, 1.5H), 0.9 (m, 3H) as a mixture of diastereomers.

Step 4: To 260 mg (0.85 mmol) of N-[(1S)-1-((1S)-oxiran-1-yl)-3-methyl-4-phenylbutyl]-t-butylcarbamate 5 in 2.5 mL of isopropanol was added 400 mg (1.88 mmol) of 1-(3-bromophenyl)cyclopropyl amine 6. The mixture was stirred at 80° C. for 2 h, concentrated in vacuo, and dissolved in ethyl acetate. The organic solution was washed twice with aqueous 10% HCl, and once each with water, 1 N NaHCO$_3$, and brine. It was dried over Na$_2$SO$_4$ and concentrated to ca. 300 mg of an oil. Chromatography on silica gel, eluting with 1% to 2% of methanol in chloroform afforded 132 mg (50%) of recovered starting material 5 and 118 mg (0.227 mmol, 54% based on unrecovered 5) of N-[(1S)-1-((1R)-2-{[1-(3-bromophenyl)cyclopropyl]amino}-1-hydroxyethyl)-3-methyl-4-phenylbutyl]-t-butylcarbamate 7 as a colorless oil. $^1$H NMR (CDCl$_3$) δ 7.45–7.11 (m, 9H), 4.52 (d, 0.5H), 4.22 (d, 0.5H), 3.64 (m, 0.5H), 3.47 (m, 0.5H), 3.31 (m, 0.5H), 3.18 (m, 0.5H), 2.81 (dd, 0.5H), 2.8 (br, 1H), 2.64 (dd, 1H), 2.59 (m, 1H), 2.51 (d, 1H), 2.19 (dd, 0.5H), 1.8 (m, 1H), 1.7–1.55 (m, 0.5H), 1.42 (s, 4.5H), 1.36 (s, 4.5H), 1.3–1.18 (m, 1.5H), 1.04–0.93 (m, 4H), 0.9 (d, 1.5H), 0.85 (d, 1.5H) as a mixture of diastereomers.

Step 5: Trifluoroacetic acid (TFA, 2 mL) and dichloromethane (2 mL) were added to N-[(1S)-1-((1R)-2-{[1-(3-bromophenyl)cyclopropyl]amino}-1-hydroxyethyl)-3-methyl-4-phenylbutyl]-t-butylcarbamate 7 (118 mg, 0.227 mmol) and the mixture was stirred for 40 min. It was concentrated in vacuo to 0.2 g of an oil, reflecting the presence of the amine and 4 equivalents (0.9 mmol) of TFA. This was dissolved in 1 mL of dimethylformamide (DMF) and neutralized with 130 μL (1.18 mmol) of 4-methyl morpholine (NMM). To this was added a pre-mixed solution of acetic acid (20 μL, 0.33 mmol), 1-(3-dimethylaminopropyl)-3-ethylcarbodiimide hydrochloride (EDC, 63 mg, 0.33 mmol), and 1-hydroxybenzotriazole hydrate (HOBT, 45 mg, 0.33 mmol) in 1 mL of dry DMF, which had been stirring together for 1.3 h. The mixture was stirred at ambient temperature for 2.5 h, quenched with 1 N KH$_2$PO$_4$, and diluted with ethyl acetate. The organic phase was washed with 1 N KH$_2$PO$_4$, 1 N NaHCO$_3$ (2×), and brine, and dried over Na$_2$SO$_4$. Concentration gave ca. 150 mg of an oil which was chromatographed over silica gel, eluting with 7% methanol (containing 1% of NH$_4$OH) in dichloromethane. A fraction of the product (58 mg) was obtained which was dissolved in ether and treated with ethereal HCl to form, after trituration with ether, 45 mg of N-[(1S)-1-((1R)-2-{[1-(3-bromophenyl)cyclopropyl]amino}-1-hydroxyethyl)-3-methyl-4-phenylbutyl] acetamide hydrochloride 8 as a white solid. The NMR spectrum (CDCl$_3$+MEOH-d$_4$) showed this to be a ca. 1:1 mixture of diastereomers, MS (CI) m/z (rel. intensity) 459 (MH$^+$, 99), 503 (4), 501 (3); HRMS (ESI) calcd for C$_{24}$H$_{31}$BRN$_2$O$_2$+H$_1$ 459.1647, found 459.1655. A second fraction of the product was likewise dissolved in ether and precipitated as the salt with ethereal HCl to afford, after ether trituration, 66 mg of a white solid shown by NMR to be a ca. 2:1 mixture of these diastereomers.

Scheme 2 illustrates the use of bromide intermediates 10, which may be converted to compounds of the invention analogous to 8 by routes similar to that outlined in Scheme 1

Scheme 2

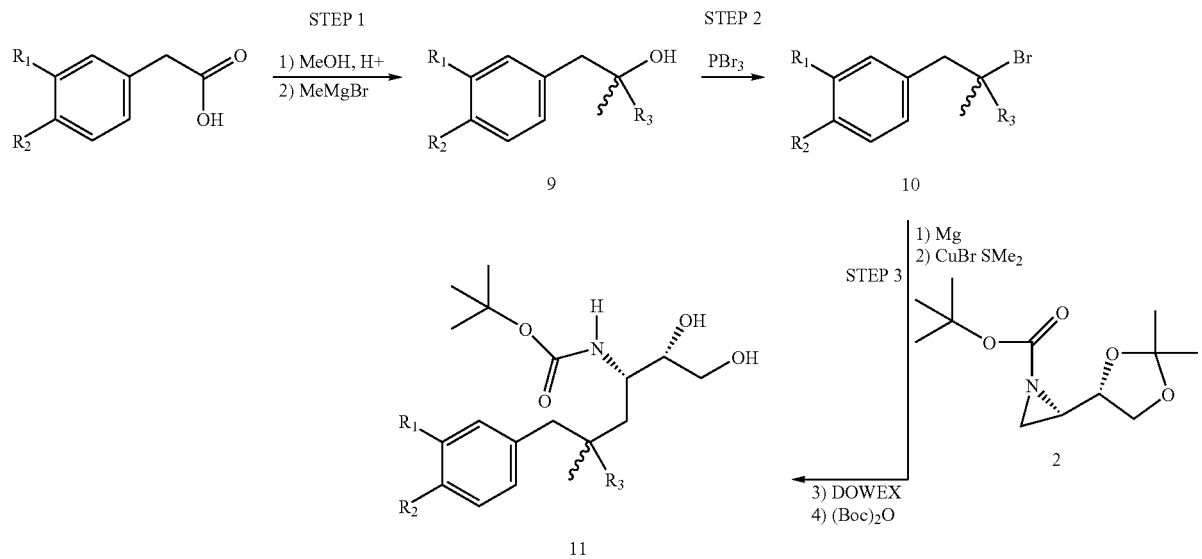

Step 1: To 3,4-dimethoxyphenyl acetic acid (4 g, 20 mmol) in 10 mL of methanol and 50 mL of dichloromethane was added 2 mL of concentrated sulfuric acid. The mixture was stirred for 2 days. The reaction mixture was poured over ice and neutralized with solid $NaHCO_3$. The mixture was extracted twice with ethyl acetate, and the combined organic phases were washed with water and brine, dried over $Na_2SO_4$, and treated with charcoal. Filtration afforded a nearly colorless solution which was concentrated to 4.34 g of a slightly yellow oil. A solution of this oil in 25 mL of dry THF was added dropwise to 25 mL of 3 M methyl magnesium bromide in THF, under nitrogen, and maintaining a temperature of 20° C. with a water bath. The addition took 10 min. After an additional 10 min, the bath was removed and the mixture was stirred at ambient temperature for 4 h. It was again cooled in a water bath and quenched by cautious dropwise addition of aqueous 5% HCl, and then 10% HCl until the pH was acidic. The product was extracted into ethyl acetate, and the organic phase was washed with water, 1 N $NaHCO_3$, and brine, and dried with $Na_2SO_4$. Concentration afforded 4 g (19 mmol, 95%) of 1-(3,4-dimethoxyphenyl)-2-methylpropan-2-ol 9 as a white solid, MS (EI) m/z (rel. intensity) 210 (M+, 95); HRMS (EI) calcd for $C_{12}H_{18}O_3$ 210.1256, found 210.1252. Anal. Calcd for $C_{12}H_{18}O_3$: C, 68.55; H, 8.63. Found: C, 68.32; H, 8.72; N, 0.20.

Step 2: To 3.15 g (15 mmol) of 1-(3,4-dimethoxyphenyl)-2-methylpropan-2-ol 9 in 30 mL of chloroform cooled to −15° C., under nitrogen, was added 0.57 mL (6 mmol) of phosphorus tribromide via syringe over 20 min. The mixture was stirred for 2.5 h as the temperature rose to 8° C. The reaction was quenched with water and diluted with ethyl acetate. The organic phase was washed with water, 1 N $NaHCO_3$, and brine, and dried over $Na_2SO_4$. Concentration afforded 4.04 g of a yellow oil, which was filtered through a short plug of silica gel, eluting with 1:1 chloroform:heptane, to afford 2.88 g (10.55 mmol, 70%) of 1-(3,4-dimethoxyphenyl)-2-methyl-2-bromo-propane 10 as a colorless oil. $^1$H NMR ($CDCl_3$) δ 6.80 (m, 3H), 3.89 (s, 3H), 3.88 (s, 3H), 3.14 (s, 2H), 1.77 (s, 6H).

Step 3: A slurry of 20 mL of Rieke magnesium (ca. 20 mmol) in THF was introduced into a dry flask under nitrogen. To the stirred suspension was added neat 1-(3,4-dimethoxyphenyl)-2-methyl-2-bromo-propane 10 (2.8 g, 10 mmol) over 10 min. The flask became warm during the addition. A hot water bath was placed under the flask, and the reaction mixture was allowed to reflux for 2 h. The resulting Grignard reagent was transferred via syringe to a flask containing 0.2 g (0.97 mmol) of cuprous bromide-dimethylsulfide complex in 5 mL of dry THF, under nitrogen, cooled to −25° C. The mixture was stirred 20 min, and then a solution of tert-butyl (2R)-2-[(4S)-2,2-dimethyl-1,3-dioxolan-4-yl]aziridine-1-carboxylate, 2 (1.2 g, 4.9 mmol) in 5 mL of THF was added over several minutes. After 0.5 h the cold bath was removed and the reaction was allowed to stir at ambient temperature ca. 18 h. It was quenched with saturated $NH_4Cl$ and diluted with ether. The organic phase was washed with saturated $NH_4Cl$ (3×), 1 N $NaHCO_3$, and brine, and dried over $Na_2SO_4$. Filtration and concentration afforded 2.76 g of a nearly colorless oil. The oil was dissolved in 50 mL of methanol. Dowex 50WX2-400 (8.2 g, washed with water, methanol, and dichloromethane) was added and the mixture was refluxed for 2.3 h. The mixture was filtered and the resin was washed extensively with methanol and dichloromethane. The resin was then washed, using a clean receiver flask, with a solution of 50% ammonium hydroxide in ethanol. The filtrate was concentrated to 0.64 g of a viscous amber oil. This was dissolved in 20 mL of dry THF, under nitrogen. The solution was stirred and di-t-butyl-dicarbonate (0.48 g, 2.2 mmol) was added. After 17 h, the mixture was concentrated, dissolved in ether, and the ether phase was washed with water (4×) and with brine. The solution was dried ($Na_2SO_4$), concentrated, and chromatographed over silica gel, eluting with 7% methanol in chloroform, to afford N-[(1S)-1-((1S)-2-hydroxy-1-hydroxyethyl)-3,3-dimethyl-4-(3,4-dimethoxyphenyl) butyl]-t-butylcarbamate 11 as a colorless oil (30 mg). $^1$H NMR ($CDCl_3$) δ 6.78 (d, 1H) 6.68 (m, 2H), 4.47 (d, 1H), 3.86 (s, 6H), 3.72–3.56 (m, 4H), 3.19 (br, 1H), 2.83 (br, 1H), 2.50 (s, 2H), 1.93 (m, 1H), 1.43 (s, 9H), 1.16 (m, 1H), 0.95 (s, 3H), 0.89 (s, 3H). A second fraction (150 mg) contained roughly equal amounts of 11 and its mono-demethylated congener.

BIOLOGY EXAMPLES

Example A

Enzyme Inhibition Assay

The compounds of the invention are analyzed for inhibitory activity by use of the MBP-C125 assay. This assay determines the relative inhibition of beta-secretase cleavage of a model APP substrate, MBP-C125SW, by the compounds assayed as compared with an untreated control. A detailed description of the assay parameters can be found, for example, in U.S. Pat. No. 5,942,400. Briefly, the substrate is a fusion peptide formed of maltose binding protein (MBP) and the carboxy terminal 125 amino acids of APP-SW, the Swedish mutation. The beta-secretase enzyme is derived from human brain tissue as described in Sinha et al, 1999, Nature 40:537–540) or recombinantly produced as the full-length enzyme (amino acids 1–501), and can be prepared, for example, from 293 cells expressing the recombinant cDNA, as described in WO0/47618.

Inhibition of the enzyme is analyzed, for example, by immunoassay of the enzyme's cleavage products. One exemplary ELISA uses an anti-MBP capture antibody that is deposited on precoated and blocked 96-well high binding plates, followed by incubation with diluted enzyme reaction supernatant, incubation with a specific reporter antibody, for example, biotinylated anti-SW192 reporter antibody, and further incubation with streptavidin/alkaline phosphatase. In the assay, cleavage of the intact MBP-C125SW fusion protein results in the generation of a truncated amino-terminal fragment, exposing a new SW-192 antibody-positive epitope at the carboxy terminus. Detection is effected by a fluorescent substrate signal on cleavage by the phosphatase. ELISA only detects cleavage following Leu 596 at the substrate's APP-SW 751 mutation site.

Specific Assay Procedure:

Compounds are diluted in a 1:1 dilution series to a six-point concentration curve (two wells per concentration) in one 96-plate row per compound tested. Each of the test compounds is prepared in DMSO to make up a 10 millimolar stock solution. The stock solution is serially diluted in DMSO to obtain a final compound concentration of 200 micromolar at the high point of a 6-point dilution curve. Ten (10) microliters of each dilution is added to each of two wells on row C of a corresponding V-bottom plate to which 190 microliters of 52 millimolar NaOAc, 7.9% DMSO, pH 4.5 are pre-added. The NaOAc diluted compound plate is spun down to pellet precipitant and 20 microliters/well is transferred to a corresponding flat-bottom plate to which 30 microliters of ice-cold enzyme-substrate mixture (2.5 microliters MBP-C125SW substrate, 0.03 microliters enzyme and 24.5 microliters ice cold 0.09% TX100 per 30 microliters) is added. The final reaction mixture of 200 micromolar compound at the highest curve point is in 5% DMSO, 20 millimolar NaOAc, 0.06% TX100, at pH 4.5.

Warming the plates to 37 degrees C. starts the enzyme reaction. After 90 minutes at 37 degrees C., 200 microliters/well cold specimen diluent is added to stop the reaction and 20 microliters/well was transferred to a corresponding anti-MBP antibody coated ELISA plate for capture, containing 80 microliters/well specimen diluent. This reaction is incubated overnight at 4 degrees C. and the ELISA is developed the next day after a 2 hour incubation with anti-192SW antibody, followed by Streptavidin-AP conjugate and fluorescent substrate. The signal is read on a fluorescent plate reader.

Relative compound inhibition potency is determined by calculating the concentration of compound that showed a fifty percent reduction in detected signal ($IC_{50}$) compared to the enzyme reaction signal in the control wells with no added compound. In this assay, the compounds of the invention exhibited an $IC_{50}$ of less than 50 micromolar.

Example B

Cell Free Inhibition Assay Utilizing a Synthetic APP Substrate

A synthetic APP substrate that can be cleaved by beta-secretase and having N-terminal biotin and made fluorescent by the covalent attachment of Oregon green at the Cys residue is used to assay beta-secretase activity in the presence or absence of the inhibitory compounds of the invention. Useful substrates include the following:

```
Biotin-SEVNL-DAEFR[Oregon green]KK                          [SEQ ID NO:1]

Biotin-SEVKM-DAEFR[Oregon green]KK                          [SEQ ID NO:2]

Biotin-GLNIKTEEISEISY-EVEFRC[Oregon green]KK                [SEQ ID NO:3]

Biotin-ADRGLTTRPGSGLTNIKTEEISEVNL-DAEF[Oregon green]KK      [SEQ ID NO:4]

Biotin-FVNQHLCoxGSHLVEALY-LVCoxGERGFFYTPKA[Oregon green]KK  [SEQ ID NO:5]
```

The enzyme (0.1 nanomolar) and test compounds (0.001–100 micromolar) are incubated in pre-blocked, low affinity, black plates (384 well) at 37 degrees for 30 minutes. The reaction is initiated by addition of 150 millimolar substrate to a final volume of 30 microliter per well. The final assay conditions are: 0.001–100 micromolar compound inhibitor; 0.1 molar sodium acetate (pH 4.5); 150 nanomolar substrate; 0.1 nanomolar soluble beta-secretase; 0.001% Tween 20, and 2% DMSO. The assay mixture is incubated for 3 hours at 37 degrees C., and the reaction is terminated by the addition of a saturating concentration of immunopure streptavidin. After incubation with streptavidin at room temperature for 15 minutes, fluorescence polarization is measured, for example, using a LJL Acqurest (Ex485 nm/Em530 nm). The activity of the beta-secretase enzyme is detected by changes in the fluorescence polarization that occur when the substrate is cleaved by the enzyme. Incubation in the presence or absence of compound inhibitor demonstrates specific inhibition of beta-secretase enzymatic cleavage of its synthetic APP substrate. In this assay, compounds of the invention exhibited an $IC_{50}$ of less than 50 micromolar.

Example C

Beta-Secretase Inhibition: P26-P4'SW Assay

Synthetic substrates containing the beta-secretase cleavage site of APP are used to assay beta-secretase activity, using the methods described, for example, in published PCT application WO00/47618.

```
                                           [SEQ ID NO: 6]
The P26-P4'SW substrate is a peptide
of the sequence:
(biotin)CGGADRGLTTRPGSGLTNIKTEEISEVNLDAEF

[SEQ ID NO: 7]
The P26-P1 standard has the sequence:
(biotin)CGGADRGLTTRPGSGLTNIKTEEISEVNL.
```

Briefly, the biotin-coupled synthetic substrates are incubated at a concentration of from about 0 to about 200 micromolar in this assay. When testing inhibitory compounds, a substrate concentration of about 1.0 micromolar is preferred. Test compounds diluted in DMSO are added to the reaction mixture, with a final DMSO concentration of 5%. Controls also contain a final DMSO concentration of 5%. The concentration of beta secretase enzyme in the reaction is varied, to give product concentrations with the linear range of the ELISA assay, about 125 to 2000 picomolar, after dilution.

The reaction mixture also includes 20 millimolar sodium acetate, pH 4.5, 0.06% Triton X100, and is incubated at 37 degrees C. for about 1 to 3 hours. Samples are then diluted in assay buffer (for example, 145.4 nanomolar sodium chloride, 9.51 millimolar sodium phosphate, 7.7 millimolar sodium azide, 0.05% Triton X405, 6 g/liter bovine serum albumin, pH 7.4) to quench the reaction, then diluted further for immunoassay of the cleavage products.

Cleavage products can be assayed by ELISA Diluted samples and standards are incubated in assay plates coated with capture antibody, for example, SW192, for about 24 hours at 4 degrees C. After washing in TTBS buffer (150 millimolar sodium chloride, 25 millimolar Tris, 0.05% Tween 20, pH 7.5), the samples are incubated with streptavidin-AP according to the manufacturer's instructions. After a one hour incubation at room temperature, the samples are washed in TTBS and incubated with fluorescent substrate solution A (31.2 g/liter 2-amino-2-methyl-1-propanol, 30 mg/liter, pH 9.5). Reaction with streptavidin-alkaline phosphate permits detection by fluorescence. Compounds that are effective inhibitors of beta-secretase activity demonstrate reduced cleavage of the substrate as compared to a control.

Example D

Assays using Synthetic Oligopeptide-Substrates

Synthetic oligopeptides are prepared that incorporate the known cleavage site of beta-secretase, and optionally detectable tags, such as fluorescent or chromogenic moieties. Examples of such peptides, as well as their production and detection methods are described in U.S. Pat. No. 5,942,400, herein incorporated by reference. Cleavage products can be detected using high performance liquid chromatography, or fluorescent or chromogenic detection methods appropriate to the peptide to be detected, according to methods well known in the art.

By way of example, one such peptide has the sequence SEVNL-DAEF [SEQ ID NO: 8], and the cleavage site is between residues 5 and 6. Another preferred substrate has the sequence ADRGLTTRPGSGLTNIKTEEISEVNL-DAEF [SEQ ID NO: 9], and the cleavage site is between residues 26 and 27.

These synthetic APP substrates are incubated in the presence of beta-secretase under conditions sufficient to result in beta-secretase mediated cleavage of the substrate. Comparison of the cleavage results in the presence of the compound inhibitor to control results provides a measure of the compound's inhibitory activity.

Example E

Inhibition of Beta-Secretase Activity—Cellular Assay

An exemplary assay for the analysis of inhibition of beta-secretase activity utilizes the human embryonic kidney cell line HEKp293 (ATCC Accession No. CRL-1573) transfected with APP751 containing the naturally occurring double mutation Lys651Met52 to Asn651Leu652 (numbered for APP751), commonly called the Swedish mutation and shown to overproduce A beta (Citron et al., 1992, *Nature* 360:672–674), as described in U.S. Pat. No. 5,604,102.

The cells are incubated in the presence/absence of the inhibitory compound (diluted in DMSO) at the desired concentration, generally up to 10 micrograms/ml. At the end of the treatment period, conditioned media is analyzed for beta-secretase activity, for example, by analysis of cleavage fragments. A beta can be analyzed by immunoassay, using specific detection antibodies. The enzymatic activity is measured in the presence and absence of the compound inhibitors to demonstrate specific inhibition of beta-secretase mediated cleavage of APP substrate.

Example F

Inhibition of Beta-Secretase in Animal Models of AD

Various animal models can be used to screen for inhibition of beta-secretase activity. Examples of animal models useful in the invention include, but are not limited to, mouse, guinea pig, dog, and the like. The animals used can be wild type, transgenic, or knockout models. In addition, mammalian models can express mutations in APP, such as APP695-SW and the like described herein. Examples of transgenic non-human mammalian models are described in U.S. Pat. Nos. 5,604,102, 5,912,410 and 5,811,633.

PDAPP mice, prepared as described in Games et al., 1995, *Nature* 373:523–527 are useful to analyze in vivo suppression of A beta release in the presence of putative inhibitory compounds. As described in U.S. Pat. No. 6,191,166, 4 month old PDAPP mice are administered compound formulated in vehicle, such as corn oil. The mice are dosed with compound (1–30 mg/ml; preferably 1–10 mg/ml). After time, e.g., 3–10 hours, the animals are sacrificed, and brains removed for analysis.

Transgenic animals are administered an amount of the compound inhibitor formulated in a carrier suitable for the chosen mode of administration. Control animals are untreated, treated with vehicle, or treated with an inactive compound. Administration can be acute, i.e., single dose or multiple doses in one day, or can be chronic, i.e., dosing is repeated daily for a period of days. Beginning at time 0, brain tissue or cerebral fluid is obtained from selected animals and analyzed for the presence of APP cleavage peptides, including A beta, for example, by immunoassay using specific antibodies for A beta detection. At the end of the test period, animals are sacrificed and brain tissue or cerebral fluid is analyzed for the presence of A beta and/or beta-amyloid plaques. The tissue is also analyzed for necrosis.

Animals administered the compound inhibitors of the invention are expected to demonstrate reduced A beta in brain tissues or cerebral fluids and reduced beta amyloid plaques in brain tissue, as compared with non-treated controls.

Example G

Inhibition of A Beta Production in Human Patients

Patients suffering from Alzheimer's Disease (AD) demonstrate an increased amount of A beta in the brain. AD patients are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; A beta deposits in the brain; amyloid plaque in the brain; and scores for cognitive and memory function, as compared with control, non-treated patients.

Example H

Prevention of A Beta Production in Patients at Risk for AD

Patients predisposed or at risk for developing AD are identified either by recognition of a familial inheritance pattern, for example, presence of the Swedish Mutation, and/or by monitoring diagnostic parameters. Patients identified as predisposed or at risk for developing AD are administered an amount of the compound inhibitor formulated in a carrier suitable for the chosen mode of administration. Administration is repeated daily for the duration of the test period. Beginning on day 0, cognitive and memory tests are performed, for example, once per month.

Patients administered the compound inhibitors are expected to demonstrate slowing or stabilization of disease progression as analyzed by changes in one or more of the following disease parameters: A beta present in CSF or plasma; brain or hippocampal volume; amyloid plaque in the brain; and scores for cognitive and memory function, as compared with control, non-treated patients.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Unless defined otherwise, all scientific and technical terms used herein have the same meaning as commonly understood by one of skill in the art to which this invention belongs.

All patents and publications referred to herein are hereby incorporated by reference for all purposes The invention has been described with reference to various specific and preferred embodiments and techniques. However, it should be understood that many variations and modifications may be made while remaining within the spirit and scope of the invention.

What is claimed is:

1. A compound of the formula:

or a pharmaceutically acceptable salt thereof, wherein

E is a bond;

$R_J$ is H;

$R_K$ is H;

K is —$(CR_4R_5)_n$—; wherein $R_4$ and $R_5$ are independently hydrogen, halogen, $C_1$–$C_6$ alkoxy or $C_1$–$C_4$ alkyl optionally substituted with halogen, —CN, —$CF_3$, or —OH;

n is 0, 1 or 2;

A is aryl optionally substituted with one, two or three independently selected $R_{100}$ groups, where $R_{100}$ is (A) —$NO_2$,
(B) —C≡N,
(C) —N(R)CO, where R and R' are independently hydrogen, $C_1$–$C_6$ alkyl, —$(CH_2)_{0-2}$-aryl, or —$(CH_2)_{0-2}$-cycloalkyl, where each aryl or cycloalkyl is optionally substituted with halogen, hydroxy, $C_1$–$C_6$ alkyl, amino, mono($C_1$–$C_6$)alkylamino, or di($C_1$–$C_6$) alkylamino,
(D) —$CO_2$—$R_{25}$, where $R_{25}$ is selected from the group consisting of:
  (a) $C_1$–$C_6$ alkyl,
  (b) —$(CH_2)_{0-2}$-cycloalkyl,
  (c) —$(CH_2)_{0-2}$-aryl, where the aryl is optionally substituted with halogen, hydroxy, $C_1$–$C_6$ alkyl, amino, mono($C_1$–$C_6$)alkylamino, or di($C_1$–$C_6$) alkylamino, and
  (d) hydrogen,
(E) —NH—$CO_2$—$R_{25}$,
(F) —O—($C_2$–$C_6$ alkyl)—$CO_2$H,
(G) —NRR',
(H) —SR,
(I) —$CH_2$OH,
(J) —C(O)—($C_1$–$C_6$)alkyl,
(K) —C(O)NRR',
(L) —$SO_2$NRR'
(M) —$CO_2$H,
(N) $C_1$–$C_6$ alkyl,
(O) $C_2$–$C_6$ alkenyl with one or two double bonds,
(P) —$C_2$–$C_6$ alkynyl with one or two triple bonds,
(Q) —$CF_3$,
(R) —F, —Cl, —Br, —I,
(S) $C_1$–$C_3$ alkoxy,
(T) —$OCF_3$,
(U) —$NH_2$,
(V) —OH, or,
(W) —$(CH_2)_{0-2}$—O—$(CH_2)_{0-2}$—OH;

W is —S—, —S(O)—, —S(O)$_2$—, —O—, or —N($R_{135}$)—, where $R_{135}$ is $C_1$–$C_6$ alkyl, $C_2$–$C_6$ alkenyl, $C_2$–$C_6$ alkynyl, $C_3$–$C_7$ cycloalkyl, —$(CH_2)_{0-2}$—(aryl), —$(CH_2)_{0-2}$—(heteroaryl), or —$(CH_2)_{0-2}$—(heterocyclyl);

L is absent when G is absent, or L is —C(O)—, —S(O)—, —$S_2$—, or —O—;

G is absent or $C_1$–$C_{10}$ alkyl;

$R_2$ is selected from the group consisting of:
(I) hydrogen, and
(II) $C_1$–$C_6$alkyl;

$R_3$ is selected from the group consisting of:
(I) —H, and
(II) $C_1$–$C_6$ alkyl;

$R_N$ is $R_{N-1}$—$X_N$—, where $X_N$ is —CO—, where $R_{N-1}$ is $R_{N-aryl}$ wherein $R_{N-aryl}$ at each occurrence is independently phenyl; naphthyl; tetralinyl; indanyl; indenyl; dihydronaphthyl; or 6,7,8,9-tetrahydro-5H-benzo[a]cycloheptenyl; each of which is optionally substituted with one, two or three of the following substituents which can be the same or different and are:

(1) $C_1$–$C_6$ alkyl, optionally substituted with one, two or three substituents selected from the group consisting of $C_1$–$C_3$ alkyl, —F, —Cl, —Br, —I, —OH, —SH, —C≡N, —$CF_3$, $C_1$–$C_3$ alkoxy, and —$NR_{1-a}R_{1-b}$, wherein $R_{1-a}$ and $R_{1-b}$ at each occurrence are independently H or $C_1$–$C_6$ alkyl,
(2) —OH,
(3) —$NO_2$,
(4) —F, —Cl, —Br, —I,
(5) —$CO_2$H,
(6) —C≡N,
(7) —$(CH_2)_{0-4}$—CO—$NR_{N-2}R_{N-3}$, where $R_{N-2}$ and $R_{N-3}$ are the same or different and are selected from the group consisting of:
  (a) —H,
  (b) —$C_1$–$C_8$ alkyl optionally substituted with one substituent selected from the group consisting of:
    (i) —OH,
    (ii) —$NH_2$, and
    (iii) phenyl, (c) —$C_1$–$C_8$ alkyl optionally substituted with 1, 2, or 3 groups that are independently —F, —Cl, —Br, or —I,
(d) —$C_3$–$C_8$ cycloalkyl,
(e) —($C_1$–$C_2$ alkyl)-($C_3$–$C_8$ cycloalkyl),
(f) —($C_1$–$C_6$ alkyl)—O—($C_1$–$C_3$ alkyl)
(g) —$C_2$–$C_6$ alkenyl,
(h) —$C_2$–$C_6$ alkynyl,
(i) —$C_1$–$C_6$ alkyl chain with one double bond and one triple bond, and
(j) —$R_{1\text{-}aryl}$, wherein $R_{1\text{-}aryl}$ at each occurrence is independently phenyl, naphthyl, indanyl, indenyl, dihydronaphthyl, or tetralinyl each of which is optionally substituted with 1, 2, 3, or 4 groups that are independently:
  (i) $C_1$–$C_6$ alkyl optionally substituted with one, two or three substituents independently selected from the group consisting of $C_1$–$C_3$ alkyl, —F, —Cl, —Br, —I, —OH, —SH, —$NR_{1\text{-}a}R_{1\text{-}b}$, —C≡N, —$CF_3$, and $C_1$–$C_3$ alkoxy,
  (ii) $C_2$–$C_6$ alkenyl with one or two double bonds, optionally substituted with one, two or three substituents independently selected from the group consisting of —F, —Cl, —OH, —SH, —C≡N, —$CF_3$, $C_1$–$C_3$ alkoxy, and —$NR_{1\text{-}a}R_{1\text{-}b}$,
  (iii) $C_2$–$C_6$ alkynyl optionally substituted with 1, 2, or 3 groups that are independently selected from the group consisting of —F, —Cl, —OH, —SH, —C≡N, —$CF_3$, $C_1$–$C_3$ alkoxy, and —$NR_{1\text{-}a}R_{1\text{-}b}$,
  (iv) —F, Cl, —Br and —I,
  (v) —$C_1$–$C_6$ alkoxy optionally substituted with 1, 2, or 3 —F,
  (vi) —OH,
  (vii) —C≡N,
  (viii) $C_3$–$C_7$ cycloalkyl, optionally substituted with 1, 2, or 3 groups that are selected from the group consisting of —F, —Cl, —OH, —SH, —C≡N, —$CF_3$, $C_1$–$C_3$ alkoxy, and —$NR_{1\text{-}a}R_{1\text{-}b}$,
  (ix) —CO—($C_1$–$C_4$ alkyl),
  (x) —$SO_2$—$NR_{1\text{-}a}R_{1\text{-}b}$,
  (xi) —CO—$NR_{1\text{-}a}R_{1\text{-}b}$, or
  (xii) —$SO_2$—($C_1$–$C_4$ alkyl)
(8) —$(CH_2)_{0\text{-}4}$—CO—($C_1$–$C_{12}$ alkyl),
(9) —$(CH_2)_{0\text{-}4}$—CO—($C_2$–$C_{12}$ alkenyl),
(10) —$(CH_2)_{0\text{-}4}$—CO—($C_2$–$C_{12}$ alkynyl),
(11) —$(CH_2)_{0\text{-}4}$—CO—($C_3$–$C_8$ cycloalkyl),
(12) —$(CH_2)_{0\text{-}4}$—CO—$R_{1\text{-}aryl}$,
(13) —$(CH_2)_{0\text{-}4}$—CO—$R_{N\text{-}4}$ wherein $R_{N\text{-}4}$ is optionally substituted with one, two, three, or four groups that are independently $C_1$–$C_6$ alkyl,
(14) —$(CH_2)_{0\text{-}4}$—CO—O—$R_{N\text{-}5}$, where $R_{N\text{-}5}$ is selected from the group consisting of:
  (a) $C_1$–$C_6$ alkyl,
  (b) —$(CH_2)_{0\text{-}2}$—($R_{1\text{-}aryl}$),
  (c) $C_2$–$C_6$ alkenyl,
  (d) $C_2$–$C_6$ alkynyl, and
  (e) —$(CH_2)_{0\text{-}2}$—$C_3$–$C_8$ cycloalkyl,
(15) —$(CH_2)_{0\text{-}4}$—$SO_2$—$NR_{N\text{-}2}R_{N\text{-}3}$,
(16) —$(CH_2)_{0\text{-}4}$—SO—($C_1$–$C_8$ alkyl),
(17) —$(CH_2)_{0\text{-}4}$—$SO_2$ ($C_1$–$C_{12}$ alkyl)
(18) —$(CH_2)_{0\text{-}4}$—$SO_2$—($C_3$–$C_8$ cycloalkyl),
(19) —$(CH_2)_{0\text{-}4}$—N(H or $R_{N\text{-}5}$)—CO—O—$R_{N\text{-}5}$,
(20) —$(CH_2)_{0\text{-}4}$—N(H or $R_{N\text{-}5}$)—CO—N($R_{N\text{-}5}$)$_2$,
(21) —$(CH_2)_{0\text{-}4}$—N—CS—N($R_{N\text{-}5}$)$_2$,
(22) —$(CH_2)_{0\text{-}4}$—N(H or $R_{N\text{-}5}$)—CO—$R_{N\text{-}2}$,
(23) —$(CH_2)_{0\text{-}4}$—$NR_{N\text{-}2}R_{N\text{-}3}$,
(24) —$(CH_2)_{0\text{-}4}$—$R_{N\text{-}4}$,
(25) —$(CH_2)_{0\text{-}4}$—O—CO—($C_1$–$C_6$ alkyl),
(26) —$(CH_2)_{0\text{-}4}$—O—CO—N($R_{N\text{-}5}$)$_2$,
(27) —$(CH_2)_{0\text{-}4}$—O—CS—N($R_{N\text{-}5}$)$_2$,
(28) —$(CH_2)_{0\text{-}4}$—O—($R_{N\text{-}5}$),
(29) —$(CH_2)_{0\text{-}4}$—O—($R_{N\text{-}5}$)—COOH,
(30) —$(CH_2)_{0\text{-}4}$—S—($R_{N\text{-}5}$),
(31) —$(CH_2)_{0\text{-}4}$—O—($C_1$–$C_6$ alkyl optionally substituted with one, two, three, four, or five of —F),
(32) $C_3$–$C_8$ cycloalkyl,
(33) $C_2$–$C_6$ alkenyl optionally substituted with $C_1$–$C_3$ alkyl, —F, —Cl, —Br, —I, —OH, —SH, —C≡N, —$CF_3$, $C_1$–$C_3$ alkoxy, or —$N_{1\text{-}a}R_{1\text{-}b}$,
(34) $C_2$–$C_6$ alkynyl optionally substituted with $C_1$–$C_3$ alkyl, —F, —Cl, —Br, —I, —OH, —SH, —C≡N, —$CF_3$, $C_1$–$C_3$ alkoxy, or —$NR_{1\text{-}a}R_{1\text{-}b}$,
(35) —$(CH_2)_{0\text{-}4}$—N(H or $R_{N\text{-}5}$)—$SO_2$—$R_{N\text{-}2}$, or
(36) —$(CH_2)_{1\text{-}4}$—($C_3$–$C_8$ cycloalkyl); and $R_C$ is selected from the group consisting of:
(I) —$C_1$–$C_{10}$ alkyl optionally substituted with one, two or three groups independently selected from the group consisting of $C_1$–$C_3$ alkyl, halogen, —OH, —SH, —C≡N, —$CF_3$, $C_1$–$C_6$ alkoxy, —O-phenyl, —$NR_{1\text{-}a}R_{1\text{-}b}$, —OC=O $NR_{1\text{-}a}R_{1\text{-}b}$, —$S(=O)_{0\text{-}2}R_{1\text{-}a}$, —$NR_{1\text{-}a}$C=O $NR_{1\text{-}a}R_{1\text{-}b}$, —C=O $NR_{1\text{-}a}R_{1\text{-}b}$, and —$S(=O)_2 NR_{1\text{-}a}R_{1\text{-}b}$ wherein
(II) —$(CH_2)_{0\text{-}3}$—($C_3$–$C_8$) cycloalkyl where cycloalkyl can be optionally substituted with one, two or three substituents independently selected from the group consisting of $C_1$–$C_3$ alkyl, halogen, —OH, —SH, —C≡N, —$CF_3$, $C_1$–$C_6$ alkoxy, —O-phenyl, —$CO_2H$, —$CO_2$—($C_1$–$C_4$ alkyl), and —$NR_{1\text{-}a}R_{1\text{-}b}$
(III) —$(CR_{C\text{-}x}R_{C\text{-}y})_{0\text{-}4}$—$R_{C\text{-}aryl}$ where $R_{C\text{-}x}$ and $R_{C\text{-}y}$ are independently selected from the group consisting of
  —H,
  $C_1$–$C_4$ alkyl optionally substituted with 1 or 2 —OH,
  $C_1$–$C_4$ alkoxy optionally substituted with 1, 2, or 3 halogen,
  —$(CH_2)_{0\text{-}4}$—$C_3$–$C_8$ cycloalkyl,
  $C_2$–$C_6$ alkenyl containing one or two double bonds,
  $C_2$–$C_6$ alkynyl containing one or two triple bonds, and
  phenyl, or
  $R_{C\text{-}x}$ and $R_{C\text{-}y}$ are taken together with the carbon to which they are attached to form a carbocycle of three, four, five, six or seven carbon atoms,
  wherein $R_{C\text{-}aryl}$ at each occurrence is independently phenyl; naphthyl; tetralinyl; indanyl; dihydronaphthyl; or 6,7,8,9-tetrahydro-5H-benzo[a]cycloheptenyl, each of which is optionally substituted with 1, 2, or 3 groups that are independently:
  (1) $C_1$–$C_6$ alkyl, optionally substituted with one, two or three substituents selected from the group consisting of $C_1$–$C_3$ alkyl, halogen, —OH, —SH, —C≡N, —$CF_3$, $C_1$–$C_3$ alkoxy, and —$NR_{1\text{-}a}R_{1\text{-}b}$,
  (2) —OH,
  (3) —$NO_2$,
  (4) halogen,
  (5) —$CO_2H$,
  (6) —C≡N,
  (7) —$(CH_2)_{0\text{-}4}$—CO—$NR_{N\text{-}2}R_{N\text{-}3}$,
  (8) —$(CH_2)_{0\text{-}4}$—CO—($C_1$–$C_{12}$ alkyl),
  (9) —$(CH_2)_{0\text{-}4}$—CO—($C_2$–$C_{12}$ alkenyl),
  (10) —$(CH_2)_{0\text{-}4}$—CO—($C_2$–$C_{12}$ alkynyl),
  (11) —$(CH_2)_{0\text{-}4}$—CO—$(CH_2)_{0\text{-}4}$ ($C_3$–$C_7$ cycloalkyl),

(12) —$(CH_2)_{0-4}$—CO—$R_{1-aryl}$,
(13) —$(CH_2)_{0-4}$—$CO_2$—$R_{N-5}$,
(14) —$(CH_2)_{0-4}$—$SO_2$—$NR_{N-2}R_{N-3}$
(15) —$(CH_2)_{0-4}$—SO—$(C_1-C_8$ alkyl),
(16) —$(CH_2)_{0-4}$—$SO_2$—$(C_1-C_{12}$ alkyl),
(17) —$(CH_2)_{0-4}$—$SO_2$—$(C_3-C_7$ cycloalkyl),
(18) —$(CH_2)_{0-4}$—N(H or $R_{N-5}$)—$CO_2$—$R_{N-5}$,
(19) —$(CH_2)_{0-4}$—N(H or $R_{N-5}$)—CO—$N(R_{N-5})_2$,
(20) —$(CH_2)_{0-4}$—N—CS—$N(R_{N-5})_2$,
(21) —$(CH_2)_{0-4}$—N(—H or $R_{N-5}$)—CO—$R_{N-2}$,
(22) —$(CH_2)_{0-4}$—$NR_{N-2}R_{N-3}$,
(23) —$(CH_2)_{0-4}$—$R_{N-4}$,
(24) —$(CH_2)_{0-4}$—O—CO—$(C_1-C_6$ alkyl),
(25) —$(CH_2)_{0-4}$—O—CO—$N(R_{N-5})_2$,
(26) —$(CH_2)_{0-4}$—O—CS—$N(R_{N-5})_2$,
(27) —$(CH_2)_{0-4}$—O—$(R_{N-5})$,
(28) —$(CH_2)_{0-4}$—O—$(R_{N-5})$—COOH,
(29) —$(CH_2)_{0-4}$—S—$(R_{N-5})$,
(30) —$(CH_2)_{0-4}$—O—$(C_1-C_6$ alkyl) wherein the alkyl group is optionally substituted with one, two, three, four, or five substituents independently selected from the group consisting of F, Cl, Br, and I,
(31) —$(CH_2)_{0-4}$—$(C_3-C_8$ cycloalkyl),
(32) $C_2-C_6$ alkenyl optionally substituted with $C_1-C_3$ alkyl, halogen, —OH, —SH, —C≡N, —$CF_3$, $C_1-C_3$ alkoxy, or —$NR_{1-a}R_{1-b}$,
(33) $C_2-C_6$ alkynyl optionally substituted with $C_1-C_3$ alkyl, —F, —Cl, —Br, —I, —OH, —SH, —C≡N, —$CF_3$, $C_1-C_3$ alkoxy, or —$NR_{1-a}R_{1-b}$, or
(34) —$(CH_2)_{0-4}$—N(—H or $R_{N-5}$)—$SO_2$—$R_{N-2}$;
(IV)  —$(CR_{c-x}R_{c-y})_{0-4}$—$R_{c-aryl}$—$R_{101}$—$R_{c-aryl}$, where $R_{101}$ is a bond, $(CH_2)_{0-4}$, —O—, —NH—, or —$N(C_1-C_6$ alkyl);
(V) —$[C(R_{C-1})(R_{C-2})]_{1-3}$—CO—$N(R_{C-3})_2$ where $R_{C-1}$ and $R_{C-2}$ are the same or different and are selected from the group consisting of:
(A) —H,
(B) —$C_1-C_6$ alkyl, optionally substituted with one, two or three substituents independently selected from the group consisting of $C_1-C_3$ alkyl, —F, —Cl, —Br, —I, —OH, —SH, —C≡N, —$CF_3$, $C_1-C_6$ alkoxy, —O-phenyl, and —$NR_{1-a}R_{1-b}$,
(C) $C_2-C_6$ alkenyl with one or two double bonds, optionally substituted with one, two or three substituents independently selected from the group consisting of $C_1-C_3$ alkyl, —F, —Cl, —Br, —I, —OH, —SH, —C≡N, —$CF_3$, $C_1-C_6$ alkoxy, —O-phenyl, and —$NR_{1-a}R_{1-b}$,
(D) $C_2-C_6$ alkynyl optionally substituted with one, two or three substituents independently selected from the group consisting of $C_1-C_3$ alkyl, —F, —Cl, —Br, —I, —OH, —SH, —C≡N, —$CF_3$, $C_1-C_6$ alkoxy, —O-phenyl, and —$NR_{1-a}R_{1-b}$,
(E) —$(CH_2)_{1-2}$—$S(O)_{0-2}$—$(C_1-C_6$ alkyl),
(F) —$(CH_2)_{0-4}$—$C_3-C_7$ cycloalkyl, optionally substituted with one, two or three substituents independently selected from the group consisting of $C_1-C_3$ alkyl, —F, —Cl, —Br, —I, —OH, —SH, —C≡N, —$CF_3$, $C_1-C_6$ alkoxy, —O-phenyl, and —$NR_{1-a}R_{1-b}$,
(G) —$(C_1-C_4$ alkyl)—$R_{1-aryl}$,
(H) —$(CH_2)_{1-4}$—$R_{C-4}$—$(CH_2)_{0-4}$—$R_{1-aryl}$ where $R_{C-4}$ is —O—, —S— or —$NR(C_1-C_6$ alkyl)—,
(I) —$R_{1-aryl}$, and where
$R_{C-3}$ at each occurrence is independently:
(A) —H,
(B) —$C_1-C_6$ alkyl optionally substituted with one, two or three substituents independently selected from the group consisting of $C_1-C_3$ alkyl, —F, —Cl, —Br, —I, —OH, —SH, —C≡N, —$CF_3$, $C_1-C_6$ alkoxy, —O-phenyl, and —$NR_{1-a}R_{1-b}$,
(C) $C_2-C_6$ alkenyl with one or two double bonds, optionally substituted with one, two or three substituents independently selected from the group consisting of $C_1-C_3$ alkyl, halogen, —OH, —SH, —C≡N, —$CF_3$, $C_1-C_6$ alkoxy, —O-phenyl, and —$NR_{1-a}R_{1-b}$,
(D) $C_2-C_6$ alkynyl with one or two triple bonds, optionally substituted with one, two or three substituents independently selected from the group consisting of $C_1-C_3$ alkyl, —F, —Cl, —Br, —I, —OH, —SH, —C≡N, —$CF_3$, $C_1-C_6$ alkoxy, —O-phenyl, and —$NR_{1-a}R_{1-b}$,
(E) —$(CH_2)_{0-4}$—$C_3-C_7$ cycloalkyl, optionally substituted with 1, 2, or 3 groups that are independently selected from the group consisting of $C_1-C_3$ alkyl, —F, —Cl, —Br, —I, —OH, —SH, —C≡N, —$CF_3$, $C_1-C_6$ alkoxy, —O-phenyl, and —$NR_{1-a}R_{1-b}$,
(F) —$R_{1-aryl}$,
(G) —$(C_1-C_4$ alkyl)—$R_{1-aryl}$,
(VI) —$CH(R_{C-aryl})_2$,
(VII) -cyclopentyl, -cyclohexyl, or -cycloheptyl ring fused to $R_{C-aryl}$, where $R_{C-aryl}$ is as defined above where cyclopentyl, cyclohexyl, or -cycloheptyl can be optionally substituted with one or two —$C_1-C_3$ alkyl, —F, —OH, —SH, —C≡N, —$CF_3$, $C_1-C_6$ alkoxy, =O, or —$NR_{1-a}R_{1-b}$,
(VIII) $C_2-C_{10}$ alkenyl optionally substituted with one, two or three substituents independently selected from the group consisting of $C_1-C_3$ alkyl, —F, —Cl, —Br, —I, —OH, —SH, —C≡N, —$CF_3$, $C_1-C_6$ alkoxy, —O-phenyl, and —$NR_{1-a}R_{1-b}$,
(IX) $C_2-C_{10}$ alkynyl optionally substituted with one, two or three substituents independently selected from the group consisting of $C_1-C_3$ alkyl, —F, —Cl, —Br, —I, —OH, —SH, —C≡N, —$CF_3$, $C_1-C_6$ alkoxy, —O-phenyl, and —$NR_{1-a}R_{1-b}$,
(X) —$(CH_2)_{0-1}$—$CHR_{C-6}$—$(CH_2)_{0-1}$—$R_{C-aryl}$ wherein $R_{C-6}$ is —$(CH_2)_{0-6}$—OH,
(XI) —$CH(—R_{C-aryl})$—CO—$O(C_1-C_4$ alkyl),
(XII) —CH(—$CH_2$OH)—CH(OH)—$(C_1-C_6$ alkyl)—$NO_2$,
(XIII) —$(C_1-C_6$ alkyl)—O—$(C_1-C_6$ alkyl)—OH,
(XIV) —$CH_2$—NH—$CH_2$—CH(—O—$CH_2$—$CH_3$)$_2$,
(XV) —H, and
(XVI) —$(CH_2)_{0-6}$—C(=$NR_{1-a}$)($NR_{1-a}R_{1-b}$).

2. A compound or salt according to claim 1, which is selected from the group consisting of N-{(1R,2R)-2-hydroxy-3-[(3-iodobenzyl)amino]-1-[(2-naphthylthio)methyl]propyl}-3-methylbenzamide;

N-{(1R,2S)-2-hydroxy-3-[(3-iodobenzyl)amino]-1-[(2-naphthylthio)methyl]propyl}-3-methylbenzamide;

N'-{(1R,2R)-2-hydroxy-3-[(3-iodobenzyl)amino]-1-[(2-naphthylthio)methyl]propyl}-5-methyl-N,N-dipropyl-isophthalamide.

3. A compound according to claim 1, wherein the formula is

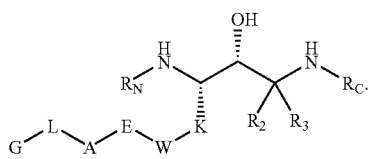

4. A compound according to claim 3, wherein
A is phenyl, or naphthyl optionally substituted with 1, 2, or 3 substituents each independently selected from the group consisting of halogen, $C_1$–$C_6$ alkyl, —O—($C_1$–$C_6$ alkyl), and —N—($C_1$–$C_6$ alkyl)($C_1$–$C_6$ alkyl);
K is —$CH_2$—; and
W is selected from the group consisting of S, S(O), and $SO_2$.

5. A compound according to claim 4, wherein
$R_C$ is benzyl or

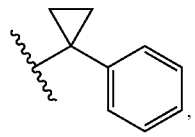

wherein each of which is substituted with at least one $R_{200}$; wherein
$R_{200}$ is $C_1$–$C_4$ alkyl, halogen, or $C_1$–$C_4$ alkoxy;
$R_N$ is —C(=O)—$R_{100}$; wherein $R_{100}$ is phenyl, optionally substituted with 1 or 2 groups independently selected from —OH, $C_1$–$C_4$ alkyl, $C_1$–$C_4$ alkoxy, halogen, —C≡N, —$SO_2R_{145}$, —C(O)NRR, and —N(R)($SO_2R_{145}$); wherein
R at each occurrence is independently H or $C_1$–$C_4$ alkyl;
$R_{145}$ is $C_1$–$C_6$ alkyl;
W is S; and
$R_2$ and $R_3$ are both hydrogen.

6. A compound according to claim 5, wherein
$R_C$ is 3-halobenzyl; and
A is naphth-2-yl optionally substituted with 1, or 2 substituents each independently selected from the group consisting of halogen, $C_1$–$C_6$ alkyl, and —O—($C_1$–$C_6$ alkyl).

7. A compound according to claim 6, wherein
$R_N$ is —C(=O)—$R_{100}$; wherein
$R_{100}$ is phenyl optionally substituted with 1 or 2 groups selected from $C_1$–$C_4$ alkyl and —C(O)NRR, wherein
R at each occurrence is independently H or $C_1$–$C_4$ alkyl.

8. A compound according to claim 7, wherein
$R_C$ is 3-iodo benzyl;
A is naphthyl-2-yl; and
$R_{100}$ is phenyl substituted with 1 group selected from methyl, ethyl, and —C(O)NRR, wherein
R at each occurrence is independently H or $C_3$–$C_4$ alkyl.

9. A compound according to claim 1, wherein
$R_C$ is benzyl or

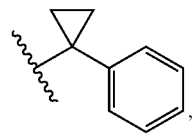

wherein each of which is substituted with at least one $R_{200}$; wherein
$R_{200}$ is $C_1$–$C_4$ alkyl, halogen, or $C_1$–$C_4$ alkoxy;
$R_N$ is —C(=O)—$R_{100}$; wherein
$R_{100}$ is phenyl optionally substituted with 1 or 2 groups independently selected from —OH, $C_1$–$C_4$ alkyl, $C_1$–$C_4$ alkoxy, halogen, —C≡N, —$SO_2R_{145}$, —C(O)NRR, and —N(R)($SO_2R_{145}$);
R at each occurrence is independently H or $C_1$–$C_4$ alkyl;
$R_{145}$ is $C_1$–$C_6$ alkyl;
A is phenyl or naphthyl, each of which is optionally substituted with 1, 2, or 3 substituents each independently selected from the group consisting of halogen, $C_1$–$C_6$ alkyl, —O—($C_1$–$C_6$ alkyl), $C_3$–$C_6$ cycloalkyl-$C_1$–$C_4$ alkyl, and —N—($C_1$–$C_6$ alkyl)($C_1$–$C_6$ alkyl);
E is a bond;
K is —$(CR_4R_5)_n$—; wherein
n is 0, 1, or 2;
L is absent or —O—; and
G is $C_1$–$C_{10}$ alkyl, optionally substituted with up to three groups independently selected from the group consisting of
(A) halogen,
(B) —OH,
(C) $C_1$–$C_6$ alkoxy, and
(D) $C_1$–$C_6$ haloalkyl; and
W is —O—, —S(O)$_{0-2}$—, or —N($R_{135}$)—.

10. A compound according to claim 9, wherein
$R_C$ is 3-methoxybenzyl.

11. A composition comprising a compound or salt according to claim 1 and at least one pharmaceutically acceptable carrier, solvent, adjuvant, additive or excipient.

* * * * *

SEQUENCE LISTING

```
<160> NUMBER OF SEQ ID NOS: 9

<210> SEQ ID NO 1
<211> LENGTH: 13
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (11)..(11)
<223> OTHER INFORMATION: covalent attachment of oregon green

<400> SEQUENCE: 1

Ser Glu Val Asn Leu Asp Ala Glu Phe Arg Cys Lys Lys
1               5                   10

<210> SEQ ID NO 2
<211> LENGTH: 13
```

-continued

```
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (11)..(11)
<223> OTHER INFORMATION: covalent attachment of oregon green

<400> SEQUENCE: 2

Ser Glu Val Lys Met Asp Ala Glu Phe Arg Cys Lys Lys
1               5                   10

<210> SEQ ID NO 3
<211> LENGTH: 22
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (20)..(20)
<223> OTHER INFORMATION: covalent attachment of oregon green

<400> SEQUENCE: 3

Gly Leu Asn Ile Lys Thr Glu Glu Ile Ser Glu Ile Ser Tyr Glu Val
1               5                   10                  15

Glu Phe Arg Cys Lys Lys
            20

<210> SEQ ID NO 4
<211> LENGTH: 34
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: N-terminal biotin
<220> FEATURE:
<221> NAME/KEY: MISC_FEATURE
<222> LOCATION: (32)..(32)
<223> OTHER INFORMATION: covalent attachment of oregon green

<400> SEQUENCE: 4

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe Arg Cys
            20                  25                  30

Lys Lys

<210> SEQ ID NO 5
<211> LENGTH: 33
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: N-terminal biotin
```

```
<220> FEATURE:
<221> NAME/KEY: MISC_FEATURE
<222> LOCATION: (7)..(7)
<223> OTHER INFORMATION: oxidized cysteine
<220> FEATURE:
<221> NAME/KEY: MISC_FEATURE
<222> LOCATION: (19)..(19)
<223> OTHER INFORMATION: oxidized cysteine
<220> FEATURE:
<221> NAME/KEY: MISC_FEATURE
<222> LOCATION: (31)..(31)
<223> OTHER INFORMATION: covalent attachment of oregon green

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Cys Lys
            20                  25                  30

Lys

<210> SEQ ID NO 6
<211> LENGTH: 33
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: N-terminal biotin

<400> SEQUENCE: 6

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu Asp Ala Glu
            20                  25                  30

Phe

<210> SEQ ID NO 7
<211> LENGTH: 29
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: N-terminal biotin

<400> SEQUENCE: 7

Cys Gly Gly Ala Asp Arg Gly Leu Thr Thr Arg Pro Gly Ser Gly Leu
1               5                   10                  15

Thr Asn Ile Lys Thr Glu Glu Ile Ser Glu Val Asn Leu
            20                  25

<210> SEQ ID NO 8
<211> LENGTH: 9
<212> TYPE: PRT
<213> ORGANISM: Artificial
<220> FEATURE:
<223> OTHER INFORMATION: synthetic

<400> SEQUENCE: 8

Ser Glu Val Asn Leu Asp Ala Glu Phe
1               5
```

```
<210> SEQ ID NO 9
<211> LENGTH: 30
<212> TYPE: PRT
<213> ORGANISM: Artificial
<220> FEATURE:
<223> OTHER INFORMATION: synthetic

<400> SEQUENCE: 9

Ala Asp Arg Gly Leu Thr Thr Arg Pro Gly Ser Gly Leu Thr Asn Ile
1               5                   10                  15

Lys Thr Glu Glu Ile Ser Glu Val Asn Leu Asp Ala Glu Phe
            20                  25                  30
```